(12) United States Patent
Ohkawa et al.

(10) Patent No.: US 7,495,018 B2
(45) Date of Patent: Feb. 24, 2009

(54) SUBSTITUTED 1,3-THIAZOLE COMPOUNDS, THEIR PRODUCTION AND USE

(75) Inventors: Shigenori Ohkawa, Takatsuki (JP); Ken-ichi Naruo, Sanda (JP); Seiji Miwatashi, Ikeda (JP); Hiroyuki Kimura, Sakai (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1388 days.

(21) Appl. No.: 10/239,692

(22) PCT Filed: Mar. 29, 2001

(86) PCT No.: PCT/JP01/02629

§ 371 (c)(1),
(2), (4) Date: Sep. 25, 2002

(87) PCT Pub. No.: WO01/74811

PCT Pub. Date: Oct. 11, 2001

(65) Prior Publication Data

US 2004/0053973 A1 Mar. 18, 2004

(30) Foreign Application Priority Data

Mar. 30, 2000 (JP) .............................. 2000-097876
Feb. 2, 2001 (JP) .............................. 2001-027571

(51) Int. Cl.
*A61K 31/4436* (2006.01)
*C07D 417/04* (2006.01)

(52) U.S. Cl. .................................. 514/342; 546/270.4

(58) Field of Classification Search ............... 546/270.4; 514/342
See application file for complete search history.

(56) References Cited

U.S. PATENT DOCUMENTS 4,612,321 A 9/1986 Shinji et al.

FOREIGN PATENT DOCUMENTS

| EP | 0 117 082 | 8/1984 |
|---|---|---|
| EP | 0 199 968 | 11/1986 |
| EP | 0 199 968 | 12/1986 |
| EP | 0 223 178 | 5/1987 |
| EP | 0 280 873 | 9/1988 |
| JP | 61-225182 | 10/1986 |
| JP | 5-70446 | 3/1993 |
| JP | 11-49762 | 2/1999 |
| WO | 93 14081 | 7/1993 |
| WO | 93 15071 | 8/1993 |
| WO | 95 13067 | 5/1995 |
| WO | 97/12876 | 4/1997 |
| WO | 99 21555 | 5/1999 |
| WO | 99 64418 | 12/1999 |
| WO | 00/64894 | * 11/2000 |
| WO | 01 10865 | 2/2001 |

OTHER PUBLICATIONS

Wagner et al., "Identification of, etc.," J. Org. Chem., 2003, 68, 4527-4530.*
Odeh, "Short Analytical Review, etc., "Clinical Immunology and Immunopathology, 83(2), 103-116, 1997.*
Campbell et al., "Molecular targets, etc.," Immunology and Cell Biology (2003) 81, 354-366.*
Bondenson, "Review the Mechanisms, etc.," Gen. Pharmaco., 29(2), 127-150, 1997.*
Database WPI, Section Ch, Week 199918, Derwent Publications Ltd., London, GB; AN 1999-210823 XP002177994 & JP 11 049762 A (Japan Tobacco Inc.), Feb. 23, 1999.
Patent Abstracts of Japan, vol. 017, No. 391, Jul. 22, 1993 & JP 05 070446, Mar. 23, 1993.
Database WPI, Section Ch, Week 198646, Derwent Publications Ltd., London, GB; AN 1986-302686 XP002178137 & JP 61 225182 A (Zenyaku Kogyo K.K.), Oct. 6, 1986.

* cited by examiner

*Primary Examiner*—Patricia L Morris
(74) *Attorney, Agent, or Firm*—Wenderoth, Lind & Ponack, L.L.P.

(57) ABSTRACT

(1) A 1,3-thiazole compound of which the 5-position is substituted with a 4-pyridyl group having a substituent including no aromatic group or (2) a 1,3-thiazole compound of which the 5-position is substituted with a pyridyl group having at the position adjacent to a nitrogen atom of the pyridyl group a substituent including no aromatic group has an excellent p38 MAP kinase inhibitory activity.

2 Claims, No Drawings

SUBSTITUTED 1,3-THIAZOLE COMPOUNDS, THEIR PRODUCTION AND USE

This application is a U.S. national stage of PCT/JP01/02629 filed Mar. 29, 2001.

TECHNICAL FIELD

The present invention relates to an excellent p38 MAP kinase inhibitor, a TNF-α production inhibitor, an adenosine receptor antagonist, and a selective phosphodiesterase IV (PDE IV) inhibitor and the like. More specifically, the present invention relates to a pharmaceutical composition comprising a 1,3-thiazole-based compound having an activity to prevent and/or treat cytokine-mediated diseases based on a p38 MAP kinase inhibiting activity, a TNF-α production inhibiting activity, a phosphodiesterase (PDE) inhibiting activity and the like, and to prevent and/or treat adenosine receptor mediated diseases based on an adenosine receptor antagonising activity.

BACKGROUND

Cytokines such as TNF-α (tumor necrosis factor-α), IL-1 (interleukin-1) and the like are biological substances produced by various cells such as monocytes, macrophages and the like in response to cellular stress such as infection and the like (Koj, A., Biochim. Biophys. Acta, 1317, 84-94 (1996)). These cytokines play an important role in immune reactions when they are present in an appropriate amount, while it is believed that excess. production thereof is related to a lot of inflammatory diseases (Dinarello, C. A., Curr. Opin. Immunol., 3, 941-948 (1991)). A p38 MAP kinase cloned as a homologue of a MAP kinase is concerned with control of the production of these cytokines, and with a signal transfer system coupled with a receptor, so inhibition of a p38 MAP kinase provides a possibility of a remedy for inflammatory diseases (Stein, B., Anderson, D., Annual Report in Medicinal Chemistry, Bristol, J. A. (ed.), Academic Press, 31, pp. 289 to 298, (1996)).

As examples having such a p38 MAP kinase inhibiting activity, imidazole derivatives are described in JP-A 7-50317 (WO 93/14081) and oxazole derivatives are described in JP-A 9-505055 (WO 95/13067), respectively.

On the other hand, as a thiazole-based compound, the following compounds, etc. are known.

1) 1,3-thiazole derivatives of the formula:

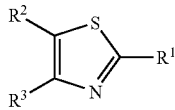

wherein $R^1$ represents a cycloalkyl group, a cyclic amino group, an amino group optionally having one or two lower alkyls, phenyls, acetyls or lower alkoxycarbonylacetyls as a substituent, an alkyl group optionally having hydroxyl, carboxyl or lower alkoxycarbonyl as a substituent, or a phenyl group optionally having carboxyl, 2-carboxyethenyl or 2-carboxy-1-propenyl as a substituent, $R^2$ represents a pyridyl group optionally having a lower alkyl as a substituent, and $R^3$ represents a phenyl group optionally having a lower alkoxy, lower alkyl, hydroxyl, halogen or methylenedioxy as a substituent, or a salt thereof, having analgesic, antipyretic, anti-inflammatory, antiulcer, thromboxane $A_2$ ($TXA_2$) synthase inhibitory, and antithrombotic activities (JP-A No. 60-58981).

2) 1,3-thiazole derivatives of the formula:

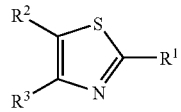

wherein $R^1$ represents an alkyl group, alkenyl group, aryl group, aralkyl group, cycloalkyl group, heterocyclic group having carbon as a connecting moiety, or amino group, $R^2$ represents a pyridyl group optionally substituted with an alkyl group, and $R^3$ represents a phenyl group optionally having a substituent, or a salt thereof, having analgesic, antipyretic, anti-inflammatory, antiulcer, $TXA_2$ synthase inhibitory, and antithrombotic activities (JP-A No. 61-10580).

3) 1,3-thiazole derivatives of the formula:

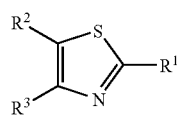

wherein $R^1$ represents an alkyl group, alkenyl group, aryl group, aralkyl group, cycloalkyl group, heterocyclic group having carbon as a connecting moiety, or amino group, $R^2$ represents a pyridyl group optionally substituted with an alkyl group, and $R^3$ represents an aryl group optionally having a substituent, or a salt thereof, having analgesic, antipyretic, anti-inflammatory, antiulcer, $TXA_2$ synthase inhibitory, and antithrombotic activities (U.S. Pat. No. 4,612,321).

4) Compounds of the formula:

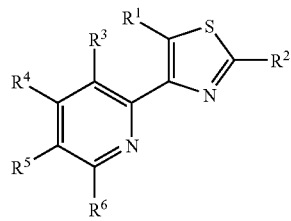

wherein $R^1$ represents phenyl optionally having a substituent, $R^2$ represents a $C_{1-6}$ alkyl or $(CH_2)_n Ar$ (n is 0 to 2, and Ar is phenyl optionally having a substituent), $R^3$ represents hydrogen or $C_{1-4}$ alkyl, $R^4$ represents hydrogen, $C_{1-4}$ alkyl or the like, $R^5$ represents hydrogen or $C_{1-4}$ alkyl, and $R^6$ represents hydrogen, $C_{1-4}$ alkyl or the like, or a salt thereof, having a gastric acid secretion inhibitory activity (JP-A No. 7-503023, WO 93/15071).

5) Compounds of the formula:

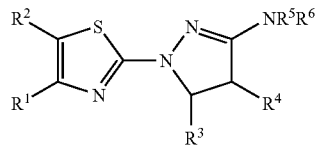

wherein $R^1$ represents pyridyl or the like, $R^2$ represents phenyl or the like, $R^3$ and $R^4$ represent hydrogen or methyl, $R^5$ represents methyl or the like, and $R^6$ represents hydrogen, methyl or the like, or a salt thereof, which are an anti-inflammatory agent and antiallergic agent (DE-A-3601411).

6) Compounds of the formula:

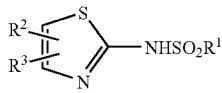

wherein $R^1$ represents a lower alkyl substituted with a halogen, $R^2$ represents pyridyl or the like, and $R^3$ represents phenyl or the like, or a salt thereof, having anti-inflammatory, antipyretic, analgesic and antiallergic activities (JP-A No. 5-70446).

7) Thiazole compounds of the formula:

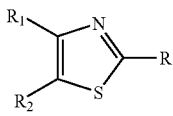

wherein R represents a lower alkyl group; lower haloalkyl group; lower hydroxyalkyl group; lower alkoxy lower alkyl group; aralkyloxy lower alkyl group or the like, $R^1$ represents a cycloalkyl group optionally substituted with a lower alkyl group and the like, and $R^2$ represents an aryl group optionally having a substituent, or the like, or a pharmaceutically acceptable salt thereof, having a TNF-α selective production inhibitory activity and/or IFN-γ production inhibitory activity (JP-A No. 11-49762).

There is a strong need to develop compounds having an excellent p38 MAP kinase inhibitory activity, TNF-α production inhibitory activity, adenosine receptor antagonizing activity and PDE IV inhibitory activity.

DISCLOSURE OF INVENTION

The present inventors have studied various compounds, and have found for the first time that 1,3-thiazole compounds having such specificity in chemical structure that the 5-position of a 1,3-thiazole skeleton is substituted with a 4-pyridyl group having a substituent including no aromatic group (hereinafter, sometimes abbreviated as compound (Ia)), 1,3-thiazole compounds having such specificity in chemical structure that the 5-position of a 1,3-thiazole skeleton is substituted with a pyridyl group having at the position adjacent to a nitrogen atom of the pyridyl group a substituent including no aromatic group (hereinafter, sometimes abbreviated as compound (Ib)) or 1,3-thiazole compounds having such specificity in chemical structure that the 5-position of a 1,3-thiazole skeleton is substituted with a 4-pyridyl group having at the position adjacent to a nitrogen atom of the 4-pyridyl group a substituent including no aromatic group (hereinafter, sometimes abbreviated as compound (Ic)) has an unexpectedly excellent p38 MAP kinase inhibitory activity, TNF-α production inhibitory activity, adenosine receptor antagonizing activity and PDE IV inhibitory activity based on their specific chemical structure, and is excellent also in pharmaceutical properties such as stability, leading to completion of the present invention based on this knowledges.

Namely, the present invention provides:

[1] A 1,3-thiazole compound of which 5-position is substituted with a 4-pyridyl group having a substituent including no aromatic group, provided that the 1,3-thiazole compound is not N-[4-(3,5-dimethylphenyl)-5-(2-hydroxy-4-pyridyl)-1,3-thiazol-2-yl]acetamide or 4-[2-(acetylamino)-4-(3,5-dimethylphenyl)-1,3-thiazol-5-yl]-2-pyridyl acetate, or a salt thereof;

[2] A compound as defined in [1] which is a compound represented by the formula:

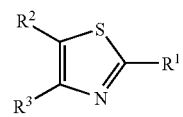

wherein $R^1$ represents a hydrogen atom, a hydrocarbon group optionally having a substituent, a heterocyclic group optionally having a substituent, an amino group optionally having a substituent or an acyl group, $R^2$ represents a 4-pyridyl group having a substituent including no aromatic group, and $R^3$ represents an aromatic group optionally having a substituent, or a salt thereof;

[3] A 1,3-thiazole compound of which 5-position is substituted with a pyridyl group having a substituent including no aromatic group, at a position adjacent to a nitrogen atom of the pyridyl group, provided that the 1,3-thiazole compound is not N-[4-(3,5-dimethylphenyl)-5-(2-hydroxy-4-pyridyl)-1,3-thiazol-2-yl]acetamide or 4-[2-(acetylamino)-4-(3,5-dimethylphenyl)-1,3-thiazol-5-yl]-2-pyridyl acetate, or a salt thereof;

[4] A compound as defined in [3] which is a compound represented by the formula:

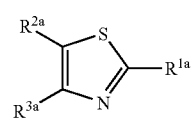

wherein $R^{1a}$ represents a hydrogen atom, a hydrocarbon group optionally having a substituent, a heterocyclic group optionally having a substituent, an amino group optionally having a substituent or an acyl group, $R^{2a}$ represents a pyridyl group having a substituent including no aromatic group, at a position adjacent to a nitrogen atom of the pyridyl group, and $R^{3a}$ represents an aromatic group optionally having a substituent, or a salt thereof;

[5] A 1,3-thiazole compound of which 5-position is substituted with a 4-pyridyl group having a substituent including no aromatic group, at a position adjacent to a nitrogen atom of the 4-pyridyl group, provided that the 1,3-thiazole compound is not N-[4-(3,5-dimethylphenyl)-5-(2-hydroxy-4-pyridyl)-1,3-thiazol-2-yl]acetamide or 4-[2-(acetylamino)-4-(3,5-dimethylphenyl)-1,3-thiazol-5-yl]-2-pyridyl acetate, or a salt thereof;

[6] A compound as defined in any one of [1] to [5] wherein the substituent including no aromatic group is a halogen atom, $C_{1-3}$ alkylenedioxy, nitro, cyano, $C_{1-6}$ alkyl which may be halogenated, $C_{2-6}$ alkenyl which may be halogenated, carboxy $C_{2-6}$ alkenyl, $C_{2-6}$ alkynyl which may be halogenated, $C_{3-8}$ cycloalkyl which may be halogenated, $C_{3-8}$ cycloalkyl-$C_{1-6}$ alkyl, $C_{1-8}$ alkoxy which may be halogenated, $C_{1-6}$ alkoxy-carbonyl-$C_{1-6}$ alkoxy, hydroxy, mercapto, $C_{1-6}$ alkylthio which may be halogenated, amino, mono-$C_{1-6}$ alkylamino, di-$C_{1-6}$ alkylamino, $C_{3-8}$ cycloalkylamino, $C_{3-8}$ cycloalkyl-$C_{1-6}$ alkylamino, N—$C_{3-8}$ cycloalkyl-N—$C_{1-6}$ alkylamino, formyl, carboxy, carboxy-$C_{2-6}$ alkenyl, carboxy-$C_{1-6}$ alkyl, $C_{1-6}$ alkyl-carbonyl which may be halogenated, $C_{3-8}$ cycloalkyl-carbonyl optionally substituted by $C_{1-6}$ alkyl, $C_{1-6}$ alkoxy-carbonyl, carbamoyl, thiocarbamoyl, mono-$C_{1-6}$ alkyl-carbamoyl, di-$C_{1-6}$ alkyl-carbamoyl, $C_{1-6}$ alkylsulfonyl, $C_{1-6}$ alkylsulfinyl, formylamino, $C_{1-6}$ alkyl-carbonylamino, $C_{3-8}$ cycloalkyl-carbonylamino which may be substituted by $C_{1-6}$ alkyl, $C_{1-6}$ alkoxy-carbonylamino, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy, 5- to 7-membered aliphatic heterocyclic group containing 1 to 4 of 1 or 2 kinds of hetero atoms selected from a nitrogen atom, a sulfur atom and an oxygen atom in addition to carbon atoms (this aliphatic heterocyclic group optionally has a substituent selected from $C_{1-6}$ alkyl, $C_{1-6}$ alkyl-carbonyl and oxo), sulfo, sulfamoyl, sulfinamoyl, sulfenamoyl or a group obtained by connecting 2 to 3 of these substituents (e.g., (i) $C_{1-6}$ alkyl, (ii) amino, (iii) $C_{1-6}$ alkylamino, (iv) $C_{3-8}$ cycloalkylamino, (v) 5- to 7-membered aliphatic heterocyclic amino containing 1 to 4 hetero atoms selected from a nitrogen atom, a sulfur atom and an oxygen atom in addition to carbon atoms, (vi) $C_{1-6}$ alkyl-carbonyl amino, (vii) $C_{3-8}$ cycloalkyl-carbonylamino or (viii) 5- to 7-membered aliphatic heterocyclic-carbonyl amino containing 1 to 4 hetero atoms selected from a nitrogen atom, a sulfur atom and an oxygen atom in addition to carbon atoms, which is substituted, respectively, by a substituent selected from the group consisting of a halogen atom, cyano, hydroxy, $C_{1-6}$ alkoxy, $C_{1-6}$ alkylthio, $C_{1-6}$ alkylsulfinyl, $C_{1-6}$ alkylsulfonyl, $C_{3-8}$ cycloalkyl, 5- to 7-membered aliphatic heterocyclic group containing 1 to 4 hetero atoms selected from a nitrogen atom, a sulfur atom and an oxygen atom in addition to carbon atoms, $C_{1-6}$ alkyl-carbonyl, $C_{3-8}$ cycloalkyl-carbonyl, 5- to 7-membered aliphatic heterocyclic-carbonyl containing 1 to 4 hetero atoms selected from a nitrogen atom, a sulfur atom and an oxygen atom in addition to carbon atoms, $C_{3-8}$ cycloalkoxy, 5- to 7-membered aliphatic heterocyclic-oxy containing 1 to 4 hetero atoms selected from a nitrogen atom, a sulfur atom and an oxygen atom in addition to carbon atoms, $C_{1-6}$ alkylamino, $C_{1-6}$ alkoxy-carbonyl, $C_{3-8}$ cycloalkoxy-carbonyl, 5- to 7-membered aliphatic heterocyclic-oxycarbonyl containing 1 to 4 hetero atoms selected from a nitrogen atom, a sulfur atom and an oxygen atom in addition to carbon atoms, etc.);

[7] A compound as defined in [2] or [4] wherein (1) the hydrocarbon group optionally having a substituent is a $C_{1-6}$ alkyl group, a $C_{2-6}$ alkenyl group, a $C_{2-6}$ alkynyl group, a $C_{3-8}$ cycloalkyl group, a $C_{6-14}$ aryl group or a $C_{7-16}$ aralkyl group, optionally having a substituent selected from Group A of substituents consisting of oxo, a halogen atom, $C_{1-3}$ alkylenedioxy, nitro, cyano, $C_{1-6}$ alkyl which may be halogenated, $C_{2-6}$ alkenyl which may be halogenated, carboxy $C_{2-6}$ alkenyl, $C_{2-6}$ alkynyl which may be halogenated, $C_{3-8}$ cycloalkyl which may be halogenated, $C_{3-8}$ cycloalkyl-$C_{1-6}$ alkyl, $C_{6-14}$ aryl, $C_{1-8}$ alkoxy which may be halogenated, $C_{1-6}$ alkoxy-carbonyl-$C_{1-6}$ alkoxy, hydroxy, $C_{6-14}$ aryloxy, $C_{7-16}$ aralkyloxy, mercapto, $C_{1-6}$ alkylthio which may be halogenated, $C_{6-14}$ arylthio, $C_{7-16}$ aralkylthio, amino, mono-$C_{1-6}$ alkylamino, mono-$C_{6-14}$ arylamino, di-$C_{1-6}$ alkylamino, $C_{3-8}$ cycloalkylamino, di-$C_{6-14}$ arylamino, $C_{3-8}$ cycloalkyl-$C_{1-6}$ alkylamino, N—$C_{3-8}$ cycloalkyl-N—$C_{1-6}$ alkylamino, formyl, carboxy, $C_{1-6}$ alkyl-carbonyl which may be halogenated, $C_{3-8}$ cycloalkyl-carbonyl optionally substituted by $C_{1-6}$ alkyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5- to 7-membered heterocyclic carbonyl containing 1 to 4 of 1 or 2 kinds of hetero atoms selected from a nitrogen atom, a sulfur atom and an oxygen atom in addition to carbon atoms, carbamoyl, thiocarbamoyl, mono-$C_{1-6}$ alkyl-carbamoyl, di-$C_{1-6}$ alkyl-carbamoyl, mono-$C_{6-14}$ aryl-carbamoyl, di-$C_{6-14}$ aryl-carbamoyl, 5- to 7-membered heterocyclic carbamoyl containing 1 to 4 of 1 or 2 kinds of hetero atoms selected from a nitrogen atom, a sulfur atom and an oxygen atom in addition to carbon atoms, $C_{1-6}$ alkylsulfonyl, $C_{6-14}$ arylsulfonyl, $C_{1-6}$ alkylsulfinyl, $C_{6-14}$ arylsulfinyl, formylamino, $C_{1-6}$ alkyl-carbonylamino, $C_{3-8}$ cycloalkyl-carbonylamino optionally substituted by $C_{1-6}$ alkyl, $C_{6-14}$ aryl-carbonylamino, $C_{1-6}$ alkoxy-carbonylamino, $C_{1-6}$ alkylsulfonylamino, $C_{6-14}$ arylsulfonylamino, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, mono-$C_{6-14}$ aryl-carbamoyloxy, di-$C_{6-14}$ aryl-carbamoyloxy, nicotinoyloxy, isonicotinoyloxy, 5- to 10-membered heterocyclic group containing 1 to 4 of 1 or 2 kinds of hetero atoms selected from a nitrogen atom, a sulfur atom and an oxygen atom in addition to carbon atoms (this heterocyclic group optionally has a substituent selected from $C_{1-6}$ alkyl, $C_{6-14}$ aryl, $C_{1-6}$ alkyl-carbonyl which may be halogenated, 5- to 10-membered aromatic heterocyclic group containing 1 to 4 of 1 or 2 kinds of hetero atoms selected from a nitrogen atom, a sulfur atom and an oxygen atom in addition to carbon atoms and oxo), sulfo, sulfamoyl, sulfinamoyl, sulfenamoyl and a group formed by connecting 2 to 3 of these substituents (e.g., (i) $C_{1-6}$ alkyl, (ii) $C_{6-14}$ aryl, (iii) amino, (iv) $C_{1-6}$ alkyl amino, (v) $C_{3-8}$ cycloalkylamino, (vi) $C_{6-14}$ arylamino, (vii) 5- to 7-membered heterocyclic amino containing 1 to 4 hetero atoms selected from a nitrogen atom, a sulfur atom and an oxygen atom in addition to carbon atoms, (viii) $C_{1-6}$ alkyl-carbonyl amino, (ix) $C_{3-8}$ cycloalkyl-carbonylamino, (x) $C_{6-14}$ aryl-carbonylamino or (xi) 5- to 7-membered heterocyclic-carbonyl amino containing 1 to 4 hetero atoms selected from a nitrogen atom, a sulfur atom and an oxygen atom in addition to carbon atoms, which is substituted, respectively, by a substituent selected from the group consisting of a halogen atom, cyano, hydroxy, $C_{1-6}$ alkoxy, $C_{6-14}$ aryloxy, $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl, $C_{3-8}$ cycloalkyl, 5- to 7-membered heterocyclic group containing 1 to 4 hetero atoms selected from a nitrogen atom, a sulfur atom and an oxygen atom in addition to carbon atoms, $C_{6-14}$ aryl, $C_{1-6}$ alkyl-carbonyl, $C_{3-8}$ cycloalkyl-carbonyl, 5- to 7-membered heterocyclic-carbonyl containing 1 to 4 hetero atoms selected from a nitrogen atom, a sulfur atom and an oxygen atom in addition to carbon atoms, $C_{6-14}$ aryl-carbonyl, $C_{3-8}$ cycloalkoxy, 5- to 7-membered heterocyclic-oxy containing 1 to 4 hetero atoms selected from a nitrogen atom, a sulfur atom and an oxygen atom in addition to carbon atoms, $C_{1-6}$ alkylamino, $C_{6-14}$ arylamino, $C_{1-6}$ alkoxy-carbonyl, $C_{3-8}$ cycloalkoxy-carbonyl, 5- to 7-membered heterocyclic-oxy-carbonyl containing 1 to 4 hetero atoms selected from a nitrogen atom, a sulfur atom and an oxygen atom in addition to carbon atoms, $C_{6-14}$ aryloxycarbonyl, etc.)

(2) the heterocyclic group optionally having a substituent is a 5- to 14-membered heterocyclic group containing 1 to 4 of 1 or 2 kinds of hetero atoms selected from a nitrogen atom, a sulfur atom and an oxygen atom in addition to carbon atoms, which optionally has a substituent selected from Group A of substituents, (3) the acyl group is an acyl group of the formula: —(C=O)—$R^{5a}$, —(C=O)—$OR^{5a}$, —(C=O)—$NR^{5a}R^{6a}$, —(C=S)-$NHR^{5a}$, —(C=O)—$N(OR^{5a})R^{6a}$, —(C=S)—$NHOR^{5a}$ or —$SO_2$—$R^{7a}$ (wherein $R^{5a}$ represents ① a hydrogen atom, ② a $C_{1-6}$ alkyl group, a $C_{2-6}$ alkenyl group, a $C_{2-6}$ alkynyl group, a $C_{3-8}$ cycloalkyl group, a $C_{6-14}$ aryl group or a $C_{7-16}$ aralkyl group, optionally having a substituent selected from Group A of substituents, or ③ a 5- to 14-membered heterocyclic group containing 1 to 4 of 1 or 2 kinds of hetero atoms selected from a nitrogen atom, a sulfur atom and an oxygen atom in addition to carbon atoms, which optionally has a substituent selected from Group A of substituents, $R^{6a}$ represents a hydrogen atom or a $C_{1-6}$ alkyl group, and $R^{7a}$ represents ① a $C_{1-6}$ alkyl group, a $C_{2-6}$ alkenyl group, a $C_{2-6}$ alkynyl group, a $C_{3-8}$ cycloalkyl group, a $C_{6-14}$ aryl group or a $C_{7-16}$ aralkyl group, optionally having a substituent selected from Group A of substituents, or ② a 5- to 14-membered heterocyclic group containing 1 to 4 of 1 or 2 kinds of hetero atoms selected from a nitrogen atom, a sulfur atom and an oxygen atom in addition to carbon atoms, which optionally has a substituent selected from Group A of substituents.), (4) the amino group optionally having a substituent is (i) an amino group optionally having 1 or 2 substituents selected from the group consisting of ① a $C_{1-6}$ alkyl group, a $C_{2-6}$ alkenyl group, a $C_{2-6}$ alkynyl group, a $C_{3-8}$ cycloalkyl group, a $C_{6-14}$ aryl group and a $C_{7-16}$ aralkyl group, optionally having a substituent selected from Group A of substituents, ② a 5- to 14-membered heterocyclic group containing 1 to 4 of 1 or 2 kinds of hetero atoms selected from a nitrogen atom, a sulfur atom and an oxygen atom in addition to carbon atoms, which optionally have a substituent selected from Group A of substituents, ③ an acyl group of the formula: —(C=O)—$R^{5a}$, —(C=O)—$OR^{5a}$, —(C=O)—$NR^{5a}R^{6a}$, —(C=S)—$NHR^{5a}$, —(C=O)—$N(OR^{5a})R^{6a}$, —(C=S)—$NHOR^{5a}$ or —$SO_2$—$R^{7a}$ (wherein each symbol is as defined above), and ④ a $C_{1-6}$ alkylidene group optionally having a substituent selected from Group A of substituents, or (ii) a 5- to 7-membered aliphatic cyclic amino group optionally containing 1 to 4 of 1 or 2 kinds of hetero atoms selected from a nitrogen atom, a sulfur atom and an oxygen atom in addition to one nitrogen atom and carbon atoms, which optionally has a substituent selected from the group consisting of $C_{1-6}$ alkyl, $C_{6-14}$ aryl, $C_{1-6}$ alkyl-carbonyl which may be halogenated, $C_{1-6}$ alkoxy-carbonyl, 5- to 10-membered aromatic heterocyclic group containing 1 to 4 of 1 or 2 kinds of hetero atoms selected from a nitrogen atom, a sulfur atom and an oxygen atom in addition to carbon atoms, and oxo, (5) the substituent containing no aromatic group is a halogen atom, $C_{1-3}$ alkylenedioxy, nitro, cyano, $C_{1-6}$ alkyl which may be halogenated, $C_{2-6}$ alkenyl which may be halogenated, carboxy $C_{2-6}$ alkenyl, $C_{2-6}$ alkynyl which may be halogenated, $C_{3-8}$ cycloalkyl which may be halogenated, $C_{3-8}$ cycloalkyl-$C_{1-6}$ alkyl, $C_{1-8}$ alkoxy which may be halogenated, $C_{1-6}$ alkoxy-carbonyl-$C_{1-6}$ alkoxy, hydroxy, mercapto, $C_{1-6}$ alkylthio which may be halogenated, amino, mono-$C_{1-6}$ alkylamino, di-$C_{1-6}$ alkylamino, $C_{3-8}$ cycloalkylamino, $C_{3-8}$ cycloalkyl-$C_{1-6}$ alkylamino, N—$C_{3-8}$ cycloalkyl-N—$C_{1-6}$ alkylamino, formyl, carboxy, carboxy-$C_{2-6}$ alkenyl, carboxy-$C_{1-6}$ alkyl, $C_{1-6}$ alkyl-carbonyl which may be halogenated, $C_{3-8}$ cycloalkyl-carbonyl optionally substituted by $C_{1-6}$ alkyl, $C_{1-6}$ alkoxy-carbonyl, carbamoyl, thiocarbamoyl, mono-$C_{1-6}$ alkyl-carbamoyl, di-$C_{1-6}$ alkyl-carbamoyl, $C_{1-6}$ alkylsulfonyl, $C_{1-6}$ alkylsulfinyl, formylamino, $C_{1-6}$ alkyl-carbonylamino, $C_{3-8}$ cycloalkyl-carbonylamino which may be substituted by $C_{1-6}$ alkyl, $C_{1-6}$ alkoxy-carbonylamino, $C_{1-6}$ alkylsulfonylamino, $C_{1-6}$ alkyl-carbonyloxy, $C_{1-6}$ alkoxy-carbonyloxy, mono-$C_{1-6}$ alkylcarbamoyloxy, di-$C_{1-6}$ alkyl-carbamoyloxy, 5- to 7-membered aliphatic heterocyclic group containing 1 to 4 of 1 or 2 kinds of hetero atoms selected from a nitrogen atom, a sulfur atom and an oxygen atom in addition to carbon atoms (this aliphatic heterocyclic group optionally has a substituent selected from $C_{1-6}$ alkyl, $C_{1-6}$ alkyl-carbonyl and oxo), sulfo, sulfamoyl, sulfinamoyl, sulfenamoyl or a group obtained by connecting 2 to 3 of these substituents (e.g., (i) $C_{1-6}$ alkyl, (ii) amino, (iii) $C_{1-6}$ alkylamino, (iv) $C_{3-8}$ cycloalkylamino, (v) 5- to 7-membered aliphatic heterocyclic amino containing 1 to 4 hetero atoms selected from a nitrogen atom, a sulfur atom and an oxygen atom in addition to carbon atoms, (vi) $C_{1-6}$ alkyl-carbonyl amino, (vii) $C_{3-8}$ cycloalkyl-carbonylamino or (viii) 5- to 7-membered aliphatic heterocyclic-carbonyl amino containing 1 to 4 hetero atoms selected from a nitrogen atom, a sulfur atom and an oxygen atom in addition to carbon atoms, which is substituted, respectively, by a substituent selected from the group consisting of a halogen atom, cyano, hydroxy, $C_{1-6}$ alkoxy, $C_{1-6}$ alkylthio, $C_{1-6}$ alkylsulfinyl, $C_{1-6}$ alkylsulfonyl, $C_{3-8}$ cycloalkyl, 5- to 7-membered aliphatic heterocyclic group containing 1 to 4 hetero atoms selected from a nitrogen atom, a sulfur atom and an oxygen atom in addition to carbon atoms, $C_{1-6}$ alkyl-carbonyl, $C_{3-8}$ cycloalkyl-carbonyl, 5- to 7-membered aliphatic heterocyclic-carbonyl containing 1 to 4 hetero atoms selected from a nitrogen atom, a sulfur atom and an oxygen atom in addition to carbon atoms, $C_{3-8}$ cycloalkoxy, 5- to 7-membered aliphatic heterocyclicoxy containing 1 to 4 hetero atoms selected from a nitrogen atom, a sulfur atom and an oxygen atom in addition to carbon atoms, $C_{1-6}$ alkylamino, $C_{1-6}$ alkoxy-carbonyl, $C_{3-8}$ cycloalkoxy-carbonyl, 5- to 7-membered aliphatic heterocyclic-oxycarbonyl containing 1 to 4 hetero atoms selected from a nitrogen atom, a sulfur atom and an oxygen atom in addition to carbon atoms, etc.), (6) the aromatic group optionally having a substituent is ① a $C_{6-14}$ mono-cyclic or fused poly-cyclic aromatic hydrocarbon group optionally having a substituent selected from Group A of substituents, or ② a 5- to 14-membered aromatic heterocyclic group containing 1 to 4 of 1 or 2 kinds of hetero atoms selected from a nitrogen atom, a sulfur atom and an oxygen atom in addition to carbon atoms;

[8] A compound as defined in [2] or [4] wherein $R^1$ represents (i) a hydrogen atom, (ii) a $C_{1-6}$ alkyl group optionally substituted by a substituent selected from the group consisting of a halogen atom, $C_{1-6}$ alkoxy-carbonyl, carboxy, cyano, $C_{1-6}$ alkylthio, $C_{1-6}$ alkylsulfinyl, $C_{1-6}$ alkylsulfonyl, hydroxy, $C_{1-6}$ alkoxy and $C_{1-6}$ alkyl-carbonyl, (iii) a $C_{6-14}$ aryl group optionally having a substituent selected from the group consisting of a halogen atom and a group of the formula: —S(O)$_n$—$R^{1bb}$ (wherein $R^{1bb}$ represents a $C_{1-6}$ alkyl group, and n represents an integer of 0 to 2), (iv) a $C_{7-15}$ aralkyl group, (v) an amino group optionally having one or two substituents selected from ① $C_{1-6}$ alkyl, ② $C_{1-6}$ alkyl-carbonyl, ③ 5- to 7-membered heterocyclic-carbonyl containing 1 to 4 hetero atoms selected from the group consisting of a nitrogen atom, an oxygen atom and a sulfur atom, in addition to carbon atoms, optionally substituted with a halogen atom, $C_{1-6}$ alkyl or $C_{1-6}$ alkoxy, ④ $C_{6-14}$ aryl-carbamoyl, ⑤ $C_{1-6}$ alkyl-carbamoyl which may be halogenated, ⑥ $C_{1-6}$ alkoxy-carbonyl which may be halogenated, ⑦ $C_{1-6}$ alkoxy-carbamoyl and ⑧ $C_{6-14}$ aryloxy-carbamoyl, (vi) a 5- to 10-membered heterocyclic group containing 1 to 4 of 1 or 2 kinds of hetero atoms selected from a nitrogen atom, a sulfur atom and an oxygen atom in addition to carbon atoms, optionally substituted by oxo, $C_{1-6}$ alkyl, $C_{6-14}$ aryl or $C_{1-6}$ alkoxy-carbonyl, (vii) an acyl group represented by the formula: —(C=O)—$R^{5b}$ (wherein $R^{5b}$ represents a hydrogen atom, a $C_{1-6}$ alkyl group which may be halogenated or a $C_{6-14}$ aryl group which may be halogenated), or (viii) an acyl group represened by the formula: —(C=O)—$OR^{5c}$ (wherein $R^{5c}$ represents a hydrogen atom or a $C_{1-6}$ alkyl group);

[9] A compound as defined in [2] or [4] wherein the substituent having no aromatic group is (1) a $C_{1-6}$ alkyl group (this $C_{1-6}$ alkyl may be substituted by a halogen atom, cyano, hydroxy, $C_{3-8}$ cycloalkyl or 5- to 7-membered aliphatic heterocyclic group containing hetero atoms selected from a nitrogen atom, an oxygen atom and a sulfur atom in addition to carbon atoms), (2) a halogen atom,
(3) an amino group optionally having a substituent selected from the group consisting of the following ① to ⑦;
① a $C_{1-6}$ alkyl group (this $C_{1-6}$ alkyl group may be substituted by a halogen atom, cyano, hydroxy, $C_{3-8}$ cycloalkyl or 5- to 7-membered aliphatic heterocyclic group having 1 to 4 hetero atoms selected from a nitrogen atom, an oxygen atom and a sulfur atom in addition to carbon atoms),
② a $C_{3-8}$ cycloalkyl group,
③ a $C_{1-6}$ alkyl-carbonyl group (this $C_{1-6}$ alkyl-carbonyl group may be substituted by a halogen atom, cyano, hydroxy, $C_{3-8}$ cycloalkyl or 5- to 7-membered aliphatic heterocyclic group having 1 to 4 hetero atoms selected from a nitrogen atom, an oxygen atom and a sulfur atom in addition to carbon atoms),
④ a $C_{1-6}$ alkoxy-carbonyl group,
⑤ a $C_{3-8}$ cycloalkyl-carbonyl group optionally substituted by $C_{1-6}$ alkyl,
⑥ a 5- to 7-membered aliphatic heterocyclic group having 1 to 4 hetero atoms selected from a nitrogen atom, an oxygen atom and a sulfur atom in addition to carbon atoms (this aliphatic heterocyclic group may be substituted by $C_{1-6}$ alkyl or $C_{1-6}$ alkyl-carbonyl),
⑦ a 5- to 7-membered aliphatic heterocyclic-carbonyl group having 1 to 4 hetero atoms selected from a nitrogen atom, an oxygen atom and a sulfur atom in addition to carbon atoms (this aliphatic heterocyclic-carbonyl group may be substituted by $C_{1-6}$ alkyl or $C_{1-6}$ alkyl-carbonyl)
(4) a 5- to 7-membered aliphatic cyclic amino group optionally further containing hetero atoms selected from a nitrogen atom, an oxygen atom and a sulfur atom in addition to carbon atoms and one nitrogen atom (this aliphatic cyclic amino group may be substituted by $C_{1-6}$ alkyl or $C_{1-6}$ alkyl-carbonyl),
(5) a hydroxy group, or
(6) a $C_{1-6}$ alkyl-carbonyloxy group.

[10] A compound as defined in [2] or [4] wherein $R^3$ is ① a $C_{6-14}$ aryl group or ② a 5- to 14-membered aromatic heterocyclic group preferably containing 1 to 4 of 1 or 2 kinds of hetero atoms selected from a nitrogen atom, a sulfur atom and an oxygen atom in addition to carbon atoms, which optionally has substituents selected from the group consisting of $C_{1-6}$ alkyl which may be halogenated, $C_{1-6}$ alkoxy, a halogen atom, carboxyl, $C_{1-6}$ alkoxy-carbonyl, cyano, $C_{1-6}$ alkylthio and $C_{1-6}$ alkylsulfonyl;

[11] A compound as defined in [3] which is a compound of the formula:

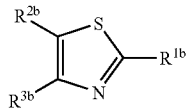

(Ibbb)

wherein $R^{1b}$ represents (i) a hydrogen atom, (ii) a $C_{1-6}$ alkyl group optionally substituted by a substituent selected from the group consisting of a halogen atom, $C_{1-16}$ alkoxy-carbonyl, carboxy, cyano, $C_{1-6}$ alkylthio, $C_{1-6}$ alkylsulfinyl, $C_{1-6}$ alkylsulfonyl, hydroxy, $C_{1-6}$ alkoxy and $C_{1-6}$ alkyl-carbonyl, (iii) a $C_{6-14}$ aryl group optionally having a substituent selected from the group consisting of a halogen atom and a group of the formula: —$S(O)_n$—$R^{1bb}$ ($R^{1bb}$ represents a $C_{1-6}$ alkyl group, and n represents an integer of 0 to 2), (iv) a $C_{7-15}$ aralkyl group, (v) an amino group optionally having one or two substituents selected from ① $C_{1-6}$ alkyl, ② $C_{1-6}$ alkyl-carbonyl, ③ $C_{1-6}$ alkoxy-carbonyl, ④ 5- to 7-membered heterocyclic-carbonyl containing 1 to 4 hetero atoms selected from the group consisting of a nitrogen atom, an oxygen atom and a sulfur atom in addition to carbon atoms, optionally substituted with a halogen atom, $C_{1-6}$ alkyl or $C_{1-6}$ alkoxy, ⑤ $C_{6-14}$ aryl-carbamoyl, ⑥ $C_{1-6}$ alkyl-carbamoyl which may be halogenated, ⑦ $C_{1-6}$ alkoxy-carbonyl which may be halogenated, ⑧ $C_{1-6}$ alkoxy-carbamoyl and ⑨ $C_{6-14}$ aryloxy-carbamoyl, (vi) a 5- to 10-membered heterocyclic group containing 1 to 4 of 1 or 2 kinds of hetero atoms selected from a nitrogen atom, a sulfur atom and an oxygen atom in addition to carbon atoms, optionally substituted by oxo, $C_{1-6}$ alkyl, $C_{6-14}$ aryl, $C_{1-6}$ alkyl-carbonyl or $C_{1-6}$ alkoxy-carbonyl, (vii) an acyl group represented by the formula: —(C=O)—$R^{5b}$ (wherein $R^{5b}$ represents a hydrogen atom, a $C_{1-6}$ alkyl group which may be halogenated or a $C_{6-14}$ aryl group which may be halogenated), or (viii) an acyl group represented by the formula: —(C=O)—$OR^{5c}$ (wherein $R^{5c}$ represents a hydrogen atom or $C_{1-6}$ alkyl group), $R^{2b}$ represents a pyridyl group having at the position adjacent to a nitrogen atom of the pyridyl group a substituent selected from the group consisting of
(1) a $C_{1-6}$ alkyl group (this $C_{1-6}$ alkyl group may be substituted by a halogen atom, cyano, hydroxy, $C_{3-8}$ cycloalkyl or a 5- to 7-membered aliphatic heterocyclic group containing hetero atoms selected from a nitrogen atom, an oxygen atom and a sulfur atom in addition to carbon atoms),
(2) a halogen atom,
(3) an amino group optionally having a substituent selected from the group consisting of the following ① to ⑦;
① a $C_{1-6}$ alkyl group (this $C_{1-6}$ alkyl group may be substituted by a halogen atom, cyano, hydroxy, $C_{3-8}$ cycloalkyl or a 5- to 7-membered aliphatic heterocyclic group having 1 to 4 hetero atoms selected from a nitrogen atom, an oxygen atom and a sulfur atom in addition to carbon atoms)
② a $C_{3-8}$ cycloalkyl group,
③ a $C_{1-6}$ alkyl-carbonyl group (this $C_{1-6}$ alkyl-carbonyl group may be substituted by a halogen atom, cyano, hydroxy, $C_{3-8}$ cycloalkyl or a 5- to 7-membered aliphatic heterocyclic group having 1 to 4 hetero atoms selected from a nitrogen atom, an oxygen atom and a sulfur atom in addition to carbon atoms),
④ a $C_{1-6}$ alkoxy-carbonyl group,
⑤ a $C_{3-8}$ cycloalkyl-carbonyl group optionally substituted by $C_{1-6}$ alkyl,
⑥ a 5- to 7-membered aliphatic heterocyclic group having 1 to 4 hetero atoms selected from a nitrogen atom, an oxygen atom and a sulfur atom in addition to carbon atoms (this aliphatic heterocyclic group may be substituted by $C_{1-6}$ alkyl or $C_{1-6}$ alkyl-carbonyl),
⑦ a 5- to 7-membered aliphatic heterocyclic-carbonyl group having 1 to 4 hetero atoms selected from a nitrogen atom, an oxygen atom and a sulfur atom in addition to carbon atoms (this aliphatic heterocyclic-carbonyl group may be substituted by $C_{1-6}$ alkyl or $C_{1-6}$ alkyl-carbonyl),
(4) a 5- to 7-membered aliphatic cyclic amino group optionally further containing 1 to 4 hetero atoms selected from a nitrogen atom, an oxygen atom and a sulfur atom in addition to carbon atoms and one nitrogen atom (this saturated cyclic amino group may be substituted by $C_{1-6}$ alkyl or $C_{1-6}$ alkyl-carbonyl),
(5) a hydroxy group, and
(6) a $C_{1-6}$ alkyl-carbonyloxy group, and
$R^{3b}$ represents ① a $C_{6-14}$ aryl group or ② a 5- to 14-membered aromatic heterocyclic group containing 1 to 4 of 1 or 2 kinds of hetero atoms selected from a nitrogen atom, a sulfur atom and an oxygen atom in addition to carbon atoms, which optionally has a substituent selected from the group consisting of $C_{1-6}$ alkyl which may be halogenated, $C_{1-6}$ alkoxy, a halogen atom, carboxyl, $C_{1-6}$ alkoxy-carbonyl, cyano, $C_{1-6}$ alkylthio and $C_{1-6}$ alkylsulfonyl, or a salt thereof;

[12] A compound as defined in [11] wherein the pyridyl group is a 4-pyridyl group;

[13] A compound as defined in [11] wherein $R^{1b}$ is a $C_{1-6}$ alkyl group optionally having a substituent selected from the group consisting of a halogen atom, hydroxy, $C_{1-6}$ alkoxy, $C_{1-6}$ alkylthio, $C_{1-6}$ alkylsulfinyl and $C_{1-6}$ alkylsulfonyl, $R^{2b}$ is a 4-pyridyl group having a $C_{1-6}$ alkyl-carbonyl-amino group or a $C_{3-8}$ cycloalkylamino group at the position adjacent to a nitrogen atom of the 4-pyridyl group, $R^{3b}$ is a $C_{6-14}$ aryl group which optionally has a substituent selected from the group consisting of $C_{1-6}$ alkyl and a halogen atom;

[14] A compound as defined in [11] wherein $R^{1b}$ is a $C_{1-3}$ alkyl group optionally having a substituent selected from the group consisting of a halogen atom, hydroxy, $C_{1-6}$ alkoxy, $C_{1-6}$ alkylthio, $C_{1-6}$ alkylsulfinyl and $C_{1-6}$ alkylsulfonyl, $R^{2b}$ is a 4-pyridyl group having a $C_{1-3}$ alkyl-carbonyl-amino group or a $C_{3-8}$ cycloalkylamino group at the position adjacent to a nitrogen atom of the 4-pyridyl group, $R^{3b}$ is a phenyl group which optionally has a substituent selected from the group consisting of methyl and a chlorine atom;

[15] A compound as defined in [5] which is 5-[2-(tert-butoxycarbonylamino)-4-pyridyl]-2-ethyl-4-(3-methylphenyl)-1,3-thiazole (Example 3),

[4-(3-methylphenyl)-5-(2-methyl-4-pyridyl)-1,3-thiazol-2-yl]amine (Example 7-4), 2-ethyl-5-(2-fluoro-4-pyridyl)-4-(3-methylphenyl)-1,3-thiazole (Example 11), 5-(2-fluoro-4-pyridyl)-4-(3-methylphenyl)-2-[4-(methylthio)phenyl]-1,3-thiazole (Example 15), 4-(3-methylphenyl)-5-(2-methyl-4-pyridyl)-2-[4(methylthio)phenyl]-1,3-thiazole (Example 16-1), 4-[2-ethyl-4-(3-methylphenyl)-1,3-thiazol-5-yl]-2-pyridylamine (Example 22), N-[4-[2-ethyl-4-(3-methylphenyl)-1,3-thiazol-5-yl]-2-pyridyl]acetamide (Example 29-2), N-[4-[2-ethyl-4-(3-methylphenyl)-1,3-thiazol-5-yl]-2-pyridyl]propionamide (Example 29-4), N-[4-[4-(3-chlorophenyl)-2-methyl-1,3-thiazol-5-yl]-2-pyridyl]acetamide (Example 30-1), N-[4-[4-(3-chlorophenyl)-2-ethyl-1,3-thiazol-5-yl]-2-pyridyl]acetamide (Example 30-2), N-[4-[4-(3-chlorophenyl)-2-propyl-1,3-thiazol-5-yl]-2-pyridyl]acetamide (Example 30-3), N-[4-[4-(3-chlorophenyl)-2-methyl-1,3-thiazol-5-yl]-2-pyridyl]propionamide (Example 30-7), N-[4-[4-(3-chlorophenyl)-2-ethyl-1,3-thiazol-5-yl]-2-pyridyl]propionamide (Example 30-8), N-[4-[4-(3-chlorophenyl)-2-propyl-1,3-thiazol-5-yl]-2-pyridyl]propionamide (Example 30-9), N-cyclohexyl-4-[2-ethyl-4-(3-methylphenyl)-1,3-thiazol-5-yl]-2-pyridylamine (Example 36-4), N-cyclohexyl-4-[4-(3-methylphenyl)-2-(4-methylsulfonylphenyl)-1,3-thiazol-5-yl]-2-pyridylamine (Example 36-5), N-cyclopentyl-4-[2-ethyl-4-(3-methylphenyl)-1,3-thiazol-5-yl]-2-pyridylamine (Example 36-6), N-cyclopentyl-4-[4-(3-methylphenyl)-2-(4-methylsulfonylphenyl)-1,3-thiazol-5-yl]-2-pyridylamine (Example 36-7), 4-[4-(3-chlorophenyl)-2-ethyl-1,3-thiazol-5-yl]-N-cyclohexyl-2-pyridylamine (Example 36-10), 4-[4-(3-chlorophenyl)-2-ethyl-1,3-thiazol-5-yl]-N-cyclopentyl-2-pyridylamine (Example 36-11), N-[4-(3-methylphenyl)-5-(2-methyl-4-pyridyl)-1,3-thiazol-2-yl]acetamide (Example 39), N-[4-(3,5-dimethylphenyl)-5-(2-methyl-4-pyridyl)-1,3-thiazol-2-yl]nicotinamide (Example 42-1), 6-chloro-N-[4-(3,5-dimethylphenyl)-5-(2-methyl4-pyridyl)-1,3-thiazol-2-yl]nicotinamide (Example 44-3), N-[4-(3,5-dimethylphenyl)-5-(2-methyl-4-pyridyl)-1,3-thiazol-2-yl]-6-methylnicotinamide (Example 46-3), N-[4-(3,5-dimethylphenyl)-5-(2-methyl-4-pyridyl)-1,3-thiazol-2-yl]-6-methoxynicotinamide (Example 48-3), 4-(3-methylphenyl)-5-(2-methyl-4-pyridyl)-2-(4-methylsulfinylphenyl)-1,3-thiazole (Example 54), 4-(3-methylphenyl)-5-(2-methyl-4-pyridyl)-2-(4-methylsulfonylphenyl)-1,3-thiazole (Example 57), 5-(2-fluoro-4-pyridyl)-4-(3-methylphenyl)-2-(4-methylsulfonylphenyl)-1,3-thiazole (Example 58-4), N-[4-[4-(3-chlorophenyl)-2-(4-methylsulfonylphenyl)-1,3-thiazol-5-yl]-2-pyridyl]acetamide (Example 58-6), N-[4-[4-(3-chlorophenyl)-2-(4-methylsulfonylphenyl)-1,3-thiazol-5-yl]-2-pyridyl]propionamide (Example 58-7), N-[4-[4-(3-chlorophenyl)-2-(4-methylsulfonylphenyl)-1,3-thiazol-5-yl]-2-pyridyl]pivalamide (Example 58-8), or a salt thereof;

[16] A pro-drug of a compound as claimed in any one as defined in [1] to [5];

[17] A method for producing a compound as defined in [1] or [3] comprising (1) reacting a compound represented by the formula:

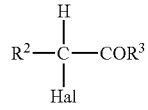

wherein Hal represents a halogen atom, $R^2$ and $R^3$ are as defined in Claim 2, or a salt thereof with a compound of the formula:

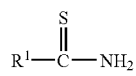

wherein $R^1$ is as defined in Claim 2, or a salt thereof, or (2) reacting a compound represented by the formula:

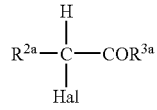

wherein Hal represents a halogen atom, $R^{2a}$ and $R^{3a}$ are as defined in Claim 4, or a salt thereof with a compound represented by the formula:

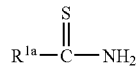

wherein $R^{1a}$ is as defined in Claim 4, or a salt thereof;

[18] A pharmaceutical composition containing the compound as claimed in any one of [1] to [5] or a prodrug thereof;

[19] The composition as defined in [18] which is a p38 MAP kinase inhibitor;

[20] The composition as defined in [18] which is a TNF-α production inhibitor;

[21] The composition as defined in [18] which is a composition for preventing or treating a cytokine-madiated disease;

[22] The composition as defined in [18] which is an adenosine receptor antagonist;

[23] The composition as defined in [18] which is a composition for preventing or treating adenosine receptor-mediated diseases;

[24] The composition as defined in [18] which is a composition for preventing or treating asthma or allergic diseases;

[25] The composition as defined in [18] which is a composition for preventing or treating inflammation, Addison's disease, autoimmune hemolytic anemia, Crohn's disease, psoriasis, rheumatism, spinal cord injury, multiple sclerosis, Alzheimer's disease, Parkinson's disease, amyotrophic lateral sclerosis, diabetes, arthritis, toxaemias, ulcerative colitis, chronic pneumonia, pulmonary silicosis, pulmonary sarcoidosis, lung tuberculosis, cachexia, arterial sclerosis, Creutzfeldt-Jakob disease, virus infection, atopic dermatitis, systemic lupus erythematosus, AIDS encephalopathy, meningitis, angina pectoris, myocardial infarction, congestive heart failure, hepatitis, transplant, dialysis hypotension or diffuse intravascular coagulation symdrome;

[26] The composition as defined in [18] which is a composition for preventing or treating chronic rheumatoid arthritis or osteoarthritis;

[27] The composition as defined in [18] which is a composition for preventing or treating cerebral edema, cerebrovascular disorder, head trauma, cerebral infarction or apoplectic stroke;

[28] A method for inhibiting p38 MAP kinase which comprises administering an effective amount of the compound as defined in any one of [1] to [5] or a pro-drug. thereof to mammals;

[29] A method for inhibiting TNF-α production which comprises administering an effective amount of the compound as defined in any one of [1] to [5] or a pro-drug thereof to mammals;

[30] A method for antagonizing an adenosine receptor which comprises administering an effective amount of the compound as defined in any one of [1] to [5] or a pro-drug thereof to mammals;

[31] A method for preventing or treating asthma or allergic diseases which comprises administering an effective amount of the compound as defined in any one of [1] to [5] or a pro-drug thereof to mammals;

[32] A method for preventing or treating inflammation, Addison's disease, autoimmune hemolytic anemia, Crohn's disease, psoriasis, rheumatism, spinal cord injury, multiple sclerosis, Alzheimer's disease, Parkinson's disease, amyotrophic lateral sclerosis, diabetes, arthritis, toxaemias, ulcerative colitis, chronic pneumonia, pulmonary silicosis, pulmonary sarcoidosis, lung tuberculosis, cachexia, arterial sclerosis, Creutzfeldt-Jakob disease, virus infection, atopic dermatitis, systemic lupus erythematosus, AIDS encephalopathy, meningitis, angina pectoris, myocardial infarction, congestive heart failure, hepatitis, transplant, dialysis hypotension or diffuse intravascular coagulation symdrome which comprises administering an effective amount of the compound as defined in [1] to [5] or a pro-drug thereof to mammals;

[33] A method for preventing or treating chronic rheumatoid arthritis or osteoarthritis which comprises administering an effective amount of the compound as defined in [1] to [5] or a pro-drug thereof to mammals;

[34] A method for preventing or treating cerebral edema, cerebrovascular disorder, head trauma, cerebral infarction or apoplectic stroke which comprises administering an effective amount of the compound as defined in any one of [1] to [5] or a pro-drug thereof to mammals;

[35] Use of the compound as defined in any one of [1] to [5] or a pro-drug thereof for producing a p38 MAP kinase inhibitor:

[36] Use of the compound as defined in any one of [1] to [5] or pro-drug thereof for producing a TNF-α production inhibitor;

[37] Use of the compound as defined in any one of [1] to [5] or a pro-drug thereof for producing an adnosine receptor antoganist;

[38] Use of the compound as defined in any one of [1] to [5] or a pro-drug thereof for producing a composition for preventing or treating asthma and allergic diseases;

[39] Use of the compound as defined in any one of [1] to [5] or a pro-drug thereof for producing a composition for preventing or treating inflammation, Addison's disease, autoimmune hemolytic anemia, Crohn's disease, psoriasis, rheumatism, spinal cord injury, multiple sclerosis, Alzheimer's disease, Parkinson's disease, amyotrophic lateral sclerosis, diabetes, arthritis, toxaemias, ulcerative colitis, chronic pneumonia, pulmonary silicosis, pulmonary sarcoidosis, lung tuberculosis, cachexia, arterial sclerosis, Creutzfeldt-Jakob disease, virus infection, atopic dermatitis, systemic lupus erythematosus, AIDS encephalopathy, meningitis, angina pectoris, myocardial infarction, congestive heart failure, hepatitis, transplant, dialysis hypotension or diffuse intravascular coagulation symdrome;

[40] Use of the compound as defined in any one of [1] to [5] or a pro-drug thereof for producing a composition for preventing or treating chronic rheumatoid arthritis or osteoarthritis; and

[41] Use of the compound as defined in any one of [1] to [5] or a pro-drug thereof for producing a composition for preventing or treating cerebral edema, cerebrovascular disorder, head trauma, cerebral infarction or apoplectic stroke.

In this specification, as the "acyl group", for example, a acyl group represented by the formula: $-(C=O)-R^5$, $-(C=O)-OR^5$, $-(C=O)-NR^5R^6$, $-(C=S)-NHR^5$, $-(C=O)-N(OR^5)R^6$, $-(C=S)-NHOR^5$ or $-SO_2-R^7$ wherein $R^5$ represents a hydrogen atom, a hydrocarbon group optionally having a substituent or a heterocyclic group optionally having a substituent, $R^6$ represents a hydrogen atom or a $C_{1-6}$ alkyl group, and $R^7$ represents a hydrocarbon group optionally having a substituent or a heterocyclic group optionally having a substituent, etc. are exemplified.

In the above-described formulae, as the "hydrocarbon group" of the "hydrocarbon group optionally having a substituent" represented by $R^5$, for example, an acyclic or cyclic hydrocarbon group (e.g., alkyl, alkenyl, alkynyl, cycloalkyl, aryl, aralkyl and the like), etc. are exemplified. Of them, an acyclic or cyclic hydrocarbon group having 1 to 16 carbon atoms, etc. are preferable.

As the "alkyl", for example, a $C_{1-6}$ alkyl group (e.g., methyl, ethyl, propyl, isopropyl, butyl, isobutyl, sec-butyl, tert-butyl, pentyl, hexyl and the like), etc. are preferable.

As the "alkenyl", for example, a $C_{2-6}$ alkenyl group (e.g., vinyl, allyl, isopropenyl, 1-butenyl, 2-butenyl, 3-butenyl, 2-methyl-2-propenyl, 1-methyl-2-propenyl, 2-methyl-1-propenyl and the like), etc. are preferable.

As the "alkynyl", for example, a $C_{2-6}$ alkynyl group (e.g., ethynyl, propargyl, 1-butynyl, 2-butynyl, 3-butynyl, 1-hexynyl and the like), etc. are preferable.

As the "cycloalkyl", for example, a $C_{3-8}$ cycloalkyl group (e.g., cyclopropyl, cyclobutyl, cyclopentyl, cyclohexyl and the like), etc. are preferable.

As the "aryl", for example, a $C_{6-4}$ aryl group (e.g., phenyl, 1-naphthyl, 2-naphthyl, 2-biphenylyl, 3-biphenylyl, 4-biphenylyl, 2-anthryl and the like), etc. are preferable.

As the "aralkyl", for example, a $C_{7-16}$ aralkyl group (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like), etc. are preferable.

As the "substituent" of the "hydrocarbon group optionally having a substituent" represented by $R^5$, for example, oxo, a halogen atom (e.g., fluorine, chlorine, bromine, iodine and the like), $C_{1-3}$ alkylenedioxy (e.g., methylenedioxy, ethylenedioxy and the like), nitro, cyano, $C_{1-6}$ alkyl which may be halogenated, $C_{2-6}$ alkenyl which may be halogenated, carboxy $C_{2-6}$ alkenyl (e.g., 2-carboxyethenyl, 2-carboxy-2-methylethenyl and the like), $C_{2-6}$ alkynyl which may be halogenated, $C_{3-8}$ cycloalkyl which may be halogenated, $C_{3-8}$ cycloalkyl-$C_{1-6}$ alkyl, $C_{6-14}$ aryl (e.g., phenyl, 1-naphthyl, 2-naphthyl, 2-biphenylyl, 3-biphenylyl, 4-biphenylyl, 2-anthryl and the like), $C_{1-8}$ alkoxy which may be halogenated, $C_{1-6}$ alkoxy-carbonyl-$C_{1-6}$ alkoxy (e.g., ethoxycarbonylmethyloxy and the like), hydroxy, $C_{6-14}$ aryloxy (e.g., phenyloxy, 1-naphthyloxy, 2-naphthyloxy and the like), $C_{7-16}$ aralkyloxy (e.g., benzyloxy, phenethyloxy and the like), mercapto, $C_{1-6}$ alkylthio which may be halogenated, $C_{6-14}$ arylthio (e.g., phenylthio, 1-naphthylthio, 2-naphthylthio and the like), $C_{7-16}$ aralkylthio (e.g., benzylthio, phenethylthio and the like), amino, mono-$C_{1-6}$ alkylamino (e.g., methylamino, ethylamino and the like), mono-$C_{6-14}$ arylamino (e.g., phenylamino, 1-naphthylamino, 2-naphthylamino and the like), di-$C_{1-6}$ alkylamino (e.g., dimethylamino, diethylamino, ethylmethylamino and the like), $C_{3-8}$ cycloalkylamino (e.g., cyclopentylamino, cyclohexylamino and the like), di-$C_{6-4}$ arylamino (e.g., diphenylamino and the like), $C_{3-8}$ cycloalkyl-$C_{1-6}$ alkylamino (e.g., cyclopentylmethylamino, cyclohexylmethylamino, cyclopentylethylamino, cyclohexylethylamino and the like), N—$C_{3-8}$ cycloalkyl-N—$C_{1-6}$ alkylamino (N-cyclopentyl-N-methylamino, N-cyclohexyl-N-methylamino, N-cyclopentyl-N-ethylamino, N-cyclohexyl-N-ethylamino and the like), formyl, carboxy, carboxy-$C_{2-6}$ alkenyl, carboxy-$C_{1-6}$ alkyl, $C_{1-6}$ alkyl-carbonyl which may be halogenated (e.g., acetyl, propionyl, pivaloyl and the like), $C_{3-8}$ cycloalkyl-carbonyl optionally substituted by $C_{1-6}$ alkyl such as methyl, ethyl, etc. (e.g., cyclopropylcarbonyl, cyclopentylcarbonyl, cyclohexylcarbonyl, 1-methyl-cyclohexyl-carbonyl and the like), $C_{1-6}$ alkoxy-carbonyl (e.g., methoxycarbonyl, ethoxycarbonyl, propoxycarbonyl, tert-butoxycarbonyl and the like), $C_{6-14}$ aryl-carbonyl (e.g., benzoyl, 1-naphthoyl, 2-naphthoyl and the like), $C_{7-16}$ aralkyl-carbonyl (e.g., phenylacetyl, 3-phenylpropionyl and the like), $C_{6-14}$ aryloxy-carbonyl (e.g., phenoxycarbonyl and the like), $C_{7-16}$ aralkyloxy-carbonyl (e.g., .benzyloxycarbonyl, phenethyloxycarbonyl and the like), 5- to 7-membered heterocyclic carbonyl containing 1 to 4 of 1 or 2 kinds of hetero atoms selected from a nitrogen atom, a sulfur atom and an oxygen atom in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl and the like), carbamoyl, thiocarbamoyl, mono-$C_{1-6}$ alkyl-carbamoyl (e.g., methylcarbamoyl, ethylcarbamoyl, and the like), di-$C_{1-6}$ alkyl-carbamoyl (e.g., dimethylcarbamoyl, diethylcarbamoyl, ethylmethylcarbamoyl and the like), mono- or di-$C_{6-14}$ aryl-carbamoyl (e.g., phenylcarbamoyl, 1-naphthylcarbamoyl, 2-naphthylcarbamoyl and the like), mono- or di-5- to 7-membered heterocyclic carbamoyl containing 1 to 4 of 1 or 2 kinds of hetero atoms selected from a nitrogen atom, a sulfur atom and an oxygen atom in addition to carbon atoms (e.g., 2-pyridylcarbamoyl, 3-pyridylcarbamoyl, 4-pyridylcarbamoyl, 2-thienylcarbamoyl, 3-thienylcarbamoyl and the like), $C_{1-6}$ alkylsulfonyl (e.g., methylsulfonyl, ethylsulfonyl and the like), $C_{1-6}$ alkylsulfinyl (e.g., methylsulfinyl, ethylsulfinyl and the like), $C_{6-14}$ arylsulfonyl (e.g., phenylsulfonyl, 1-naphthylsulfonyl, 2-naphthylsulfonyl and the like), $C_{6-14}$ arylsulfinyl (e.g., phenylsulfinyl, 1-naphthylsulfinyl, 2-naphthylsulfinyl and the like), formylamino, $C_{1-6}$ alkyl-carbonylamino (e.g., acetylamino, propionylamino, pivaloylamino and the like), $C_{3-8}$ cycloalkyl-carbonylamino optionally substituted by $C_{1-6}$ alkyl (e.g., cyclopropylcarbonylamino, cyclopentylcarbonylamino, cyclohexylcarbonylamino and the like), $C_{6-14}$ arylcarbonylamino (e.g., benzoylamino, naphthoylamino and the like), $C_{1-6}$ alkoxy-carbonylamino (e.g., methoxycarbonylamino, ethoxycarbonylamino, propoxycarbonylamino, butoxycarbonylamino and the like), $C_{1-6}$ alkylsulfonylamino (e.g., methylsulfonylamino, ethylsulfonylamino and the like), $C_{6-14}$ arylsulfonylamino (e.g., phenylsulfonylamino, 2-naphthylsulfonylamino, 1-naphthylsulfonylamino and the like), $C_{1-6}$ alkyl-carbonyloxy (e.g., acetoxy, propionyloxy and the like), $C_{6-14}$ aryl-carbonyloxy (e.g., benzoyloxy, naphthylcarbonyloxy and the like), $C_{1-6}$ alkoxy-carbonyloxy (e.g., methoxycarbonyloxy, ethoxycarbonyloxy, propoxycarbonyloxy, butoxycarbonyloxy and the like), mono-$C_{1-6}$ alkyl-carbamoyloxy (e.g., methylcarbamoyloxy, ethylcarbamoyloxy and the like), di-$C_{1-6}$ alkyl-carbamoyloxy (e.g., dimethylcarbamoyloxy, diethylcarbamoyloxy and the like), mono- or di-$C_{6-14}$ aryl-carbamoyloxy (e.g., phenylcarbamoyloxy, naphthylcarbamoyloxy and the like), nicotinoyloxy, isonicotinoyloxy, 5- to 10-membered heterocyclic group containing 1 to 4 of 1 or 2 kinds of hetero atoms selected from a nitrogen atom, a sulfur atom and an oxygen atom in addition to carbon atoms (e.g. 5- to 7-membered aliphatic heterocyclic group, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like) optionally having a substituent, sulfo, sulfamoyl, sulfinamoyl, sulfenamoyl, a group obtained by connecting two or more (e.g., 2 to 3) of these substituents (e.g., (i) $C_{1-6}$ alkyl, (ii) $C_{6-14}$ aryl, (iii) amino, (iv) $C_{1-6}$ alkylamino, (v.) $C_{3-8}$ cycloalkylamino, (vi) $C_{6-14}$ arylamino, (vii) 5- to 7-membered heterocyclic amino containing 1 to 4 hetero atoms selected from a nitrogen atom, a sulfur atom and an oxygen atom in addition to carbon atoms, (viii) $C_{1-6}$ alkyl-carbonyl amino, (ix) $C_{3-8}$ cycloalkyl-carbonylamino, (x) $C_{6-14}$ aryl-carbonylamino or (xi) 5- to 7-membered heterocyclic-carbonyl amino containing 1 to 4 hetero atoms selected from a nitrogen atom, a sulfur atom and an oxygen atom in addition to carbon atoms, which is substituted, respectively, by a substituent selected from the group consisting of a halogen atom, cyano, hydroxy, $C_{1-6}$ alkoxy, $C_{6-14}$ aryloxy, $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl, $C_{3-8}$ cycloalkyl, 5- to 7-membered heterocyclic group containing 1 to 4 hetero atoms selected from a nitrogen atom, a sulfur atom and an oxygen atom in addition to carbon atoms, $C_{6-14}$ aryl, $C_{1-6}$ alkyl-carbonyl, $C_{3-8}$ cycloalkyl-carbonyl, 5- to 7-membered heterocyclic-carbonyl containing 1 to 4 hetero atoms selected from a nitrogen atom, a sulfur atom and an oxygen atom in addition to carbon atoms, $C_{6-14}$ aryl-carbonyl, $C_{3-8}$ cycloalkoxy, 5- to 7-membered heterocyclic-oxy containing 1 to 4 hetero atoms selected from a nitrogen atom, a sulfur atom and an oxygen atom in addition to carbon atoms, $C_{1-6}$ alkylamino, $C_{6-14}$ arylamino, $C_{1-6}$ alkoxy-carbonyl, $C_{3-8}$ cycloalkoxy-carbonyl, 5- to 7-membered heterocyclic-oxycarbonyl containing 1 to 4 hetero atoms selected from a nitrogen atom, a sulfur atom and an oxygen atom in addition to carbon atoms, $C_{6-14}$ aryloxycarbonyl, etc.) (sometimes referred to as Group A of substituents).

The above-mentioned "hydrocarbon group" may have, for example, the 1 to 5, preferably 1 to 3 above-mentioned substituents at substitutable positions, and when the number of the substituent is 2 or more, they may be the same or different.

As the above-mentioned "$C_{1-6}$ alkyl which may be halogenated", for example, $C_{1-6}$ alkyl (e.g., methyl, ethyl, propyl, isopropyl, butyl, isobutyl, sec-butyl, tert-butyl, pentyl, hexyl and the like) which may have 1 to 5, preferably 1 to 3 halogen atoms (e.g., fluorine, chlorine, bromine, iodine and the like), etc. are exemplified. As specific examples thereof, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. are exemplified.

As the above-mentioned "$C_{2-6}$ alkenyl which may be halogenated", for example, $C_{2-6}$ alkenyl (e.g., vinyl, propenyl, isopropenyl, 2-buten-1-yl, 4-penten-1-yl, 5-hexen-1-yl and the like) which may have 1 to 5, preferably 1 to 3 halogen atoms (e.g. fluorine, chlorine, bromine, iodine and the like), etc. are exemplified.

As the above-mentioned "$C_{2-6}$ alkynyl which may be halogenated", for example, $C_{2-6}$ alkynyl (e.g., 2-butyn-1-yl, 4-pentyn-1-yl, 5-hexyn-1-yl and the like) which may have 1 to 5, preferably 1 to 3 halogen atoms (e.g., fluorine, chlorine, bromine, iodine and the like), etc. are exemplified.

As the above-mentioned "$C_{3-8}$ cycloalkyl which may be halogenated", for example, $C_{3-8}$ cycloalkyl (e.g., cyclopropyl, cyclobutyl, cyclopentyl, cyclohexyl and the like) which may have 1 to 5, preferably 1 to 3 halogen atoms (e.g., fluorine, chlorine, bromine, iodine and the like), etc. are exemplified. As specific examples thereof, cyclopropyl, cyclobutyl, cyclopentyl, cyclohexyl, 4,4-dichlorocyclohexyl, 2,2,3,3-tetrafluorocyclopentyl, 4-chlorocyclohexyl, etc. are exemplified.

As the above-mentioned "$C_{1-8}$ alkoxy which may be halogenated", for example, $C_{1-8}$ alkoxy (e.g., methoxy, ethoxy, propoxy, isopropoxy, butoxy, isobutoxy, sec-butoxy, pentyloxy, hexyloxy and the like) which may have 1 to 5, preferably 1 to 3 halogen atoms (e.g., fluorine, chlorine, bromine, iodine and the like), etc. are exemplified. As specific examples thereof, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. are exemplified.

As the above-mentioned "$C_{1-6}$ alkylthio which may be halogenated", for example, $C_{1-6}$ alkylthio (e.g., methylthio, ethylthio, propylthio, isopropylthio, butylthio, sec-butylthio, tert-butylthio and the like) which may have 1 to 5, preferably 1 to 3 halogen atoms (e.g., fluorine, chlorine, bromine, iodine and the like), etc. are exemplified. As specific examples thereof, methylthio, difluoromethylthio, trifluoromethylthio, ethylthio, propylthio, isopropylthio, butylthio, 4,4,4-trifluorobutylthio, pentylthio, hexylthio, etc. are exemplified.

As the "5- to 7-membered aliphatic heterocyclic group" of the above-mentioned "5- to 7-membered aliphatic heterocyclic group optionally having a substituent", for example, 5- to 7-membered aliphatic heterocyclic group containing 1 to 4 of 1 or 2 kinds of hetero atoms selected from a nitrogen atom, a sulfur atom and an oxygen atom in addition to carbon atoms are exemplified, and as specific examples thereof, 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl, etc. are exemplified.

As the "substituent" of the above-mentioned "5- to 7-membered aliphatic heterocyclic group optionally having a substituent", for example, 1 to 3 of $C_{1-6}$ alkyl (e.g., methyl, ethyl, propyl, isopropyl, butyl, isobutyl, sec-butyl, tert-butyl, pentyl, hexyl and the like), $C_{6-14}$ aryl (e.g., phenyl, 1-naphthyl, 2-naphthyl, 2-biphenylyl, 3-biphenylyl, 4-biphenylyl, 2-anthryl and the like), $C_{1-6}$ alkyl-carbonyl (e.g., acetyl, propionyl and the like) which may be halogenated, $C_{1-6}$ alkoxy-carbonyl (e.g., methoxycarbonyl, ethoxycarbonyl, propoxycarbonyl), 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2benzothiazolyl, 2-benzo[b]thienyl, 3-benzo[b]thienyl, 2-benzo[b]furanyl, 3-benzo[b]furanyl and the like), oxo, etc. are exemplified.

As the "heterocyclic group" of the "heterocyclic group optionally having a substituent" represented by $R^5$, for example, a 5- to 14-membered (monocyclic, bicyclic or tricyclic) heterocyclic ring which may contain 1 to 4 of 1 or 2 kinds of hetero atoms selected from a nitrogen atom, a sulfur atom and an oxygen atom in addition to carbon atoms are exemplified, preferably, mono-valent groups obtained by removing any one hydrogen atom from (i) a 5- to 14-membered (preferably, 5- to 10-membered) aromatic heterocyclic ring, (ii) a 5- to 10-membered aliphatic heterocyclic ring or (iii) a 7- to 10-membered bridged heterocyclic ring, etc. are exemplified.

As the above-mentioned 5- to 14-membered (preferably, 5- to 10-membered) aromatic heterocyclic ring, for example, an aromatic heterocyclic ring such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isooxazole, furazane, phenoxazine and the like, or rings formed by fusing these rings (preferably, monocyclic ring) with 1 or plural (preferably, 1 or 2) aromatic rings (for example, benzene ring and the like), etc. are exemplified.

As the above-mentioned "5- to 10-membered aliphatic heterocyclic ring", for example, pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, etc. are exemplified.

As the above-mentioned "7- to 10-membered bridged heterocyclic ring", for example, quinuclidine, 7-azabicyclo[2.2.1]heptane, etc. are exemplified.

The above-mentioned "heterocyclic group" is preferably a 5- to 14-membered (preferably, 5- to 10membered) (monocyclic or bicyclic) heterocyclic group which contains preferably 1 to 4 of 1 or 2 kinds of hetero atoms selected from a nitrogen atom, a sulfur atom and an oxygen atom in addition to carbon atoms. Specifically, an aromatic heterocyclic group such as, for example, 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pirazinyl, 2-pyrimidinyl, 4-pyrimidinyl, 3-pyrrolyl, 2-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo [b]furanyl, .3-benzo[b]furanyl and the like, and aliphatic heterocylic groups such as, for example, 1-pyrrolidinyl, 2-pyrrolidinyl, 3-pyrrolidinyl, 3-oxazolidinyl, 1-imidazolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholin0 and the like, etc. are exemplified.

Of them, for example, a 5- or 6-membered heterocyclic group containing 1 to 3 hetero atoms selected from a nitrogen atom, a sulfur atom and an oxygen atom in addition to carbon atoms are further preferable. Specifically, 2-thienyl, 3-thienyl, 2-pyridyl, 3-pyridyl, 4-pyridyl, 2-furyl, 3-furyl, pirazinyl, 2-pyrimidinyl, 3-pyrrolyl, 3-pyridazinyl, 3-isothiazolyl, 3-isooxazolyl, 1-pyrrolidinyl, 2-pyrrolidinyl, 3-pyrrolidinyl, 3-oxazolidinyl, 1-imidazolidinyl, 2-imidazolidinyl, 4-imidazolidinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc. are exemplified.

As the "substituent" of the above-mentioned "heterocyclic group optionally having a substituent", for example, the same moieties as for the "substituent" of the above-mentioned "hydrocarbon group optionally having a substituent" represented by $R^5$, etc. are exemplified.

The above-mentioned "heterocyclic group" may have, for example, 1 to 5, preferably 1 to 3 of the above-mentioned substituents at substitutable positions, and when the number of the substituent is 2 or more, they may be the same or different.

As the "$C_{1-6}$ alkyl group" represented by $R^6$, for example, methyl, ethyl, propyl, isopropyl, butyl, isobutyl, sec-butyl, tert-butyl, pentyl, hexyl, etc. are exemplified.

As the "hydrocarbon group optionally having a substituent" and "heterocyclic group optionally having a substituent" represented by $R^7$, for example, the above-mentioned "hydrocarbon group optionally having a substituent" and "heterocyclic group optionally having a substituent" represented by $R^5$ are exemplified, respectively.

As the "hydrocarbon group optionally having a substituent" represented by $R^1$ and $R^{1a}$, for example, the "hydrocarbon group optionally having a substituent" represented by $R^5$ is exemplified.

As the "heterocyclic group optionally having a substituent" represented by $R^1$ and $R^{1a}$, for example, the "heterocyclic group optionally having a substituent" represented by $R^5$ is exemplified.

As the "amino group optionally having a substituent" represented by $R^1$ and $R^{1a}$, for example, (1) an amino group optionally having 1 or 2 substituents and (2) a cyclic amino group optionally having a substituent are exemplified.

As the "substituent" of the above-mentioned "(1) amino group optionally having 1 or 2 substituents", for example, a hydrocarbon group optionally having a substituent, a heterocyclic group optionally having a substituent, an acyl group, an alkylidene group optionally having a substituent, etc. are exemplified. As the "hydrocarbon group optionally having a substituent" and "heterocyclic group optionally having a substituent", for example, the same moieties as for the above-mentioned "hydrocarbon group optionally having a substituent" and "heterocyclic group optionally having a substituent" represented by $R^5$ are exemplified, respectively.

As the "alkylidene group" of the above-mentioned "alkylidene group optionally having a substituent", for example, $C_{1-6}$ alkylidene (e.g., methylidene, ethylidene, propylidene and the like), etc. are exemplified. As the "substituent" of the above-mentioned "alkylidene group optionally having a substituent", for example, 1 to 5, preferably 1 to 3 of the same moieties as for the "substituent" of the above-mentioned "hydrocarbon group optionally having a substituent" represented by $R^5$ are exemplified.

When the number of the "substituent" of the above-mentioned "amino group optionally having 1 or 2 substituents" is two, these substituents may be the same or different.

As the "cyclic amino group" of the above-mentioned "(2) cyclic amino group optionally having a substituent", for example, a 5- to 7-membered aliphatic cyclic amino group which may contain 1 to 4 of 1 or 2 kinds of hetero atoms selected from a nitrogen atom, a sulfur atom and an oxygen atom in addition to one nitrogen atom and carbon atoms are exemplified, and as specific examples thereof, 1-pyrrolidinyl, piperidino, 1-piperazinyl, morpholino, thiomorpholino, hexahydroazepin-1-yl, 1-imidazolidinyl, 2,3-dihydro-(1H)-imidazolyl, tetrahydro-1(2H)-pyrimidinyl, 3,6-dihydro-1(2H)-pyrimidinyl, 3,4-dihydro-1(2H)-pyrimidinyl, etc. are exemplified. As the "substituent" of the "cyclic amino group optionally having a substituent", for example, 1 to 3 of the same moieties as for the "substituent" of the "5- to 7-membered aliphatic heterocyclic group optionally having a substituent" described in detail as the "substituent" of the "hydrocarbon group optionally having a substituent" represented by $R^5$.

As specific examples of the 5- to 7-membered aliphatic cyclic amino group having one oxo, for example, 2-oximidazolidin-1-yl, 2-oxo-2,3-dihydro-1-H-imidazol-1-yl, 2-oxoteterahydro-1(2H)-pyrimidinyl, 2-oxo-3,6-dihydro-1(2H)-pyrimidinyl, 2-oxo-3,4-dihydro-1(2H)-pyrimidinyl, 2-oxopyrrolidin-1-yl, 2-oxopiperidino, 2-oxopiperazin-1-yl, 3-oxopiperazin-1-yl, 2-oxo-2,3,4,5,6,7-hexahydroazepin-1-yl, etc. are exemplified.

$R^1$ or $R^{1a}$ is preferably an alkyl group optionally having a substituent, an aryl group optionally having a substituent, an amino group optionally having a substituent, a heterocyclic group optionally having a substituent, an acyl group represented by the formula; —(C=O)—$R^5$ (wherein $R^5$ is as defined above), an acyl group represented by the formula: —(C=O)—OR$^5$ (wherein $R^5$ is as defined above), or the like.

As the "alkyl group optionally having a substituent", for example, a $C_{1-6}$ alkyl group (preferably, methyl, ethyl, propyl, butyl and the like) optionally having 1 to 5 substituents selected from a halogen atom, carboxy, hydroxy, $C_{1-6}$ alkoxy, $C_{1-6}$ alkoxy-carbonyl, $C_{1-6}$ alkylthio, $C_{1-6}$ alkylsulfinyl, $C_{1-6}$ alkylsulfonyl, and the like, etc. are preferably exemplified.

As the above-mentioned "aryl group optionally having a substituent", for example, a $C_{6-14}$ aryl group (preferably, phenyl and the like) optionally having 1 to 5 substituents selected from a halogen atom, $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl, carboxy and the like, etc. are preferably exemplified.

As the above-mentioned "amino group optionally having a substituent", an amino group optionally having 1 or 2 acyl represented by the formula: —(C=O)—$R^5$, —(C=O)—OR$^5$, —(C=O)—NR$^5$R$^6$, —(C=S)—NHR$^5$, —(C=O)—N(OR$^5$)R$^6$, —(C=S)—NHOR$^5$ or —SO$_2$—R$^7$ (wherein each symbol is as defined above), etc. are preferably exemplified.

Further preferably, $R^1$ is an amino group optionally having 1 or 2 acyls represented by the formula: —(C=O)—$R^5$ or —(C=O)—$NR^5R^6$ (wherein each symbol is as defined above), etc. are exemplified.

As the "heterocyclic group" of the "heterocyclic group optionally having a substituent", for example, a 5- to 14-membered (monocyclic, bicyclic or tricyclic) heterocyclic group which contain 1 to 4 of 1 or 2 kinds of hetero atoms selected from a nitrogen atom, a sulfur atom and an oxygen atom in addition to carbon atoms are used, and of them, a 5- to 10-membered aliphatic heterocyclic group, a 5- to 7-membered aromatic heterocyclic group, etc. are preferable.

As the "substituent" of the "heterocyclic group optionally having a substituent", for example, an oxo group, a $C_{1-6}$ alkyl group (e.g., methyl, ethyl, etc.), a $C_{6-14}$ aryl group (e.g., phenyl, etc.), a $C_{1-6}$ alkyl-carbonyl group (e.g., acetyl, etc.), a $C_{1-6}$ alkoxy-carbonyl group (e.g., methoxycarbonyl, ethoxycarbonyl, etc.) and the like are used, and the number of substituents is 1 to 3.

As $R^5$ of the "acyl group represented by the formula: —(C=O)—$R^5$", a hydrogen atom, a hydrocarbon group optionally having a substituent and an aromatic heterocyclic group optionally having a substituent are preferable, and particularly, ① a hydrogen atom, ② a $C_{1-6}$ alkyl group which may be halogenated (e.g., methyl, ethyl, propyl, trifluoromethyl, etc.), ③ a $C_{6-14}$ aryl group which may be halogenated (e.g., phenyl, naphthyl, fluorophenyl, chlorophenyl, etc.), ④ a 5- to 7-membered aromatic heterocyclic group (e.g., pyridyl, thienyl, pyrrolyl, furyl, pyridazinyl, pyrimidinyl, etc.) which may be substituted by a halogen atom (e.g., fluorine, chlorine, bromine, etc.), optionally halogenated $C_{1-6}$ alkyl (e.g., methyl, ethyl, propyl, trifluoromethyl, etc.), $C_{1-6}$ alkoxy group (e.g., methoxy, ethoxy, propoxy, butoxy, etc.), and the like are preferable.

As $R^5$ of the "acyl group represented by the formula: —(C=O)—$OR^5$", a hydrogen atom and a hydrocarbon group optionally substituted are preferable, and particularly, a hydrogen atom and a $C_{1-6}$ alkyl group (e.g., methyl, ethyl, propyl, etc.), and the like are preferable.

As $R^1$ or $R^{1a}$, (i) a hydrogen atom, (ii) a $C_{1-6}$ alkyl group optionally substituted by a substituent selected from the group consisting of a halogen atom, $C_{1-6}$ alkoxy-carbonyl, carboxy, cyano, $C_{1-6}$ alkylthio, $C_{1-6}$ alkylsulfinyl, $C_{1-6}$ alkylsulfonyl, hydroxy, $C_{1-6}$ alkoxy and $C_{1-6}$ alkyl-carbonyl, (iii) a $C_{6-14}$ aryl group optionally having a substituent selected from the group consisting of a halogen atom and a group of the formula: —S(O)$_n$—$R^{1bb}$ ($R^{1bb}$ represents a $C_{1-6}$ alkyl group, and n represents an integer of 0 to 2), (iv) a $C_{7-15}$ aralkyl group, (v) an amino group optionally having one or two substituents selected from ① $C_{1-6}$ alkyl, ② $C_{1-6}$ alkyl-carbonyl, ③ 5- to 7-membered heterocyclic-carbonyl containing 1 to 4 hetero atoms selected from the group consisting of a nitrogen atom, an oxygen atom and a sulfur atom in addition to carbon atoms, optionally substituted with a halogen atom, $C_{1-6}$ alkyl or $C_{1-6}$ alkoxy, ④ $C_{6-14}$ aryl-carbamoyl, ⑤ $C_{1-6}$ alkyl-carbamoyl which may be halogenated, ⑥ $C_{1-6}$ alkoxy-carbonyl which may be halogenated, ⑦ $C_{1-6}$ alkoxy-carbamoyl and ⑧ $C_{6-14}$ aryloxy-carbamoyl, (vi) a 5- to 10-membered heterocyclic group containing 1 to 4 of 1 or 2 kinds of hetero atoms selected from a nitrogen atom, a sulfur atom and an oxygen atom in addition to carbon atoms, optionally substituted by oxo, $C_{1-6}$ alkyl, $C_{6-14}$ aryl, $C_{1-6}$ alkoxy-carbonyl or $C_{1-6}$ alkyl-carbonyl, (vii) an acyl group represented by the formula: —(C=O)—$R^{5b}$ (wherein $R^{5b}$ represents a hydrogen atom, a $C_{1-6}$ alkyl group which may be halogenated or a $C_{6-14}$ aryl group which may be halogenated), or (viii) an acyl group represented by the formula: —(C=O)—$OR^{5c}$ (wherein $R^{5c}$ represents a hydrogen atom or a $C_{1-6}$ alkyl group), and the like are suitable.

As the $C_{1-6}$ alkyl group represented by $R^1$ or $R^{1a}$, for example, methyl, ethyl, propyl, isopropyl, butyl, isobutyl, sec-butyl, tert-butyl, pentyl, hexyl, etc. are used, and particularly, $C_{1-4}$ alkyl groups such as methyl, ethyl, propyl, butyl and the like are preferable.

As the halogen atom which is a substituent of the $C_{1-6}$ alkyl group represented by $R^1$ or $R^{1a}$, for example, a fluorine atom, a chlorine atom, a bromine atom and an iodine atom are preferable.

As the $C_{1-6}$ alkoxy-carbonyl which is a substituent of the $C_{1-6}$ alkyl group represented by $R^1$ or $R^{1a}$, for example, methoxycarbonyl, ethoxycarbonyl and the like are preferable.

As the $C_{1-6}$ alkylthio which is a substituent of the $C_{1-6}$ alkyl group represented by $R^1$ or $R^{1a}$, for example, methylthio, ethylthio and the like are preferable.

As the $C_{1-6}$ alkylsulfinyl which is a substituent of the $C_{1-6}$ alkyl group represented by $R^1$ or $R^{1a}$, for example, methylsulfinyl, ethylsulfinyl and the like are preferable.

As the $C_{1-6}$ alkylsulfonyl which is a substituent of the $C_{1-6}$ alkyl group represented by $R^1$ or $R^{1a}$, for example, methylsulfonyl, ethylsulfonyl and the like are preferable.

As the $C_{1-6}$ alkoxy which is a substituent of the $C_{1-6}$ alkyl group represented by $R^1$ or $R^{1a}$, for example, methoxy, ethoxy, propoxy and the like are preferable.

As the $C_{1-6}$ alkyl-carbonyl which is a substituent of the $C_{1-6}$ alkyl group represented by $R^1$ or $R^{1a}$, for example, acetyl, propionyl and the like are preferable.

As the $C_{1-6}$ alkyl group represented by $R^{1bb}$, for example, methyl, ethyl, propyl, isopropyl, butyl, isobutyl, sec-butyl, tert-butyl, pentyl, hexyl, etc. are used, and of them, $C_{1-4}$ alkyl groups such as methyl, ethyl, propyl, butyl and the like are preferable, and methyl is particularly preferable.

As the $C_{6-14}$ aryl group represented by $R^1$ or $R^{1a}$, for example, phenyl, naphthyl, etc. are preferable, and of them, phenyl is particularly preferable.

As the halogen atom which is a substituent of the $C_{6-14}$ aryl group represented by $R^1$ or $R^{1a}$, a fluorine atom, a chlorine atom, a bromine atom and an iodine atom are used.

As the $C_{7-15}$ aralkyl group represented by $R^1$ or $R^{1a}$, for example, phenyl-$C_{1-3}$ alkyl groups such as benzyl, phenylethyl, phenylpropyl and the like are preferable.

As the $C_{1-6}$ alkyl group which is a substituent of an amino group represented by $R^1$ or $R^{1a}$, for example, methyl, ethyl, propyl, isopropyl, butyl, isobutyl, sec-butyl, tert-butyl, pentyl, hexyl, etc. are used, and of them, $C_{1-3}$ alkyl groups such as methyl, ethyl, propyl and the like are preferable, particularly, methyl is preferable.

As the $C_{1-6}$ alkyl-carbonyl which is a substituent of an amino group represented by $R^1$ or $R^{1a}$, for example, a $C_{1-3}$ alkyl-carbonyl group such as acetyl, propionyl and the like are preferable.

As the "5- to 7-membered heterocyclic-carbonyl containing 1 to 4 hetero atoms selected from the group consisting of a nitrogen atom, an oxygen atom and a sulfur atom in addition to carbon atoms" which is a substituent of an amino group represented by $R^1$ or $R^{1a}$, for example, a 5- to 7-membered heterocyclic (e.g., furyl, thienyl, pyrrolyl, pyridyl, pyrimidinyl, pyridazinyl and the like)-carbonyl group containing 1 or 2 hetero atoms selected from the group consisting of a nitrogen atom, an oxygen atom and a sulfur atom, etc. are preferable. As the substituent of the heterocyclic group of this heterocyclic-carbonyl group, a halogen atom such as a chlorine atom and the like, $C_{1-6}$ alkyl group such as methyl, ethyl and the like, and $C_{1-6}$ alkoxy such as methoxy, ethoxy and the like are preferable.

As the $C_{6-14}$ aryl-carbamoyl which is a substituent of an amino group represented by $R^1$ or $R^{1a}$, for example, phenylcarbamoyl, etc. are preferable.

As the $C_{1-6}$ alkyl-carbamoyl which may be halogenated which is a substituent of an amino group represented by $R^1$ or $R^{1a}$, for example, methylcarbamoyl, ethylcarbamoyl, propylcarbamoyl optionally substituted by a halogen atom (e.g., chlorine atom) and the like are preferable.

As the $C_{1-6}$ alkoxy-carbonyl which may be halogenated which is a substituent of an amino group represented by $R^1$ or $R^{1a}$, for example, methoxycarbonyl, ethoxycarbonyl, propoxycarbonyl optionally substituted by halogen atoms (e.g., a chlorine atom) and the like are preferable.

As the $C_{1-6}$ alkoxy-carbamoyl which is a substituent of an amino group represented by $R^1$ or $R^{1a}$, for example, methoxycarbamoyl, ethoxycarbamoyl, propoxycarbamoyl and the like are preferable.

As the $C_{6-14}$ aryloxy-carbamoyl which is a substituent of an amino group represented by $R^1$ or $R^{1a}$, for example, phenyloxy-carbamoyl and the like are preferable.

As the 5- to 10-membered aliphatic heterocyclic group represented by $R^1$ or $R^{1a}$, for example, 1-pyrrolidinyl, 2-pyrrolidinyl, 3-pyrrolidinyl, 3-oxazolidinyl, 1-imidazolidinyl, 2-imidazolidinyl, 4-imidazolidinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like, are used, and of them, 4-piperidyl, 1-piperazinyl, 3-oxazolidinyl, 1-imidazolidinyl and the like are preferable.

As the 5- to 10-membered aliphatic heterocyclic group optionally substituted by oxo, $C_{1-6}$ alkyl (preferably, methyl, ethyl), $C_{6-14}$ aryl (preferably, phenyl), $C_{1-6}$ alkyl-carbonyl (preferably, acetyl) or $C_{1-6}$ alkoxy-carbonyl (preferably, methoxycarbonyl, ethoxycarbonyl) represented by $R^1$ or $R^{1a}$, 1-methyl-4-piperidyl, 4-methyl-1-piperazinyl, 2-oxo-3-oxazolidinyl, 2-oxo-1-imidazolidinyl, 2-oxo-3-phenyl-1-imidazolidinyl and the like are preferable.

As $R^{5b}$ of the formula: —(C=O)—$R^{5b}$ represented by $R^1$ or $R^{1a}$, a hydrogen atom, a $C_{1-6}$ alkyl group which may be halogenated by a fluorine atom, a chlorine atom and the like (e.g., methyl, ethyl, trifluoromethyl, etc.), a $C_{6-14}$ aryl group which may be halogenated by a fluorine atom, a chlorine atom and the like (e.g., phenyl, naphthyl, fluorophenyl, chlorophenyl, etc.) are preferable.

As $R^{5c}$ of the formula: —(C=O)—$OR^{5c}$, a hydrogen atom and a $C_{1-3}$ alkyl group (methyl, ethyl, etc.) are preferable.

As the "substituent containing no aromatic group" carried by a 4-pyridyl group substituted at the 5-position of a compound (Ia), the "substituent containing no aromatic group" substituted at the position adjacent to a nitrogen atom of a pyridyl group substituted at the 5-position of a compound (Ib) the "substituent containing no aromatic group" substituted at the position adjacent to a nitrogen atom of a 4-pyridyl group substituted at the 5-position of a compound (Ic), the "substituent containing no aromatic group" of the "4-pyridyl group having a substituent containing no aromatic group" represented by $R^2$, and "the substituent containing no aromatic group" of the "pyridyl group having at the position adjacent to a nitrogen atom of the pyridyl group a substituent containing no aromatic group" represented by $R^{2a}$, for example, a halogen atom (e.g., fluorine, chlorine, bromine, iodine and the like), $C_{1-3}$ alkylenedioxy (e.g., methylenedioxy, ethylenedioxy and the like), nitro, cyano, $C_{1-6}$ alkyl which may be halogenated, $C_{2-6}$ alkenyl which may be halogenated, carboxy $C_{2-6}$ alkenyl (e.g., 2-carboxyethenyl, 2-carboxy-2-methylethenyl and the like), $C_{2-6}$ alkynyl which may be halogenated, $C_{3-8}$ cycloalkyl which may be halogenated, $C_{3-8}$ cycloalkyl-$C_{1-6}$ alkyl, $C_{1-8}$ alkoxy which may be halogenated, $C_{1-6}$ alkoxy-carbonyl-$C_{1-6}$ alkoxy (e.g., ethoxycarbonylmethyloxy and the like), hydroxy, mercapto, $C_{1-6}$ alkylthio which may be halogenated, amino, mono-$C_{1-6}$ alkylamino (e.g., methylamino, ethylamino and the like), di-$C_{1-6}$ alkylamino (e.g., dimethylamino, diethylamino, ethylmethylamino and the like), $C_{3-8}$ cycloalkylamino (e.g., cyclopentylamino, cyclohexylamino and the like), $C_{3-8}$ cycloalkyl-$C_{1-6}$ alkyl amino (e.g., cyclopentylmethylamino, cyclohexylmethylamino, cyclopentylethylamino, cyclohexylethylamino and the like), N—$C_{3-8}$ cycloalkyl-N—$C_{1-6}$ alkylamino (e.g., N-cyclopentyl-N-methylamino, N-cyclohexyl-N-methylamino, N-cyclopentyl-N-ethylamino, N-cyclohexyl-N-ethylamino and the like), formyl, carboxy, carboxy-$C_{2-6}$ alkenyl, carboxy-$C_{1-6}$ alkyl, $C_{1-6}$ alkyl-carbonyl which may be halogenated (e.g., acetyl, propionyl, 2,2,2-trifluoroacetyl, 3,3,3-trifluoropropionyl, 2,2-difluoropropionyl and the like), $C_{3-8}$ cycloalkyl-carbonyl optionally substituted by $C_{1-6}$ alkyl (e.g., cyclopropylcarbonyl, cyclopentylcarbonyl, cyclohexylcarbonyl, 1-methyl-cyclohexylcarbonyl and the like), $C_{1-6}$ alkoxy-carbonyl (e.g., methoxycarbonyl, ethoxycarbonyl, propoxycarbonyl, tert-butoxycarbonyl and the like), carbamoyl, thiocarbamoyl, mono-$C_{1-6}$ alkyl-carbamoyl (e.g., methylcarbamoyl, ethylcarbamoyl, and the like), di-$C_{1-6}$ alkyl-carbamoyl (e.g., dimethylcarbamoyl, diethylcarbamoyl, ethylmethylcarbamoyl and the like), $C_{1-6}$ alkylsulfonyl (e.g., methylsulfonyl, ethylsulfonyl and the like), $C_{1-6}$ alkylsulfinyl (e.g., methylsulfinyl, ethylsulfinyl and the like), formylamino, $C_{1-6}$ alkyl-carbonylamino (e.g., acetylamino, propionylamino, pivaloylamino and the like), $C_{3-8}$ cycloalkyl-carbonylamino optionally substituted by $C_{1-6}$ alkyl (e.g., cyclopropylcarbonylamino, cyclopentylcarbonylamino, cyclohexylcarbonylamino, 1-methyl-cyclohexylcarbonylamino and the like), $C_{1-6}$ alkoxy-carbonylamino (e.g., methoxycarbonylamino, ethoxycarbonylamino, propoxycarbonylamino, butoxycarbonylamino and the like), $C_{1-6}$ alkylsulfonylamino (e.g., methylsulfonylamino, ethylsulfonylamino and the like), $C_{1-6}$ alkyl-carbonyloxy (e.g., acetoxy, propionyloxy and the like), $C_{1-6}$ alkoxy-carbonyloxy (e.g., methoxycarbonyloxy, ethoxycarbonyloxy, propoxycarbonyloxy, butoxycarbonyloxy and the like), mono-$C_{1-6}$ alkylcarbamoyloxy (e.g., methylcarbamoyloxy, ethylcarbamoyloxy and the like), di-$C_{1-6}$-alkyl-carbamoyloxy (e.g., dimethylcarbamoyloxy, diethylcarbamoyloxy and the like), 5- to 7-membered aliphatic heterocyclic group having a substituent, sulfo, sulfamoyl, sulfinamoyl, sulfenamoyl, a group formed by connecting 2 to 3 of these substituents (e.g., (i) $C_{1-6}$ alkyl, (ii) amino, (iii) $C_{1-6}$ alkylamino, (iv) $C_{3-8}$ cycloalkylamino, (v) 5- to 7-membered aliphatic heterocyclic amino containing 1 to 4 hetero atoms selected from a nitrogen atom, a sulfur atom and an oxygen atom in addition to carbon atoms, (vi) $C_{1-6}$ alkyl-carbonyl amino, (vii) $C_{3-8}$ cycloalkyl-carbonylamino or (viii) 5- to 7-membered aliphatic heterocyclic-carbonyl amino containing 1 to 4 hetero atoms selected from a nitrogen atom, a sulfur atom and an oxygen atom in addition to carbon atoms, which is substituted, respectively, by a substituent selected from the group consisting of a halogen atom, cyano, hydroxy, $C_{1-6}$ alkoxy, $C_{1-6}$ alkylthio, $C_{1-6}$ alkylsulfinyl, $C_{1-6}$ alkylsulfonyl, $C_{3-8}$ cycloalkyl, 5- to 7-membered aliphatic heterocyclic group containing 1 to 4 hetero atoms selected from a nitrogen atom, a sulfur atom and an oxygen atom in addition to carbon atoms, $C_{1-6}$ alkyl-carbonyl, $C_{3-8}$ cycloalkyl-carbonyl, 5- to 7-membered aliphatic heterocyclic-carbonyl containing 1 to 4 hetero atoms selected from a nitrogen atom, a sulfur atom and an oxygen atom in addition to carbon atoms, $C_{3-8}$ cycloalkoxy, 5- to 7-membered aliphatic heterocyclicoxy containing 1 to 4 hetero atoms selected from a nitrogen atom, a sulfur atom and an oxygen atom in addition to carbon atoms, $C_{1-6}$ alkylamino, $C_{1-6}$ alkoxy-carbonyl, $C_{3-8}$ cycloalkoxy-carbonyl, 5- to 7-membered aliphatic heterocyclic-oxycarbonyl containing 1 to 4 hetero atoms selected from a nitrogen atom, a sulfur atom and an oxygen atom in addition to carbon atoms, etc.) and the like are exemplified.

As the above-mentioned "$C_{1-6}$ alkyl which may be halogenated", for example, $C_{1-6}$ alkyl (e.g., methyl, ethyl, propyl, isopropyl, butyl, isobutyl, sec-butyl, tert-butyl, pentyl, hexyl and the like) which may have 1 to 5, preferably 1 to 3 halogen atoms (e.g., fluorine, chlorine, bromine, iodine and the like), etc. are exemplified. As specific examples thereof, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. are exemplified.

As the above-mentioned "$C_{2-6}$ alkenyl which may be halogenated", for example, $C_{2-6}$ alkenyl (e.g., vinyl, propenyl, isopropenyl, 2-buten-1-yl, 4-penten-1-yl, 5-hexen-1-yl and the like) which may have 1 to 5, preferably 1 to 3 halogen atoms (e.g., fluorine, chlorine, bromine, iodine and the like), etc. are exemplified.

As the above-mentioned "$C_{2-6}$ alkynyl which may be halogenated", for example, $C_{2-6}$ alkynyl (e.g., 2-butyn-1-yl, 4-pentyn-1-yl, 5-hexyn-1-yl and the like) which may have 1 to 5, preferably 1 to 3 halogen atoms (e.g., fluorine, chlorine, bromine, iodine and the like), etc. are exemplified.

As the above-mentioned "$C_{3-8}$ cycloalkyl which may be halogenated", for example, $C_{3-8}$ cycloalkyl (e.g., cyclopropyl, cyclobutyl, cyclopentyl, cyclohexyl and the like) which may have 1 to 5, preferably 1 to 3 halogen atoms (e.g., fluorine, chlorine, bromine, iodine and the like), etc. are exemplified. As specific examples thereof, cyclopropyl, cyclobutyl, cyclopentyl, cyclohexyl, 4,4-dichlorocyclohexyl, 2,2,3,3-tetrafluorocyclopentyl, 4-chlorocyclohexyl, etc. are exemplified.

As the above-mentioned "$C_{1-18}$ alkoxy which may be halogenated", for example, $C_{1-8}$ alkoxy (e.g., methoxy, ethoxy, propoxy, isopropoxy, butoxy, isobutoxy, sec-butoxy, pentyloxy, hexyloxy and the like) which may have 1 to 5, preferably 1 to 3 halogen atoms (e.g., fluorine, chlorine, bromine, iodine and the like), etc. are exemplified. As specific examples thereof, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. are exemplified.

As the above-mentioned "$C_{1-6}$ alkylthio which may be halogenated", for example, $C_{1-6}$ alkylthio (e.g., methylthio, ethylthio, propylthio, isopropylthio, butylthio, sec-butylthio, tert-butylthio and the like) which may have 1 to 5, preferably 1 to 3 halogen atoms (e.g., fluorine, chlorine, bromine, iodine and the like), etc. are exemplified. As specific examples thereof, methylthio, difluoromethylthio, trifluoromethylthio, ethylthio, propylthio, isopropylthio, butylthio, 4,4,4-trifluorobutylthio, pentylthio, hexylthio, etc. are exemplified.

As the "5- to 7-membered aliphatic heterocyclic group" of the above-mentioned "5- to 7-membered aliphatic heterocyclic group optionally having a substituent", for example, 5- to 7-membered aliphatic heterocyclic group containing 1 to 4 of 1 or 2 kinds of hetero atoms selected from a nitrogen atom, a sulfur atom and an oxygen atom in addition to carbon atoms are exemplified, and as specific examples thereof, 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl, etc. are exemplified.

As the "substituent" of the above-mentioned "5- to 7-membered aliphatic heterocyclic group optionally having a substituent", for example, 1 to 3 of $C_{1-6}$ alkyl (e.g., methyl, ethyl, propyl, isopropyl, butyl, isobutyl, sec-butyl, tert-butyl, pentyl, hexyl and the like), $C_{1-6}$ alkyl-carbonyl (e.g., acetyl, propionyl and the like), oxo, etc. are exemplified.

Provided that, when
(i) $R^1$ or $R^{1a}$ is an acetylamino group, and $R^3$ or $R^{3a}$ is a 3,5-dimethylphenyl group,
(ii) $R^1$ or $R^{1a}$ is a $C_{1-6}$ alkyl-carbonylamino group, and $R^3$ or $R^{3a}$ is a $C_{6-14}$ aryl group substituted by a $C_{1-6}$ alkyl group, or
(iii) $R^1$ or $R^{1a}$ is an amino group optionally having a substituent, and R3 or $R^{3a}$ is an aromatic hydrocarbon group optionally having a substituent, there are exemplified, as the "substituent containing no aromatic group", a halogen atom (e.g., fluorine, chlorine, bromine, iodine and the like), $C_{1-3}$ alkylenedioxy (e.g., methylenedioxy, ethylenedioxy and the like), nitro, cyano, $C_{1-6}$ alkyl which may be halogenated, $C_{2-6}$ alkenyl which may be halogenated, carboxy $C_{2-6}$ alkenyl (e.g., 2-carboxyethenyl, 2-carboxy-2-methylethenyl and the like), $C_{2-6}$ alkynyl which may be halogenated, $C_{3-8}$ cycloalkyl which may be halogenated, $C_{3-8}$ cycloalkyl-$C_{1-6}$ alkyl, $C_{1-8}$ alkoxy which may be halogenated, $C_{1-6}$ alkoxy-carbonyl-$C_{1-6}$ alkoxy (e.g., ethoxycarbonylmethyloxy and the like), mercapto, $C_{1-6}$ alkylthio which may be halogenated, amino, mono-$C_{1-6}$ alkylamino (e.g., methylamino, ethylamino and the like), di-$C_{1-6}$ alkylamino (e.g., dimethylamino, diethylamino, ethylmethylamino and the like), $C_{3-8}$ cycloalkylamino (e.g., cyclopentylamino, cyclohexylamino and the like), $C_{3-8}$ cycloalkyl-$C_{1-6}$ alkyl amino (e.g., cyclopentylmethylamino, cyclohexylmethylamino and the like)., N—$C_{3-8}$ cycloalkyl-N—$C_{1-6}$ alkylamino (e.g., N-cyclopentyl-N-methylamino, N-cyclohexyl-N-methylamino, N-cyclopentyl-N-ethylamino, N-cyclohexyl-N-ethylamino and the like), formyl, carboxy, carboxy-$C_{2-6}$ alkenyl, carboxy-$C_{1-6}$ alkyl, $C_{1-6}$ alkyl-carbonyl (e.g., acetyl, propionyl and the like), $C_{3-8}$ cycloalkyl-carbonyl optionally substituted by $C_{1-6}$ alkyl (e.g., cyclopropylcarbonyl, cyclopentylcarbonyl, cyclohexylcarbonyl, 1-methyl-cyclohexyl-carbonyl and the like), $C_{1-6}$ alkoxy-carbonyl (e.g., methoxycarbonyl, ethoxycarbonyl, propoxycarbonyl, tert-butoxycarbonyl and the like), carbamoyl, thiocarbamoyl, mono-$C_{1-6}$ alkyl-carbamoyl (e.g., methylcarbamoyl, ethylcarbamoyl, and the like), di-$C_{1-6}$ alkyl-carbamoyl (e.g., dimethylcarbamoyl, diethylcarbamoyl, ethylmethylcarbamoyl and the like), $C_{1-6}$ alkylsulfonyl (e.g., methylsulfonyl, ethylsulfonyl and the like), $C_{1-6}$ alkylsulfinyl (e.g., methylsulfinyl, ethylsulfinyl and the like), formylamino, $C_{1-6}$ alkyl-carbonylamino (e.g., acetylamino, propionylamino, pivaloylamino and the like), $C_{3-8}$ cycloalkyl-carbonylamino optionally substituted by $C_{1-6}$ alkyl (e.g., cyclopropylcarbonylamino, cyclopentylcarbonylamino, cyclohexylcarbonylamino and the like), $C_{1-6}$ alkoxy-carbonylamino (e.g., methoxycarbonylamino, ethoxycarbonylamino, propoxycarbonylamino, butoxycarbonylamino and the like), $C_{1-6}$ alkylsulfonylamino (e.g., methylsulfonylamino, ethylsulfonylamino and the like), $C_{1-6}$ alkoxy-carbonyloxy (e.g., methoxycarbonyloxy, ethoxycarbonyloxy, propoxycarbonyloxy, butoxycarbonyloxy and the like), mono-$C_{1-6}$ alkyl-carbamoyloxy (e.g., methylcarbamoyloxy, ethylcarbamoyloxy and the like), di-$C_{1-6}$ alkyl-carbamoyloxy (e.g., dimethylcarbamoyloxy, diethylcarbamoyloxy and the like), 5- to 7-membered aliphatic heterocyclic group optionally having a substituent (preferably, 5- to 7-membered aliphatic heterocyclic group having 1 to 4 hetero atoms selected from a nitrogen atom, an oxygen atom and a sulfur atom in addition to carbon atoms), sulfo, sulfamoyl, sulfinamoyl, sulfenamoyl and the like are exemplified. Further, a group obtained by connecting two or more (e.g., (i) $C_{1-6}$ alkyl, (ii) amino, (iii) $C_{1-6}$ alkylamino, (iv) $C_{3-8}$ cycloalkylamino, (v) 5- to 7-membered aliphatic heterocyclic amino containing 1 to 4 hetero atoms selected from a nitrogen atom, a sulfur atom and an oxygen atom in addition to carbon atoms, (vi) $C_{1-6}$ alkyl-carbonyl amino, (vii) $C_{3-8}$ cycloalkyl-carbonylamino or (viii) 5- to 7-membered aliphatic heterocyclic-carbonyl amino containing 1 to 4 hetero atoms selected from a nitrogen atom, a sulfur atom and an oxygen atom in addition to carbon atoms, which is substituted, respectively, by a substituent selected from the group consisting of a halogen atom, cyano, hydroxy, $C_{1-6}$ alkoxy, $C_{1-6}$ alkylthio, $C_{1-6}$ alkylsulfinyl, $C_{1-6}$ alkyl sulfonyl, $C_{3-8}$ cycloalkyl, 5- to 7-membered aliphatic heterocyclic group containing 1 to 4 hetero atoms selected from a nitrogen atom, a sulfur atom and an oxygen atom in addition to carbon atoms, $C_{1-6}$ alkyl-carbonyl, $C_{3-8}$ cycloalkyl-carbonyl, 5- to 7-membered aliphatic heterocyclic-carbonyl containing 1 to 4 hetero atoms selected from a nitrogen atom, a sulfur atom and an oxygen atom in addition to carbon atoms, $C_{3-8}$ cycloalkoxy, 5- to 7-membered aliphatic heterocyclic-oxy containing 1 to 4 hetero atoms selected from a nitrogen atom, a sulfur atom and an oxygen atom in addition to carbon atoms, $C_{1-6}$ alkylamino, $C_{1-6}$ alkoxy-carbonyl, $C_{3-8}$ cycloalkoxy-carbonyl, 5- to 7-membered aliphatic heterocyclic-oxydarbonyl containing 1 to 4 hetero atoms selected from a nitrogen atom, a sulfur atom and an oxygen atom in addition to carbon atoms, etc.), etc. can also be used as a substituent.

Among these substituents, specifically, 1 to 3, preferably 1 or 2 substituents selected from the following (1) to (6), particularly (1) to (4) are preferably used.

(1) a $C_{1-6}$ alkyl group (e.g., methyl, ethyl, propyl, isopropyl, butyl, isobutyl, sec-butyl, tert-butyl, pentyl, hexyl and the like, preferably a $C_{1-4}$ alkyl group such as methyl, ethyl, propyl, butyl and the like): this $C_{1-6}$ alkyl group may be substituted by a halogen atom, cyano, hydroxy, $C_{3-8}$ cycloalkyl or a 5- to 7-membered aliphatic heterocyclic group containing hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like), (2) a halogen atom (e.g., fluorine atom, chlorine atom, bromine atom, iodine atom), (3) an amino group optionally having a substituent selected from the group consisting of the following ①to ⑦:

①a $C_{1-6}$ alkyl group (e.g., methyl, ethyl, propyl, isopropyl, butyl, isobutyl, sec-butyl, tert-butyl, pentyl, hexyl and the like, preferably $C_{1-3}$ alkyl groups such as methyl, ethyl, propyl and the like), this $C_{1-6}$ alkyl group may be substituted by a halogen atom, cyano, hydroxy, $C_{3-8}$ cycloalkyl or 5- to 7-membered aliphatic heterocyclic group containing 1 to 4 hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, hexahydroazepin-1-yl and the like), ②a $C_{3-8}$ cycloalkyl group (e.g., cyclopropyl, cyclobutyl, cyclopentyl, cyclohexyl and the like), ③a $C_{1-6}$ alkyl-carbonyl group.(e.g., acetyl, propionyl, butyryl, valeryl, isovaleryl, 2-methylpropionyl, pivaloyl and the like), this $C_{1-6}$ alkyl-carbonyl group may be substituted by a halogen atom, cyano, hydroxy, $C_{3-8}$ cycloalkyl or 5- to 7-membered aliphatic heterocyclic group optionally containing 1 to 4 hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like), ④a $C_{1-6}$ alkoxy-carbonyl group (e.g., methoxycarbonyl, ethoxycarbonyl, propoxycarbonyl, butoxycarbonyl, isobutoxycarbonyl, sec-butoxycarbonyl, tert-butoxycarbonyl and the like), ⑤a $C_{3-8}$ cycloalkyl-carbonyl group optionally substituted by $C_{1-6}$ alkyl such as methyl, ethyl (e.g., cyclopropylcarbonyl, cyclobutylcarbonyl, cyclopentylcarbonyl, cyclohexylcarbonyl, 1-methyl-cyclohexylcarbonyl and the like), ⑥a 5- to 7-membered aliphatic heterocyclic group optionally having 1 to 4 hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, (e.g, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl, etc.). This aliphatic heterocyclic group may be substituted by $C_{1-6}$ alkyl (e.g., methyl, ethyl), $C_{1-6}$ alkyl-carbonyl (e.g., acetyl, propionyl) and the like.

⑦a 5- to 7-membered aliphatic heterocyclic (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl, etc.)-carbonyl group optionally having 1 to 4 hetero atoms selected from a nitrogen atom, an oxygen atom and a sulfur atom in addition to carbon atoms . This aliphatic heterocyclic-carbonyl group may be substituted by $C_{1-6}$ alkyl (e.g., methyl, ethyl), $C_{1-6}$ alkyl-carbonyl (e.g., acetyl, propionyl) and the like.

(4) a 5- to 7-membered aliphatic cyclic amino group which may contain further 1 to 4 hetero atoms selected from a nitrogen atom, an oxygen atom and a sulfur atom in addition to carbon atoms and one nitrogen atom (e.g., 1-pyrrolidinyl, piperidino, morpholino, 1-piperazinyl and the like). This aliphatic cyclic amino group may be substituted with $C_{1-6}$ alkyl (e.g., methyl, ethyl), $C_{1-6}$ alkyl-carbonyl (e.g., acetyl, propionyl) and the like.

(5) a hydroxyl group, (6) a $C_{1-6}$ alkyl-carbonyloxy group (e.g., acetyloxy, propionyloxy, butyryloxy and the like).

The "pyridyl group" represented by $R^2$ and $R^{2a}$ may have, for example, 1 to 5, preferably 1 to 3 of the above-mentioned substituents at substitutable positions, and when the number of substituents is 2 or more, they may be the same or different. Further, an endocyclic nitrogen atom of the "pyridyl group" may be N-oxidized.

As the "pyridyl group" of the "pyridyl group having at the position adjacent to a nitrogen atom of the pyridyl group a substituent including no aromatic group" represented by $R^{2a}$, 1-, 2-, 3- and 4-pyridyl group are exemplified, and 4-pyridyl group is particularly preferable.

As the "aromatic group" of the "aromatic group optionally having a substituent," represented by $R^3$ and $R^{3a}$, an aromatic hydrocarbon group, an aromatic heterocyclic group, etc. are exemplified.

As the "aromatic hydrocarbon group", for example, a monocyclic or fused polycyclic (bicyclic or tricyclic) aromatic hydrocarbon group having 6 to 14 carbon atoms are exemplified. As specific examples thereof, for example, $C_{6-14}$ aryl such as phenyl, 1-naphthyl, 2-naphthyl, 2-biphenylyl, 3-biphenylyl, 4-biphenylyl, 2-anthryl and the like, etc. are exemplified.

As the "aromatic heterocyclic group", for example, a 5- or 14-membered (preferably, 5- or 10-membered) monocyclic or bicyclic aromatic heterocyclic groups preferably containing 1 to 4 of 1 or 2 kinds of hetero atoms selected from a nitrogen atom, a sulfur atom and an oxygen atom in addition to carbon atoms, are exemplified. Specifically, an aromatic heterocyclic group such as, for example, 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pirazinyl, 2-pyrimidinyl, 4-pyrimidinyl, 3-pyrrolyl, 2-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, are exemplified.

As the "substituent" of the above-mentioned "aromatic group optionally having a substituent", for example, 1 to 5, preferably 1 to 3 of the same moieties as for the "substituent" of the above-mentioned "hydrocarbon group optionally having a substituent" represented by $R^5$ are exemplified. When the number of the substituents is two or more, these substituents may be the same or different. Further, adjacent two substituents may form a 4- to 7-membered aliphatic carbon ring. Preferable is a 5- or 6-membered aliphatic carbon ring.

$R^3$ and $R^3a$ preferably represent a $C_{6-14}$ aryl group, or a 5- to 14-membered aromatic heterocyclic group preferably containing 1 to 4 of 1 or 2 kinds of hetero atoms selected from a nitrogen atom, a sulfur atom and an oxygen atom in addition to carbon atoms. More preferably, they represent a phenyl group optionally having a substituent or a thienyl group optionally having a substituent, and a phenyl group optionally having a substituent is particularly preferable.

As the substituent on the $C_{6-10}$ aryl group, a phenyl group, a 5- to 14-membered aromatic heterocyclic group and a thienyl group, preferable are 1 to 3 substituents selected from a halogen atom, $C_{1-3}$ alkylenedioxy, $C_{1-6}$ alkyl which may be halogenated, carboxy $C_{2-6}$ alkenyl, $C_{3-8}$ cycloalkyl, $C_{1-8}$ alkoxy which may be halogenated, hydroxy, $C_{7-16}$ aralkyloxy, $C_{1-6}$ alkyl-carbonyloxy, carboxy, $C_{1-6}$ alkoxy-carbonyl, cyano, $C_{1-6}$ alkylthio, $C_{1-6}$ alkylsulfonyl and particularly, a halogen atom, $C_{1-6}$ alkyl which may be halogenated (e.g., $C_{1-3}$ alkyl such as methyl, ethyl, propyl and the like), $C_{1-8}$ alkoxy which may be halogenated (e.g., $C_{1-3}$ alkoxy such as methoxy, ethoxy and the like), carboxy, $C_{1-6}$ alkoxy-carbonyl, cyano, $C_{1-6}$ alkylthio (e.g., methylthio, ethylthio), $C_{1-6}$ alkylsulfonyl (e.g., methylsulfonyl, ethylsulfonyl), etc. are preferable. Further, two alkyl groups adjacent as substituents may form a 5-membered aliphatic carbocyclic ring.

As the compound (Ibb), specifically, compounds represented by the following formula are preferably used:

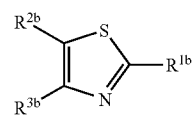

(Ibbb)

wherein $R^{1b}$ represents (i) a hydrogen atom, (ii) a $C_{1-6}$ alkyl group optionally substituted by a substituent selected from the group consisting of a halogen atom, $C_{1-6}$ alkoxy-carbonyl, carboxy, cyano, $C_{1-6}$ alkylthio, $C_{1-6}$ alkylsulfinyl, $C_{1-6}$ alkylsulfonyl, hydroxy, $C_{1-6}$ alkoxy and $C_{1-6}$ alkyl-carbonyl, (iii) a $C_{6-14}$ aryl group optionally having a substituent selected from the group consisting of a halogen atom and a group represented by the formula: —S(O)$_n$—R$^{1bb}$ (R$^{1bb}$ represents a $C_{1-6}$ alkyl group, and n represents an integer of 0 to 2), (iv) a $C_{7-15}$ aralkyl group, (v) an amino group optionally having one or two substituents selected from ① $C_{1-6}$ alkyl, ② $C_{1-6}$ alkyl-carbonyl, ③ $C_{1-6}$ alkoxy-carbonyl, ④ 5- to 7-membered heterocyclic-carbonyl containing 1 to 4 hetero atoms selected from the group consisting of a nitrogen atom, an oxygen atom and a sulfur atom, in addition to carbon atoms, optionally substituted with a halogen atom, $C_{1-6}$ alkyl group or $C_{1-6}$ alkoxy, ⑤ $C_{6-14}$ aryl-carbamoyl, ⑥ $C_{1-6}$ alkyl-carbamoyl which may be halogenated, ⑦ $C_{1-16}$ alkoxy-carbonyl which may be halogenated, ⑧ $C_{1-6}$ alkoxy-carbamoyl and ⑨ $C_{6-14}$ aryloxy-carbamoyl, (vi) a 5- to 10-membered aliphatic heterocyclic group containing 1 to 4 of 1 or 2 kinds of hetero atoms selected from a nitrogen atom, a sulfur atom and an oxygen atom in addition to carbon atoms, optionally substituted by oxo, $C_{1-6}$ alkyl, $C_{6-14}$ aryl, $C_{1-6}$ alkyl-carbonyl or $C_{1-6}$ alkoxy-carbonyl, (vii) an acyl group represented by the formula: —(C=O)—R$^{5b}$ (wherein R$^{5b}$ represents a hydrogen atom, a $C_{1-6}$ alkyl group which may be halogenated or a $C_{6-14}$ aryl group which may be halogenated), or (viii) an acyl group represented by the formula: —(C=O)—OR$^{5c}$ (wherein R$^{5c}$ represents a hydrogen atom or a $C_{1-6}$ alkyl group), $R^{2b}$ represents a pyridyl group (preferably, 4-pyridyl group and this pyridyl group may be N-oxidized.) having at the position adjacent to a nitrogen atom of the pyridyl group a substituent selected from the group (particularly, consisting of (1) to (4)) consisting of (1) a $C_{1-6}$ alkyl group (this $C_{1-6}$ alkyl group may be substituted by a halogen atom, cyano, hydroxy, $C_{3-8}$ cycloalkyl or a 5- to 7-membered aliphatic heterocyclic group containing hetero atoms selected from a nitrogen atom, an oxygen atom and a sulfur atom in addition to carbon atoms), (2) a halogen atom, (3) an amino group optionally having a substituent selected from the group consisting of the following ① to ①;

① $C_{1-6}$ alkyl group (this $C_{1-6}$ alkyl group may be substituted by halogen atoms, cyano, hydroxy, $C_{3-8}$ cycloalkyl or 5- to 7-membered aliphatic heterocyclic group having 1 to 4 hetero atoms selected from a nitrogen atom, an oxygen atom and a sulfur atom in addition to carbon atoms), ② a $C_{3-8}$ cycloalkyl group, ③ a $C_{1-6}$ alkyl-carbonyl group (this $C_{1-6}$ alkyl-carbonyl group may be substituted by halogen atoms, cyano, hydroxy, $C_{3-8}$ cycloalkyl or 5- to 7-membered aliphatic heterocyclic group having 1 to 4 hetero atoms selected from a nitrogen atom, an oxygen atom and a sulfur atom in addition to carbon atoms), ④ a $C_{1-6}$ alkoxy-carbonyl group, ⑤ a $C_{3-8}$ cycloalkyl-carbonyl group optionally substituted by $C_{1-6}$ alkyl, ⑥ a 5- to 7-membered aliphatic heterocyclic group having 1 to 4 hetero atoms selected from a nitrogen atom, an oxygen atom and a sulfur atom in addition to carbon atoms (this aliphatic heterocyclic group may be substituted by $C_{1-6}$ alkyl or $C_1$ alkyl-carbonyl), ⑦ a 5- to 7-membered aliphatic heterocyclic-carbonyl group having 1 to 4 hetero atoms selected from a nitrogen atom, an oxygen atom and a sulfur atom in addition to carbon atoms (this aliphatic heterocyclic-carbonyl group may be substituted by $C_{1-6}$ alkyl or $C_{1-6}$ alkyl-carbonyl), (4) a 5- to 7-membered aliphatic cyclic amino group optionally further containing hetero atoms selected from a nitrogen atom, an oxygen atom and a sulfur atom in addition to carbon atoms and one nitrogen atom (this aliphatic cyclic amino group may be substituted by $C_{1-6}$ alkyl or $C_{1-6}$ alkyl-carbonyl), (5) a hydroxy group, and (6) a $C_{1-6}$ alkyl-carbonyloxy group, and $R^{3b}$ represents ① a $C_{6-14}$ aryl group or ② a 5- to 14-membered aromatic heterocyclic group preferably containing 1 to 4 of 1 or 2 kinds of hetero atoms selected from a nitrogen atom, a sulfur atom and an oxygen atom in addition to carbon atoms, which optionally has a substituent selected from the group consisting of $C_{1-16}$ alkyl which may be halogenated, $C_{1-6}$ alkoxy, a halogen atom, carboxyl, $C_{1-6}$ alkoxy-carbonyl, cyano, $C_{1-6}$ alkylthio and $C_{1-6}$ alkylsulfonyl.

As the $C_{1-6}$ alkyl group represented by $R^{1b}$, for example, methyl, ethyl, propyl, isopropyl, butyl, isobutyl, sec-butyl, tert-butyl, pentyl, hexyl, etc. are used, and particularly, a $C_{1-4}$ alkyl group such as methyl, ethyl, propyl, butyl and the like are preferable, and a $C_{1-3}$ alkyl group such as methyl, ethyl, propyl, etc. are particularly preferable.

As the halogen atom which is a substituent of the $C_{1-6}$ alkyl group represented by $R^{1b}$, a fluorine atom, a chlorine atom, a bromine atom and an iodine atom and the like are used.

As the $C_{1-6}$ alkoxy-carbonyl which is a substituent of the $C_{1-6}$ alkyl group represented by $R^{1b}$, for example, methoxycarbonyl, ethoxycarbony and the like are preferable.

As the $C_{1-6}$ alkylthio which is a substituent of the $C_{1-6}$ alkyl group represented by $R^{1b}$, for example, methylthio, ethylthio and the like are preferable.

As the $C_{1-6}$ alkylsulfinyl which is a substituent of the $C_{1-6}$ alkyl group represented by $R^{1b}$, for example, methylsulfinyl, ethylsulfinyl and the like are preferable.

As the $C_{1-6}$ alkylsulfonyl which is a substituent of the $C_{1-6}$ alkyl group represented by $R^{1b}$, for example, methylsulfonyl, ethylsulfonyl and the like are preferable.

As the $C_{1-6}$ alkoxy which is a substituent of the $C_{1-6}$ alkyl group represented by $R^{1b}$, for example, methoxy, ethoxy, propoxy and the like are preferable.

As the $C_{1-6}$ alkyl-carbonyl which is a substituent of the $C_{1-6}$ alkyl group represented by $R^{1b}$, for example, acetyl, propionyl and the like are preferable.

As the $C_{1-6}$ alkyl group represented by $R^{1bb}$, for example, methyl, ethyl, propyl, isopropyl, butyl, isobutyl, sec-butyl, tert-butyl, pentyl, hexyl, etc. are used, and particularly, a $C_{1-3}$ alkyl group such as methyl, ethyl, propyl and the like are preferable, particularly, methyl is preferable.

As the $C_{6-14}$ aryl group represented by $R^{1b}$, for example, phenyl, naphthyl, etc. are preferable, and of them, phenyl is particularly preferable.

As the halogen atom which is a substituent of the $C_{6-14}$ aryl group represented by $R^{1b}$, a fluorine atom, a chlorine atom, a bromine atom and an iodine atom are used.

As the $C_{7-15}$ aralkyl group represented by $R^{1b}$, for example, a phenyl-$C_{1-3}$ alkyl group such as benzyl, phenylethyl, phenylpropyl and the like are preferable.

As the $C_{1-6}$ alkyl group which is a substituent of an amino group represented by $R^{1b}$, for example, methyl, ethyl, propyl, isopropyl, butyl, isobutyl, sec-butyl, tert-butyl, pentyl, hexyl, etc. are used, and particularly, a $C_{1-3}$ alkyl group such as methyl, ethyl, propyl and the like are preferable, particularly, methyl is preferable.

As the $C_{1-6}$ alkyl-carbonyl which is a substituent of an amino group represented by $R^{1b}$, for example, a $C_{1-3}$ alkyl-carbonyl group such as acetyl, propionyl and the like are preferable.

As the "5- to 7-membered heterocyclic-carbonyl containing 1 to 4 hetero atoms selected from the group consisting of a nitrogen atom, an oxygen atom and a sulfur atom, in addition to carbon atoms" which is a substituent of an amino group represented by $R^{1b}$, for example, a 5- to 7-membered heterocyclic (e.g., pyridyl and the like)-carbonyl group containing 1 or 2 hetero atoms selected from the group consisting of a nitrogen atom, an oxygen atom and a sulfur atom, etc. are preferable. As the substituent of the heterocyclic group of this heterocyclic-carbonyl group, a halogen atom such as a chlorine atom, a $C_{1-6}$ alkyl group such as methyl, ethyl and the like, and a $C_{1-6}$ alkoxy group such as methoxy, ethoxy and the like are preferable.

As the $C_{6-14}$ aryl-carbamoyl which is a substituent of an amino group represented by $R^{1b}$, for example, phenyl-carbamoyl, etc. are preferable.

As the $C_{1-6}$ alkyl-carbamoyl which may be halogenated which is a substituent of an amino group represented by $R^{1b}$, for example, methylcarbamoyl, ethylcarbamoyl, propylcarbamoyl optionally substituted by a halogen atom (e.g., chlorine atom) and the like are preferable.

As the $C_{1-6}$ alkoxy-carbonyl which may be halogenated which is a substituent of an amino group represented by $R^{1b}$, for example, methoxycarbamoyl, ethoxycarbamoyl, propoxycarbamoyl optionally substituted by halogen atoms (e.g., chlorine atom) and the like are preferable.

As the $C_{1-6}$ alkoxy-carbamoyl which is a substituent of an amino group represented by $R^{1b}$, for example, methoxycarbamoyl, ethoxycarbamoyl, propoxycarbamoyl and the like are preferable.

As the $C_{6-14}$ aryloxy-carbamoyl which is a substituent of an amino group represented by $R^{1b}$, for example, phenyloxy-carbamoyl and the like are preferable.

As the 5- to 10-membered aliphatic heterocyclic group represented by $R^{1b}$, for example, 1-pyrrolidinyl, 2-pyrrolidinyl, 3-pyrrolidinyl, 3-oxazolidinyl, 1-imidazolidinyl, 2-imidazolidinyl, 4-imidazolidinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like, are used, and of them, 4-piperidyl, 1-piperazinyl, 3-oxazolidinyl, 1-imidazolidinyl and the like are preferable.

As the 5- to 10-membered aliphatic heterocyclic group optionally substituted by oxo, $C_{1-6}$ alkyl (preferably, methyl, ethyl), $C_{6-14}$ aryl (preferably, phenyl), $C_{1-6}$ alkyl-carbonyl (preferably, acetyl, propionyl) or $C_{1-6}$ alkoxy-carbonyl (preferably, methoxycarbonyl, ethoxycarbonyl, tert-butoxycarbonyl) represented by $R^{1b}$, 1-methyl-4-piperidyl, 4-methyl-1-piperazinyl, 2-oxo-3-oxazolidinyl, 2-oxo-1-imidazolidinyl, 2-oxo-3-phenyl-1-imidazolidinyl and the like are preferable.

As $R^{5b}$ of the formula: —(C=O)—$R^{5b}$ represented by $R^{1b}$, a hydrogen atom, a $C_{1-6}$ alkyl group which may be halogenated (methyl, ethyl, trifluoromethyl and the like), a $C_{6-14}$ alkyl group which may be halogenated (phenyl, naphthyl, fluorophenyl, chlorophenyl and the like), etc. are preferable.

As $R^{5c}$ of the formula —(C=O)—$OR^{5c}$ represented by $R^{1b}$, a hydrogen atom, a $C_{1-3}$ alkyl group (methyl, ethyl, etc.), etc. are preferable.

As $R^{1b}$, a $C_{1-6}$ alkyl group (e.g., methyl, ethyl, propyl, isopropyl, butyl, isobutyl, sec-butyl, tert-butyl, pentyl, hexyl, etc.) is preferable, particularly, a $C_{1-3}$ alkyl group such as methyl, ethyl, propyl, etc. is preferable.

As specific examples of a substituent of the pyridyl group represented by $R^{2b}$, 1 to 3, preferably 1 or 2 substituents selected from the following (1) to (6), particularly (1) to (4) are used.

(1) a $C_{1-6}$ alkyl group (e.g., methyl, ethyl, propyl, isopropyl, butyl, isobutyl, sec-butyl, tert-butyl, pentyl, hexyl and the like, preferably a $C_{1-4}$ alkyl group such as methyl, ethyl, propyl, butyl and the like): this $C_{1-6}$ alkyl group may be substituted by a halogen atom, cyano, hydroxy, $C_{3-8}$ cycloalkyl or 5- to 7-membered aliphatic heterocyclic group containing hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like), (2) a halogen atom (e.g., fluorine atom, chlorine atom, bromine atom, iodine atom), (3) an amino group optionally having a substituent selected from the group consisting of the following ① to ⑦:

① a $C_{1-6}$ alkyl group (e.g., methyl, ethyl, propyl, isopropyl, butyl, isobutyl, sec-butyl, tert-butyl, pentyl, hexyl and the like, preferably a $C_{1-3}$ alkyl group such as methyl, ethyl, propyl and the like): this $C_{1-6}$ alkyl group may be substituted by a halogen atom, cyano, hydroxy, $C_{3-8}$ cycloalkyl or 5- to 7-membered aliphatic heterocyclic group optionally containing hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like), ② a $C_{3-8}$ cycloalkyl group (e.g., cyclopropyl, cyclobutyl, cyclopentyl, cyclohexyl and the like), ③ a $C_{1-6}$ alkyl-carbonyl group (e.g., acetyl, propionyl, butylyl, valeryl, isovaleryl, 2-methylbutyryl, pivaloyl and the like): this $C_{1-6}$ alkyl-carbonyl group maybe substituted by a halogen atom, cyano, hydroxy , $C_{3-8}$ cycloalkyl or 5- to 7-membered aliphatic heterocyclic group optionally containing hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like), ④ a $C_{1-6}$ alkoxy-carbonyl group (e.g., methoxycarbonyl, ethoxy carbonyl, propoxycarbonyl, butoxycarbonyl, isobutoxycarbonyl, sec-butoxycarbonyl, tert-butoxycarbonyl and the like), ⑤ a $C_{3-8}$ cycloalkyl-carbonyl group optionally substituted by $C_{1-6}$ alkyl such as methyl, ethyl (e.g., cyclopropylcarbonyl, cyclobutylcarbonyl, cyclopentylcarbonyl, cyclohexylcarbonyl, 1-methylcyclohexyl-carbonyl and the like), ⑥ a 5- to 7-membered aliphatic heterocyclic group optionally having 1 to 4 hetero atoms selected from a nitrogen atom, an oxygen atom and a sulfur atom in addition to carbon atoms (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like). This aliphatic heterocyclic group may be substituted by $C_{1-6}$ alkyl (e.g., methyl, ethyl) or $C_{1-6}$ alkyl-carbonyl (e.g., acety, propionyl), ⑦ a 5- to 7-membered aliphatic heterocyclic (e.g., 1-pyrrolidinyl, 2-pyrrolidinyl, 3-pyrrolidinyl, piperidino, 2-piperidyl, 3-piperidyl, 4-piperidyl, 1-piperazinyl, 2-piperazinyl, 3-piperazinyl, 4-piperazinyl, morpholino, 2-morpholinyl, 3-morpholinyl, thiomorpholino, 2-thiomorpholinyl, 3-thiomorpholinyl, hexahydroazepin-1-yl and the like)-carbonyl group having 1 to 4 hetero atoms selected from a nitrogen atom, an oxygen atom and a sulfur atom in addition to carbon atoms This heterocyclic-carbonyl group may be substituted by $C_{1-6}$ alkyl (e.g., methyl, ethyl) or $C_{1-6}$ alkyl-carbonyl (e.g., acety, propionyl), (4) a 5- or 7-membered aliphatic cyclic amino group which may contain hetero atoms selected from a nitrogen atom, an oxygen atom and a sulfur atom in addition to carbon atoms and one nitrogen atom (e.g., 1-pyrrolidinyl, piperidino, morpholino, 1-piperazinyl and the like). This aliphatic cyclic amino group may be substituted with $C_{1-6}$ alkyl (e.g., methyl, ethyl), $C_{1-6}$ alkyl-carbonyl (e.g., acety, propionyl) and the like;

(5) a hydroxyl group, (6) a $C_{1-6}$ alkyl-carbonyloxy group (e.g., acetyloxy, propionyloxy, butyryloxy and the like).

Of them, as a substituent of the pyridyl group represented by $R^{2b}$, for example, a $C_{1-6}$ alkyl-carbonylamino group (e.g., acetylamino, propionylamino, butylylamino, valerylamino, isovalerylamino, 2-methylbutyrylamino, pivaloylamino and the like) is preferable, and particularly, a $C_{1-3}$ alkyl-carbonylamino group such as acetyl, propionylamino, etc. is preferable.

As the $C_{6-14}$ aryl group represented by $R^{3b}$, for example, phenyl, naphthyl, etc. are preferable, and of them, phenyl is particularly preferable.

As the 5- to 14-membered aromatic heterocyclic group preferably containing 1 to 4 of 1 or 2 kinds of hetero atoms selected from a nitrogen atom, a sulfur atom and an oxygen atom in addition to carbon atoms, represented by $R^{3b}$, for example, a 5- or 6-membered aromatic heterocyclic group preferably containing 1 to 4 of 1 or 2 kinds of hetero atoms selected from a nitrogen atom, a sulfur atom and an oxygen atom in addition to carbon atoms, such as thienyl and the like, are preferable.

As the $C_{1-6}$ alkyl group which may be halogenated, which is a substituent of the $C_{6-14}$ aryl group or the aromatic heterocyclic group, for example, methyl, ethyl, propyl, isopropyl, butyl, isobutyl, sec-butyl, tert-butyl, pentyl, hexyl, etc. which may be substituted by a halogen atom (e.g., fluorine, chlorine and the like) are used, and particularly, a $C_{1-3}$ alkyl group which may be halogenated such as methyl, ethyl, propyl, trifluoromethyl and the like are preferable.

As the $C_{1-6}$ alkoxy which is a substituent of the $C_{6-14}$ aryl group or the aromatic heterocyclic group, for example, methoxy, ethoxy, propoxy, etc. are used, and of them, methoxy is particularly preferable.

As the halogen atom which is a substituent of the $C_{6-14}$ aryl group or the aromatic heterocyclic group, a fluorine atom, a chlorine atom, a bromine atom and an iodine atom are used, and of them, a fluorine atom and a chlorine atom, etc. are preferable.

As the $C_{1-6}$ alkoxy-carbonyl which is a substituent of the $C_{6-14}$ aryl group or the aromatic heterocyclic group, for example, methoxycarbonyl, ethoxycarbonyl and the like are preferable.

As the $C_{1-6}$ alkylthio which is a substituent of the $C_{6-14}$ aryl group or the aromatic heterocyclic group, for example, methylthio, ethylthio and the like are preferable.

As the $C_{1-6}$ alkylsulfonyl which is a substituent of the $C_{6-14}$ aryl group or the aromatic heterocyclic group, for example, methylsulfonyl, ethylsulfonyl and the like are preferable.

As $R^{3b}$, a $C_{6-14}$ aryl group optionally having a substituent selected from the group consisting of $C_{1-6}$ alkyl and a halogen atom is preferable, and a phenyl group optionally substituted by methyl or a chlorine atom is more preferable.

As the compound (Ibbb), for example, (1) the compound (Ibbb) wherein $R^{1b}$ is a $C_{1-6}$ alkyl group optionally having a substituent selected from the group consisting of a halogen atom, hydroxy, $C_{1-6}$ alkoxy, $C_{1-6}$ alkylthio, $C_{1-6}$ alkylsulfinyl and $C_{1-6}$ alkylsulfonyl, $R^{2b}$ is a $C_{1-6}$ alkyl-carbonylamino group or a $C_{3-8}$ cycloalkylamino group, $R^{3b}$ is a $C_{6-14}$ aryl group optionally having a substituent selected from the group consisting of $C_{1-6}$ alkyl and a halogen atom, (2) the compound (Ibbb) wherein $R^{1b}$ is a $C_{1-3}$ alkyl group optionally having a substituent selected from the group consisting of a halogen atom, hydroxy, $C_{1-6}$ alkoxy, $C_{1-6}$ alkylthio, $C_{1-6}$ alkylsulfinyl and $C_{1-6}$ alkylsulfonyl, $R^{2b}$ is a $C_{1-3}$ alkyl-carbonylamino group or a $C_{3-8}$ cycloalkylamino group, $R^{3b}$ is a phenyl group optionally having a substituent selected from the group consisting of methyl or a chlorine atom, and the like are preferable.

As preferable specific examples of the compound (Ibbb), compounds produced in Examples 1 to 113 described later are exemplified, and of them, 5-[2-(tert-butoxycarbonylamino)-4-pyridyl]-2-ethyl-4-(3-methylphenyl)-1,3-thiazol (Example 3), [4-(3-methylphenyl)-5-(2-methyl-4-pyridyl)-1,3-thiazol-2-yl]amine (Example 7-4), 2-ethyl-5-(2-fluoro-4-pyridyl)-4-(3-methylphenyl)-1,3-thiazole (Example 11), 5-(2-fluoro-4-pyridyl)-4-(3-methylphenyl)-2-[4-(methylthio)phenyl]-1,3-thiazole (Example 15), 4-(3-methylphenyl)-5-(2-methyl-4-pyridyl)-2-[4-(methylthio)phenyl]-1,3-thiazole (Example 16-1), 4-[2-ethyl-4-(3-methylphenyl)-1,3-thiazol-5-yl]-2-pyridylamine (Example 22), N-[4-[2-ethyl-4-(3-methylphenyl)-1-1,3-thiazol-5-yl]-2-pyridyl]acetamide (Example 29-2), N-[4-[2-ethyl-4-(3-methylphenyl)-1,3-thiazol-5-yl]-2-pyridyl]propionamide (Example 29-4), N-[4-[4-(3-chlorophenyl)-2-methyl-1,3-thiazol-5-yl]-2-pyridyl]acetamide (Example 30-1), N-[4-[4-(3-chlorophenyl)-2-ethyl-1,3-thiazol-5-yl]-2-pyridyl]acetamide (Example 30-2), N-[4-[4-(3-chlorophenyl)-2-propyl-1,3-thiazol-5-yl]-2-pyridyl]acetamide (Example 30-3), N-[4-[4-(3-chlorophenyl)-2-methyl-1,3-thiazol-5-yl]-2pyridyl]propionamide (Example 30-7), N-[4-[4-(3-chlorophenyl)-2-ethyl-1,3-thiazol-5-yl]-2-pyridyl]propionamide (Example 30-8), N-[4-[4-(3-chlorophenyl)-2-propyl-1,3-thiazol-5-yl]-2-pyridyl]propionamide (Example 30-9), N-cyclohexyl-4-[2-ethyl-4-(3-methylphenyl)-1,3-thiazol-5-yl]-2-pyridylamine (Example 36-4), N-cyclohexyl-4-[4-(3-methylphenyl)-2-(4-methylsulfonylphenyl)-1,3-thiazol-5-yl]-2-pyridylamine (Example 36-5), N-cyclopentyl-4-[2-ethyl-4-(3-methylphenyl)-1,3-thiazol-5yl]-2-pyridylamine (Example 36-6), N-cyclopentyl-4-[4-(3-methylphenyl)-2-(4-methylsulfonylphenyl)-1,3-thiazol-5-yl]-2-pyridylamine (Example 36-7), 4-[4-(3-chlorophenyl)-2-ethyl-1,3-thiazol-5-yl]-N-cyclohexyl-2-pyridylamine (Example 36-10), 4-[4-(3-chlorophenyl)-2-ethyl-1,3-thiazol-5-yl]-N-cyclopentyl-2-pyridylamine (Example 36-11), N-[4-(3-methylphenyl)-5-(2-methyl-4-pyridyl)-1,3-thiazol-2-yl]acetamide (Example 39), N-[4-(3,5-dimethylphenyl)-5-(2-methyl-4-pyridyl)-1,3-thiazol-2-yl] nicotimide (Example 42-1), 6-chloro-N-[4-(3,5-dimethylphenyl)-5-(2-methyl-4-pyridyl)-1,3-thiazol-2-yl] nicotinamide (Example 44-3), N-[4-(3,5-dimethylphenyl)-5-(2methyl-4-pyridyl)-1,3-thiazol-2-yl]-6methylnicotinamide (Example 46-3), N-[4-(3,5-dimethylphenyl)-5-(2-methyl-4-pyridyl)-1,3-thiazol-2-yl]-6-methoxynicotinamide (Example 48-3), 4-(3-methylphenyl)-5-(2-methyl-4-pyridyl)-2-(4-methylsulfinylphenyl)-1,3-thiazole (Example 54), 4-(3-methylphenyl)-5-(2-methyl-4-pyridyl)-2-(4-methylsulfonylphenyl)-1,3-thiazole (Example 57), 5-(2-fluoro-4-pyridyl)-4-(3-methylphenyl)-2-(4-methylsulfonylphenyl)-1,3-thiazole (Example 58-4), N-[4-[4-(3-chlorophenyl)-2-(4-methylsulfonylphenyl)-1,3-thiazol-5-yl]-2-pyridyl]acetamide (Example 58-6), N-[4-[4-(3-chlorophenyl)-2-(4-methylsulfonylphenyl)-1,3-thiazol-5-yl-]-2-pyridyl]propionamide (Example 58-7), N-[4-[4-(3-chlorophenyl)-2-(4-methylsulfonylphenyl)-1,3-thiazol-5-yl]-2-pyridyl]pivalamide (Example 58-8) and the like are preferable.

As a salt of the compound (Ia), (Ib) or (Ic), for example, metal salts, ammonium salts, salts with organic bases, salts with inorganic acids, salts with organic acids, salts with basic or acidic amino acids, etc. are exemplified. As suitable examples of metal salts, for example, alkali metal salts such as sodium salts, potassium salts and the like; alkaline earth metal salts such as potassium salts, magnesium salts, barium salts and the like; aluminum salts; etc. are exemplified. As suitable examples of salts with organic bases, for example, salts with trimethylamine, triethylamine, pyridine, picoline, 2,6-lutidine, ethanolamine, diethanolamine, triethanolamin, cyclohexylamine, dicyclohexyamine, N,N'-dibenzylethylenediamine, etc. are exemplified. As suitable examples of salts with inorganic acids, for example, salts with hydrochloric acid, hydrobromic acid, nitric acid, sulfuric acid, phosphoric acid, etc. are exemplified. As suitable examples of salts with organic acids, for example, salts with formic acid, acetic acid, trifluroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. are exemplified. As suitable examples of salts with basic amino acids, for example, salts with arginine, lysine, ornithine, etc. are exemplified, and as suitable examples of salts with acidic amino acids, for example, salts with aspartic acid, glutamic acid, etc. are exemplified.

Of them, pharmaceutically acceptable salts are preferable. When an acidic functional group is contained in a compound, for example, inorganic salts such as alkali metal salts (e.g., sodium salts, potassium salts and the like), alkaline earth metal salts (e.g., calcium salts, magnesium salts, barium salts and the like), and ammonium salts, etc. are exemplified, and when a basic functional group is contained in a compound, for example, salts with inorganic acids such as hydrochloric acid, hydrobromic acid, nitric acid, sulfuric acid, phosphoric acid, etc. or salts with organic acids such as acetic acid, phthalic acid, fumaric acid, oxalic acid, tartaric acid, maleic acid, citric acid, succinic acid, methanesulfonic acid, p-toluenesulfonic acid, etc. are preferable.

A pro-drug of the compound (Ia), compound (Ib), compound (Ic), compound (Iaa), compound (Ibb) or a salt thereof of the present invention (hereinafter, sometimes referred to as compound (I) of the present invention) means a compound which is converted into the compound (I) of the present invention by reactions of enzymes, gastric acid and the like under physiological conditions in organisms, namely, a compound which causes enzymatic oxidation, reduction, hydrolysis and the like to be converted into the compound (I) of the present invention, and a compound which causes hydrolysis and the like by gastric acid, etc. to be converted into a compound (I) of the present invention.

As the pro-drug of the compound (I) of the present invention, compounds obtained by acylation, alkylation and phosphorylation of an amino group of the compound (I) of the present invention (e.g., compounds obtained by eicosanoylation, alanylation, pentylaminocarbonylation, (5-methyl-2-oxo-1,3-dioxolen-4yl)-methoxycarbonylation, tetrahydrofuranylation, pyrrolidylmethylation, pivaloyloxymethylation, tertbutylation of an amino group of the compound (I) of the present invention, etc.); compounds obtained by acylation, alkylation, phosphorylation and boration of a hydroxyl group of the compound (I) of the present invention (e.g., compounds obtained by acetylation, palmitoylation, propanoylation, pivaloylation, succinylation, fumarylation, alanylation, dimethylaminomethylcarbonylation of a hydroxyl group of the compound (I) of the present invention, etc.); compounds obtained by esterification and amidation of a carboxyl group of the compound (I) of the present invention (e.g., compounds obtained by ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolene-4-yl)methylesterification, cyclohexyloxycarbonylethylesterification, methylamidation of a carboxyl group of the compound (I) of the present invention, etc.), etc. are exemplified. These compounds can be produced from the compound (I) of the present invention according to methods known per se.

Further, a prodrug of the compound (I) of the present invention may also be one which is converted into the compound (I) of the present invention under physiological conditions as described in "Iyakuhin no Kaihatsu", vol. 7, Bunshi Sekkei, pp. 163to 198, Hirokawa Shoten, 1990.

A method for producing the compound (Ia), (Ib), (Ic) or a salt thereof of the present invention will be illustrated below. Hereinafter, the compound (I) means a compound including compounds (Ia), (Ib), (Ic), (Ibb) and (Ibbb).

The compound (I) of the present invention is obtained by a method represented by the following reaction formula 1 or methods according to this method, and additionally, obtained, for example, by methods described in JP-A No. 60-58981, JP-A No. 61-10580, JP-T No. 7-503023, WO 93/15071, DE-A-3601411, JP-A No. 5-70446 and methods according to them.

Symbols of compounds in the following reaction formulae 1 to 2 are as defined above. Compounds in the reaction formulae also include salts, and as this salt, for example, the same salts as for the compound (Ia) are exemplified.

Reaction Formula 1

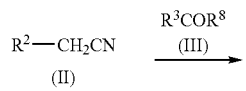

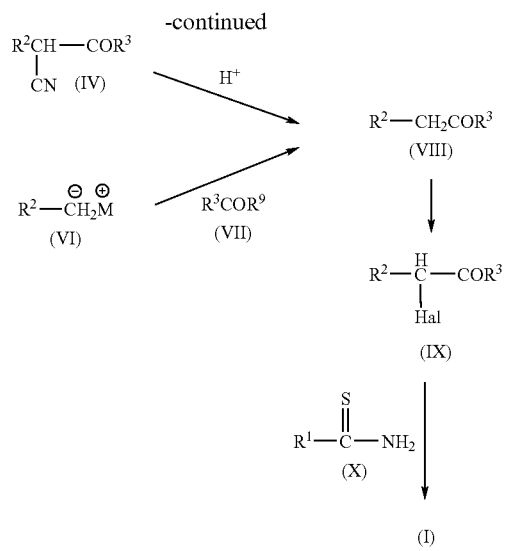

When compounds (II), (III), (V), (VII), (XI), (XIII) and (XIV) are commercially available, they may be used without any treatment, and also can be produced by methods known per se or methods according to them.

The compound (IV) is obtained by condensing a compound (II) with a compound (III) in the presence of a base.

In the compound (III), $R^8$ represents, for example, ① a $C_{1-6}$ alkoxy (e.g., methoxy, ethoxy and the like), ② a di-$C_{1-6}$ alkylamino (e.g., dimethylamino, diethylamino and the like), ③ an N—$C_{6-10}$ aryl-N—$C_{1-6}$ alkylamino (e.g., N-phenyl-N-methylamino and the like), ④ a 3- to 7-membered cyclic amino optionally substituted with a $C_{6-10}$ aryl and (or) $C_{1-6}$ alkyl (e.g., pyrrolidin-1-yl, morpholino, methylaziridin-1-yl, and the like), etc.

The amount of the compound (III) used is about 0.5 to about 3.0 mol, preferably about 0.8 to about 2.0 mol per mol of the compound (II).

The amount of a base used is about 1.0 to about 30 mol, preferably about 1.0 to about 10 mol per mol of the compound (II).

As the "base", for example, basic salts such as sodium carbonate, potassium carbonate, cesium carbonate and the like, inorganic bases such as sodium hydroxide, potassium hydroxide and the like, aromatic amines such as pyridine, lutidine and the like, tertiary amines such triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, etc. are exemplified.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, ethers, amides, alcohols, water or mixtures of two or more of them, etc. are used.

The reaction temperature is usually from about −5° C. to about 200° C., preferably from about 5° C. to about 150° C.

The reaction time is usually from about 5 minutes to about 72 hours, preferably from about 0.5 to about 30 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (VIII) is obtained by treating a compound (IV) with an acid.

The amount of an acid used is about 1.0 to about 100 mol, preferably about 1.0 to about 30 mol per mol of the compound (IV).

As the "acid", for example, mineral acids such as hydrochloric acid, hydrobromic acid, sulfuric acid, etc. are used.

The present reaction is conducted in the presence of a solvent inactive to the reaction. The solvent is not particularly restricted providing the reaction can progress, and for example, water, mixtures of water with amides, mixtures of water with alcohols, etc. are used.

The reaction temperature is usually from about 20° C. to about 200° C., preferably from about 60° C. to about 150° C. The reaction time is usually from about 30 minutes to about 72 hours, preferably from about 1 hour to about 30 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (VIII) can also be obtained by condensing a compound (VII) with a compound (VI) obtained by treating a compound (V) with a base.

In the compound (VI), M represents, for example, an alkali metal such as lithium, sodium, potassium and the like.

In the compound (VII), as $R^9$, for example, the same moieties as for $R^8$ are exemplified.

The amount of a base used is about 1.0 to about 30 mol, preferably about 1.0 to about 10 mol per mol of the compound (V).

As the "base", for example, metal amides such as sodium amide, lithium diisopropylamide, lithium hexamethyldisilazide and the like, and alkyl metal compounds such as alkyllithium and the like are used.

The present reaction is advantageously conducted in the absence or presence of a solvent inactive to the reaction. This solvent is not particularly restricted providing the reaction can progress, and for example, aliphatic hydrocarbons, aromatic hydrocarbons, ethers, or mixtures of two or more of them, etc. are used.

The reaction temperature is usually from about −78° C. to about 60° C., preferably from about −78° C. to about 20° C. The reaction time is usually from about 5 minutes to about 24 hours, preferably from about 0.5 to about 3 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (IX) is obtained by treating a compound (VIII) with halogens. This reaction is conducted in the presence of a base or basic salt, if necessary.

In the compound (IX), Hal represents halogens.

The amount of halogens used is about 1.0 to about 5.0 mol, preferably about 1.0 to about 2.0 mol per mol of the compound (VIII).

As the "halogens", bromine, chlorine, iodine, etc. are exemplified.

The amount of a base used is about 1.0 to about 10.0 mol, preferably about 1.0 to about 3.0 mol per mol of the compound (VIII).

As the "base", for example, aromatic amines such as pyridine, lutidine and the like, tertiary amines such triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, etc. are exemplified.

The amount of a basic salt used is about 1.0 to about 10.0 mol, preferably about 1.0 to about 3.0 mol per mol of the compound (VIII).

As the "basic salt", for example, sodium carbonate, potassium carbonate, cesium carbonate, sodium hydrogen carbonate, sodium acetate, potassium acetate, etc. are exemplified.

The present reaction is advantageously conducted in the absence or presence of a solvent inactive to the reaction. This solvent is not particularly restricted providing the reaction can progress, and for example, ethers, aromatic hydrocarbons, aliphatic hydrocarbons, amides, halogenated hydrocarbons, nitriles, sulfoxides, organic acids, aromatic amines, or mixtures of two or more of them, etc. are used.

The reaction temperature is usually from about −20° C. to about 150° C., preferably from about 0° C. to about 100° C. The reaction time is usually from about 5 minutes to about 24 hours, preferably from about 10 minutes to about 5 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (I) can be obtained by condensing a compound (IX) with a compound (X). The present reaction is conducted in the presence of a base, if necessary.

When the compound (X) is commercially available, it may be used without any treatment, and also can be obtained by methods known per se or methods according to them, further, can be obtained by a method of the following reaction formula 2, etc.

The amount of the compound (X) used is about 0.5 to about 3.0 mol, preferably about 0.8 to about 2.0 mol per mol of the compound (IX).

The amount of a base used is about 1.0 to about 30 mol, preferably about 1.0 to about 10 mol per mol of the compound (IX).

As the "base", for example, basic salts such as sodium carbonate, potassium carbonate, cesium carbonate, sodium hydrogen carbonate and the like, aromatic amines such as pyridine, lutidine and the like, tertiary amines such triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, etc. are exemplified.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, ethers, amides, alcohols, nitrites, or mixtures of two or more of them, etc. are used.

The reaction temperature is from about −5° C. to about 200° C., preferably from about 5° C. to about 150° C. The reaction time is usually from about 5 minutes to about 72 hours, preferably from about 0.5 to about 30 hours.

The product can be used in the following reaction as the reaction solution itself or as a crude product, and can also be isolated from the reaction mixture according to an ordinary method, and can be easily purified by separation means such as recrystallization, distillation, chromatography and the like.

Reaction formula 2:

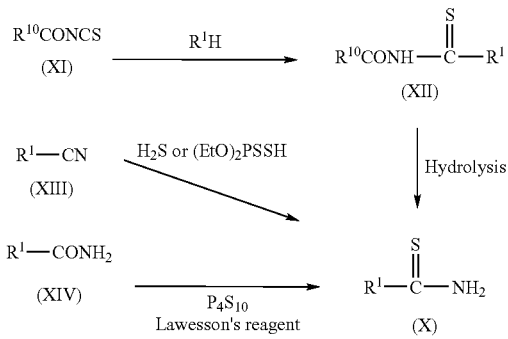

A compound (XII) can be obtained by condensing a compound (XI) with amines represented by $R^1H$.

In the compound (XI), $R^{10}$ represents an aromatic hydrocarbon group or alkoxy. As the "aromatic hydrocarbon group", a phenyl group optionally having a substituent, etc. are listed. As the "alkoxy", for example, $C_{1-6}$ alkoxys such as methoxy, ethoxy, propoxy, isopropoxy, butoxy and the like, etc. are exemplified.

The amount of the "amines" used is about 1.0 to about 30 mol, preferably about 1.0 to about 10 mol per mol of the compound (XI).

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, ethers, amides, alcohols, nitriles, ketones, or mixtures of two or more of them, etc. are used.

The reaction temperature is from about –5° C. to about 200° C., preferably from about 5° C. to about 120° C. The reaction time is usually from about 5 minutes to about 72 hours, preferably from about 0.5 to about 30 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (X) can be obtained by hydrolyzing the compound (XII) with an acid or base.

The amount of the acid or base used is about 0.1 to about 50 mol, preferably about 1 to about 20 mol, respectively, per mole of the compound (XII).

As the "acid", for example, mineral acids such as hydrochloric acid, hydrobromic acid, sulfuric acid and the like, Lewis acids such as boron trichloride, boron tribromide and the like, co-use of Lewis acids with thiols or sulfides, and organic acids such as trifluoroacetic acid, p-toluenesulfonic acid and the like, etc. are used.

As the "base", for example, metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like, etc. are used.

The present reaction is advantageously conducted in the absence or presence of a solvent inactive to the reaction. This solvent is not particularly restricted providing the reaction can progress, and for example, alcohols, ethers, aromatic hydrocarbons, aliphatic hydrocarbons, halogenated hydrocarbons, sulfoxides, water or mixtures of two or more of them, etc. are used.

The reaction time is usually from about 10 minutes to about 50 hours, preferably from about 30 minutes to about 12 hours. The reaction temperature is usually from about 0° C. to about 200° C., preferably from about 20° C. to about 120° C.

A compound (X) can also be obtained by treating a compound (XIII) with hydrogen sulfide in the presence of a base.

The amount of hydrogen sulfide used is about 1 to about 30 mol per mol of the compound (XIII).

The amount of a base used is about 1.0 to about 30 mol, preferably about 1.0 to about 10 mol per mol of the compound (XIII).

As the "base", for example, aromatic amines such as pyridine, lutidine and the like, tertiary amines such triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, etc. are used.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, ethers, aromatic amines, or mixtures of two or more of them, etc. are used.

The present reaction is effected under normal pressure or positive pressure. The reaction temperature is usually from about –20° C. to about 80° C., preferably from about –10° C. to about 30° C. The reaction time is usually from about 5 minutes to about 72 hours, preferably from about 0.5 to about 30 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (X) can also be obtained by treating a compound (XIII) with dithiophosphoric acid 0,0-diethyl ester in the presence of an acid.

The amount of dithiophosphoric acid 0,0-diethyl ester used is about 0.9 to about 2 mol per mole of the compound (XIII).

The amount of an acid used is about 3.0 to about 30 mol, preferably about 3.0 to about 10 mol per mol of the compound (XIII).

As the "acid", for example, hydrogen halides such as hydrogen chloride, hydrogen bromide and the like, and mineral acids such as hydrochloric acid, hydrobromic acid and the like, etc. are exemplified.

The present reaction is advantageously conducted in the absence or presence of a solvent inactive to the reaction. This solvent is not particularly restricted providing the reaction can progress, and for example, halogenated hydrocarbons, alcohols, amides, ethers, esters, water, or mixtures of two or more of them, etc. are used.

The reaction temperature is usually from about 0° C. to about 80° C., preferably from about 0° C. to about 30° C. The reaction time is usually from about 5 minutes to about 72 hours, preferably from about 0.5 hours to about 30 hours.

The product can be used in the following reaction as the reaction solution itself or as a crude product, and can also be isolated from the reaction mixture according to an ordinary method, and can be easily purified by separation means such as recrystallization, distillation, chromatography and the like.

A compound (X) can also be obtained by treating a compound (XIV) with phosphorus pentasulfide or a Lawesson's reagent.

The amount of the phosphorus pentasulfide or Lawesson's reagent used is about 0.5 to about 10 mol, preferably about 0.5 to about 3 mol per mole of the compound (XIV).

The present reaction is advantageously conducted in the absence or presence of a solvent inactive to the reaction. This solvent is not particularly restricted providing the reaction can progress, and for example, ethers, aromatic hydrocarbons, aliphatic hydrocarbons, halogenated hydrocarbons, or mixtures of two or more of them, etc. are used.

The reaction time is usually from about 10 minutes to about 50 hours, preferably from about 30 minutes to about 12 hours. The reaction temperature is usually from about 0° C. to about 150° C., preferably from about 20° C. to about 120° C.

The product (X) can be used in the following reaction as the reaction solution itself or as a crude product, and can also be isolated from the reaction mixture according to an ordinary method, and can be easily purified by separation means such as recrystallization, distillation, chromatography and the like.

When the compound (I) is an acylamino compound, the corresponding amine can be subjected to an acylation reaction known per se to obtain the intended substance.

For example, of compounds (I), that in which a substituent at the 2-position of a thiazole ring is acyamino optionally having a substituent is obtained by reacting the corresponding 2-thiazolamine and acylating agent, if necessary in the presence of a base or acid.

The amount of the acylating agent used is about 1.0 to about 5.0 mol, preferably about 1.0 to about 2.0 mol per mol of the corresponding 2-thiazolamine.

As the "acylating agent", for example, carboxylic acids corresponding to the acyl group of the intended substance, or reactive derivatives thereof (e.g., acid halide, acid anhydride, ester and the like), etc. are exemplified.

The amount of a base or acid used is about 0.8 to about 5.0 mol, preferably about 1.0 to about 2.0 mol per mol of the corresponding 2-thiazolamine.

As the "base", for example, triethylamine, pyridine, 4-dimethylaminopyridine, etc. are exemplified.

As the "acid", for example, methanesulfonic acid, p-toluenesulfonic acid, camphor-sulfonic acid, etc. are exemplified.

The present reaction is advantageously conducted in the absence or presence of a solvent inactive to the reaction. This solvent is not particularly restricted providing the reaction can progress, and for example, ethers, aromatic hydrocarbons, aliphatic hydrocarbons, amides, halogenated hydrocarbons, nitriles, sulfoxides, aromatic amines, or mixtures of two or more of them, etc. are used.

The reaction temperature is from about −20° C. to about 150° C., preferably from about 0° C. to about 100° C. The reaction time is usually from about 5 minutes to about 24 hours, preferably from about 10 minutes to about 5 hours.

The product can be used in the following reaction as the reaction solution itself or as a crude product, and can also be isolated from the reaction mixture according to an ordinary method, and can be easily purified by separation means such as recrystallization, distillation, chromatography and the like.

Further, of compounds (I), that in which a substituent at the 5-position of a thiazole ring is acylaminopyridyl optionally having a substituent is obtained by reacting the corresponding 5-(2-aminopyridyl)thiazole and acylating agent, if necessary in the presence of a base or acid.

The amount of the acylation agent used is from about 1.0 to about 5.0 mol, preferably from about 1.0 to about 2.0 mol per mol of the corresponding 5-(2-aminopyridyl)thiazole.

As the "acylating agent", for example, carboxylic acids corresponding to the acyl group of the intended substance, or reactive derivatives thereof (e.g., acid halide, acid anhydride, ester and the like), etc. are exemplified.

The amount of a base or acid used is from about 0.8 to about 5.0 mol, preferably from about 1.0 to about 2.0 mol per mol of the corresponding 5-(2-aminopyridyl)thiazole.

As the "base", for example, triethylamine, pyridine, 4-dimethylaminopyridine, etc. are exemplified.

As the "acid", for example, methanesulfonic acid, p-toluenesulfonic acid, camphor-sulfonic acid, etc. are exemplified.

The present reaction is advantageously conducted in the absence or presence of a solvent inactive to the reaction. This solvent is not particularly restricted providing the reaction can progress, and for example, ethers, aromatic hydrocarbons, aliphatic hydrocarbons, amides, halogenated hydrocarbons, nitrites, sulfoxides, aromatic amines, or mixtures of two or more of them, etc. are used.

The reaction temperature is from about −20° C. to about 150° C., preferably from about 0° C. to about 100° C. The reaction time is usually from about 5 minutes to about 24 hours, preferably from about 10 minutes to about 5 hours.

The product can be used in the following reaction as the reaction solution itself or as a crude product, and can also be isolated from the reaction mixture according to an ordinary method, and can be easily purified by separation means such as recrystallization, distillation, chromatography and the like.

Of compounds (I), that in which a substituent at the 5-position of a thiazole ring is alkylaminopyridyl optionally having a substituent is obtained by reducing the corresponding acylaminopyridine with a reducing agent.

The amount of the reducing agent used is from about 1.0 to about 5.0 mol, preferably from about 1.0 to about 3.0 mol per mol of the corresponding acylaminopyridine.

As the "reducing agent", for example, metal hydrides such as aluminum hydride, diisobutylaluminum hydride and the like, metal hydrogen complex compounds such as lithium aluminum hydride, sodium boron hydride and the like, borane complexes such as borane tetrahydrofuran complex, borane dimethylsulfide complex and the like, alkyl boranes such as thexyl borane, dicyamyl borane and the like, etc. are exemplified.

In the present reaction, an acid is also added together with a reducing agent, if necessary.

The amount of an acid used is from about 0.8 to about 5.0 mol, preferably from about 1.0 to about 3.0 mol per mol of the corresponding acylaminopyridine.

As the "acid", for example, Lewis acids such as aluminum chloride and the like, are exemplified.

The present reaction is advantageously conducted in the absence or presence of a solvent inactive to the reaction. This solvent is not particularly restricted providing the reaction can progress, and for example, ethers, aromatic hydrocarbons, aliphatic hydrocarbons, halogenated hydrocarbons, or mixtures of two or more of them, etc. are used.

The reaction temperature is from about −78° C. to about 150° C., preferably from about 0° C. to about 100° C. The reaction time is usually from about 5 minutes to about 24 hours, preferably from about 10 minutes to about 5 hours.

The product can be used in the following reaction as the reaction solution itself or as a crude product, and can also be isolated from the reaction mixture according to an ordinary method, and can be easily purified by separation means such as recrystallization, distillation, chromatography and the like.

Of compounds (I), that in which a substituent at the 5-position of a thiazole ring is alkylaminopyridyl optionally having a substituent is obtained by condensing the corresponding 5-(2-halogenopyridyl)thiazole with amines.

The amount of the amine used is from about 1.0 to about 100.0 mol, preferably from about 1.0 to about 20.0 mol per mol of the corresponding 5-(2-halogenopyridyl)thiazole.

As the halogen of the "5-(2-halogenopyridyl)thiazole", fluorine, chlorine, bromine, iodine, etc. are exemplified.

As the "amines", for example, aliphatic amines and cyclic amines corresponding to the intended alkylamine, etc. are exemplified.

The present reaction is conducted, if necessary in the presence of a base or basic salt.

The amount of the base used is from about 1.0 to about 10.0 mol, preferably from about 1.0 to about 3.0 mol per mol of the corresponding 5-(2-halogenopyridyl)thiazole.

As the "base", for example, aromatic amines such as pyridine, lutidine and the like, tertiary amines such triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, etc. are used.

The amount of the basic salt used is from about 1.0 to about 10.0 mol, preferably from about 1.0 to about 3.0 mol per mol of the corresponding 5-(2-halogenopyridyl)thiazole.

As the "basic salt", for example, sodium carbonate, potassium carbonate, cesium carbonate, sodium hydrogen carbonate, sodium acetate, potassium acetate, etc. are used.

The present reaction is advantageously conducted in the absence or presence of a solvent inactive to the reaction. This solvent is not particularly restricted providing the reaction can progress, and for example, ethers, aromatic hydrocarbons, aliphatic hydrocarbons, amides, halogenated hydrocarbons, nitrites, water or mixtures of two or more of them, etc. are used.

The reaction temperature is from about 0° C. to about 300° C., preferably from about 20° C. to about 200° C. The reaction time is usually from about 5 minutes to about 48 hours, preferably from about 10 minutes to about 15 hours.

The product can be used in the following reaction as the reaction solution itself or as a crude product, and can also be isolated from the reaction mixture according to an ordinary method, and can be easily purified by separation means such as recrystallization, distillation, chromatography and the like.

When the compound (I) is an N-oxide, it is obtained by treating the corresponding pyridyl compound with an organic peracid.

The amount of the organic peracid used is from about 0.8 to about 10 mol, preferably from about 1.0 to about 3.0 mol per mol of the corresponding pyridyl compound.

As the above-mentioned "organic peracid", for example, peracetic acid, pertrifluoroacetic acid, m-chloroperbenzoic acid, etc. are exemplified.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, organic acids, ethers, amides, sulfoxides, alcohols, nitriles, ketones or mixtures of two or more of them, etc. are used.

The reaction temperature is from about −20° C. to about 130° C., preferably from about 0° C. to about 100° C. The reaction time is usually from about 5 minutes to about 72 hours, preferably from about 0.5 to about 12 hours.

Further, an N-oxide can also be obtained by treating the corresponding pyridyl compound with hydrogen peroxide or alkyl hydroperoxide, if necessary in the presence of a base, acid or metal oxide.

The amount of the hydrogen peroxide or alkyl hydroperoxide used is from about 0.8 to about 10 mol, preferably from about 1.0 to about 3.0 mol per mol of the corresponding pyridyl compound.

As the above-mentioned "alkyl hydroperoxide", for example, tert-butylhydroperoxide, cumene hydroperoxide, etc. are exemplified.

The amount of the base, acid or metal oxide used is from about 0.1 to about 30 mol, preferably from about 0.8 to about 5 mol per mol of the corresponding pyridyl compound.

As the above-mentioned "base", for example, inorganic bases such as sodium hydroxide, potassium hydroxide and the like, basic salts such as sodium carbonate, potassium carbonate and the like, etc. are exemplified.

As the above-mentioned "acid", for example, mineral acids such as hydrochloric acid, sulfuric acid, perchloric acid and the like, Lewis acids such as boron trifluoride, aluminum chloride, titanium tetrachloride and the like, organic acids such as formic acid, acetic acid and the like, etc. are exemplified.

As the above-mentioned "metal oxide", for example, vanadium oxide ($V_2O_5$), osmium tetraoxide ($OsO_4$), tungsten oxide ($WO_3$), molybdenum oxide ($MoO_3$), selenium dioxide ($SeO_2$), chromium oxide ($CrO_3$), etc. are exemplified.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, organic acids, ethers, amides, sulfoxides, alcohols, nitrites, ketones or mixtures of two or more of them, etc. are used.

The reaction temperature is from about −20° C. to about 130° C., preferably from about 0° C. to about 100° C. The reaction time is usually from about 5 minutes to about 72 hours, preferably from about 0.5 to about 12 hours.

The product can be used in the following reaction as the reaction solution itself or as a crude product, and can also be isolated from the reaction mixture according to an ordinary method, and can be easily purified by separation means such as recrystallization, distillation, chromatography and the like.

When the compound (I) is an S-oxide, it is obtained by treating the corresponding sulfide with a peroxide.

The amount of the peroxide used is from about 0.8 to about 10 mol, preferably from about 1.0 to about 3.0 mol per mol of the corresponding sulfide.

As the above-mentioned "peracid", for example, peracetic acid, pertrifluoroacetic acid, m-chloroperbenzoic acid, potassium persulfate, meta-periodic acid, etc. are exemplified.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, organic acids, ethers, amides, sulfoxides, alcohols, nitrites, ketones or mixtures of two or more of them, etc. are used.

The reaction temperature is from about −20° C. to about 130° C., preferably from about 0° C. to about 100° C. The reaction time is usually from about 5 minutes to about 72 hours, preferably from about 0.5 to about 12 hours.

Further, an S-oxide can also be obtained by treating the corresponding sulfide with hydrogen peroxide or alkyl hydroperoxide, if necessary in the presence of a base, acid or metal oxide.

The amount of the hydrogen peroxide or alkyl hydroperoxide used is from about 0.8 to about 10 mol, preferably from about 1.0 to about 3.0 mol per mol of the corresponding sulfide.

As the above-mentioned "alkyl hydroperoxide", for example, tert-butylhydroperoxide, cumene hydroperoxide, etc. are exemplified.

The amount of the "base, acid or metal oxide" used is from about 0.1 to about 30 mol, preferably from about 0.8 to about 5 mol per mol of the corresponding sulfide.

As the above-mentioned "base", for example, inorganic bases such as sodium hydroxide, potassium hydroxide and the like, basic salts such as sodium carbonate, potassium carbonate and the like, etc. are exemplified.

As the above-mentioned "acid", for example, mineral acids such as hydrochloric acid, sulfuric acid, perchloric acid and the like, Lewis acids such as boron trifluoride, aluminum chloride, titanium tetrachloride and the like, organic acids such as formic acid acetic acid and the like, etc. are exemplified.

As the above-mentioned "metal oxide", for example, vanadium oxide ($V_2O_5$), osmium tetraoxide ($OsO_4$), tungsten oxide ($WO_3$), molybdenum oxide ($MoO_3$), selenium dioxide ($SeO_2$), chromium oxide ($CrO_3$), etc. are exemplified.

The present reaction is advantageously conducted in the absence or presence of a solvent inactive to the reaction. This solvent is not particularly restricted providing the reaction can progress, and for example, halogenated hydrocarbons, aliphatic hydrocarbons, aromatic hydrocarbons, organic acids, ethers, amides, sulfoxides, alcohols, nitriles, ketones or mixtures of two or more of them, etc. are used.

The reaction temperature is from about –20° C. to about 130° C., preferably from about 0° C. to about 100° C. The reaction time is usually from about 5 minutes to about 72 hours, preferably from about 0.5 to about 12 hours.

The product can be used in the following reaction as the reaction solution itself or as a crude product, and can also be isolated from the reaction mixture according to an ordinary method, and can be easily purified by separation means such as recrystallization, distillation, chromatography and the like.

In the above-mentioned reactions, when a starting material has amino, carboxy, hydroxy as a substituent, a protective group as generally used may be introduced into these groups by peptide chemistry and the like, and the intended compound can be obtained by removing the protective group after the reaction, if necessary.

As the protective group for amino, for example, formyl or, $C_{1-6}$ alkyl-carbonyls (e.g., acetyl, propionyl and the like), phenylcarbonyl, $C_{1-6}$ alkoxy-carbonyls (e.g. methoxycarbony, ethoxycarbonyl and the like), phenyloxycarbonyl, $C_{7-10}$ aralkyloxy-carbonyls (e.g., benzyloxycarbonyl and the like), trityl, phthaloyl, each optionally having a substituent, etc. are used. As these substituents, halogen atoms (e.g., fluorine, chlorine, bromine, iodine and the like), $C_{1-6}$ alkyl-carbonyls (e.g., acetyl, propionyl, valeryl and the like), nitro, etc. are used, and the number of the substituent is 1 to 3.

As the protective group for carboxy, for example, $C_{1-6}$ alkyls (e.g.,methyl, ethyl, propyl, isopropyl, butyl, tert-butyl and the like), phenyl, trityl, silyl, each optionally having a substituent, etc. are used. As these substituents, halogen atoms (e.g., fluorine, chlorine, bromine, iodine and the like), formyl, $C_{1-6}$ alkyl-carbonyls (e.g., acetyl, propionyl, butylcarbonyl and the like), nitro, $C_{1-6}$ alkyls (e.g., methyl, ethyl, tert-butyl and the like), $C_{6-10}$ aryls (e.g., phenyl, naphthyl and the like), etc. are used, and the number of the substituent is 1 to 3.

As the protective group for hydroxy, for example, $C_{1-6}$ alkyls (e.g., methyl, ethyl, propyl, isopropyl, butyl, tert-butyl and the like), phenyl, $C_{7-11}$ aralkyls (e.g., benzyl and the like), formyl, $C_{1-6}$ alkyl-carbonyls (e.g., acetyl, propionyl and the like), phenyloxycarbonyl, $C_{7-11}$ aralkyloxy-carbonyls (e.g., benzyloxycarbonyl and the like), tetrahydropyranyl, tetrahydrofuranyl, and silyl, each optionally having a substituent, and so on are used. As these substituents, halogen atoms (e.g., fluorine, chlorine, bromine, iodine and the like), $C_{1-6}$ alkyls (e.g. methyl, ethyl, tert-butyl and the like), $C_{7-11}$ aralkyls (e.g., benzyl and the like), $C_{6-10}$ aryls (e.g., phenyl, naphthyl and the like), nitro, etc. are used, and the number of the substituent is 1 to 4.

For removing a protective group, method known per se or methods according to them are used, and for example, methods for treating with an acid, a base, ultraviolet ray, hydrazine, phenylhydrazine, sodium N-methyldithiocarbamate, tetrabutylammonium fluoride, palladium acetate and the like, or reducing methods are used.

In any case, further if necessary, the compound (I) can be synthesized by using known de-protection reactions, acylation reactions, alkylation reactions, hydrogenation reactions, oxidation reactions, reduction reactions, carbon chain extension reactions, substituent interchange reactions, each alone or in combination of two or more of them. As these reactions, for example, methods described in Shin Jikken Kagaku Koza 14, 15, 1977 (Maruzen), etc. are adopted.

As the above-mentioned "alcohols", for example, methanol, ethanol, propanol, isopropanol, tert-butanol, etc. are exemplified.

As the above-mentioned "ethers", for example, diethyl ether, diisopropyl ether, diphenyl ether, tetrahydrofuran, dioxane, 1,2-dimethoxyethane, etc. are exemplified.

As the above-mentioned "halogenated hydrocarbons", for example, dichloromethane, chloroform, 1,2-dichloroethane, carbon tetrachloride, etc. are exemplified.

As the above-mentioned "aliphatic hydrocarbons", for example, hexane, pentane, cyclohexane, etc. are exemplified.

As the above-mentioned "aromatic hydrocarbons", for example, benzene, toluene, xylene, chlorobenzene, etc. are exemplified.

As the above-mentioned "aromatic amines", for example, pyridine, lutidine, quinoline, etc. are exemplified.

As the above-mentioned "amides", for example, N,N-dimethylformamide, N,N-dimethylacetamide, hexamethylphosphoric triamide, etc. are exemplified.

As the above-mentioned "ketones", for example, acetone, methyl ethyl ketone, etc. are exemplified.

As the above-mentioned "sulfoxides", for example, dimethylsulfoxide, etc. are exemplified.

As the above-mentioned "nitriles", for example, acetonitrile, propionitrile, etc. are exemplified.

As the above-mentioned "organic acids", for example, acetic acid, propionic acid, trifluoroacetic acid, etc. are exemplified.

As the above-mentioned "esters", for example, methyl acetate, ethyl acetate, amyl acetate, ethyl propionate, etc. are exemplified.

When the intended substance is obtained in the free form by the above-mentioned reaction, it may be converted into a salt according to an ordinary method, while when obtained in the form of a salt, it can also be converted into a free form or other salt according to an ordinary method. Thus obtained compound (I) can be isolated and purified from a reaction solution by known means, for example, rolling, concentration, solvent extraction, fractionation, crystallization, recrystallization, chromatography and the like.

When the compound (I) is present as a configuration isomer, diastereomer, conformer or the like, if necessary, each can be isolated by the above-mentioned separation and purification means. When the compound (I) is a racemate, it can be separated into an S form and R form by a usual optical resolution.

When a stereoisomer is present in the compound (I), this isomer alone and mixtures thereof are also included in the present invention.

Further, the compound (I) may be a hydrate or non-hydrate.

The compound (I) may be labeled with an isotope (e.g. $^3$H, $^{14}$C, $^{35}$S), etc.

The compound (I) of the present invention or a pro-drug thereof (hereinafter also referred to as the compound of the present invention) has an excellent p38 MAP kinase inhibitory activity, TNF-α inhibitory activity (TNF-α production inhibitory activity, TNF-α action inhibitory activity), phosphodiesterase IV (PDE IV) inhibitory activity, adenosine receptor (e.g., adenosine $A_1$, $A_{2a}$, $A_{2b}$, $A_3$ receptors) antagonizing activity and the like, further has low toxicity and few side effects. Therefore, the compound of the present invention is useful as a safe medicine such as a p38 MAP kinase inhibitor, a TNF-α production inhibitor, a PDE IV inhibitor, an adenosine receptor (e.g., adenosine $A_1$, $A_{2a}$, $A_{2b}$ or $A_3$ receptor) antagonist, etc.

A pharmaceutical composition comprising the compound of the present invention shows an excellent p38 MAP kinase inhibitory activity and TNF-α inhibitory activity on mammals (e.g., mouse, rat, hamster, rabbit, felis, canis, bovine, ovis, monkey, human and the like) and has also an excellent (oral)absorbing property, (metabolic) stability and the like. Therefore, this composition can be used as a pharmaceutical composition for preventing and/or treating p38 MAP kinase-mediated diseases and TNF-α production-mediated diseases, for example, asthma, allergic diseases, atopic dermatitis, inflammation, inflammatory eye diseases, Addison's disease, autoimmune hemolytic anemia, systemic lupus erythematosus, psoriasis, rheumatism, central nerve disorders (e.g., cerebrovascular disorders such as encephalorrhagy, cerebral infarction and the like, head trauma, spinal cord injury, cerebral edema, multiple sclerosis and the like), neuro-degenerative diseases (e.g., Alzheimer's disease, Parkinson's disease, amyotrophic lateral sclerosis (ALS), aquired immune deficiency syndrome (AIDS) encephalopathy), meningitis, diabetes, arthritis (e.g., chronic rheumatoid arthritis, osteoarthritis, rheumatoid spondylitis, gouty arthritis, synovitis), toxaemias (e.g., sepsis, septic shock, endotoxic shock, Gram-negative sepsis, toxic shock syndrome), inflammatory bowel diseases (e.g., Crohn's disease, ulcerative colitis), inflammatory lung diseases (e.g., chronic pneumonia, pulmonary silicosis, pulmonary sarcoidosis, lung tuberculosis), or cachexias (e.g., cachexy due to infection, cancerous cachexia, cachexy due to acquired immune deficiency syndrome (AIDS)), arterial sclerosis, Creutzfeldt-Jakob disease, virus infection (e.g., virus infection by cytomegalovirus, influenza virus, herpes virus and the like), angina pectoris, myocardial infarction, congestive heart failure, hepatitis, transplant, dialysis hypotension, diffuse intravascular coagulation syndrome, etc.

A pharmaceutical composition comprising the compound of the present invention shows an excellent adenosine receptor antagonizing activity on mammals (e.g., mouse, rat, hamster, rabbit, felis, canis, bovine, ovis, monkey, human and the like) and has also an excellent (oral) absorbing property, (metabolic) stability and the like. Therefore, this composition can be used as a pharmaceutical composition for preventing and/or treating adenosine receptor-mediated diseases (particulaly, adenosine $A_3$ receptor-mediated diseases), for example, asthma, allergic diseases, inflammation, Addison's disease, autoimmune hemolytic anemia, Crohn's disease, psoriasis, rheumatism, central nerve disorders (e.g., cerebrovascular disorders such as encephalorrhagy, cerebral infarction, apoplectic stroke and the like, head trauma, spinal cord injury, cerebral edema, multiple sclerosis and the like), neuro-degenerative diseases (e.g., Alzheimer's disease, Parkinson's disease, amyotrophic lateral sclerosis. (ALS), diabetes and the like, preferably, central nerve disorders, asthma, allergic disorders and the like).

Further, a pharmaceutical composition comprising the compound of the present invention shows an excellent PDE IV inhibitory activity, and can be used as a pharmaceutical composition for preventing and/or treating diseases caused by inflammation, for example, bronchial asthma, chronic obstructive pulmonary disease (COPD), chronic rheumatoid arthritis, autoimmune diseases, diabetes mellitus, graft versus host disease, multiple sclerosis, sepsis, psoriasis, osteoporosis, depression, central function degradation after cerebrovascular obturation, cerebrovascular dementia, Alzheimer's dementia, obesity, cardiac insufficiency, etc.

A pharmaceutical composition comprising the compound of the present invention has a low toxicity, and can be formulated, according to means known per se generally used in production of medicinal preparations, as it is or in admixture with a pharmacologically acceptable carrier, into for example tablets (including sugar-coated tablet and film-coated tablet), powders, granules, capsules (including soft capsule), liquid, injections, suppository, sustained release preparations and the like, and safely administered orally or parenterally (e.g., topical, rectal, intravenous administrations, etc.). The content of the compound of the present invention in the preparation of the present invention is from about 0.01 to about 100 wt % based on the whole preparation. This dose varies depending on the subject to be dosed, dose route, disease, symptom and the like, and it may advantageously be administered orally, as a p38 MAP kinase-mediated disease preventive and therapeutic agent, for example to an arthritis patient (body weight: about 60 kg), in a dosage of about 0.01 to about 30 mg/kg-body weight/day, preferably about 0.1 to about 20 mg/kg-body weight/day, further preferably about 1 to about 20 mg/kg-body weight/day in terms of the effective component [the compound of the present invention], in one time or divided into several times a day.

As a pharmacologically acceptable carrier which may be used in production of a preparation of the present invention, various conventional organic or inorganic carrier substances are exemplified as preparation raw materials, and for example, an excipient, brightener, binder and disintegrating agent in a solid preparation, and a solvent, solubilizer, suspending agent, isotonization agent, buffer, soothing agent and the like in a liquid preparation, etc. are exemplified. Further, if necessary, usual additives such as a preservative, antioxidant, coloring agent, sweetener, adsorbent, wetting agent and the like can be appropriately used in suitable amount.

As the exipient, for example, lactose, sucrose, D-mannitol, starch, corn starch, crystalline cellulose, light anhydrous silic acid, etc. are exemplified.

As the brightener, for example, magnesium stearate, calcium stearate, talc, colloidal silica, etc. are exemplified.

As the binder, for example, crystalline cellulose, sucrose, D-mannitol, dextrin, hydroxypropyl cellulose, hydroxypropylmethyl cellulose, polyvinylpyrrolidone, starch, saccharose, gelatin, methyl cellulose, carboxymethyl cellulose sodium, etc. are exemplified.

As the disintegrating agent, for example, starch, carboxymethyl cellulose, carboxymethyl cellulose calcium, carboxymethyl starch sodium, L-hydroxypropyl cellulose, etc. are exemplified.

As the solvent, for example, injection water, alcohol, propylene glycol, Macrogol, sesame oil, corn oil, olive oil, etc. are exemplified.

As the dissociation aid, for example, polyethylene glycol, propylene glycol, D-mannitol, benzyl benzoate, ethanol, trisaminomethane, cholesterol, triethanolamine, sodium carbonate, sodium citrate, etc. are exemplified.

As the suspending agent, for example, surfactants such as stearyltriethanolamine, sodium laurylsulfate, laurylaminopropionic acid, lecithin, benzalkonium chloride, benzethonium chloride, glycerine monostearate and the like; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose and the like, etc. are exemplified.

As the isotonization agent, for example, glucose, D-sorbitol, sodium chloride, glycerine, D-mannitol, etc. are exemplified.

As the buffer, for example, buffering solutions of a phosphate, acetate, carbonate, citrate, etc. are exemplified.

As the soothing agent, for example, benzyl alcohol, etc. are exemplified.

As the preservative, for example, p-hydroxybenzoates, chlorobutanol, benzyl alcohol, phenethyl alcohol, dehydroacetic acid, sorbic acid, etc. are exemplified.

As the antioxidant, for example, a sulfite, ascorbic acid, α-tocopherol, etc. are exemplified.

Further, the compound of the present invention can be used in combination with other drugs than the compound of the present invention.

Examples of the drug which can be combined with the compound of the present invention (hereinafter, sometimes referred to as combination drug) include the following compounds.

(1) Non-steroidal Anti-inflammatory Drugs (NSAIDs)
① Classical NSAIDs
Alcofenac, acechrofenac, sulindac, tolmetin, etodolac, fenoprofen, tiaprofenic acid, meclofenamic acid, meroxicam, theoxicam, lolnoxicam, nabtomen, acetaminophen, phenacetin, ethenzamide, sulpyrine, antipyrine, migrenin, aspirin, mefenamic acid, flufenamic acid, dichlorophenac sodium, loxoprofen sodium, phenylbutazone, indomethacin, ibuprofen, ketoprofen, naproxen, pxaprozin, flurbiprofen, fenbufen, pranoprofen, frotacfenin, piroxicam, epirizole, tiaramide hydrochloride, sartoprofen, gabexate mesilate, camostat mesilate, urinastatin, colchicines, probenezide, sulfinpyrazon, benzbromarone, allopurinol, sodium aurothiomalate, sodium hyaluronate, sodium salicylate, morphine hydrochloride, salicylic acid, atropine, scopolamine, morphine, pethidine, levorphanol, oxymorphone, or a salt thereof, and the like.

② Cyclooxygenase depressants (COX-1 selective inhibitor, COX-2 Selective Inhibitor and the Like)
Salicylic acid derivatives (e.g., cerecoxiv, lofecoxiv, aspirin), MK-663, baldecoxiv, SC-57666, thylacoxiv, S-2474, dichlofenac, indomethacin, loxoprofen, and the like.

③ drugs having simultaneous COX inhibition and 5-lipoxygenase inhibition
ML-300, p54 (COX inhibition & 5-lipoxygenase inhibition) and the like.

④ nitric oxide free type NSAIDs (2) Disease Modifying Anti-rheumatic Drugs (DMARDs)
① Gold preparation
Auranofin and the like.
② Penicillamine
D-penicillamine
③ Sulfasalazine
④ Anti-malarial agent
Chloroquine and the like.
⑤ Pyrimidine synthesis inhibitor
Refulnomide and the like.
⑥ Prograph (3) Anti-cytokine Agents
(I) Protein preparations
(i) TNF inhibitors
Ethanarcept, infliximav, D2E7, CDP-571, PASSTNF-α, soluble TNF receptor, TNF-α binding protein, anti-TNF-α antibody and the like.
(ii) Interleukin-1 inhibitors
Anaquinra (interleukin-1 receptor antagonist), soluble interleukin-1 receptor and the like.
(iii) Interleukin-6 inhibitors
MRA (anti-interleukin-6 receptor antibody), anti-interleukin-6 antibody, Sant-7 (interleukin-6 receptor antagonist) and the like.
(iv) Interleukin-10 drugs
Interleukin-10 and the like.
(v) Interleukin-12 inhibitors
Anti-interleukin-12 antibody and the like.
(v) Drugs having interferon-α and -γ inhibition and TNF-α inhibition simultaneously AGT-1.
(II) Nonprotein preparations
(i) MAP kinase inhibitors
PD-98059 and the like.
(ii) Gene regulators
Inhibitors of a molecule related to signal transfer such as SP-100030, NF-κ, NF-κ B, IKK-1, IKK-2, AP-1 etc., and the like.
(iii) Cytokine production suppressors
T-614, SR-31747, sonatimod and the like.
(iv) TNF-α converting enzyme inhibitors
(v) Interleukin-1β converting enzyme inhibitors
HMR3480/VX-740 and the Like.
(vi) Interleukin-6 antagonists
SANT-7 and the like.
(vii) Interleukin-8 inhibitors
IL-8 antagonist, CXCR1 & CXCR2 antagonist and the like.
(viii) Chemokine antagonists
MCP-1 antagonist and the like.
(ix) Interleukin-2 receptor antagonists
Denileukin, diftitox and the like.
(x) Therapeutic vaccines
TNF-α vaccine and the like.
(xi) Gene therapeutic agents
Gene therapeutic agents intended to accentuate expression of a gene having an anti-inflammatory action such as interleukin-4, interleukin-10, soluble interleukin-1 receptor, soluble TNF-α receptor, HSV-tk and the like.
(xii) Anti-sense compounds
ISIS-104838 and the like.

(4) Immunomodulators (Immunosuppressant)
(i) T-cell differentiation modifiers
Ethyl 6,7-dimethoxy-4-(3,4-dimethoxyphenyl)-2-(1,2,4-triazol-1-ylmethyl)quinoline-3-carboxylate (JP-A No. 7-118266)
(ii) Others
Methotrexate, cyclophosphamide, MX-68, atiprimode dihydrochloride, BMS-188667, CKD-461, limexolone, cyclosporin, tacrolimus, gusperimus, azathipurine, antilymphocyte serum, dry sulfonated immunoglobulin, erythropoietin, colony stimulation factor, interleukin, interferon and the like.

(5) Steroid Drugs

Dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone propionate, erythritol and the like.

(6) c-JUN N-terminal Kinase (JNK) Inhibitor

Compounds described in WO00/35906, WO00/35909, WO00/35921, WO00/64872 or WO00/75118.

(7) Others (i) T-cell inhibitors
IR-501 (T-cell receptor peptide) and the like.
(ii) Inosine monophosphate dehydrogenase (IMPDH) inhibitors
Micophenolate mophetyl, VX-497 and the like.
(iii) Adhesive molecule inhibitors
ISIS-2302, selectin inhibitor, ELAM-1, VCAM-1, ICAM-1 and the like.
(iv) Thalidomide
(v) Monocyte therapeutic agents
Leukobax and the like.
(vi) Cathapsin inhibitors
(vii) Matrix MMPs inhibitors
BB-3644, CGS-27023A, Bay-12-9566, KB-R7785, L-758354, POL-641 and the like.
(viii) Glucose-6-phosphate dehydrogenase inhibitors
CBF-BS2 and the like.
(ix) Hydroortate dehydrogenase (DHODH) inhibitors
(x) Phosphodiesterase IV (PDE IV) inhibitors
CG-1088 and the like.
(xi) Phospholipase $A_2$ inhibitors
(xii) iNOS inhibitors
NOX-200 and the like.
(xiii) Microtuble stimulants
Pacritaxel and the like.
(xiv) Microtuble inhibitors
Leumacon and the like.
(xv) MHC class II antagonists
ZD-2315 and the like.
(xvi) Prostacyclin agonists
Iloprost and the like.
(xvii) CD4 antagonists
4162W94, kelliximav and the like.
(xviii) CD23 Antagonists
(xix) LTB4 receptor antagonists
CGS-25019C and the like.
(xx) 5-lipoxygenase inhibitors
Dileuton and the like.
(xxi) Cholinesterase inhibitors
Galanthamine and the like.
(xxii) Thyrosinkinase inhibitors
YT-146 and the like.
(xxiii) Carepsin B inhibitors
(xxiv) Adenosine deaminase inhibitors
Pentostatin and the like.
(xxv) Osteogenesis stimulants
(2R, 4S)-(−)-N-[4-(diethoxyphosphorylmethyl)phenyl]-1,2,4,5-tetrahydro-4-methyl-7,8-methylenedioxy-5-oxo-3-benzothiepin-2-carboxamide or a salt thereof (JP-A No. 8-231659) and the like.
(xxvi) Dipeptidyl peptitase inhibitors
TMC-2A and the like.
(xxvii) TRK-530, TOK-8801
(xxviii) Collagen agonists
AI-200 and the like.
(xxix) Capsaicin cream
(xxx) Hyaluronic acid derivatives
Sinvisc 8hylan G-F 20), othovisc and the like.
(xxxi) Glucosamine sulfate
(xxxii) Amyprilose (6) Used after Synovia Excision.

(7) Used after Therapy Using Prosorba Column.

Examples of the combination drug other than the above-mentioned compounds include antibacterial agents, antifungal agents, antiprotozoan agents, antibiotics, antitussive and expectorants, sedatives, narcotics, antiulcer agents, antiarrhythmic agents, hypotensive diuretics, anticoagulants, tranquilizers, antipsychotics, antitumor agents, anti-hyperlipidemia agents, muscle relaxants, anticonvulsants, antidepressants, antiallergic agents, cardiac restoratives, arrhythmia therapeutic agents, vasodilators, vasoconstrictors, hypotensive diuretics, diabetes therapeutic agents, antinarcotics, vitamin agents, vitamin derivatives, antiasthmatic agents, thamuria and acrasia therapeutic agents, atopic dermatitis therapeutic agents, allergic gastritis therapeutic agents, vasopressor agents, endotoxin antagonists or antibories, signal transfer inhibitors, inflammatory mediator action suppressants, inflammatory mediator action suppressing antibodies, anti-inflammatory mediator action suppressants, anti-inflammatory mediator action suppressing antibodies, and the like. Specific examples thereof are listed below.

(1) Antibacterial Agents

①Sulfa drugs
Sulfamethizole, sulfisoxazole, sulfamonomethoxin, sulfamethyzole, salazosulfapyridine, sulfadiazine silver and the like.

②Quinoline-based antibacterial agents
Nalidixic acid, pipemidic acid trihydrate, enoxacin, norfloxacin, ofloxacin, tosfloxacin tosilate, cyprofloxacin hydrochloride, lomefloxacin hydrochloride, sparfloxacin, fleloxacin and the like.

③Anti-tuberculous agents
Isoniazid, ethambutol (ethambutol hydrochloride), p-aminosalicylic acid (calcium p-aminosalicylate), pyradinamide, ethionamide, prothionamide, rifampicin, streptomycin sulfate, kanamycin sulfate, cycloserine and the like.

④Anti-acid fast bacteria drugs
Diaphenylsulfone, rifampicin and the like.

⑤Anti-viral drugs
Idoxuridine, aciclovir, vitalavin, ganciclovir and the like.

⑥Anti-HIV drugs
Didopsin, didanosin, sarcitavin, indinavir sulfate ethanol adduct, litonavir and the like.

⑦Anti-spirochaeta drugs

⑧Antibiotics
Tetracyclin hydrochloride, ampicillin, piperacillin, gentamycin, dibekacin, kanendomycin, lipidmycin, tobramycin, amikacin, fradiomycin, sisomycin, tetracycline, oxytetracycline, rolitetracycline, doxycycline, ampicillin, piperacillin, ticarcillin, cephalothin, cefapirin, cefaloridine, cefaclor, cefalexin, cefuroxadine, cefadroxil, defamandole, cefatoam, cefuroxime, cefathiam, cefathiamhexetyl, cefuroxime akycetyl, cefdinyl, cefditorenepivoxyl, ceftazidime, cefpiramide, cefsulodin, cefmenoxime, cefpodoxime proxetyl, cefpirom, cefazopurane, cefepim, cefsulodin, cefmenoxime, cefmethazole, cefminox, cefaxytin, cefbuperazone, latamoquinacef, flomoquinacef, cefazolin, cefataxime, cefoperazone,ceftizoxime, moxalactam, thienamycin, sulfazesin, azthreonam, or a salt thereof, griseofulvin, lancasidines [Journal of Antibiotics, 38, 877-885 (9185)], azole-based compounds [2-[(2R, 2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl-3-(2H, 4H)-1,2,4-triazolone, fulconazole, itraconazole, etc.] and the like.

(2) Antifungal Agents
① Polyethylene-based antibiotics (e.g., amphotericin, B, nystatin, trichomycin)
② Griseofulvin, pyrrole nitrin and the like
③ Cytosine metabolism antagonists (e.g., flucytosine)
④ Imidazole derivatives (e.g., econazole, clotrimazole, miconazole nitrate, bihonazole, cloconazole)
⑤ Triazole derivatives (e.g., fulconazole, itraconazole)
⑥ Thiocarbamic acid derivatives (e.g., trinaphthol and the like)

(3) Anti-protozoan Agents
Metronidazole, tinidazole, diethyl citrate carbamycin, quinine hydrochloride, quinine sulfate and the like.

(4) Antitussive and Expectorants
Ephedrine hydrochloride, noscapine hydrochloride, dihydrocodeine phosphate, isoproterenol hydrochloride, ephedrine hydrochloride, methylephedrine hydrochloride, noscapine hydrochloride, allocramide, chlorophedianole, picoperidamine, chloperastine, protokylol, isoproterenol, salbutamol, terebuthaline, oxypetebanol, morphine hydrochloride, dextropetolfan hydrobromide, oxycodone hydrochloride, dimorfan phosphate, tipepidine hibenzate, pentoxyverine citrate, clofedanole hydrochloride, benzonatate, guaifenesin, bromhexine hydrochloride, ambroxol hydrochloride, acetylcysteine, ethylcycteine hydrochloride, carbocysteine and the like.

(5) Sedatives
Chlorpromazine hydrochloride, atropine hydrochloride, phenobarbitol, barbitol, amobarbitol, pentobarbitol, thiopentanol sodium, thiamylal sodium, nitrazepam, estazolam, flurazepam, haloxazolam, triazolam, flunitrazepam, bromovalerylurea, chloral hydrate, triclofos sodium and the like.

(6) Narcotics
(6-1) Local Anesthetics
Cocaine hydrochloride, procaine hydrochloride, lidocaine, dibucaine hydrochloride, tetracaine hydrochloride, mepivacaine hydrochloride, bupivacaine hydrohcloride, oxybuprocaine hydrochloride, ethyl aminobenzoate, oxethazeine, and the like.
(6-2) General Anesthetics
① Inhalation anesthetics (e.g., ether, halothane, nitrous oxide, influrane, enflurane)
② Vein anesthetics (e.g., ketamine hydrochloride, droperidol, thiopental sodium, thiamylal sodium, pentobarbitol), and the like.

(7) Anti-ulcer Agents
Methacropromide, histidin hydrochloride, lansoprazole, methocropramide, pirenzepine, cimetidine, ranitidine, famotidine, urogastrin, oxathezeine, proglumide, omeprazole, sucralfate, sulpiride, cetraxate, gefalnate, aldioxa, teprenone, prostaglandin and the like.

(8) Arrhythmia Therapeutic Agents
① Sodium channel blockers (e.g., chinidine, procaineamide, disopyramide, ajmaline, lidocaine, mexiletine, phenytoin)
② Blockers (e.g., propranolol, alprenolol, bufetolol, oxprenolol, atenolol, acebutolol, metoprolol, bisoprolol, hindrol, carteolol, allotilol)
③ Potassium channel blockers (e.g., amiodarone)
④ Calcium channel blockers (e.g., verapamil, diltiazem), and the like.

(9) Hypotensive Diuretics
Hexamethonium bromide, clonidine hydrochloride, hydrochlorothiazide, trichlormetiazide, furosemide, ethacrynic acid, bumetanide, mefruside, azosemide, spironolactone, potassium canrenoate, triamterene, amiloride, acetazolamide, D-mannitol, isosorubide, aminoferine and the like.

(10) Anticoagulants
Heparin sodium, sodium citrate, activated protein C, tissue factor route inhibitor, antithrombin III, dalteparin sodium, warfarin potassium, algatrovane, gabexate, sodium citrate, ozacrel sodium, ethyl icosapentaenoate, varaprosto sodium, alprostadil, ticlopidine hydrochloride, pentoxyfylline, dipyridamole, thiokinase, urokinase, streptokinase, and the like.

(11) Tranquilizers
Diazepam, lorazepam, oxazepam, chlordiazepoxide, medazepam, oxazolam, cloxazolam, clotiazepam, bromazepam, etizolam, fludiazepamm, hydroxydine, and the like.

(12) Antiphychotics
Chlorpromazine hydrochloride, prochlorperazine, trifluoroperazine, thiolidazine hydrochloride, perphenazine malate, fluphenazine enantate, prochlorperazine maleate, levomepromazine maleate, promethazine hydrochloride, haloperidol, bromperidol, spiperone, reserpine, clocapramine hydrochloride, sulpiride, zotepine and the like.

(13) Anti-tumor Agents
6-O-(N-chloroacetylcarbamoyl)fumagylol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lenthinan, levamisole, bestatin, ajmexone, glycyrrhizin, doxorubicin hydrochloride, aclarubicin hydrochloride, bleomycin hydrochloride, peplomycin sulfate, vincristine sulfate, illinotecane hydrochloride, cyclophosphamide, melphalan, disulfane, thiotepa, procarbazine hydrochloride, cisplatin, azathiopurine, mercaptopurine, tegafur, carmofur, cytarabine, methyltestosterone, testosterone propioante, testosterone enantate, mepitiostane, phosphestolol, chlormazinone acetate, eupurine acetate, bucelerin acetate and the like.

(14) Anti-hyperlipidemia Agents
Clofibrate, etheyl 2-chloro-3-[4-(2-methyl-2-pheylpropoxy)phenyl]propioante (Chemical and Pharmaceutical Bulletin, 38, 2792 to 2796 (1990)), pravastatine, sinvastatine, probucol, bezafibrate, clinofibrate, nicomol, cholestyramine, dextran sulfate sodium and the like.

(15) Muscle Relaxants
Pridinol, tubocurarine, pancuronium, tolperisone hydrochloride, chlorphenesin carbamate, baclofen, chlormezanone, mephenesin, clozoxazone, epirizone, thizanidine and the like.

(16) Anti-convulsants
Phenytoin, ethosuximide, acetazolamide, chloridiazepoxide, tripetadione, carbamazepine, phenobarbitol, primidone, sulthiam, sodium palpuroate, clonazepam, nitrazepam and the like.

(17) Anti-depressants

Imipramine, clomipramine, noxiptiline, phenelzine, amytriptiline hydrochloride, nortriptiline hydrochloride, amoxapine, mianserin hydrochloride, maprotiline hydrochloride, sulpiride, fluboxamine maleate, trazodone hydrochloride and the like.

(18) Anti-allergic Agents

Diphenhydramine, chlorpheniramine, tripelenamine, methoziramine, clemizole, diphenylpyraline, methoxyphenamine, sodium cromoglycate, tranilast, lepirinast, anlexanone, ibudilast, ketotifen, terphenazine, mequitazine, azelastin, epinastin, ozagrel hydrochloride, planlucast-hydrate, ceratrodust and the like.

(19) Cardiac Restorative

Transbiooxocamphor, telefinol, aminophylin, etilefrine, dopamine, dobutamine, denopamine, aminophylin, paecinaline, amlinone, pimobendane, ubidecarenone, digitoxin, digoxin, methyldigoxin, lanatoside C, G-strophanthin, and the like.

(20) Vasodilators

Oxyfedrine, diltiazem, tolazoline, hexobendine, bamethane, clonidine, methyldopa, guanabenz and the like.

(21) Vasoconstrictors

Dopamine, dobutamine, denopamine and the like.

(22) Hypotensive Diuretics

Hexamethonium bromide, pentolinium, mecamylamine, ecarazine, clonidine, diltiazem, nifedipine and the like.

(23) Diabetes Ttherapeutic Agents

Tolbutamide, chlorpropamide, acetohexamide, glibenclamide, tolazamide, acalbose, epalrestat, troglytazone, glucagon, glymidine, glypzide, phenformin, puformin, metformin and the like.

(24) Antinarcotics

Levallolphan, nalorphine, naloxone, or salt thereof, and the like.

(25) Fat Soluble Vitamins

①Vitamins A: vitamin $A_1$, vitamin $A_2$ and retinol palmitate

②Vitamins D: vitamins $D_1$, $D_2$, $D_3$, $D_4$ and $D_5$

③Vitamins E: α-tocopherol, β-tocopherol, γ-tocopherol, δ-tocopherol, dl-α-tocopherol nicotinate ④Vitamins K: vitamins $K_1$, $K_2$, $K_3$ and $K_4$ ⑤Folic Acid (vitamin M), and the Like.

(26) Vitamin Derivatives

Various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5.6-trans-ergocalciferol, and the like.

(27) Anti-asthmatic Agents

Isoprenaline hydrochloride, salbutamol sulfate, procatechol hydrochloride, terbutaline sulfate, trimetoquinol hydrochloride, tulobuterol hydrochloride, orciprenaline sulfate, fenoterol hydrobromide, ephedrine hydrochloride, iprotropium bromide, oxytropium bromide, fultropium bromide, theophyline, aminophyline, sodium cromoglycate, tranilast, lepirinast, anlexanone, ibudilast, ketotifen, terphenazine, mequitazine, azelastin, epinastin, ozagrel hydrochloride, planlucast-hydrate, ceratrodust, dexamethasone, prednisolone, hydrocortiaone, vecropetazone propionate, and the like.

(28) Thamuria and Acrasia Therapeutic Agents flavoxate hydrochloride and the like.

(29) Atopic Dermatitis Therapeutic Agents

Sodium cromoglycate and the like.

(30) Allergic Rhinitis Therapeutic Agents

Sodium cromoglycate, chlorpheniramine maleate, alimemazine tartarate, clemastine fumarate, homochlorcyclizine hydrochloride, terfenazine, mequitazine and the like.

(31) Vasopressors

Dopamine, dobutamine, denopamine, digitoxin, digoxin, methyldigoxin, lanatoside C, G-strophanthin, and the like.

(32) Others

Hydroxicam, diaserine, megestrol acetate, nicerogoline, prostaglandin and the like.

Combination of compounds of the present invention with combination drugs provide the following excellent effects:

(1) The dose can be reduced in comparison with a case in which the compound of the present invention or a combination drug is administered alone.

(2) A drug to be combined with the compound of the present invention can be selected depending on symptoms (mild, serious and the like) of patients.

(3) The therapeutic period can be lengthened by selecting a combination drug having a different action mechanism than that of the compound of the present invention.

(4) The therapeutic effect can be sustained by selecting a combination drug having a different action mechanism than that of the compound of the present invention.

(5) By combining the compound of the present invention with a combination drug, synergic effect can be obtained.

Hereinafter, combined use of the compound (I) of the present invention with a combination drug is referred to as "combination agent of the present invention".

In use of a combination agent of the present invention, the administration time of the compound of the present invention and a combination drug is not restricted, and the compound of the present invention or a pharmaceutical composition thereof and a combination drug or a pharmaceutical composition thereof can be administered to an administration subject simultaneously, or may be administered at different times. The dosage, of a combination drug may be determined according to the administration amount clinically used, and can be appropriately selected depending on an administration subject, administration route, disease, combination and the like.

The administration mode of a combination agent of the present invention is not particularly restricted, and it is sufficient that the compound of the present invention and a combination drug are combined in administration. Examples of such administration mode include the following methods:

(1) The compound of the present invention and a combination drug are simultaneously produced to give a single preparation which is administered. (2) The compound of the present invention and a combination drug are separately produced to give two kinds of preparations which are administered simultaneously by the same administration route. (3) The compound of the present invention and a combination drug are separately produced to give two kinds of preparations which are administered by the same administration route only at the different times. (4) The compound of the present invention and a combination drug are separately produced to give two kinds of preparations which are administered simultaneously by the different administration routes. (5) The compound of the present invention and a combination drug are separately produced to give two kinds of preparations which are administered by the different administration routes only at different times (for example, the compound of the present invention and a combination drug are administered in this order, or in the reverse order).

The combination agent of the present invention has low toxicity, and for example, the compound of the present invention or (and) the above-mentioned combination drug can be mixed, according to a method known per se, with a pharmacologically allowable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like). An injection can be administered by intravenous, intramuscular, subcutaneous or intraorgan route, or directly to the lesion.

As the pharmacologically allowable carrier which may be used in production of a combination agent of the present invention, various organic or inorganic carrier substances conventionally used as a preparation raw material are exemplified, and for example, an excipient, lubricant, binder and disintegrating agent in a solid preparation, or a solvent, dissolution aid, suspending agent, isotonizing agent, buffer, soothing agent and the like in a liquid preparation, are listed. Further, if desirable, usual additives such as a preservative, antioxidant, coloring agent, sweetening agent, adsorbent, wetting agent and the like can also be appropriately used in suitable amount.

As the excipient, for example, lactose, sucrose, D-mannitol, starch, corn starch, crystalline cellulose, light anhydrous silicic acid and the like are listed.

As the lubricant, for example, magnesium stearate, calcium stearate, talc, colloidal silica and the like are listed.

As the binder, for example, crystalline cellulose, sucrose, D-mannitol, dextrin, hydroxypropylcellulose, hydroxypropylmethylcllulose, polyvinylpyrrolidone, starch, sucrose, gelatin, methylcellulose, carboxymethylcellulose sodium and the like are listed.

Examples of the disintegrating agent include starch, carboxymethylcellulose, carboxymethylcellulose calcium, carboxymethylstarch sodium, L-hydroxypropylcellulose and the like.

Examples of the solvent include injection water, alcohol, propylene glycol, macrogol, sesame oil, corn oil, olive oil and the like.

Disclosed as examples of the dissolution aid are polyethylene glycol, propylene glycol, D-mannitol, benzyl benzoate, ethanol, trisaminomethane, cholesterol, triethanolamine, sodium carbonate, sodium citrate and the like.

Disclosed as examples of the suspending agent are surfactants such as stearyl triethanolamine, sodium laurylsulfate, laurylaminopropionic acid, lecithine, benzalkonium chloride, benzetonium chloride, glycerin monostearate and the like; hydrophilic polymers such as polyvinyl alcohol, polyvinyl pyrrolidone, carboxymethylcellulose sodium, methylcellulose, hydroxymethylcellulose, hydroxyethylceluose, hydroxypropylcellulose and the like.

As the isotonizing agent, for example, glucose, D-sorbitol, sodium chloride, glycerin, D-mannitol and the like are listed.

As the buffer, for example, buffer solutions of a phosphate, acetate, carbonate, citrate and the like, etc., are listed.

As the soothing agent, benzyl alcohol and the like are listed.

Examples of the preservative include p-oxybenzoates, chlorobutanol, benzyl alcohol, phenetyl alcohol, dehydroacetic acid, sorbic acid and the like.

Example of the antioxidant include sulfites, ascorbic acid, α-tocopherol and the like.

The compounding ratio of the compound of the present invention to a combination drug in a combination agent in the present invention can be appropriately selected depending on an administration subject, administration route, diseases and the like.

For example, the content of the compound of the present invention in a combination agent of the present invention differs depending on the form of a preparation, and usually from about 0.01 to 100% by weight, preferably from about 0.1 to 50% by weight, further preferably from about 0.5 to 20% by weight, based on the preparation.

The content of a combination drug in a combination agent of the present invention differs depending on the form of a preparation, and usually from about 0.01 to 100% by weight, preferably from about 0.1 to 50% by weight, further preferably from about 0.5 to 20% by weight, based on the preparation.

The content of additives such as a carrier and the like in a combination agent of the present invention differs depending on the form of a preparation, and usually from about 1 to 99.99% by weight, preferably from about 10 to 90% by weight, based on the preparation.

In the case when the compound of the present invention and a combination drug are separately prepared respectively, the same contents may be adopted.

These preparations can be produced by a method known per se usually used in a preparation process.

For example, the compound of the present invention and a combination drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and molded into an oily injection.

In the case of a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxpropylcellulose and the like), a lubricant (e.g., talc, magnesium stearate, polyethylene glycol 6000 and the like) and the like, for example, can be added to the compound of the present invention or a combination drug, according to a method known per se, and the mixture can be compression-molded, then if desirable, the molder product can be coated by a method known per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose stearate succinate, Eudoragit (methacrylic acid•acrylic acid copolymer, manufactured by Rohm, D E), pigment (e.g., iron oxide red, titanium dioxide, et.) and the like can be used. The preparation for oral administration may be any of a quick release preparation and a sustained release preparation.

For example, in the case of a suppository, the compound of the present invention and a combination drug can be made into an oily or aqueous solid, semisolid or liquid suppository according to a method known per se.

As the oily substrate used in the above-mentioned composition, for example, glycerides of higher fatty acids [e.g., cacao butter, Witebsols (manufactured by Dynamite Novel, D E), etc.], intermediate grade fatty acids [e.g., Myglyols (manufactured by Dynamite Novel, D E), etc.], or vegetable oils (e.g., sesame oil, soy bean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release agent, sustained release microcapsules and the like are listed.

For obtaining a sustained release microcapsule, a method known per se can be adopted, and for example, it is preferably molded into a sustained release preparation shown in the following [2] before administration.

The compound of the present invention is preferably molded into an oral administration preparation such as a solid preparation (e.g., powder, granule, tablet, capsule) and the like, or molded into a rectum administration preparation such as a suppository. Particularly, an oral administration preparation is preferable.

A combination drug can be made into the above-mentioned drug form depending on the kind of the drug.

[1] An injection of the compound of the present invention or a combination drug, and preparation thereof, [2] a sustained release preparation or quick release preparation of the compound of the present invention or a combination drug, and preparation thereof, [3] a sublingual, buccal or intraoral quick disintegrating agent of the compound of the present invention or a combination drug, and preparation thereof, will be specifically described below.

[1] Injection and Preparation Thereof

An injection prepared by dissolving the compound of the present invention or a combination drug into water is preferable. This injection may be allowed to contain a benzoate and/or salicylate.

The injection is obtained by dissolving the compound of the present invention or a combination drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, organic acid salts such as tromethamol and the like, etc. are listed.

The concentration of the compound of the present invention or a combination drug in an injection is from 0.5 to 50 w/v %, preferably from about 3 to 20 w/v %. The concentration of a benzoate salt or/and salicylate salt is from 0.5 to 50 w/v %, preferably from 3 to 20 w/v %.

Into a preparation of the present invention, additives usually used in an injection, for example, a stabilizer (ascorbic acid, sodium pyrosulfite, and the like), a surfactant (Polysorbate 80, macrogol and the like), a solubilizer (glycerin, ethanol and the like), a buffer (phosphoric acid and alkali metal salt thereof, citric acid and alkali metal salt thereof, and the like), an isotonizing agent (sodium chloride, potassium chloride, and the like), a dispersing agent (hydroxypropylmethylcellulose, dextrin), a pH regulator (hydrochloric acid, sodium hydroxide and the like), a preservative (ethyl p-oxybenzoate, benzoic acid and the like), a dissolving agent (conc. glycerin, meglumine and the like), a dissolution aid (propylene glycol, sucrose and the like), a soothing agent (glucose, benzyl alcohol and the like), and the like, can be appropriately compounded. These additives are generally compounded in a proportion usually used in an injection.

It is advantageous that pH of an injection is controlled from 2 to 12, preferably from 2.5 to 8.0 by addition of a pH regulator.

An injection is obtained by dissolving the compound of the present invention or a combination drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously be heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation which is divided and administered multiple-times.

[2] Sustained Release Preparation or Quick Release Preparation, and Preparation Thereof A sustained release preparation is preferable which is obtained, if desirable, by coating a nucleus containing the compound of the present invention or a combination drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose stearate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacryalte/aminoalkyl methacrylate copolymers, polyacrylic acid, polymethacrylic acid, methacrylic acid alkylamide copolymers poly(methyl methacrylate), polymethacrylate, polymethacrylamide, aminoalkyl methacryalte copolymers, poly(methacrylic anhydride), glycidyl methacrylate copolymer, particularly, acrylic acid-based polymers such as Eudoragits (Rhom Farma) such as Eudoragit RS-100, RL-100, RS-30D, RL-30D, RL-PO, RS-PO (ethyl acryalte•methyl methacryalte•trimethyl chloride methacryalte•ammoniumethyl copolymer), Eudoragit NE-30D (methyl methacryalte•ethyl acrylate copolymer), and the like, hardened oils such as hardened castor oil (e.g., Lovery wax (Freunt) and the like), waxes such as carnauba wax, fatty acid glycerin ester, paraffin and the like, polyglycerin fatty esters, and the like.

As the swellable polymer, polymers having an acidic dissociating group and showing pH dependent swell are preferable, and polymers manifesting small swelling in acidic regions such as in stomach and large swelling in neutral regions such as in small intestine and large intestine are preferable.

As such a polymer having an acidic dissociating group and showing pH dependent swell, cross-linkable polyacrylic acid copolymers such as, for example, Carbomer 934P, 940, 941, 974P, 980, 1342 and the like, polycarbophil (calcium polycarbophil (last two are manufactured by B F Goodrich), Hibiswako 103, 104, 105, 304 (all are manufactured by Wako Purechemical Co., Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like are listed.

The content of a water-insoluble substance in the film agent of a sustained release preparation is from about 30 to 90% (w/w), preferably from about 35 to 80% (w/w), further preferably from about 40 to 75% (w/w), the content of a swellable polymer is from about 3 to 30% (w/w), preferably from about 3 to 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drug as exemplified below, then, coating the resulting nucleus with a film agent solution prepared by heat-solvating a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to 2000 μm, further preferably, from about 500 to 1400 μm.

Preparation of the nucleus can be effected by a usual production method. For example, a suitable excipient, binding agent, integrating agent, lubricant, stabilizer and the like are mixed into a drug, and the mixture is subjected to a wet extrusion granulating method, fluidized bed granulating method or the like, to prepare a nucleus.

The content of drugs in a nucleus is from about 0.5 to 95% (w/w), preferably from about 5.0 to 80% (w/w), further preferably from about 30 to 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binder, for example, polyvinyl alcohol, hydroxypropyl cellulose, polyethylene glycol, polyvinyl pyrrolidone, Pluronic F68, gum Arabic, gelatin, starch and the like are used. As the disintegrating agent, for example, carboxymethylcellulose calcium (ECG505), crosscarmelose sodium (Ac-Di-Sol), crosslinked polyvinylpyrrolidone (Crosspovidone), lower substitution hydroxypropylcellulose (L-HPC) and the like are used. Among them, hydroxypropylcellulose, polyvinylpyrrolidone, lower substitution hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the abovementioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose, waxes can be used, and the average particle size thereof is preferably from about 100 μm to 1500 μm.

For separating a drug and a film agent contained in a nucleus, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are used. The protective agent may contain, as a stabilizer, acids such as tartaric acid, citric acid, succinic acid, fumaric acid, maleic acid and the like, and lubricants such as talc and the like. When the protective agent is used, the coating amount is from about 1 to 15% (w/w), preferably from about 1 to 10% (w/w), further preferably from about 2 to 8% (w/w), based on the nucleus.

The protective agent can be coated by a usual coating method, and specifically, the protective agent can be coated, for example, by a fluidized bed coating method, pan coating method and the like.

II. Coating of Nucleus with Film Agent

A nucleus obtained in the above-mentioned step I is coated with a film agent solution obtained by heat-solvating the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer and hydrophilic substance in a film agent solution is appropriately selected so that the contents of these components in a coated film are the above-mentioned contents, respectively.

The coating amount of a film agent is from about 1 to 90% (w/w), preferably from about 5 to 50% (w/w), further preferably from about 5 to 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick release preparation may be liquid (solution, suspension, emulsion and the like) or solid (particle, pill, tablet and the like). Oral agents and parenteral agents such as an injection and the like are used, and oral agents are preferable.

The quick release preparation, usually, may contain, in addition to an active component drug, also carriers, additives and excipients conventionally used in the production field (hereinafter, sometimes abbreviated as excipient). The preparation excipient used is not particularly restricted providing it is an excipient ordinarily used as a preparation excipient. For example, as the exipient for an oral solid preparation, lactose, starch, corn starch, crystalline cellulose (Acevil PH101, manufactured by Asahi Chemical Industry Co., Ltd., and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to 99.4 w/w %, preferably from about 20 to 98.5 w/w %, further preferably from about 30 to 97 w/w %, based on the total amount of the quick release preparation.

The content of a drug in the quick release preparation can be appropriately selected in the range from about 0.5 to 95%, preferably from about 1 to 60% based on the total amount of the quick release preparation.

When the quick release preparation is an oral solid preparation, it usually contains, in addition to the above-mentioned components, also a disintegrating agent. As this disintegrating agent, there are used, for example, carboxymethylcellulose calcium (ECG-505, manufactured by Gotoku Yakuhin), crosscarmelose sodium (for example, Actisol, manufactured by Asahi Chemical Industry Co., Ltd.), crosspovidone (for example, Colicone CL, manufactured by BASF), lower substitution hydroxypropylcellulose (manufactured by Shin-Etsu Chemical Co., Ltd.), carboxymethylstarch (manufactured by Matsutani Kagaku K. K.), carboxymethylstarch sodium (Exprotab, manufactured by Kimura Sangyo), partially α-nized starch (PCS, manufactured by Asahi Chemical Industry Co., Ltd.), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and compounding amount of a drug used, design of releasing property, and the like, and for example, from about 0.05 to 30 w/w %, preferably from about 0.5 to 15 w/w %, based on the total amount of the quick releasing agent.

When the quick release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxylmethylcellulose, polybinylpyrrolidone, pluran, dextrin and the like), a lubricant (e.g., polyethylene glycol, magnesium stearate, talc, light anhydrous silicic acid (for example, aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar coloring matter, caramel, iron oxide red, titanium oxide, riboflavins), if necessary, an appetizing agent (e.g., sweetening agent, aroma and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick releasing reparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a quick release preparation is formed, for example, into a particle, it can be prepared., according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Pulek), and the like, then, subjecting the mixture to a wet extrusion granulation method, fluidized bed granulation method and the like.

Thus obtained quick releasing preparation and sustained releasing preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation together with preparation excipients and the like. It may also be permissible that they are made into granules or fine particles, and filled in the same capsule to be used as a preparation for oral administration.

[3] Sublinguial, Buccal or Intraoral Quick Disintegrating Agent and Preparation thereof Sublinguial, buccal or intraoral quick disintegrating agents may be a solid preparation such as tablet and the like, or may be an oral mucosa membrane patch (film).

As the sublinguial, buccal or intraoral quick disintegrating agent, a preparation containing the compound of the present invention or a combination drug and an excipient is preferable. It may contain also auxiliary agents such as a lubricant, isotonizing agent, hydrophilic carrier, water-dispersible polymer, stabilizer and the like. Further, for easy absorption and increase in in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., fine crystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolicone, polycarbofil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublinguial, buccal or intraoral quick disintegrating agent can be produced by mixing the compound of the present invention or a combination drug and an excipient by a method known per se. Further, is desirable, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or a combination drug and the above-mentioned water-dispersible polymer (preferably, hydroxypropylcellulose, hydroxypropylmethylcellulose), excipient and the like are dissolved in a solvent such as water and the like, and the resulted solution is cast, to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbofil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into given area.

As the preferable intraoral quick disintegrating agent, there are listed solid quick scattering dose agents composed of a network body comprising the compound of the present invention or a combination drug, and a water-soluble or water-diffusible carrier which is inert to the compound of the present invention or combination drug, are listed. This network body is obtained by sublimating a solvent from the solid composition constituted from a solution prepared by dissolving the compound of the present invention or a combination drug in a suitable solvent.

It is preferable that the composition of an intraoral quick disintegrating agent contains a matrix forming agent and a secondary component, in addition to the compound of the present invention or a combination drug.

Examples of the matrix forming agent include animal proteins or vegetable proteins such as gelatins, dextrins and, soybean, wheat and psyllium seed protein and the like; rubber substances such as gum Arabic, guar gum, agar, xathane gum and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-asparatic acid, L-glutamic acid, L-hydroxyproline, L-isoleucine, L-leucine, L-phenylalanine and the like, are losted.

One or more of the matrix forming agents can be introduced in a solution or suspension before solidification. Such a matrix forming agent may be present in addition to a surfactant, or may be present while a surfactant is being excluded. The matrix forming agent aids to maintain the compound of the present invention or a combination drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD &. C Red 40 and the like manufactured by Elis and Eberald. Examples of the suitable flavoring agent include mint, raspberry licorice, orange, lemon, grape fruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-containing compounds, adsorbent substances and microcapsulated compounds.

The preparation contains the compound of the present invention or a combination drug in an amount usually from about 0.1 to 50% by weight, preferably from about 0.1 to 30% by weight, and preferable are preparations (such as the above-mentioned sublingual agent, buccal and the like) which can dissolve 90% or more the compound of the present invention or a combination drug (into water) within the time range of about 1 to 60 minutes, preferably of about 1 to 16 minutes, more preferably of about 2 to 5 minutes, and intraoral quick disintegrating preparations which are disintegrated within the range of 1 to 60 seconds, preferably of 1 to 30 seconds, further preferably of 1 to 10 seconds after being placed in an oral cavity.

The content of the above-mentioned exipient in the whole preparation is from about 10 to 99% by weight, preferably from about 30 to 90% by weight. The content of β-cyclodextrin or β-cyclodextrin derivative in the whole preparation is from 0 to about 30% by weight. The content of the lubricant in the whole preparation is from about 0.01 to 10% by weight, preferably from about 1 to 5% by weight. The content of the isotonizing agent in the whole preparation is from about 0.1 to 90% by weight, preferably, from about 10 to 70% by weight. The content of the hydrophilic carrier agent in the whole preparation is from about 0.1 to 50% by weight, preferably, from about 10 to 30% by weight. The content of the water-dispersible polymer in the whole preparation is from about 0.1 to 30% by weight, preferably from about 10 to 25% by weight. The content of the stabilizer in the whole preparation is from about 0.1 to 10% by weight, preferably, from about 1 to 5% by weight. The above-mentioned preparation may further contain additives such as a coloring agent, sweetening agent, preservative and the like, if necessary.

The dosage of a combination agent of the present invention differs depending on the kind of compound (I), age, body weight, condition, drug form, administration method, administration period and the like, and for example, for one sepsis patient (adult, body weight: about 60 kg), the combination agent is administered intravenously, at a dose of about 0.01 to 1000 mg/kg/day, preferably about 0.01 to 100 mg/kg/day, more preferably about 0.1 to 100 mg/kg/day, particularly about 0.1 to 50 mg/kg/day, especially about 1.5 to 30 mg/kg/day, in terms of the compound of the present invention or a combination drug, respectively, once or apportioned to several times in a day. Of course, since the dose as described above varies depending on various conditions, amounts smaller than the above-mentioned dosage may sometimes be sufficient, further, amounts over that range sometimes have to be administered.

The amount of a combination drug can be set at any value unless side effects are problematic. The daily dosage in terms of a combination drug differs depending on the severity, age, sex, body weight, sensitivity difference of the subject, administration period, interval, and nature, pharmacy, kind of the pharmaceutical preparation, kind of effective ingredient, and the like, and is not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once or divided into 4-times a day.

In the administration of a medicine of the present invention, the compound of the present invention may be administered after administration of a combination drug or a combination drug may be administered after administration of the compound of the present invention, though they may be administered simultaneously. When administered at a time interval, the interval differs depending on the effective ingredient, drug form and administration method, and for example, when a combination drug is administered first, a method in which the compound of the present invention is administered within a time range of from 1 minute to 3 days, preferably from 10 minutes to 1 day, more preferably from 15 minutes to 1 hour after administration of the combination drug is exemplified. When the compound of the present invention is administered first, a method in which a combination drug is administered within a time range of from 1 minute to 1 day, preferably from 10 minutes to 6 hours, more preferably from 15 minutes to 1 hour after administration of the compound of the present invention is exemplified.

In a preferable administration method, for example, a combination drug which has been formed into an oral administration preparation is administered orally at a daily dose of about 0.001 to 200 mg/kg, and 15 minutes after, the compound of the present invention which has been formed into an oral administration preparation is administered orally at a daily dose of about 0.005 to 100 mg/kg.

BEST MODE OF CARRYING OUT THE INVENTION

The following reference examples, examples, preparation examples and experiments will illustrate the present invention further in detail below, but these are only examples and do not limit the scope of the present invention, and further, may be varied within a range which is not outside the range of the present invention.

In the following reference examples and example, room temperature" means usually temperatures from about 10° C. to about 35° C. "%" is by weight unless otherwise stated. Yield is represented by mol/mol %.

Abbreviations used in this text have the following meanings.

| | |
|---|---|
| S; | singlet |
| d: | doublet |
| t: | triplet |
| q: | quartet |
| dd: | double doublet |
| ddd: | double double doublet |
| dt: | double triplet |
| br: | broad |
| J: | coupling constant |
| Hz: | Hertz |
| $CDCl_3$: | deuterium chloroform |
| $DMSO-d_6$: | dimethylsulfoxide-$d_6$ |
| $^1$H-NMR: | proton nuclear magnetic resonance spectrum |
| Me: | methyl |

Sequence numbers in the sequence table of the present specification mean the following sequences.

[SEQ ID No. 1]

It indicates a nucleotide sequence of a primer p38-U used in Example 1.

[SEQ ID No. 2]

It indicates a nucleotide sequence of a primer PAG-L used in Example 1.

[SEQ ID No. 3]

It indicates a nucleotide sequence of a primer MKK-U used in Example 1.

[SEQ ID No. 4]

It indicates a nucleotide sequence of a primer MKK-L used in Example 1.

[SEQ ID No. 5]

It indicates a nucleotide sequence of a primer SER-U used in Example 1.

[SEQ ID No. 6]

It indicates a nucleotide sequence of a primer SER-L used in Example 1.

WORKING EXAMPLE

Reference Example 1

1-bromo-3-ethylbenzene

To a solution of 3-ethylaniline (10.0 g, 82.5 mmol) in 50% sulfanic acid (43.6 g) was added dropwise an aqueous solution (16.5 mL) of sodium nitrite (6.83 g, 99.0 mmol) over 30 minutes at 0° C. The resulting reaction mixture was stirred for 45 minutes at 0° C. This diazonium salt solution was added dropwise to a solution of copper (I) bromide (12.4 g, 86.6 mmol) in a 48% hydrobromic acid (82.5 mL) while heating gently under reflux. After the addition, the reaction mixture was heated to reflux for 30 minutes. The reaction mixture was cooled to room temperature, and extracted with ether. The extracts were sequentially washed with a 1N-aqueous sodium hydroxide solution and brine, and filtrated, dried, and concentrated. The residue was purified by silica gel column chromatography (hexane-ethyl acetate=20:1) to obtain a title compound (6.13 g, yield 40%).

Oil $^1$H-NMR (CDCl$_3$) δ: 1.23 (3H, t, J=7.5 Hz), 2.63 (2H, q, J=7.5 Hz), 7.11-7.20 (2H, m), 7.28-7.38 (2H, m).

Reference Example 2

The following reference example compound 2 was synthesized according to Reference Example 1, using 3-(1-methylethyl)aniline instead of 3-ethylaniline.

Reference Example Compound 2

1-bromo-3-(1-methylethyl)benzene

Oil $^1$H-NMR (CDCl$_3$) δ: 1.24 (6H, d, J=7.0 Hz), 2.77-2.99 (1H, m), 7.03-7.16 (2H, m), 7.27-7.34 (1H, m), 7.37 (1H, s).

Reference Example 3

3-ethylbenzoic acid

Under an argon atmosphere, a solution of 1-bromo-3-ethylbenzene (5.1 g, 28 mmol) in tetrahydrofuran (45 mL) was added dropwise to a mixture of magnesium turnings (0.74 g, 31 mmol) in tetrahydrofuran (5.0 mL), and the mixture was stirred for 30 minutes under the same condition. The reaction mixture was added to crashed dry ice, and the mixture was stirred for 1 hour. To the reaction mixture was added 1N-hydrochloric acid, and extracted with ethyl acetate. The extracts were dried, filtrated and concentrated. The residue was purified by silica gel column chromatography (hexane-ethyl acetate=5:1) to obtain a title compound (3.87 g, yield 93%).

Oil $^1$H-NMR (CDCl$_3$) δ: 1.28 (3H, t, J=7.5 Hz), 2.73 (2H, q, J=7.5 Hz), 7.34-7.50 (2H, m), 7.92-7.98 (2H, m).

Reference Example 4

The following reference example compounds 4-1 and 4-2 were synthesized according to Reference Example 3, using 1-bromo-3-(1-methylethyl)benzene, 1-bromo-4-fluoro-3-methylbenzene instead of 1-bromo-3-ethylbenzene.

Reference Example Compound 4-1

3-(1-methylethyl)benzoic acid

Oil $^1$H-NMR (CDCl$_3$) δ: 1.29 (6H, d, J=7.0 Hz), 2.98-3.06 (1H, m), 7.38-7.54 (2H, m), 7.90-8.02 (2H, m).

Reference Example Compound 4-2

4-fluoro-3-methylbenzoic acid m.p. 165-167° C.

Reference Example 5

3-ethylbenzoyl chloride 3-ethylbenzoic acid (9.40 g, 62.6 mmol) was added slowly to thionyl chloride (45 mL), and N,N-dimethylformamide (3 drops) was added dropwise. The resulting reaction mixture was heated under reflux for 2 hours under the same condition. The reaction mixture was concentrated, and used in the subsequent reaction without further purification.

Reference Example 6

The following reference example compounds 6-1 to 6-4 were synthesized according to Reference Example 5, using 3-(1-methylethyl)benzoic acid, 4-fluoro-3-methylbenzoic acid, 4-cyclohexylbenzoic acid and 3,5-dimethylbenzoic acid instead of 3-ethylbenzoic acid.

Reference Example Compound 6-1

3-(1-methylethyl)benzoyl chloride

This was used in the subsequent reaction without purification.

Reference Example Compound 6-2

4-fluoro-3-methylbenzoyl chloride

This was used in the subsequent reaction without purification.

Reference Example Compound 6-3

4-cyclohexylbenzoyl chloride

This was used in the subsequent reaction without purification.

Reference Example Compound 6-4

3,5-dimethylbenzoyl chloride b.p. 82-85° C. (933 Pa).

Reference Example 7

N-(4-chlorobenzoyl)propyleneimine,

A solution of propyleneimine (12 mL, 0.15 mol) in tetrahydrofuran (160 mL) was added to an 1 N-aqueous sodium hydroxide solution. To this mixture was added dropwise 4-chlorobenzoyl chloride (25 g, 0.14 mol) at 0° C. After completion of the addition, the mixture was further stirred for 30 minutes. The reaction mixture was extracted with ethyl acetate. The extract was dried, and the solvent was distilled off to obtain a title compound (25 g, yield 89%).
Oil
¹H-NMR (CDCl₃) δ: 1.39 (3H, d, J=5.5 Hz), 2.15 (1H, d, J=2.9 Hz), 2.51-2.66 (2H, m), 7.39-7.47 (2H, m), 7.93-8.01 (2H, m).

Reference Example 8

The following reference example compounds 8-1 to 8-16 were synthesized according to Reference Example 7, using 3-chlorobenzoyl chloride, 3-methylbenzoyl chloride, 3,5-dimethylbenzoyl chloride, 4-fluorobenzoyl chloride, benzoyl chloride, 3-bromobenzoyl chloride, 4-(methylthio)benzoyl chloride, 2-thiophenecarbonyl chloride, 3-propylbenzoyl chloride, 3-trifluoromethylbenzoyl chloride, 3-ethylbenzoyl chloride, 3-(1-methylethyl)benzoyl chloride, 4-fluoro-3-methylbenzoyl chloride, 3-fluorobenzoyl chloride, 3-methoxybenzoyl chloride and 4-methoxybenzoyl chloride, respectively, instead of 4-chlorobenzoyl chloride.

Reference Example Compound 8-1

N-(3-chlorobenzoyl)propyleneimine,
Oil
¹H-NMR (CDCl₃) δ: 1.40 (3H, d, J=5.1 Hz), 2.17 (1H, d, J=3.3 Hz), 2.53-2.68 (2H, m), 7.40 (1H, dd, J=7.7, 8.1 Hz), 7.53 (1H, ddd, J=1.5, 2.2, 8.1 Hz), 7.90 (1H, dt, J=7.7, 1.5 Hz), 8.00-(1H, dd, J=1.5, 2.2 Hz).

Reference Example Compound 8-2

N-(3-methylbenzoyl)propyleneimine,
Oil
¹H-NMR (CDCl₃) δ: 1.39 (3H, d, J=5.5 Hz), 2.14 (1H, d, J=3.3 Hz), 2.41 (3H, s), 2.51-2.66 (2H, m), 7.32-7.39 (2H, m), 7.79-7.87 (2H, m).

Reference Example Compound 8-3

N-(3,5-dimethylbenzoyl)propyleneimine,
Oil
¹H-NMR (CDCl₃) δ: 1.39 (3H, d, J=5.5 Hz), 2.13 (1H, d, J=3.7 Hz), 2.37 (6H, s), 2.47-2.62 (2H, m), 7.19 (1H, s), 7.64 (2H, s).

Reference Example Compound 8-4

N-(4-fluorobenzoyl)propyleneimine,
Oil
¹H-NMR (CDCl₃) δ: 1.39 (3H, d, J=5.2 Hz), 2.14-2.15 (1H, m), 2.52-2.63 (2H, m), 7.08-7.19 (2H, m), 8.00-8.10 (2H, m).

Reference Example Compound 8-5

N-benzoylpropyleneimine,
Oil
¹H-NMR (CDCl₃) δ: 1.40 (3H, d, J=6.0 Hz), 2.15 (1H, d, J=3.2 Hz), 2.52-2.67 (2H, m), 7.40-7.61 (3H, m), 7.98-8.07 (2H, m).

Reference Example Compound 8-6

N-(3-bromobenzoyl)propyleneimine,
Oil
¹H-NMR (CDCl₃) δ: 1.40 (3H, d, J=5.2 Hz), 2.16-2.18 (1H, m), 2.53-2.65 (2H, m), 7.34 (1H, t, J=7.9 Hz), 7.65-7.71 (1H, m), 7.95 (1H, d, J=7.9 Hz), 8.16 (1H, t, J=1.8 Hz).

Reference Example Compound 8-7

N-[4-(methylthio)benzoyl]propyleneimine,
Oil
¹H-NMR (CDCl₃) δ: 1.49 (3H, d, J=6.0 Hz), 2.13 (1H, d, J=3.2 Hz), 2.49-2.60 (5H, m), 7.24-7.30 (2H, m), 7.90-7.96 (2H, m).

Reference Example Compound 8-8

N-(2-thiophenecarbonyl)propyleneimine,
Oil
¹H-NMR (CDCl₃) δ: 1.43 (3H, d, J=5.2 Hz), 2.14 (1H, d, J=3.6 Hz), 2.56-2.72 (2H, m), 7.08-7.16 (1H, m), 7.53-7.60 (1H, m), 7.75-7.81 (1H, m).

Reference Example Compound 8-9

N-(3-propylbenzoyl)propyleneimine,
Oil
¹H-NMR (CDCl₃) δ: 0.95 (3H, t, J=7.3 Hz), 1.40 (3H, d, J=4.8 Hz), 1.59-1.78 (2H, m), 2.14 (1H, d, J=2.8 Hz), 2.52-2.74 (4H, m), 7.34-7.43 (2H, m), 7.81-7.89 (2H, m).

Reference Example Compound 8-10

N-(3-trifluoromethylbenzoyl)propyleneimine,
Oil
¹H-NMR (CDCl₃) δ: 1.42 (3H, d, J=5.5 Hz), 2.20 (1H, d, J=3.3 Hz), 2.56-2.67 (2H, m), 7.61 (1H, t, J=7.7 Hz), 7.81 (1H, d, J=7.7 Hz), 8.21 (1H, d, J=7.7 Hz), 8.30 (1H, s).

Reference Example Compound 8-11

N-(3-ethylbenzoyl)propyleneimine,
Oil
¹H-NMR (CDCl₃) δ: 1.27 (3H, t, J=7.5 Hz), 1.40 (3H, d, J=5.5 Hz), 2.14 (1H, d, J=2.9 Hz), 2.52-2.61 (2H, m), 2.71 (2H, q, J=7.5 Hz), 7.32-7.41 (2H, m), 7.81-7.89 (2H, m).

Reference Example Compound 8-12

N-[3-(1-methylethyl)benzoyl]propyleneimine,
Oil
¹H-NMR (CDCl₃) δ: 1.29 (6H, t, J=7.0 Hz), 1.40 (3H, d, J=5.9 Hz), 2.14 (1H, d, J=3.7 Hz), 2.51-2.64 (2H, m), 2.87-3.10 (1H, m), 7.33-7.46 (2H, m), 7.84 (1H, dt, J=7.0, 1.8 Hz). 7.91 (1H, s).

Reference Example Compound 8-13

N-(4-fluoro-3-methylbenzoyl)propyleneimine,
Oil
¹H-NMR (CDCl₃) δ: 1.39 (3H, d, J=5.4 Hz), 2.14 (1H, d, J=3.4 Hz), 2.33 (3H, s), 2.51-2.61 (2H, m), 7.06 (1H, t, J=8.8 Hz), 7.81-7.90 (2H, m).

Reference Example Compound 8-14

N-(3-fluorobenzoyl)propyleneimine,
Oil
¹H-NMR (CDCl₃) δ: 1.40 (3H, d, J=5.5 Hz), 2.16 (1H, d, J=3.3 Hz), 2.52-2.68 (2H, m), 7.25 (1H, ddd, J=1.1, 2.6, 8.4

Hz), 7.43 (1H, ddd, J=5.5, 7.7, 8.1 Hz), 7.69 (1H, ddd, J=1.5, 2.6, 8.1 Hz), 7.81 (1H, ddd, J=1.1, 1.5, 7.7 Hz).

Reference Example Compound 8-15

N-(3-methoxybenzoyl)propyleneimine,
Oil
$^1$H-NMR (CDCl$_3$) δ: 1.40 (3H, d, J=5.9 Hz), 2.14 (1H, d, J=2.9 Hz), 2.52-2.65 (2H, m), 3.86 (3H, s), 7.10 (1H, ddd, J=1.1, 2.6, 8.4 Hz), 7.37 (1H, dd, J=8.4, 7.3 Hz), 7.55 (1H, dd, J=1.5, 2.6 Hz), 7.63 (1H, ddd, J=1.1, 1.5, 7.3 Hz).

Reference Example Compound 8-16

N-(4-methoxyphenyl)propyleneimine,
Oil
$^1$H-NMR (CDCl$_3$) δ: 1.39 (3H, d, J=5.9 Hz), 2.11 (1H, d, J=3.3 Hz), 2.50-2.63 (2H, m), 3.87 (3H, s), 6.94 (2H, d, J=9.2 Hz), 8.00 (1H, d, J=9.2 Hz).

Reference Example 9

2-fluoro-4-methylpyridine
This was synthesized according to a method described in Journal of Medicinal Chemistry, 33, 1667-1675, 1990.
m.p. 82-86° C. (10 kPa).

Reference Example 10

2-phenylmethyloxy-4-methylpyridine
Sodium hydride (60% paraffin dispersion, 5.0 g, 120 mmol) was washed with hexane (5 mL) twice, and suspended in tetrahydrofuran (200 mL). To this suspension was added dropwise a solution of benzyl alcohol (14 g, 120 mol) in tetrahydrofuran (50 mL) at 0° C., and the mixture was allowed to warm to room temperature and stirred for 15 minutes. To this solution was added a solution of 2-bromo-4-methylpyridine (20 mL, 110 mol) in tetrahydrofuran (50 mL), and the mixture was heated to reflux for 14 hours. Water (200 mL) was added to the reaction mixture, and extracted with ethyl acetate. The extracted solution was dried, and the solvent was distilled off. The crude product was distilled under reduced pressure to obtain a title compound (13 g, yield 67%).
b.p. 116-118° C. (400 Pa).
$^1$H-NMR (CDCl$_3$) δ: 2.30 (3H, s), 5.37 (2H, s), 6.63 (1H, s), 6.72 (1H, d, J=5.1 Hz), 7.29-7.50 (5H, m), 8.03 (1H, d, J=5.1 Hz).

Reference Example 11

2-tert-butoxycarbonylamino-4-methylpyridine
It was synthesized according to a method described in Synthesis, pp. 877 to 882, 1996 or Journal of Organic Chemistry, 61, pp. 4810 to 4811, 1996.

Reference Example 12

2-(2-fluoro-4-pyridyl)-1-(3-methylphenyl)ethanone
Under an argon atmosphere, a solution of diisopropylamine (44 mL, 0.31 mol) in anhydrous tetrahydrofuran (300 mL) was cooled to −78° C., and to this was added dropwise a 1.6 M n-butyllithium hexane solution (190 mL, 0.31 mol) with stirring. After completion of the addition, the solution was stirred for 10 minutes, subsequently, a solution of 2-fluoro-4-methylpyridine (34.5 g, 0.31 mol) in anhydrous tetrahydrofuran (30 mL) was added. The reaction mixture was stirred for 30 minutes at −10° C. The reaction solution was cooled to −78° C., and a solution of N-(3-methylbenzoyl)propyleneimine (52 g, 0.30 mol) in anhydrous tetrahydrofuran (30 mL) was added dropwise. After completion of the addition, the mixture was stirred for 2 hours at room temperature. To the reaction mixture was added water (100 mL), and extracted with ethyl acetate. The extracted solution was washed with water, dried, then, the solvent was distilled off. The residue was recrystallized from isopropyl ether to obtain a title compound (35 g, yield 52%).
m.p. 66-67° C.

Reference Example 13

The following reference example compounds 13-1 to 13-3 were synthesized according to Reference Example 12, using N-(3-methoxybenzoyl)propyleneimine, N-(4-fluorobenzoyl)propyleneimine and N-(3-chlorobenzoyl)propyleneimine instead of N-(3-methylbenzoyl)propyleneimine.

Reference Example Compound 13-1

2-(2-fluoro-4-pyridyl)-1-(3-methoxyphenyl)ethanone
Oil
$^1$H-NMR (CDCl$_3$) δ: 3.86 (3H, s), 4.31 (2H, s), 6.86 (1H, s), 7.03-7.19 (2H, m), 7.31-7.59 (3H, m), 8.18 (1H, d, J=5.6 Hz).

Reference Example Compound 13-2

1-(4-fluorophenyl)-2-(2-fluoro-4-pyridyl)ethanone
m.p. 100-101° C.

Reference Example Compound 13-3

1-(3-chlorophenyl)-2-(2-fluoro-4-pyridyl)ethanone
m.p. 84-86° C.

Reference Example 14

1-(3-methylphenyl)-2-(2-methyl-4-pyridyl)ethanone
A solution of diisopropylamine (112 mL) in anhydrous tetrahydrofuran (760 mL) was cooled to −50° C., and to this was added dropwise a 1.6 M n-butyllithium hexane solution (500 mL) with stirring. After completion of the addition, the solution was stirred for 10 minutes, subsequently, a solution of 2,4-lutidine (87.9 mL) in anhydrous tetrahydrofuran (76 mL) was added dropwise at −30° C. The reaction mixture was stirred for 1 hour, then, a solution of N-(3-methylbenzoyl) propyleneimine (134 g) in anhydrous tetrahydrofuran (76 mL) was added dropwise at −78° C. After completion of the addition, the mixture was stirred for 2 hours at −78° C. The reaction mixture was allowed to warm to room temperature, to this was added water (800 mL), and extracted with ethyl acetate. The extracts were washed with water, dried, then, the solvent was distilled off. The resulted residue was crystallized from isopropyl ether-hexane to obtain a title compound (156 g, yield 91%).
m.p. 56-57° C.

Reference Example 15

The following reference example compounds 15-1 and 15-2 were synthesized according to Reference Example 14, using N-(3,5-dimethylbenzoyl)propyleneimine and N-(4-fluorobenzoyl)propyleneimine instead of N-(3-methylbenzoyl)propyleneimine.

Reference Example Compound 15-1

1-(3,5-dimethylphenyl)-2-(2-methyl-4-pyridyl)ethanone
Oil
$^1$H-NMR (CDCl$_3$) δ: 2.38 (6H, s), 2.54 (3H, s), 4.21 (2H, s), 6.98-7.10 (1H, m), 7.01 (1H, m), 7.06 (1H, s), 7.23 (1H, s), 7.60 (2H, s), 8.42-8.45 (1H, m).

Reference Example Compound 15-2

2-(2-methyl-4-pyridyl)-1-(4-fluorophenyl)ethanone
m.p. 79-81° C.

Reference Example 16

The following reference example compounds 16-1 and 16-2 were synthesized according to Reference Examples 14 and 15, using γ-choline instead of 2,4-lutidine.

Reference Example Compound 16-1

2-(2,6-dimethyl-4-pyridyl)-1-(3-methylphenyl)ethanone
m.p. 46-48° C.

Reference Example Compound 16-2

1-(3,5-dimethylphenyl)-2-(2,6-dimethyl-4-pyridyl)ethanone
m.p. 135-136° C.

Reference Example 17

2-(2-tert-butoxycarbonylamino-4-pyridyl)-1-(4-methoxyphenyl)ethanone
A solution of 2-tert-butoxycarbonylamino-4-methylpyridine (20 g, 97 mmol) in anhydrous tetrahydrofuran (300 mL) was cooled to −78° C., and to this was added dropwise a 1.6 M n-butyllithium hexane solution (140 mL, 0.23 mol) with stirring. After completion of the addition, the solution was stirred for 30 minutes at 0° C., then, the solution was cooled to −78° C. A solution of N-(4-methoxybenzoyl)propyleneimine (25 g, 0.13 mol) in anhydrous tetrahydrofuran (50 mL) was added dropwise. After completion of the addition, the reaction mixture was stirred for 2 hours at room temperature. To the reaction mixture was added water (100 mL) and isopropyl ether (300 mL), and the resulted crude crystal was filtrated. This crude crystal was recrystallized from tetrahydrofuran-hexane to obtain a title compound (23 g, yield: 69%).
m.p. 187-190° C.

Reference Example 18

The following reference example compounds 18-1 to 18-15 were synthesized according to Reference Example 17, using N-(3-methylbenzoyl)propyleneimine, N-(3,5-dimethylbenzoyl)propyleneimine, N-(3-chlorobenzoyl)propyleneimine, N-benzoylpropyleneimine, N-(4-fluorobenzoyl)propyleneimine, N-[3-(trifluoromethyl)benzoyl]propyleneimine, N-(3-bromobenzoyl)propyleneimine, N-[4-(methylthio)benzoyl]propyleneimine, N-(2-thiophenecarbonyl)propyleneimine, N-(3-propylbenzoyl)propyleneimine, N-[3-(1-methylethyl)benzoyl]propyleneimine, N-(4-fluoro-3-methylbenzoyl)propyleneimine, N-(3-fluorobenzoyl)propyleneimine, N-(4-chlorobenzoyl)propyleneimine and N-(3-ethylbenzoyl)propyleneimine instead of N-(4-methoxybenzoyl)propyleneimine.

Reference Example Compound 18-1

2-(2-tert-butoxycarbonylamino-4-pyridyl)-1-(3-methylphenyl)ethanone
m.p. 144-146° C.

Reference Example Compound 18-2

2-(2-tert-butoxycarbonylamino-4-pyridyl)-1-(3,5-dimethylphenyl)ethanone
m.p. 133-136° C.

Reference Example Compound 18-3

2-(2-tert-butoxycarbonylamino-4-pyridyl)-1-(3-chlorophenyl)ethanone
m.p. 152-153° C.

Reference Example Compound 18-4

2-(2-tert-butoxycarbonylamino-4-pyridyl)-1-phenylethanone
m.p. 162-163° C.

Reference Example Compound 18-5

2-(2-tert-butoxycarbonylamino-4-pyridyl)-1-(4-fluorophenyl)ethanone
m.p. 139-141° C.

Reference Example Compound 18-6

2-(2-tert-butoxycarbonylamino-4-pyridyl)-1-[3-(trifluoromethyl)phenyl]ethanone
m.p. 149-150° C.

Reference Example Compound 18-7

1-(3-bromophenyl)-2-(2-tert-butoxycarbonylamino-4-pyridyl)ethanone
m.p. 132-133° C.

Reference Example Compound 18-8

2-(2-tert-butoxycarbonylamino-4-pyridyl)-1-[4-(methylthio)phenyl]ethanone
m.p. 177-178° C.

Reference Example Compound 18-9

2-(2-tert-butoxycarbonylamino-4-pyridyl)-1-(2-thienyl)ethanone
m.p. 161-162° C.

Reference Example Compound 18-10

2-(2-tert-butoxycarbonylamino-4-pyridyl)-1-(3-propylphenyl)ethanone
m.p. 110-111° C.

Reference Example Compound 18-11

2-(2-tert-butoxycarbonylamino-4-pyridyl)-1-[(1-methylethyl)phenyl]ethanone
m.p. 176-177° C.

Reference Example Compound 18-12

2-(2-tert-butoxycarbonylamino-4-pyridyl)-1-(4-fluoro-3-methylphenyl)ethanone
m.p. 143-144° C.

Reference Example Compound 18-13

2-(2-tert-butoxycarbonylamino-4-pyridyl)-1-(3-fluorophenyl)ethanone
m.p. 164-165° C.

Reference Example Compound 18-14

2-(2-tert-butoxycarbonylamino-4-pyridyl)-1-(4-chlorophenyl)ethanone
m.p. 155-156° C.

Reference Example Compound 18-15

2-(2-tert-butoxycarbonylamino-4-pyridyl)-1-(3-ethylphenyl)ethanone
m.p. 122-123° C.

Reference Example 19

1-(3,5-dimethylphenyl)-2-(2-phenylmethyloxy-4-pyridyl)ethanone
A solution of diisopropylamine (9.6 mL, 69 mmol) in anhydrous tetrahydrofuran (60 mL) was cooled to −50° C., and to this was added dropwise a 1.6 M n-butyllithium hexane solution (43 mL, 69 mmol) with stirring. After completion of the addition, the solution was stirred for 10 minutes, subsequently, a solution of 2-phenylmethyloxy-4-methylpyridine (12 g, 62 mmol) in anhydrous tetrahydrofuran (12 mL) was dropped at −30° C. After stirring for 1 hour, a solution of N-(3,5-dimethylbenzoyl)propyleneimine (12 g, 62 mmol) in anhydrous tetrahydrofuran (12 mL) was added dropwise at −30° C. After completion of the addition, the mixture was allowed to warm to room temperature gradually, and stirred for 2 hours. Water (60 mL) was added to the reaction mixture, and extracted with ethyl acetate. The extracted solution was washed with water, dried, then, the solvent was distilled off. The residue was purified by silica gel column chromatography (hexane-ethyl acetate=5:1) to obtain a title compound (9.1 g, yield 44%).
Oil
$^1$H-NMR (CDCl$_3$) δ: 2.37 (6H, s), 4.20 (2H, s), 5.37 (2H, s), 6.72 (1H, s), 6.81 (1H, d, J=5.1 Hz), 7.22 (1H, s), 7.30-7.49 (5H, m), 7.59 (2H, s), 8.12 (1H, d, J=5.1 Hz).

Reference Example 20

2-bromo-2-(2-tert-butoxycarbonylamino-4-pyridyl)-1-(4-methoxyphenyl)ethanone hydrobromide
To a solution of 2-(2-tert-butoxycarbonylamino-4-pyridyl)-1-(4-methoxyphenyl)ethanone (0.36 g, 1.1 mmol) in acetic acid (5 mL) was added bromine (0.058 mL, 1.1 mmol), and the mixture was stirred for 1 hour at room temperature. The reaction mixture was concentrated, and the residue was washed with isopropyl ether to obtain a title compound (0.44 g, yield 82%).
Amorphous.
$^1$H-NMR (CDCl$_3$) δ: 1.55 (6H, s), 3.92 (3H, s), 6.35 (1H, s), 6.99-7.03 (2H, m), 7.66 (1H, dd, J=6:6, 1.8 Hz), 8.02-8.07 (2H, m), 8.20 (1H, d, J=6.6 Hz), 8.70 (2H, d, J=1.8 Hz), 11.02 (1H, br s).

Reference Example 21

The following reference example compounds 21-1 to 21-4 were synthesized according to Reference Example 20, using 2-(2-tert-butoxycarbonylamino-4-pyridyl)-1-(3-methylphenyl)ethanone, 2-(2-tert-butoxycarbonylamino-4-pyridyl)-1-(3,5-dimethylphenyl)ethanone, 1-(3,5-dimethylphenyl)-2-(2-phenylmethyloxy-4-pyridyl)ethanone and 1-(3-bromophenyl)-2-(2-tert-butoxycarbonylamino-4-pyridyl) ethanone, respectively, instead of 2-(2-tert-butoxycarbonylamino-4-pyridyl)-1-(4-methoxyphenyl) ethanone.

Reference Example Compound 21-1

2-bromo-2-(2-tert-butoxycarbonylamino-4-pyridyl)-1-(3-methylphenyl)ethanone hydrobromide
This was used in the subsequent reaction without purification.

Reference Example Compound 21-2

2-bromo-2-(2-tert-butoxycarbonylamino-4-pyridyl)-1-(3,5-dimethylphenyl)ethanone hydrobromide
This was used in the subsequent reaction without purification.

Reference Example Compound 21-3

2-bromo-1-(3,5-dimethylphenyl)-2-(2-phenylmethyloxy-4-pyridyl)ethanone hydrobromide
m.p. 88 to 90° C.

Reference Example Compound 21-4

2-bromo-1-(3-bromophenyl)-2-(2-tert-butoxycarbonylamino-4-pyridyl)ethanone hydrobromide
This was used in the subsequent reaction without purification.

Reference Example 22

2-bromo-1-(3-methylphenyl)-2-(2-methyl-4-pyridyl)ethanone hydrobromide
1-(3-methylphenyl)-2-(2-methyl-4-pyridyl)ethanone (150 g) was dissolved in acetic acid (450 mL), bromine (34.3 mL) was added to this, and the mixture was stirred for 3 hours at 70° C. The reaction solution was cooled by ice water, and the deposited crystal was filtrated off. The crystal was washed with ethyl acetate to obtain a title compound (168 g, yield 66%).
m.p. 144-146° C.

Reference Example 23

The following reference example compounds 23-1 to 23-22 were synthesized according to Reference Example 22, using 2-(2-fluoro-4-pyridyl)-1-(3-methylphenyl)ethanone, 2-(2-fluoro-4-pyridyl)-1-(3-methoxyphenyl)ethanone, 2-(2-fluoro-4-pyridyl)-1-(4-fluorophenyl)ethanone, 2-(2-fluoro-4-pyridyl)-1-(3-chlorophenyl)ethanone, 1-(3,5-dimethylphenyl)-2-(2-methyl-4-pyridyl)ethanone, 2-(2-methyl-4-pyridyl)-1-(4-fluorophenyl)ethanone, 2-(2,6-dimethyl-4-pyridyl)-1-(3-methylphenyl)ethanone, 1-(3,5-dimethylphenyl)-2-(2,6-dimethyl-4-pyridyl)ethanone, 2-(2-tert-butoxycarbonylamino-4-pyridyl)-1-(3-methylphenyl) ethanone, 2-(2-tert-butoxycarbonylamino-4-pyridyl)-1-(3- chlorophenyl)ethanone, 2-(2-tert-butoxycarbonylamino-4-pyridyl)-1-phenylethanone, 2-(2-tert-butoxycarbonylamino-4-pyridyl)-1-(4-fluorophenyl)ethanone, 2-(2-tert-butoxycarbonylamino-4-pyridyl)-1-[3-(trifluoromethyl)phenyl]ethanone, 2-(2-tert-butoxycarbonylamino-4-pyridyl)-1-(3-bromophenyl)ethanone, 2-(2-tert-butoxycarbonylamino-4-pyridyl)-1-[4-(methylthio)phenyl]ethanone, 2-(2-tert-butoxycarbonylamino-4-pyridyl)-1-(2-thienyl)ethanone, 2-(2-tert-butoxycarbonylamino-4-pyridyl)-1-(3-propylphenyl)ethanone, 2-(2-tert-butoxycarbonylamino-4-pyridyl)-1-[(1-methylethyl)phenyl]ethanone, 2-(2-tert-butoxycarbonylamino-4-pyridyl)-1-(3-fluorophenyl)ethanone, 2-(2-tert-butoxycarbonylamino-4-pyridyl)-1-(4-chlorophenyl)ethanone, 2-(2-tert-butoxycarbonylamino-4-pyridyl)-1-(3-ethylphenyl)ethanone and 2-(2-tert-butoxycarbonylamino-4-pyridyl)-1-(4-fluoro-3-methylphenyl)ethanone, respectively, instead of 1-(3-methylphenyl)-2-(2-methyl-4-pyridyl)ethanone.

Reference Example Compound 23-1

2-bromo-2-(2-fluoro-4-pyridyl)-1-(3-methylphenyl)ethanone hydrobromide
This was used in the subsequent reaction without purification.

Reference Example Compound 23-2

2-bromo-2-(2-fluoro-4-pyridyl)-1-(3-methoxyphenyl)ethanone hydrobromide
This was used in the subsequent reaction without purification.

Reference Example Compound 23-3

2-bromo-2-(2-fluoro-4-pyridyl)-1-(4-fluorophenyl)ethanone hydrobromide
Amorphous
$^1$H-NMR (DMSO-$d_6$) δ: 7.16 (1H, s), 7.37-7.54 (4H, m), 8.11-8.24 (2H, m), 8.30 (1H, d, J=5.0 Hz).

Reference Example Compound 23-4

2-bromo-1-(3-chlorophenyl)-2-(2-fluoro-4-pyridyl)ethanone hydrobromide
Amorphous
$^1$H-NMR (DMSO-$d_6$) δ: 7.19 (1H, s), 7.38 (1H, s), 7.52-7.56 (1H, m), 7.64 (1H, t, J=8.0 Hz), 7.77-7.82 (1H, m), 8.05-8.09 (1H, m), 8.16 (1H, t, J=1.8 Hz), 8.32 (1H, d, J=5.2 Hz), 10.23 (1H, br s).

Reference Example Compound 23-5

2-bromo-1-(3,5-dimethylphenyl)-2-(2-methyl-4-pyridyl)ethanone hydrobromide
This was used in the subsequent reaction without purification.

Reference Example Compound 23-6

2-bromo-1-(4-fluorophenyl)-2-(2-methyl-4-pyridyl)ethanone hydrobromide
Amorphous
$^1$H-NMR (DMSO-$d_6$) δ: 3.02 (3H, s), 6.68 (1H, s), 7.23 (2H, t, J=8.4 Hz), 8.05 (1H, s), 8.10-8.22 (3H, m), 8.65 (1H, br s).

Reference Example Compound 23-7

2-bromo-2-(2,6-dimethyl-4-pyridyl)-1-(3-methylphenyl)ethanone hydrobromide
This was used in the subsequent reaction without purification.

Reference Example Compound 23-8

2-bromo-1-(3,5-dimethylphenyl)-2-(2,6-dimethyl-4-pyridyl)ethanone hydrobromide
m.p. 208-212° C.

Reference Example Compound 23-9

2-(2-amino-4-pyridyl)-2-bromo-1-(3-methylphenyl)ethanone hydrobromide
m.p. 182-185° C.

Reference Example Compound 23-10

2-(2-amino-4-pyridyl)-2-bromo-1-(3-chlorophenyl)ethanone hydrobromide
m.p. 199-200° C.

Reference Example Compound 23-11

2-(2-amino-4-pyridyl)-2-bromo-1-phenylethanone hydrobromide
m.p. 155-156° C.

Reference Example Compound 23-12

2-(2-amino-4-pyridyl)-2-bromo-1-(4-fluorophenyl)ethanone hydrobromide
m.p. 171-172° C.

Reference Example Compound 23-13

2-(2-amino-4-pyridyl)-2-bromo-1-[3-(trifluoromethyl)phenyl]ethanone hydrobromide
m.p. 174-175° C.

Reference Example Compound 23-14

2-(2-amino-4-pyridyl)-2-bromo-1-(3-bromophenyl)ethanone hydrobromide
This was used in the subsequent reaction without purification.

Reference Example Compound 23-15

2-(2-amino-4-pyridyl)-2-bromo-1-[4-(methylthio)phenyl]ethanone hydrobromide
Amorphous
$^1$H-NMR (DMSO-$d_6$) δ: 6.96-7.09 (2H, m), 7.24 (1H, s), 7.32-7.43 (1H, m), 7.98 (1H, d, J=6.6 Hz), 8.12-8.36 (2H, m).

Reference Example Compound 23-16

2-(2-amino-4-pyridyl)-2-bromo-1-(2-thienyl)ethanone hydrobromide
Amorphous

Reference Example Compound 23-17

2-(2-amino-4-pyridyl)-2-bromo-1-(3-propylphenyl)ethanone hydrobromide
Amorphous
$^1$H-NMR (DMSO-d$_6$) δ: 0.90 (3H, t, J=7.3 Hz), 1.53-1.73 (2H, m), 2.65 (2H, t, J=7.5 Hz), 3.40-(2H, br s), 6.97 (1H, dd, J=1.8, 6.6 Hz), 7.13 (1H, s), 7.19 (1H, s), 7.46-7.59 (2H, m), 7.89-7.99 (3H, m), 8.14 (1H, br d, J=6.6 Hz).

Reference Example Compound 23-18

2-(2-amino-4-pyridyl)-2-bromo-1-[3-(1-methylethyl)phenyl]ethanone hydrobromide
Amorphous
$^1$H-NMR (DMSO-d$_6$) δ: 1.24 (6H, d, J=6.6 Hz), 3.00 (1H, septet, J=6.6 Hz), 7.15 (1H, s), 7.17 (1H, s), 7.46-7.65 (2H, m), 7.88-7.98 (4H, m), 8.09 (1H, br s).

Reference Example Compound 23-19

2-(2-amino-4-pyridyl)-2-bromo-1-(3-fluorophenyl)ethanone hydrobromide
m.p. 206-207° C.

Reference Example Compound 23-20

2-(2-amino-4-pyridyl)-2-bromo-1-(4-chlorophenyl)ethanone hydrobromide
m.p. 202-203° C.

Reference Example Compound 23-21

2-(2-amino-4-pyridyl)-2-bromo-1-(3-ethylphenyl)ethanone hydrobromide
m.p. 46-47° C.

Reference Example Compound 23-22

2-(2-amino-4-pyridyl)-2-bromo-1-(4-fluoro-3-methylphenyl)ethanone hydrobromide
m.p. 225-226° C.

Reference Example 24

4-(methylthio)thiobenzamide
4-(methylthio)benzonitrile (12 g, 80 mmol) was dissolved in a solution of 4 N hydrogen chloride in ethyl acetate (130 mL). To this solution was added dithiophosphoric acid O,O-diethyl ester(15 mL, 88 mmol), and the mixture was stirred for 22 hours at room temperature. Water (100 mL) was added to the reaction mixture, and extracted with ethyl acetate. The insoluble material was filtrated off, then, the filtrate was washed with brine, dried, then, the solvent was distilled off. The residue was recrystallized from ethyl acetate to obtain a title compound (10 g, yield 67%).
m.p. 176-178° C.

Reference Example 25

The following reference example compounds 25-1 to 25-10 were synthesized according to Reference Example 24, using 2-chlorobenzonitrile, 4-chlorobenzonitrile, 2-fluorobenzonitrile, 4-fluorobenzonitrile, 2,4-difluorobenzonitrile, butyronitrile, valeronitrile, 3-phenylpropionitrile, 4-phenylbutyronitrile, 1-methylpiperidine-4-carbonitrile, respectively, instead of 4-(methylthio)benzonitrile.

Reference Example Compound 25-1

2-chlorothiobenzamide
m.p. 58-59° C.

Reference Example Compound 25-2

4-chlorothiobenzamide
m.p. 130-131° C.

Reference Example Compound 25-3

2-fluorothiobenzamide
m.p. 113-114° C.

Reference Example Compound 25-4

4-fluorothiobenzamide
m.p. 156-157° C.

Reference Example Compound 25-5

2,4-difluorothiobenzamide
m.p. 127-128° C.

Reference Example Compound 25-6 thiobutyramide
Oil
$^1$H-NMR (CDCl$_3$) δ: 0.99 (3H, t, J=7.6 Hz), 1.72-1.93 (2H, m), 2.64 (2H, t, J=7.6 Hz), 7.02 (1H, br s), 7.77 (1H, br s).

Reference Example Compound 25-7 thiovaleramide
Oil
$^1$H-NMR (CDCl$_3$) δ: 0.94 (3H, t, J=7.3 Hz), 1.31-1.49 (2H, m), 1.68-1.83 (2H, m), 2.67 (2H, t, J=7.7 Hz), 6.92 (1H, br s), 7.73 (1H, br s).

Reference Example Compound 25-8

3-phenyl(thiopropionamide)
m.p. 83-84° C.

Reference Example Compound 25-9

4-phenyl(thiobutyramide)
m.p. 60-61° C.

Reference Example Compound 25-10

1-methylpiperidine-4-carbothioamide
m.p. 216-220° C.

Reference Example 26 ethyl (4-phenyl-1-piperazinyl)carbothioylcarbamate
To a solution of ethyl isothiocyanatoformate (8.1 g, 62 mmol) in acetone (30 mL) was added 1-phenylpiperazine (10 g, 62 mmol), and the mixture was heated to reflux for 1 hour.

85

The reaction mixture was concentrated, and the crude crystal was recrystallized from ethyl acetate to obtain a title compound (13 g, yield 73%).
m.p. 134-135° C.

Reference Example 27

The following reference example compound 27 was synthesized according to Reference Example 26 using 1-methylpiperazine instead of 1-phenylpiperazine.

Reference Example Compound 27 ethyl (4-methyl-piperazinyl)carbothioylcarbamate
m.p. 155-157° C.

Reference Example 28

4-phenyl-1-piperazinecarbothioamide
Ethyl (4-phenyl-1-piperazinyl)carbothioylcarbamate (13 g, 44 mmol) was added to conc. hydrochloric acid (44 mL), and the mixture was stirred for 2 hours at 80° C. The reaction mixture was made basic with an 8N-aqueous sodium hydroxide solution, and the crystal was collected by filtration. The crystal was washed with water, and dried to obtain a title compound (6.1 g, yield 63%).
m.p. 178-179° C.

Reference Example 29

The following reference example compound 29 was synthesized according to Reference Example 28 using ethyl (4-methyl-1-piperazinyl)carbothioylcarbamate instead of ethyl (4-phenyl-1-piperazinyl)carbothioylcarbamate.

Reference Example Compound 29

4-methyl-1-piperazinecarbothioamide
m.p. 173-175° C.

Reference Example 30

3,3,3-trifluorothiopropionamide
To a solution of 3,3,3-trifluoropropionamide (2.00 g, 15.7 mmol) in anhydrous tetrahydrofuran (100 mL) was added a Lawesson's reagent (3.79 g, 9.37 mmol), and the mixture was heated under reflux for 2 hours. The mixture was cooled to room temperature, then, an aqueous saturated sodium hydrogen carbonate solution was added to the reaction mixture, and extracted with ethyl acetate. The extracts were dried, to distill off the solvent. The residue was purified by silica gel column chromatography (hexane-ethyl acetate=10:1 to 4:1) to give a title compound (1.85 g, yield: 82%).
Oil
$^1$H-NMR (CDCl$_3$) δ: 3.61 (2H, q, J=10.4 Hz), 6.70-8.00 (2H, m).

Reference Example 31

The following reference example compounds 31-1 and 31-2 were synthesized according to Reference Example 30, using ethyl 3-amino-3-oxopropanate and ethyl 2-amino-2-oxoacetate instead of 3,3,3-trifluoropropionamide.

Reference Example Compound 31-1 ethyl 3-amino-3-thioxopropanate
Oil

86

$^1$H-NMR (CDCl$_3$) δ: 1.31 (3H, t, J=7.1 Hz), 3.85 (2H, s), 4.22 (2H, q, J=7.1 Hz), 7.74 (1H, br s), 8.92 (1H, br s).

Reference Example Compound 31-2 ethyl 2-amino-2-thioxoacetate
$^1$H-NMR (CDCl$_3$) δ: 1.41 (3H, t, J=7.2 Hz), 4.38 (2H, q, J=7.2 Hz), 7:68 (1H, br s), 8.24 (1H, br s).

Reference Example 32

The following reference example compound 32 was synthesized according to Example 33 described later, using 4-(3-methylphenyl)-2-[4-(methylthio)phenyl]-5-(4-pyridyl)-1,3-thiazole instead of 4-(3,5-dimethylphenyl)-5-(2-methyl-4-pyridyl)-2-[4-(methylthio)phenyl]-1,3-thiazole.

Reference Example Compound 32

4-[4-(3-methylphenyl)-2-(4-methylsulfonylphenyl)-1,3-thiazol-5-yl]pyridine N-oxide
m.p. 196-197° C.

Reference Example 33

1-tert-butoxycarbonylpiperidine-4-carboxamide
To a solution of piperidine-4-carboxamide (5.0 g, 39 mmol) in water (30 mL) was added di-tert-butyl dicarbonate (9.2 mL, 40 mmol) slowly, and then the reaction mixture was stirred at room temperature for 24 hours. The resulting mixture was extracted with ethyl acetate, and the extracts were washed with brine, dried, and concentrated in vacuo. The residue was crystallized from ethyl acetate to give a title compound (6.9 g, yield 78%).
m.p. 163-165° C.

Reference Example 34

The following reference example compound 34 was synthesized according to Reference example 30, using 1-tert-butoxycarbonylpiperidine-4-carboxamide instead of 3,3,3-trifluoropropionamide.

Reference Example Compound 34

1-tert-butoxycarbonylpiperidine-4-carbothioamide
m.p. 129-131° C.

Reference Example 35

The following reference example compound 35 was synthesized according to Reference example 12, using N-(3-ethylbenzoyl)propyleneimine instead of N-(3-methylbenzoyl)propyleneimine

Reference Example Compound 35

1-(3-ethylphenyl)-2-(2-fluoro-4-pyridyl)ethanone
m.p. 59-60° C.

Reference Example 36

The following reference example compound 36 was synthesized according to Reference example 22, using 1-(3-ethylphenyl)-2-(2-fluoro-4-pyridyl)ethanone instead of 1-(3-methylphenyl)-2-(2-methyl-4-pyridyl)ethanone Reference Example Compound 36

2-bromo-1-(3-ethylphenyl)-2-(2-fluoro-4-pyridyl)ethanone hydrobromide
amorphous
$^1$H-NMR(DMSO-$d_6$) d: 1.22 (3H, t, J=7.6 Hz), 2.70 (2H, q, J=7.6 Hz), 7.19 (1H, s), 7.39 (1H, s), 7.45-7.58 (3H, m), 7.77 (1H, br s), 7.92-7.97 (2H, m), 8.30 (1H, d, J=5.6 Hz).

Reference Example 37 ethyl 2,2-difluoropropionate
To ethyl pyruvate (3.0 g, 26 mmol) was added dropwise dimethylaminosulfur trifluoride (3.4 mL, 26 mmol) over 1 hour and the reaction mixture was stirred at 60° C. for 4 hours. The resulting mixture was poured into ice-water and extracted with ethyl acetate. The extracts were washed with brine, dried, and concentrated under reduced pressure to give a title compound (1.2 g, yield 78%).
Oil
$^1$H-NMR(CDCl$_3$) d: 1.36 (3H, t, J=7.2 Hz), 1.81 (3H, t, J=19.0 Hz), 4.33 (2H, q, J=7.2 Hz).

Reference Example 38

2,2-difluoropropionic acid
A solution of ethyl 2,2-difluoropropionate (1.2 g, 8.8 mmol) methanol (26 mL) was added to 2N aqueous sodium hydroxide (26 mL) and the resulting mixture was stirred at room temperature for 14 hours. The reaction mixture was acidified with 2N hydrochloric acid and extracted with ether. The extracts were dried, and concentrated under reduced pressure to give a title compound (0.90 g, yield 92%).
Oil
$^1$H-NMR(CDCl$_3$) d: 1.85 (3H, t, J=19.0 Hz), 6.21 (1H, br s).

Reference Example 39

2,2-difluoropropionamide
To a solution of 2,2-difluoropropionic acid (7.8 g, 71 mmol) in tetrahydrofuran (80 mL) was added oxalyl chloride (6.6 mL, 78 mmol) at room temperature and then N,N-dimethylformamide (2 drops) was added to the solution. The reaction mixture was stirred at room temperature for 2 hours. The resulting solution was added dropwise to 25% aqueous ammonia at 0° C. over 15 minutes, and stirred for 1 hour. The reaction mixture was extracted with ethyl acetate. The extracts were dried, and concentrated under reduced pressure. The obtained crude mixture was crystallized from hexane to give a title compound (3.7 g, yield 49%).
m.p. 70-71° C.

Reference Example 40

The following reference example compound 40 was synthesized according to Reference example 24, using (methylthio)acetonitrile instead of 4-(methylthio)benzonitrile.

Reference Example Compound 40

(methylthio)thioacetamide
m.p. 66-67° C.

Reference Example 41

The following reference example compound 41-1 and 41-2 were synthesized according to Reference example 30, using 3-(methylthio)propionamide and 2,2-difluoropropionamide instead of 3,3,3-trifluoropropionamide.

Reference Example Compound 41-1

3-(methylthio)thiopropionamide
Oil
$^1$H-NMR(CDCl$_3$) d: 2.17 (3H, s), 2.93 (4H, s), 7.52 (2H, br s).

Reference Example Compound 41-2

2,2-difluorothiopropionamide
Oil
$^1$H-NMR(CDCl$_3$) d: 1.98 (3H, t, J=18.5 HZ), 7.56 (1H, br s), 7.72 (1H, br s).

Reference Example 42

2-amino-1-methyl-2-oxoethyl benzoate
To a solution of 2-hydroxypropionamide (10.8 g, 121 mmol) in pyridine (40 mL) was added benzoyl chloride (14.2 mL, 122 mmol) at 0° C. and the reaction mixture was allowed to warm up to room temperature. The resulting mixture was stirred at room temperature for 3 hours and the solvent was removed under reduced pressure to give a residue. To the residue an aqueous sodium hydrogen carbonate solution was added and the mixture was extracted with ethyl acetate. The extracts were washed with an 1N hydrochloric acid twice and brine. The organic solution was dried, and concentrated under reduced pressure. The obtained crude crystal was recrystallized from ethyl acetate-hexane to give a title compound (17.9 g, yield 77%).
m.p. 116-117° C.

Reference Example 43

2-amino-1-methyl-2-thioxoethyl benzoate
To a solution of 2-amino-1-methyl-2-oxoethyl benzoate (10.0 g, 52.0 mmol) in 1,2-dimethoxyethane (90 mL) was added Lawesson's reagent (11.2 g, 27.7 mmol) at 0° C. and the reaction mixture was allowed to warm up to room temperature. The resulting mixture was stirred at room temperature for 24 hours and the precipitate was removed by filtration. The resulting solution was concentrated under reduced pressure to give a residue. The residue was dissolved in ethyl acetate and the solution was washed with brine. The organic solution was dried, and concentrated under reduced pressure to give a residue. The residue was purified by silica gel column chromatography (hexane-ethyl acetate=2:1) to obtain a crude crystal. The crude crystal was recrystallized from ethyl acetate-hexane to give a title compound (8.60 g, yield 79%).
m.p. 100-101° C.

Example 1

[5-(2-amino-4-pyridyl)-4-(4-methoxyphenyl)-1,3-thiazol-2-yl]amine
To a solution of 2-bromo-2-(2-tert-butoxycarbonylamino-4-pyridyl)-1-(4-methoxyphenyl)ethanone hydrobromide (synthesized from 2-(2-tert-butoxycarbonylamino-4-pyridyl)-1-(4-methoxyphenyl)ethanone (4.5 g, 13 mmol) according to the method described in Reference Example 20)

in acetonitrile (40 mL) were added thiourea (1.1 g, 14 mmol) and triethylamine (1.9 mL, 14 mmol), and the mixture was stirred for 2 hours at 80° C. The reaction mixture was cooled to room temperature, then, concentrated. To the residue was added a saturated aqueous sodium hydrogen carbonate solution (200 mL), and the resulting solid was filtrated, and washed with water. To this solid was added 2N-hydrochloric acid (35 mL), and the mixture was stirred for 45 minutes at 100° C. The reaction mixture was cooled to room temperature, then, 8N-sodium hydroxide aqueous solution (10 mL) and aqueous sodium hydrogen carbonate solution (100 mL) were added. The resulted crude crystal was filtrated, and washed with water. This crude crystal was recrystallized from ethanol to obtain a title compound (2.7 g, yield 69%).

m.p. 251 to 254° C.

Example 2

[5-(2-tert-butoxycarbonylamino-4-pyridyl)-3-(4-methoxyphenyl)-1,3-thiazol-2-yl]amine To a solution of 2-(2-tert-butoxycarbonylamino-4-pyridyl)-1-(4-methoxyphenyl)ethanone (6.1 g, 18 mmol) in acetic acid (100 mL) was added bromine (1.0 mL), and the mixture was stirred for 2 hours at room temperature. The reaction mixture was concentrated. The residue was dissolved in acetonitrile (100 mL), and to this solution were added thiourea (1.1 g, 14 mmol) and triethylamine (3.0 mL, 22 mmol), and the mixture was stirred at room temperature for 2 hours, then, concentrated. To the residue was added a saturated aqueous sodium hydrogen carbonate solution (50 mL), and the resulted solid was filtrated, washed with water, and recrystallized from ethanol to give a title compound (1.7 g, yield: 24%).

m.p. 270° C. or more (dec.)

Example 3

[5-(2-tert-butoxycarbonylamino)-4-pyridyl]-2-ethyl-4-(3-methylphenyl)-1,3-thiazole A solution of 2-bromo-2-(2-tert-butoxycarbonylamino-4-pyridyl)-1-(3-methylphenyl)ethanone hydrobromide (synthesized from 2-(2-tert-butoxycarbonylamino-4-pyridyl)-1-(3-methylphenyl)ethanone (5.0 g, 24 mmol) according to the method described in Reference Example 21) and thiopropionamide (1.4 g, 16 mmol) in N,N-dimethylformamide (50 mL) was stirred for 14 hours at room temperature. To the reaction mixture was poured an aqueous sodium hydrogen carbonate solution, and extracted with ethyl acetate. The extracts were washed with water, then, dried and concentrated. The residue was purified by silica gel column chromatography (hexane-ethyl acetate=4:1) to obtain a crystal. This crystal was washed with hexane to obtain a title compound (2.43 g, yield 39%).

m.p. 162-163° C.

Example 4

The following example compounds 4-1 and 4-2 were synthesized according to Example 3, using thioacetamide and 4-(methylthio)thiobenzamide instead of thiopropionamide.

Example Compound 4-1

5-[2-(tert-butoxycarbonylamino)-4-pyridyl]-2-methyl-4-(3-methylphenyl)-1,3-thiazole This was used in the subsequent reaction without purification.

Example Compound 4-2

[5-[2-(tert-butoxycarbonylamino)-4-pyridyl]-4-(3-methylphenyl)-2-[4-(methylthio)phenyl]-1,3-thiazole This was used in the subsequent reaction without purification.

Example 5

The following example compound 5 was synthesized according to Example 4, using 2-bromo-2-(2-tert-butoxycarbonylamino-4-pyridyl)-1-(4-methoxyphenyl)ethanone hydrobromide instead of 2-bromo-2-(2-tert-butoxycarbonylamino-4-pyridyl)-1-(3-methylphenyl)ethanone hydrobromide.

Example Compound 5

5-[2-(tert-butoxycarbonylamino)-4-pyridyl]-4-(4-methoxyphenyl)-2-methyl-1,3-thiazole This was used in the subsequent reaction without purification.

Example 6

[5-(2-fluoro-4-pyridyl)-4-(3-methylphenyl)-1,3-thiazol-2-yl]amine

To a mixture of 2-bromo-2-(2-fluoro-4-pyridyl)-1-(3-methylphenyl)ethanone hydrobromide and thiourea (3.03 g, 39.8 mmol) in acetonitrile (50 mL) was added triethylamine (5.2 mL, 37.3 mmol), and the mixture was stirred for 2 hours at 80° C. Aqueous sodium hydrogen carbonate solution was poured into the reaction mixture, and the deposited solid was collected by filtration. The resulted solid was washed with water, then, dried. The crude crystal was recrystallized from ethanol to obtain a title compound (3.67 g, yield 35%).

m.p. 214-218° C.

Example 7

The following example compounds 7-1 to 7-8 were synthesized according to Example 6, using 2-bromo-2-(2-fluoro-4-pyridyl)-1-(3-methoxyphenyl)ethanone hydrobromide, 2-bromo-1-(3-chlorophenyl)-2-(2-fluoro-4-pyridyl)ethanone hydrobromide, 2-bromo-1-(4-fluorophenyl)-2-(2-fluoro-4-pyridyl)ethanone hydrobromide, 2-bromo-1-(3-methylphenyl)-2-(2-methyl-4-pyridyl)ethanone hydrobromide, 2-bromo-1-(3,5-dimethylphenyl)-2-(2-methyl-4-pyridyl)ethanone hydrobromide, 2-bromo-1-(3,5-dimethylphenyl)-2-(2,6-dimethyl-4-pyridyl)ethanone hydrobromide and 2-bromo-1-(3,5-dimethylphenyl)-2-(2,6-dimethyl-4-pyridyl)ethanone hydrobromide, 2-bromo-1-(4-fluorophenyl)-2-(2-methyl-4-pyridyl)ethanone hydrobromide, respectively, instead of 2-bromo-2-(2-fluoro-4-pyridyl)-1-(3-methylphenyl)ethanone hydrobromide.

Example Compound 7-1

[5-(2-fluoro-4-pyridyl)-4-(3-methoxyphenyl)-1,3-thiazol-2-yl]amine m.p. 190-191° C.

Example Compound 7-2

4-(3-chlorophenyl)-5-(2-fluoro-4-pyridyl)-1,3-thiazol-2-yl]amine m.p. 227-228° C.

Example Compound 7-3

[4-(4-fluorophenyl)-5-(2-fluoro-4-pyridyl)-1,3-thiazol-2-yl]amine
m.p. 243-245° C.

Example Compound 7-4

[4-(3-methylphenyl)-5-(2-methyl-4-pyridyl)-1,3-thiazol-2-yl]amine
m.p. 205-206° C.

Example Compound 7-5

[4-(3,5-dimethylphenyl)-5-(2-methyl-4-pyridyl)-1,3-thiazol-2-yl]amine
m.p. 219-220° C.

Example Compound 7-6

[5-(2,6-dimethyl-4-pyridyl)-3-(3-methylphenyl)-1,3-thiazol-2-yl]amine
m.p. 214-216° C.

Example Compound 7-7

[4-(3,5-dimethylphenyl)-5-(2,6-dimethyl-4-pyridyl)-1,3-thiazol-2-yl]amine
m.p. 256-258° C.

Example Compound 7-8

[4-(4-fluorophenyl)-5-(2-methyl-4-pyridyl)-1,3-thiazol-2-yl]amine
m.p. 233-234° C.

Example 8

The following example compound 8 was synthesized according to Example 6, using N-methylthiourea instead of thiourea.

Example Compound 8

N-methyl-[5-(2-fluoro-4-pyridyl)-4-(3-methylphenyl)-1,3-thiazol-2-yl]amine
m.p. 186-187° C.

Example 9

The following example compound 9 was synthesized according to Example 8, using 2-bromo-2-(2-methyl-4-pyridyl)-1-(3-methylphenyl)ethanone hydrobromide instead of 2-bromo-2-(2-fluoro-4-pyridyl)-1-(3-methylphenyl)ethanone hydrobromide.

Example Compound 9

N-methyl-[4-(3-methylphenyl)-5-(2-methyl-4-pyridyl)-1,3-thiazol-2-yl]amine
m.p. 164-165° C.

Example 10

The following example compound 10 was synthesized according to Example 9, using N,N-dimethylthiourea instead of N-methylthiourea.

Example Compound 10

N,N-dimethyl-[4-(3-methylphenyl)-5-(2-methyl-4-pyridyl)-1,3-thiazol-2-yl]amine
m.p. 77-79° C.

Example 11

2-ethyl-5-(2-fluoro-4-pyridyl)-4-(3-methylphenyl)-1,3-thiazole
A solution of 2-bromo-2-(2-fluoro-4-pyridyl)-1-(3-methylphenyl)ethanone hydrobromide (11 g, 29 mmol) and thiopropionamide (2.7 g, 30 mmol) in N,N-dimethylformamide (30 mL) was stirred for 14 hours at room temperature. Aqueous sodium hydrogen carbonate solution was added to the reaction mixture, and extracted with ethyl acetate. The extracts were washed with water, dried, then, the solvent was distilled off. The residue was purified by silica gel column chromatography (hexane-ethyl acetate=4:1) to obtain a title compound (3.3 g, yield 38%).
Oil
$^1$H-NMR (CDCl$_3$) δ: 1.64 (3H, t, J=7.6 Hz), 2.34 (3H, s), 3.10 (2H, q, J=7.6 Hz), 6.84-6.86 (1H, m), 7.05-7.09 (1H, m), 7.13-7.25 (3H, m), 7.37 (1H, s), 8.10 (1H, d, J=5.6 Hz).

Example 12

The following example compound 12 was synthesized according to Example 11, using 2-bromo-1-(3-chlorophenyl)-2-(2-fluoro-4-pyridyl)ethanone hydrobromide instead of 2-bromo-2-(2-fluoro-4-pyridyl)-1-(3-methylphenyl)ethanone hydrobromide.

Example Compound 12

2-ethyl-4-(3-chlorophenyl)-5-(2-fluoro-4-pyridyl)-1,3-thiazole
m.p. 102-103° C.

Example 13

The following example compound 13 was synthesized according to Example 11, using 2-bromo-1-(3-methylphenyl)-2-(2-methyl-4-pyridyl)ethanone hydrobromide instead of 2-bromo-2-(2-fluoro-4-pyridyl)-1-(3-methylphenyl)ethanone hydrobromide.

Example Compound 13

2-ethyl-4-(3-methylphenyl)-5-(2-methyl-4-pyridyl)-1,3-thiazole
Oil
$^1$H-NMR (CDCl$_3$) δ: 1.45 (3H, t, J=7.6 Hz), 2.33 (3H, s), 2.51 (3H, s), 3.09 (2H, q, J=7.6 Hz), 6.99 (1H, dd, J=1.2, 5.2 Hz), 7.13-7.30 (4H, m), 7.39 (1H, s), 8.38 (1H, d, J=5.2 Hz).

Example 14

The following example compounds 14-1 to 14-14 were synthesized according to Example 13, using 2-chlorothiobenzamide, 4-chlorothiobenzamide, 2-fluorothiobenzamide, 4-fluorothiobenzamide, 2,4-difluorothiobenzamide, thiobenzamide, phenyl(thioacetamide), 3-phenyl(thiopropionamide), 4-phenyl(thiobutyramide), thiovaleramide, thiobutyramide, ethyl 2-amino-2-thioxoacetate, 4-methyl-1-piperazinecarbothioamide and 1-methylpiperidine-4-carbothioamide, respectively, instead of thiopropionamide.

Example Compound 14-1

2-(2-chlorophenyl)-4-(3-methylphenyl)-5-(2-methyl-4-pyridyl)-1,3-thiazole
m.p. 83-84° C.

Example Compound 14-2

2-(4-chlorophenyl)-4-(3-methylphenyl)-5-(2-methyl-4-pyridyl)-1,3-thiazole
m.p. 104-105° C.

Example Compound 14-3

2-(2-fluorophenyl)-4-(3-methylphenyl)-5-(2-methyl-4-pyridyl)-1,3-thiazole
m.p. 73-74° C.

Example Compound 14-4

2-(4-fluorophenyl)-4-(3-methylphenyl)-5-(2-methyl-4-pyridyl)-1,3-thiazole
m.p. 89-91° C.

Example Compound 14-5

2-(2,4-difluorophenyl)-4-(3-methylphenyl)-5-(2-methyl-4-pyridyl)-1,3-thiazole
m.p. 90-91° C.

Example Compound 14-6

4-(3-methylphenyl)-5-(2-methyl-4-pyridyl)-2-phenyl-1,3-thiazole
m.p. 79-80° C.

Example Compound 14-7

4-(3-methylphenyl)-5-(2-methyl-4-pyridyl)-2-(phenylmethyl)-1,3-thiazole
m.p. 82-84° C.

Example Compound 14-8

4-(3-methylphenyl)-5-(2-methyl-4-pyridyl)-2-(2-phenylethyl)-1,3-thiazole
m.p. 64-65° C.

Example Compound 14-9

4-(3-methylphenyl)-5-(2-methyl-4-pyridyl)-2-(3-phenylpropyl)-1,3-thiazole
Oil
$^{1}$H-NMR (CDCl$_3$) δ: 2.12-2.27 (2H, m), 2.33 (3H, s), 2.50 (3H, s), 2.79 (2H, t, J=7.7 Hz), 3.08 (2H, t, J=7.9 Hz), 6.98 (1H, dd, J=1.4, 5.6 Hz), 7.10-7.35 (9H, m), 7.38 (1H, s), 8.38 (1H, d, J=5.6 Hz).

Example Compound 14-10

2-butyl-4-(3-methylphenyl)-5-(2-methyl-4-pyridyl)-1,3-thiazole
Oil
$^{1}$H-NMR (CDCl$_3$) δ: 0.99 (3H, t, J=7.1 Hz), 1.43-1.56 (2H, m), 1.76-1.91 (2H, m), 2.33 (3H, s), 2.50 (3H, s), 3.05 (2H, t, J=7.9 Hz), 6.99 (1H, d, J=5.4 Hz), 7.10-7.20 (4H, m), 7.38 (1H, s), 8.37 (1H, d, J=5.4 Hz).

Example Compound 14-11

4-(3-methylphenyl)-5-(2-methyl-4-pyridyl)-2-propyl-1,3-thiazole
Oil
$^{1}$H-NMR (CDCl$_3$) δ: 1.08 (3H, t, J=7.4 Hz), 1.79-2.00 (2H, m), 2.33 (3H, s), 2.50 (3H, s), 3.03 (2H, t, J=7.4 Hz), 6.99 (1H, d, J=5.3 Hz), 7.10-7.20 (4H, m), 7.39 (1H, s), 8.37 (1H, d, J=5.3 Hz).

Example Compound 14-12

Ethyl [4-(3-methylphenyl)-5-(2-methyl-4-pyridyl)-1,3-thiazol-2-yl]carboxylate
m.p. 97-98° C.

Example Compound 14-13

4-(3-methylphenyl)-2-(4-methylpiperazin-1-yl)-5-(2-methyl-4-pyridyl)-1,3-thiazole
m.p. 115-116° C.

Example Compound 14-14

4-(3-methylphenyl)-2-(1-methylpiperazin-4-yl)-5-(2-methyl-4-pyridyl)-1,3-thiazole
m.p. 127-130° C.

Example 15

The following example compound 15 was synthesized according to Example 11, using 4-(methylthio)thiobenzamide, instead of thiopropionamide.

Example Compound 15

5-(2-fluoro-4-pyridyl)-4-(3-methylphenyl)-2-[4-(methylthio)phenyl]-1,3-thiazole
m.p. 97-100° C.

Example 16

The following example compounds 16-1 to 16-6 were synthesized according to Example 15, using 2-bromo-1-(3-methylphenyl)-2-(2-methyl-4-pyridyl)ethanone hydrobromide, 2-bromo-1-(3,5-dimethylphenyl)-2-(2-methyl-4-pyridyl)ethanone hydrobromide, 2-bromo-1-(3,5-dimethylphenyl)-2-(2,6-dimethyl-4-pyridyl)ethanone hydrobromide, 2-bromo-1-(3,5-dimethylphenyl)-2-(2,6-dimethyl-4-pyridyl)ethanone hydrobromide, 2-bromo-1-(4-fluorophenyl)-2-(2-methyl-4-pyridyl)ethanone hydrobromide and 2-(2-amino-4-pyridyl)-2-bromo-1-(3-chlorophenyl)ethanone hydrobromide, respectively, instead of 2-bromo-2-(2-fluoro-4-pyridyl)-1-(3-methylphenyl)ethanone hydrobromide.

Example Compound 16-1

4-(3-methylphenyl)-5-(2-methyl-4-pyridyl)-2-[4-(methylthio)phenyl]-1,3-thiazole
m.p. 119-122° C.

Example Compound 16-2

4-(3,5-dimethylphenyl)-5-(2-methyl-4-pyridyl)-2-[4-(methylthio)phenyl]-1,3-thiazole
m.p. 123-125° C.

Example Compound 16-3

5-(2,6-dimethyl-4-pyridyl)-4-(3-methylphenyl)-2-[4-(methylthio)phenyl]-1,3-thiazole
m.p. 112-114° C.

Example Compound 16-4

4-(3,5-dimethylphenyl)-5-(2,6-dimethyl-4-pyridyl)-2-[4-(methylthio)phenyl]-1,3-thiazole
m.p. 134-136° C.

Example Compound 16-5

4-(4-fluorophenyl)-5-(2-methyl-4-pyridyl)-2-[4-(methylthio)phenyl]-1,3-thiazole
m.p. 99-100° C.

Example Compound 16-6

4-[4-(3-chlorophenyl)-2-[4-(methylthio)phenyl-1,3-thiazol-5-yl]-2-pyridylamine
m.p. 183-184° C.

Example 17

4-[2-(2-chlorophenyl)-4-(3-methylphenyl)-1,3-thiazol-5-yl]-2-pyridylamine
A solution of 2-(2-amino-4-pyridyl)-2-bromo-1-(3-methylphenyl)ethanone hydrobromide (5.00 g, 12.3 mmol) and 2-chlorothiobenzamide (1.06 g, 11.9 mmol) in N,N-dimethylformamide (40 mL) was stirred for 14 hours at room temperature. Aqueous sodium hydrogen carbonate solution was poured into the reaction mixture, and extracted with ethyl acetate. The extracts were washed with water, dried, and concentrated. The residue was purified by silica gel column chromatography (hexaneethyl acetate=4:1 to 2:1) to obtain a crystal. This crystal was washed with isopropyl ether, to obtain a title compound (3.15 g, yield 81%).
m.p. 175-177° C.

Example 18

The following example compounds 18-1 to 18-6 were synthesized according to Example 17, using 4-fluorothiobenzamide, thiovaleramide, 3,3,3-trifluorothiopropionamide, thiobutyramide, ethyl 3-amino-3-thioxopropanate, ethyl 2-amino-2-thioxoacetate, respectively, instead of 2-chlorothiobenzamide.

Example Compound 18-1

4-[2-(4-fluorophenyl)-4-(3-methylphenyl)-1,3-thiazol-5-yl]-2-pyridylamine
m.p. 160-162° C.

Example Compound 18-2

4-[2-butyl-4-(3-methylphenyl)-1,3-thiazol-5-yl]-2-pyridylamine
Oil
$^1$H-NMR (CDCl$_3$) δ: 0.98 (3H, t, J=7.3 Hz), 1.39-1.59 (2H, m), 1.76-1.92 (2H, m), 2.34 (3H, s), 3.04 (2H, t, J=7.4 Hz), 4.14 (2H, br s), 6.44 (1H, s), 6.56 (1H, dd, J=1.5, 5.4 Hz), 7.09-7.26 (3H, m), 7.41 (1H, s), 7.96 (1H, d, J=5.4 Hz).

Example Compound 18-3

4-[4-(3-methylphenyl)-2-(2,2,2-trifluoroethyl)-1,3-thiazol-5-yl]-2-pyridylamine
m.p. 131-132° C.

Example Compound 18-4

4-[4-(3-methylphenyl)-2-propyl-1,3-thiazol-5-yl]-2-pyridylamine
m.p. 113-115° C.

Example Compound 18-5

Ethyl [5-(2-amino-4-pyridyl)-4-(3-methylphenyl)-1,3-thiazol-2-yl]acetate
m.p. 128-129° C.

Example Compound 18-6

Ethyl [5-(2-amino-4-pyridyl)-4-(3-methylphenyl)-1,3-thiazol-2-yl]carboxylate
m.p. 147-148° C.

Example 19

The following example compound 22 was synthesized according to Example 17, using thiopropionamide instead of 2-chlorothiobenzamide.

Example 20

The following example compounds 20-1 to 20-12 were synthesized according to Example 19, using 2-(2-amino-4-pyridyl)-2-bromo-1-(3-chlorophenyl)ethanone hydrobromide, 2-(2-amino-4-pyridyl)-2-bromo-1-phenylethanone hydrobromide, 2-(2-amino-4-pyridyl)-2-bromo-1-(4-fluorophenyl)ethanone hydrobromide, 2-(2-amino-4-pyridyl)-2-bromo-1-[3-(trifluoromethyl)phenyl]ethanone hydrobromide, 2-(2-amino-4-pyridyl)-2-bromo-1-[4-(methylthio)phenyl]ethanone hydrobromide, 2-(2-amino-4-pyridyl)-2-bromo-1-(3-fluorophenyl)ethanone ( hydrobromide, 2-(2-amino-4-pyridyl)-2-bromo-1-(4-chlorophenyl)ethanone hydrobromide, 2-(2-amino-4-pyridyl)-2-bromo-1-(3-ethylphenyl)ethanone hydrobromide, 2-(2-amino-4-pyridyl)-2-bromo-1-(4-fluoro-3-methylphenyl)ethanone hydrobromide, 2-(2-amino-4-pyridyl)-2-bromo-1-[3-(1-methylethyl)phenyl]ethanone hydrobromide, 2-(2-amino-4-pyridyl)-2-bromo-1-(3-propylphenyl)ethanone hydrobromide, 2-(2-amino-4-pyridyl)-2-bromo-1-(2-thienyl)ethanone hydrobromide, respectively, instead of 2-(2-amino-4-pyridyl)-2-bromo-1-(3-methylphenyl)ethanone hydrobromide.

Example Compound 20-1

4-[2-ethyl-4-(3-chlorophenyl)-1,3-thiazol-5-yl]-2-pyridylamine
m.p. 132-133° C.

Example Compound 20-2

4-(2-ethyl-4-phenyl-1,3-thiazol-5-yl)-2-pyridylamine
m.p. 158-159° C.

Example Compound 20-3

4-[2-ethyl-4-(4-fluorophenyl)-1,3-thiazol-5-yl]-2-pyridylamine
m.p. 140-141° C.

Example Compound 20-4

4-[2-ethyl-4-[3-(trifluoromethyl)phenyl]-1,3-thiazol-5-yl]-2-pyridylamine
m.p. 117-118° C.

Example Compound 20-5

4-[2-ethyl-4-[4-(methylthio)phenyl]-1,3-thiazol-5-yl]-2-pyridylamine
m.p. 119-120° C.

Example Compound 20-6

4-[2-ethyl-4-(3-fluorophenyl)-1,3-thiazol-5-yl]-2-pyridylamine
m.p. 153-154° C.

Example Compound 20-7

4-[4-(4-chlorophenyl)-2-ethyl-1,3-thiazol-5-yl]-2-pyridylamine
m.p. 136-137° C.

Example Compound 20-8

4-[2-ethyl-4-(3-ethylphenyl)-1,3-thiazol-5-yl]2-pyridylamine
m.p. 128-129° C.

Example Compound 20-9

4-[2-ethyl-4-(4-fluoro-3-methylphenyl)-1,3-thiazol-5-yl]-2-pyridylamine
m.p. 134-135° C.

Example Compound 20-10

4-[2-ethyl-4-[3-(1-methylethyl)phenyl]-1,3-thiazol-5-yl]-2-pyridylamine
m.p. 80-81° C.

Example Compound 20-11

4-[2-ethyl-4-(3-propylphenyl)-1,3-thiazol-5-yl]-2-pyridylamine
m.p. 72-74° C.

Example Compound 20-12

4-[2-ethyl-4-(2-thienyl)-1,3-thiazol-5-yl]-2-pyridylamine
m.p. 159-160° C.

Example 21

The following example compounds 21-1 and 21-2 were synthesized according to Example 18, using 2-(2-amino-4-pyridyl)-2-bromo-1-(3-chlorophenyl)ethanone hydrobromide instead of 2-(2-amino-4-pyridyl)-2-bromo-1-(3-methylphenyl)ethanone hydrobromide.

Example Compound 21-1

4-[4-(3-chlorophenyl)-2-propyl-1,3-thiazol-5-yl]-2-pyridylamine
m.p. 99-100° C.

Example Compound 21-2

Ethyl [5-(2-amino-4-pyridyl)-4-(3-chlorophenyl)-1,3-thiazol-2-yl]acetate
m.p. 154-155° C.

Example 22

4-[2-ethyl-4-(3-methylphenyl)-1,3-thiazol-5-yl]-2-pyridylamine

To 5-[2-(tert-butoxycarbonylamino)-4-pyridyl]-2-ethyl-4-(3-methylphenyl)-1,3-thiazole (synthesized from 2-(2-tert-butoxycarbonylamino-4-pyridyl)-1-(3-methylphenyl)ethanone (35 g, 170 mmol) according to the method described in Example 3) was added 2N-hydrochloric acid (200 mL), and the mixture was stirred for 1 hour at 100° C. The reaction mixture was cooled to room temperature, then, made alkaline with a 2N aqueous sodium hydrogen carbonate solution (200 mL) and aqueous sodium hydrogen carbonate solution. The resulted mixture was extracted by ethyl acetate, and the extracts were washed with water. This extracts were dried and concentrated. The residue was purified by silica gel column chromatography (hexane-ethyl acetate=1:1) to obtain a crystal. This crystal was washed with isopropyl ether, to obtain a title compound (17 g, yield 55%).
m.p. 144-146° C.

Example 23

The following example compounds 23-1 to 23-3 were synthesized according to Example 22, using 5-[2-(tert-butoxycarbonylamino)-4-pyridyl]-2-methyl-4-(3-methylphenyl)-1,3-thiazole, 5-[2-(tert-butoxycarbonylamino)-4-pyridyl]-4-(3-methylphenyl)-2-[4-(methylthio)phenyl]-1,3-thiazole and 5-[2-(tert-butoxycarbonylamino)-4-pyridyl]-4-(4-methoxyphenyl)-2-methyl-1,3-thiazole, respectively, instead of 5-[2-(tert-butoxycarbonylamino)-4-pyridyl]-2-ethyl-4-(3-methylphenyl)-1,3-thiazole.

Example Compound 23-1

4-[2-methyl-4-(3-methylphenyl)-1,3-thiazol-5-yl]-2-pyridylamine
m.p. 152-153° C.

Example Compound 23-2

4-[4-(3-methylphenyl)-2-[4-(methylthio)phenyl]-1,3-thiazol-5-yl]-2-pyridylamine
m.p. 181-183° C.

Example Compound 23-3

4-[4-(4-methoxyphenyl)-2-methyl-1,3-thiazol-5-yl]-2-pyridylamine
m.p. 140-141° C.

Example 24

[5-(2-amino-4-pyridyl)-4-(3-methylphenyl)-1,3-thiazol-2-yl]acetic acid

To a suspension of ethyl [5-(2-amino-4-pyridyl)-4-(3-methylphenyl)-1,3-thiazol-2-yl]acetate (7.00 g, 19.8 mmol) in ethanol (40 mL) was added a 1N aqueous sodium hydroxide solution (40 mL), and the mixture was stirred for 2 hours at the room temperature under the same condition, The reaction mixture was neutralized with 2N hydrochloric acid (20 mL), then, the produced solid was collected by filtration. The crude product was washed with water, and dried to obtain a title compound (6.10 g, yield: 95%).

m.p. 132-133° C.

Example 25

The following example compounds 25-1 to 25-3 were synthesized according to Example 24, using ethyl [5-(2-amino-4-pyridyl)-4-(3-methylphenyl)-1,3-thiazol-2-yl]carboxylate, ethyl [5-(2-methyl-4-pyridyl)-4-(3-methylphenyl)-1,3-thiazol-2-yl]carboxylate and ethyl [5-(2-amino-4-pyridyl)-4-(3-chlorophenyl)-1,3-thiazol-2-yl]acetate, respectively, instead of ethyl [5-(2-amino-4-pyridyl)-4-(3-methylphenyl)-1,3-thiazol-2-yl]acetate.

Example Compound 25-1

5-(2-amino-4-pyridyl)-4-(3-methylphenyl)-1,3-thiazole-2-carboxylic acid m.p. 156-157° C.

Example Compound 25-2

5-(2-methyl-4-pyridyl)-4-(3-methylphenyl)-1,3-thiazole-2-carboxylic acid m.p. 135-136° C.

Example Compound 25-3

[5-(2-methyl-4-pyridyl)-4-(3-chlorophenyl)-1,3-thiazol-2-yl]acetic acid

This was used in the subsequent reaction without purification.

Example 26

4-(3-methylphenyl)-5-(2-methyl-4-pyridyl)-1,3-thiazole 4-(3-methylphenyl)-5-(2-methyl-4-pyridyl)-1,3-thiazole-2-carboxylic acid (0.20 g, 0.64 mmol) was stirred for 15 minutes at 150° C. It was cooled to room temperature, then, the crude product was purified by silica gel column chromatography (ethyl acetate) to obtain a title compound (0.17 g, yield 98%).

Oil $^1$H-NMR (CDCl$_3$) δ: 2.34 (3H, s), 2.53 (3H, s), 7.04 (1H, d, J=5.1 Hz), 7.16-7.24 (4H, m), 7.43 (1H, s), 8.42 (1H, d, J=5.1 Hz), 8.88 (1H, s).

Example 27

The following example compounds 27-1 and 27-2 were synthesized according to Example 26, using 5-(2-amino-4-pyridyl)-4-(3-methylphenyl)-1,3-thiazole-2-carboxylic acid and [5-(2-amino-4-pyridyl)-4-(3-chlorophenyl)-1,3-thiazol-2-yl]acetic acid.

Example Compound 27-1

4-[4-(3-methylphenyl)-1,3-thiazol-5-yl]-2-pyridylamine m.p. 91-92° C.

Example Compound 27-2

4-[4-(3-chlorophenyl)-2-methyl-1,3-thiazol-5-yl]-2-pyridylamine m.p. 142-143° C.

Example 28

N-[4-[2-ethyl-4-(3-methylphenyl)-1,3-thiazol-5-yl]-2-pyridyl]cyclohexanecarboxamide To a solution of 4-[2-ethyl-4-(3-methylphenyl)-1,3-thiazol-5-yl]-2-pyridylamine (0.80 g, 2.7 mmol) in tetrahydrofuran (10 mL) were added cyclohexanecarbonyl chloride (0.40 mL, 3.0 mmol) and triethylamine (0.39 mL, 2.8 mmol) sequentially, and the mixture was stirred for 1 hour at room temperature. To the reaction mixture was added an aqueous sodium hydrogen carbonate solution, and extracted with ethyl acetate. The extracts were washed with an aqueous sodium hydrogen carbonate solution, then, dried and concentrated. The residue was purified by silica gel column chromatography (hexane-ethyl acetate=20:1 to 4:1) to obtain a crystal. This crystal was washed with hexane to obtain a title compound (0.83 g, yield 75%).

m.p. 98-100° C.

Example 29

The following example compounds 29-1 to 29-5 were synthesized according to Example 28, using cyclopentanecarbonyl chloride, acetyl chloride, 1-methylcyclohexanecarbonyl chloride, propionyl chloride and pivaloyl chloride instead of cyclohexanecarbonyl chloride.

Example Compound 29-1

N-[4-[2-ethyl-4-(3-methylphenyl)-1,3-thiazol-5-yl]-2-pyridyl]cyclopentanecarboxamide m.p. 123-125° C.

Example Compound 29-2

N-[4-[2-ethyl-4-(3-methylphenyl)-1,3-thiazol-5-yl]-2-pyridyl]acetamide m.p. 119-120° C.

Example Compound 29-3

N-[4-[2-ethyl-4-(3-methylphenyl)-1,3-thiazol-5-yl]-2-pyridyl]-1-methylcyclohexanecarboxamide Oil $^1$H-NMR (CDCl$_3$) δ: 1.28 (3H, s), 1,30-1.75 (11H, m), 1.98-2.12 (2H, m), 2,33 (3H, s), 3.08 (2H, q, J=7.6 Hz), 6.79-6.85 (1H, m), 7.10-7.25 (3H, m), 7.38-7.42 (1H, m), 8.04-8.07 (2H, m), 8.40-8.43 (1H, m).

Example Compound 29-4

N-[4-[2-ethyl-4-(3-methylphenyl)-1,3-thiazol-5-yl]-2-pyridyl]propionamide m.p. 103-104° C.

Example Compound 29-5

N-[4-[2-ethyl-4-(3-methylphenyl)-1,3-thiazol-5-yl]-2-pyridyl]pivalamide
Oil
$^1$H-NMR (CDCl$_3$) δ: 1.34 (9H, s), 1.44 (3H, t, J=7.6 Hz), 2.33 (3H, s) , 3.08 (2H, q, J=7.6 Hz), 6.79-6.84 (1H, m), 7.09-7.27 (3H, m), 7.36-7.39 (1H, m), 8.03-8.10 (2H, m), 8.38-8.42 (1H, m).

Example 30

The following example compounds 30-1 to 30-12 were synthesized according to Example 29, using 4-[4-(3-chlorophenyl)-2-methyl-1,3-thiazol-5-yl]-2-pyridylamine, 4-[4-(3-chlorophenyl)-2-ethyl-1,3-thiazol-5-yl]-2-pyridylamine, 4-[4-(3-chlorophenyl)-2-propyl-1,3-thiazol-5-yl]-2-pyridylamine, 4-[2-ethyl-4-(2-thienyl)-1,3-thiazol-5-yl]-2-pyridylamine and 4-[4-(3-chlorophenyl)-2-[4-(methylthio)phenyl]-1,3-thiazol-5-yl]-2-pyridylamine, respectively, instead of 4-[2-ethyl-4-(3-methylphenyl)-1,3-thiazol-5-yl]-2-pyridylamine.

Example Compound 30-1

N-[4-[4-(3-chlorophenyl)-2-methyl-1,3-thiazol-5-yl]-2-pyridyl]acetamide
m.p. 112-115° C.

Example Compound 30-2

N-[4-[4-(3-chlorophenyl)-2-ethyl-1,3-thiazol-5-yl]-2-pyridyl]acetamide
m.p. 149-150° C.

Example Compound 30-3

N-[4-[4-(3-chlorophenyl)-2-propyl-1,3-thiazol-5-yl]-2-pyridyl]acetamide
m.p. 144-145° C.

Example Compound 30-4

N-[4-[2-ethyl-4-(2-thienyl)-1,3-thiazol-5-yl]-2-pyridyl]acetamide
m.p. 154-155° C.

Example Compound 30-5

N-[4-[4-(3-chlorophenyl)-2-[4-(methylthio)phenyl]-1,3-thiazol-5-yl]-2-pyridyl]acetamide
m.p. 207-208° C.

Example Compound 30-6

N-[4-[4-(3-chlorophenyl)-2-ethyl-1,3-thiazol-5-yl]-2-pyridyl]-1-methylcyclohexanecarboxamide
Oil
$^1$H-NMR (CDCl$_3$) δ: 1.28 (3H, s), 1.35-1.82 (11H, m), 1.95-2.13 (2H, m), 3.08 (2H, q, J=7.8 Hz), 6.80-6.84 (1H, m), 7.19-7.37 (3H, m), 7.53-7.62 (1H, m), 8.07-8.12 (1H, m), 8.25-8.35 (1H, m), 8.40-8.43 (1H, m).

Example Compound 30-7

N-[4-[4-(3-chlorophenyl)-2-methyl-1,3-thiazol-5-yl]-2-pyridyl]propionamide.
m.p. 134-135° C.

Example Compound 30-8

N-[4-[4-(3-chlorophenyl)-2-ethyl-1,3-thiazol-5-yl]-2-pyridyl]propionamide
m.p. 132-133° C.

Example Compound 30-9

N-[4-[4-(3-chlorophenyl)-2-propyl-1,3-thiazol-5-yl]-2-pyridyl]propionamide
m.p. 103-104° C.

Example Compound 30-10

N-[4-[2-ethyl-4-(2-thienyl)-1,3-thiazol-5-yl]2-pyridyl]propionamide
m.p. 187-188° C.

Example Compound 30-11

N-[4-[4-(3-chlorophenyl)-2-[4-(methylthio)phenyl]-1,3-thiazol-5-yl]-2-pyridyl]propionamide
m.p. 187-188° C.

Example Compound 30-12

N-[4-[4-(3-chlorophenyl)-2-[4-(methylthio)phenyl]-1,3-thiazol-5-yl]-2-pyridyl]pivalamide
m.p. 119-120° C.

Example 31

N-(cyclohexylmethyl)-4-[2-ethyl-4-(3-methylphenyl)-1,3-thiazol-5-yl]-2-pyridylamine To a solution of aluminum chloride (0.40 g, 3.0 mmol) in tetrahydrofuran (40 mL) was added lithium aluminum hydride (0.12 g, 3.0 mmol) at 0° C. To this solution was added dropwise a solution of N-[4-[2-ethyl-4-(3-methylphenyl)-1,3-thiazol-5-yl]-2-pyridyl]cyclohexanecarboxamine (0.40 g, 0.99 mmol) in tetrahydrofuran (10 mL), and the mixture was heated under reflux for 1 hour. The reaction mixture was cooled to room temperature, to this was added ice water, and extracted with ethyl acetate. The extracts were washed with an aqueous sodium hydrogen carbonate solution, then, dried and concentrated. The residue was purified by silica gel column chromatography (hexane-ethyl acetate=20:1 to 4:1) to obtain a crystal. This crystal was washed with hexane to obtain a title compound (0.27 g, yield 70%).
m.p. 74-75° C.

Example 32

The following example compound 32 was synthesized according to Example 31, using N-[4-[2-ethyl-4-(3-methylphenyl)-1,3-thiazol-5-yl]-2-pyridyl]cyclopentanecarboxamine instead of N-[4-[2-ethyl-4-(3-methylphenyl)-1,3-thiazol-5-yl]-2-pyridyl]cyclohexanecarboxamine.

Example Compound 32

N-(cyclopentylmethyl)-4-[2-ethyl-4-(3-methylphenyl)-1,3-thiazol-5-yl]-2-pyridylamine
m.p. 67-69° C.

Example 33

[4-(3-methylphenyl)-5-(2-pyperidino-4-pyridyl)-1,3-thiazol-2-yl]amine 5-(2-fluoro-4-pyridyl)-4-(3-methylphenyl)-1,3-thiazol-2-yl]amine (0.70 g, 2.5 mmol) and piperidine (2.0 mL, 20 mmol) were stirred at 150° C. for 3 hours. The reaction mixture was purified by silica gel column chromatography (hexane-ethyl acetate=1:1) to obtain a title compound (0.62 g, yield 72%).
m.p. 181-182° C.

Example 34

The following example compounds 34-1 to 34-3 were synthesized according to Example 33, using morpholine, cyclohexylamine and cyclopentylamine instead of piperidine.

Example Compound 34-1

[4-(3-methylphenyl)-5-(2-morpholino-4-pyridyl)-1,3-thiazol-2-yl]amine
m.p. 188-189° C.

Example Compound 34-2

[5-(2-cyclohexylamino-4-pyridyl)-4-(3-methylphenyl)-1,3-thiazol-2-yl]amine
m.p. 168-169° C.

Example Compound 34-3

[5-(2-cyclopentylamino-4-pyridyl)-4-(3-methylphenyl)-1,3-thiazol-2-yl]amine
m.p. 169-170° C.

Example 35

The following example compounds 35-1 and 35-2 were synthesized according to Example 34, using 4-(3-chlorophenyl)-5-(2-fluoro-4-pyridyl)-1,3-thiazol-2-yl]amine and 5-(2-fluoro-4-pyridyl)-4-(3-methylphenyl)-2-(4-methylsulfonylphenyl)-1,3-thiazole instead of 5-(2-fluoro-4-pyridyl)-4-(3-methylphenyl)-1,3-thiazol-2-yl]amine

Example Compound 35-1

[4-(3-chlorophenyl)-5-(2-piperidino-4-pyridyl)-1,3-thiazol-2-yl]amine
m.p. 206-208° C.

Example Compound 35-2

4-(3-methylphenyl)-2-(4-methylsulfonylphenyl)-5-(2-piperidino-1-pyridyl)-1,3-thiazole
m.p. 155-157° C.

Example 36

The following example compounds 36-1 to 36-11 were synthesized according to Example 34, using 5-(2-fluoro-4-pyridyl)-4-(4-fluorophenyl)-1,3-thiazol-2-yl]amine, N-methyl-[5-(2-fluoro-4-pyridyl)-4-(3-methylphenyl)-1,3-thiazol-2-yl]amine, 2-ethyl-5-(2-fluoro-4-pyridyl)-4-(3-methylphenyl)-1,3-thiazole, 5-(2-fluoro-4-pyridyl)-4-(3-methylphenyl)-2-(4-methylsulfonylphenyl)-1,3-thiazole and 4-(3-chlorophenyl)-2-ethyl-5-(2-fluoro-4-pyridyl)-1,3-thiazole, respectively, instead of 5-(2-fluoro-4-pyridyl)-4-(3-methylphenyl)-1,3-thiazol-2-yl]amine.

Example Compound 36-1

[5-(2-cyclohexylamino-4-pyridyl)-4-(4-fluorophenyl)-1,3-thiazol-2-yl]amine
m.p. 194-195° C.

Example Compound 36-2

N-methyl-[5-(2-cyclohexylamino-4-pyridyl)-4-(3-methylphenyl)-1,3-thiazol-2-yl]amine
m.p. 211-212° C.

Example Compound 36-3

N-methyl-[5-(2-cyclopentylamino-4-pyridyl)-4-(3-methylphenyl)-1,3-thiazol-2-yl]amine
m.p. 170-172° C.

Example Compound 36-4

N-cyclohexyl-4-[2-ethyl-4-(3-methylphenyl)-1,3-thiazol-5-yl]-2-pyridylamine
m.p. 110-112° C.

Example Compound 36-5

N-cyclohexyl-4-[4-(3-methylphenyl)-2-(4-methylsulfonylphenyl)-1,3-thiazol-5-yl]-2-pyridylamine
m.p. 197-199° C.

Example Compound 36-6

N-cyclopentyl-4-[2-ethyl-4-(3-methylphenyl)-1,3-thiazol-5-yl]-2-pyridylamine
m.p. 117-118° C.

Example Compound 36-7

N-cyclopentyl-4-[4-(3-methylphenyl)-2-(4-methylsulfonylphenyl)-1,3-thiazol-5-yl]-2-pyridylamine
m.p. 154-156° C.

Example Compound 36-8

4-(3-methylphenyl)-2-(4-methylsulfonylphenyl)-5-(2-morpholino-4-pyridyl)-1,3-thiazole
m.p. 200-202° C.

Example Compound 36-9

2-ethyl-4-(3-methylphenyl)-5-(2-morpholino-4-pyridyl)-1,3-thiazole
m.p. 69-71° C.

Example Compound 36-10

4-[4-(3-chlorophenyl)-2-ethyl-1,3-thiazol-5-yl]-N-cyclohexyl-2-pyridylamine
m.p. 106-107° C.

Example Compound 36-11

4-[4-(3-chlorophenyl)-2-ethyl-1,3-thiazol-5-yl]-N-cyclopentyl-2-pyridylamine
m.p. 110-111° C.

Example 37

The following example compounds 37-1 to 37-5 were synthesized according to Example 36, using pyrrolidine, N-methylcyclohexylamine, (cyclohexylmethyl)amine and 1-methylpiperazine, respectively, instead of cyclohexylamine.

Example Compound 37-1

2-ethyl-4-(3-methylphenyl)-5-[2-(1-pyrrolidinyl)-4-pyridyl]-1,3-thiazole
m.p. 108-109° C.

Example Compound 37-2

N-cyclohexyl-N-methyl-4-[4-(3-methylphenyl)-2-(4-methylsulfonylphenyl)-1,3-thiazol-5-yl]-2-pyridylamine
m.p. 173-174° C.

Example Compound 37-3

N-cyclohexylmethyl-4-[4-(3-methylphenyl)-2-(4-methylsulfonylphenyl)-1,3-thiazol-5-yl]-2-pyridylamine
m.p. 157-159° C.

Example Compound 37-4

4-(3-methylphenyl)-2-(4-methylsulfonylphenyl)-5-[2-(1-pyrrolidinyl)-4-pyridyl]-1,3-thiazole
m.p. 199-201° C.

Example Compound 37-5

4-(3-methylphenyl)-5-[2-(4-methyl-1-piperazinyl)-4-pyridyl]-2-(4-methylsulfonylphenyl)-1,3-thiazole
m.p. 153-154° C.

Example 38

N-[5-(2-acetylamino-4-pyridyl)-4-(4-methoxyphenyl)-1,3-thiazol-2-yl]acetamide
To a solution of 4-[2-amino-4-(4-methoxyphenyl)-1,3-thiazol-5-yl]-2-pyridylamine (0.40 g, 1.4 mmol) and 4-dimethylaminopyridine (0.055 g, 0.45 mmol) in N,N-dimethylacetamide (10 mL) was added acetyl chloride (0.3 mL, 4.2 mmol), and the mixture was stirred for 14 hours at 70° C. An aqueous sodium hydrogen carbonate solution was poured into the reaction mixture, and extracted with ethyl acetate. The extracts were washed with brine, then, dried and concentrated. The crude crystal was recrystallized from ethanol to obtain a title compound (0.30 g, yield 58%).
m.p. 262-264° C.

Example 39

N-[4-(3-methylphenyl)-5-(2-methyl-4-pyridyl)-1,3-thiazol-2-yl]acetamide
To a solution of [4-(3-methylphenyl)-5-(2-methyl-4-pyridyl)-1,3-thiazol-2-yl]amine (0.50 g, 1.8 mmol) and 4-dimethylaminopyridine (0.061 g, 0.50 mmol) in N,N-dimethylacetamide (15 mL) was added acetyl chloride (0.19 mL, 2.7 mmol), and the mixture was stirred for 14 hours at 80° C. An aqueous sodium hydrogen carbonate solution was poured into the reaction mixture, and the deposited solid was filtrated. The resulted solid was washed with water, then, dried. The crude crystal was recrystallized from ethanol, to obtain a title compound (0.39 g, yield 67%).
m.p. 230-231° C.

Example 40

The following example compounds 40-1 to 40-3 were synthesized according to Example 39, using [4-(3,5-dimethylphenyl)-5-(2-methyl-4-pyridyl)-1,3-thiazol-2-yl]amine, [5-(2,6-dimethyl-4-pyridyl)-4-(3-methylphenyl)-1,3-thiazol-2-yl]amine and [4-(3,5-dimethylphenyl)-5-(2,6-dimethyl-4-pyridyl)-1,3-thiazol-2-yl]amine, respectively, instead of [4-(3-methylphenyl)-5-(2-methyl-4-pyridyl)-1,3-thiazol-2-yl]amine.

Example Compound 40-1

N-[4-(3,5-dimethylphenyl)-5-(2-methyl-4-pyridyl)-1,3-thiazol-2-yl]acetamide
m.p. 236-237° C.

Example Compound 40-2

N-[5-(2,6-dimethyl-4-pyridyl)-4-(3-methylphenyl)-1,3-thiazol-2-yl]acetamide
m.p. 185-187° C.

Example Compound 40-3

N-[4-(3,5-dimethylphenyl)-5-(2,6-dimethyl-4-pyridyl)-1,3-thiazol-2-yl]acetamide
m.p. 266-267° C.

Example 41

The following example compound 41 was synthesized according to Example 39, using nicotinoyl chloride hydrochloride instead of acetyl chloride.

Example Compound 41

N-[4-(3-methylphenyl)-5-(2-methyl-4-pyridyl)-1,3-thiazol-2-yl]nicotinamide
m.p. 175-178° C.

Example 42

The following example compounds 42-1 to 42-10 were synthesized according to Example 41, using [4-(3,5-dimethylphenyl)-5-(2-methyl-4-pyridyl)-1,3-thiazol-2-yl]amine, [4-(3,5-dimethylphenyl)-5-(2,6-dimethyl-4-pyridyl)-1,3-thiazol-2-yl]amine, [5-(2-cyclohexylamino-4-pyridyl)-4-(3-methylphenyl)-1,3-thiazol-2-yl]amine, [5-(2-cyclopentylamin-4-pyridyl)-4-(3-methylphenyl)-1,3-thiazol-2-yl]amine, [5-(2-cyclohexylamino-4-pyridyl)-4-(4-fluorophenyl)-1,3-thiazol-2-yl]amine, [5-(2-fluoro-4-pyridyl)-4-(3-methylphenyl)-1,3-thiazol-2-yl]amine, [4-(4-fluorophenyl)-5-(2-methyl-4-pyridyl)-1,3-thiazol-2-yl]amine, N-[5-(2-cyclohexylamino-4-pyridyl)-4-(3-methylphenyl)-1,3-thiazol-2-yl]-N-methylamine, N-[5-(2-cyclopentylamino-4-pyridyl)-4-(3-methylphenyl)-1,3-thiazol-2-yl]-N-methylamine and N-methyl-N-[5-(2-methyl-4-pyridyl)-4-(3-methylphenyl)-1,3-thiazol-2-yl]amine, respectively, instead of [4-(3-methylphenyl)-5-(2-methyl-4-pyridyl)-1,3-thiazol-2-yl]amine.

Example Compound 42-1

N-[4-(3,5-dimethylphenyl)-5-(2-methyl-4-pyridyl)-1,3-thiazol-2-yl]nicotinamide
m.p. 203-206° C.

Example Compound 42-2

N-[4-(3,5-dimethylphenyl)-5-(2,6-dimethyl-4-pyridyl)-1,3-thiazol-2-yl]nicotinamide
m.p. 267-268° C.

Example Compound 42-3

N-[5-(2-cyclohexylamino-4-pyridyl)-4-(3-methylphenyl)-1,3-thiazol-2-yl]nicotinamide
m.p. 201-203° C.

Example Compound 42-4

N-[5-(2-cyclopentylamino-4-pyridyl)-4-(3-methylphenyl)-1,3-thiazol-2-yl]nicotinamide
m.p. 215-216° C.

Example Compound 42-5

N-[5-(2-cyclohexylamino-4-pyridyl)-4-(4-fluorophenyl)-1,3-thiazol-2-yl]nicotinamide
m.p. 136-138° C.

Example Compound 42-6

N-[(5-(2-fluoro-4-pyridyl)-4-(3-methylphenyl)-1,3-thiazol-2-yl]nicotinamide
m.p. 229-231° C.

Example Compound 42-7

N-[4-(4-fluorophenyl)-5-(2-methyl-4-pyridyl)-1,3-thiazol-2-yl]nicotinamide
m.p. 261-262° C.

Example Compound 42-8

N-[5-(2-cyclohexylamino-4-pyridyl)-4-(3-methylphenyl)-1,3-thiazol-2-yl]-N-methylnicotinamide
m.p. 147-148° C.

Example Compound 42-9

N-[5-(2-cyclopentylamino-4-pyridyl)-4-(3-methylphenyl)-1,3-thiazol-2-yl]N-methylnicotinamide
m.p. 148-148° C.

Example Compound 42-10

N-methyl-N-[5-(2-methyl-4-pyridyl)-4-(3-methylphenyl)-1,3-thiazol-2-yl]nicotinamide
Oil
$^1$H-NMR (CDCl$_3$) δ: 2.35 (3H, s), 2.53 (3H, s), 3,78 (3H, s), 7.05 (1H, d, J=5.2 Hz), 7.06-7.30 (4H, m), 7.41 (1H, s), 7.49 (1H, dd, J=5.2, 7.0 Hz), 7.95 (1H, d, J=7,0 Hz), 8,40 (1H, d, J=5.2 Hz), 8.80 (1H, d, J=5.2 Hz), 8.88 (1H, s).

Example 43

The following example compound 43 was synthesized according to Example 39 using 6-chloro-3-pyridylcarbonyl chloride hydrochloride instead of acetyl chloride.

Example Compound 43

6-chloro-N-[4-(3-methylphenyl)-5-(2-methyl-4-pyridyl)-1,3-thiazol-2-yl]nicotinamide
m.p. 228-230° C.

Example 44

The following example compounds 44-1 to 44-4 were synthesized according to Example 43, using [5-(2-cyclohexylamino-4-pyridyl)-4-(3-methylphenyl)-1,3-thiazol-2-yl]amine, [5-(2-cyclopentylamino-4-pyridyl)-4-(3-methylphenyl)-1,3-thiazol-2-yl]amine, [4-(3,5-dimethylphenyl)-5-(2-methyl-4-pyridyl)-1,3-thiazol-2-yl]amine and N-methyl-[5-(2-cyclopentylamino-4-pyridyl)-4-(3-methylphenyl)-1,3-thiazol-2-yl]amine, respectively, instead of [4-(3-methylphenyl)-5-(2-methyl-4-pyridyl)-1,3-thiazol-2-yl]amine.

Example Compound 44-1

6-chloro-N-[5-(2-cyclohexylamino-4-pyridyl)-4-(3-methylphenyl)-1,3-thiazol-2-yl]nicotinamide
m.p. 255-256° C.

Example Compound 44-2

6-chloro-N-[5-(2-cyclopentylamino-4-pyridyl)-4-(3-methylphenyl)-1,3-thiazol-2-yl]nicotinamide
m.p. 211-212° C.

Example Compound 44-3

6-chloro-N-[4-(3,5-dimethylphenyl)-5-(2-methyl-4-pyridyl)-1,3-thiazol-2-yl]nicotinamide
m.p. 271-273° C.

Example Compound 44-4

6-chloro-N-[5-(2-cyclohexylamino-4-pyridyl)-4-(3-methylphenyl)-1,3-thiazol-2-yl]-N-methylnicotinamide
m.p. 171-172° C.

Example 45

The following example compound 45 was synthesized according to Example 39, using 6-methyl-3-pyridylcarbonyl chloride hydrochloride instead of acetyl chloride.

Example Compound 45

6-methyl-N-[4-(3-methylphenyl)-5-(2-methyl-4-pyridyl)-1,3-thiazol-2-yl]nicotinamide
m.p. 233-234° C.

Example 46

The following example compounds 46-1 to 46-4 were synthesized according to Example 45, using [5-(2-cyclohexylamino-4-pyridyl)-4-(3-methylphenyl)-1,3-thiazol-2-yl] amine, [5-(2-cyclopentylamino-4-pyridyl)-4-(3-methylphenyl)-1,3-thiazol-2-yl]amine, [4-(3,5-dimethylphenyl)-5-(2-methyl-4-pyridyl)-1,3-thiazol-2-yl] amine and N-methyl-[5-(2-cyclopentylamino-4-pyridyl)-4-(3-methylphenyl)-1,3-thiazol-2-yl]amine, respectively, instead of [4-(3-methylphenyl)-5-(2-methyl-4-pyridyl)-1,3-thiazol-2-yl]amine.

Example Compound 46-1

N-[5-(2-cyclohexylamino-4-pyridyl)-4-(3-methylphenyl)-1,3-thiazol-2-yl]-6-methylnicotinamide
m.p. 242-243° C.

Example Compound 46-2

N-[5-(2-cyclopentylamino-4-pyridyl)-4-(3-methylphenyl)-1,3-thiazol-2-yl]-6-methylnicotinamide
m.p. 213-214° C.

Example Compound 46-3

N-[4-(3,5-dimethylphenyl)-5-(2-methyl-4-pyridyl)-1,3-thiazol-2-yl]-6-methylnicotinamide
m.p. 252-253° C.

Example Compound 46-4

N-[5-(2-cyclopentylamino-4-pyridyl)-4-(3-methylphenyl)-1,3-thiazol-2-yl]-N,6-dimethylnicotinamide
m.p. 117-118° C.

Example 47

The following example compound 47 was synthesized according to Example 39, using 6-methoxy-3-pyridylcarbonyl chloride hydrochloride instead of acetyl chloride.

Example Compound 47

6-methoxy-N-[4-(3-methylphenyl)-5-(2-methyl-4-pyridyl)-1,3-thiazol-2-yl]nicotinamide
m.p. 224-226° C.

Example 48

The following example compounds 48-1 and 48-3 were synthesized according to Example 47, using [5-(2-cyclohexylamino-4-pyridyl)-4-(3-methylphenyl)-1,3-thiazol-2-yl] amine, [5-(2-cyclopentylamino-4-pyridyl)-4-(3-methylphenyl)-1,3-thiazol-2-yl]amine and [4-(3,5-dimethylphenyl)-5-(2-methyl-4-pyridyl)-1,3-thiazol-2-yl]amine, respectively, instead of [4-(3-methylphenyl)-5-(2-methyl-4-pyridyl)-1,3-thiazol-2-yl]amine.

Example Compound 48-1

N-[5-(2-cyclohexylamino-4-pyridyl)-4-(3-methylphenyl)-1,3-thiazol-2-yl]-6-methoxynicotinamide
m.p. 191-192° C.

Example Compound 48-2

N-[5-(2-cyclopentylamino-4-pyridyl)-4-(3-methylphenyl)-1,3-thiazol-2-yl]-6-methoxynicotinamide
m.p. 219-221° C.

Example Compound 48-3

N-[4-(3,5-dimethylphenyl)-5-(2-methyl-4-pyridyl)-1,3-thiazol-2-yl]-6-methoxynicotinamide
m.p. 242-244° C.

Example 49

The following example compound 49 was synthesized according to Example 39, using 2-methoxy-3-pyridylcarbonyl chloride hydrochloride instead of acetyl chloride.

Example Compound 49

2-methoxy-N-[4-(3-methylphenyl)-5-(2-methyl-4-pyridyl)-1,3-thiazol-2-yl]nicotinamide
m.p. 169-170° C.

Example 50

The following example compound 50 was synthesized according to Example 39, using [5-(2-tert-butoxycarbonylamino-4-pyridyl)-3-(4-methoxyphenyl)-1,3-thiazol-2-yl] amine instead of [4-(3-methylphenyl)-5-(2-methyl-1-pyridyl)-1,3-thiazol-2-yl]amine.

Example Compound 50

N-[5-(2-amino-4-pyridyl)-4-(4-methoxyphenyl)-1,3-thiazol-2-yl]acetamide
m.p. 247-250° C.

Example 51

The following example compound 51 was synthesized according to Example 50, using benzoyl chloride instead of acetyl chloride.

Example Compound 51

N-[5-(2-amino-4-pyridyl)-4-(4-methoxyphenyl)-1,3-thiazol-2-yl]benzamide
m.p. 219-222° C.

Example 52

N-[4-(2,6-dimethyl-4-pyridyl)-5-(3-methylphenyl)-1,3-thiazol-2-yl]-N'-phenylurea
To a solution of [4-(2,6-dimethyl-4-pyridyl)-5-(3-methylphenyl)-1,3-thiazol-2-yl]amine (0.50 g, 1.7 mmol) in N,N-dimethylacetamide (20 mL) was added phenyl isocyanate (0.28 mL, 2.6 mmol), and the mixture was stirred for 14 hours at 80° C. Aqueous sodium hydrogen carbonate was poured into the reaction mixture, and extracted with ethyl acetate. The extracts were washed with brine, then, dried to be concentrated. The residue was purified by silica gel column chromatography (hexane-ethyl acetate=1:1). The resulted crude crystal was recrystallized from ethyl acetate-hexane to obtain a title compound (0.34 g, yield 48%).
m.p. 173-174° C.

Example 53

The following example compounds 53-1 to 53-4 were synthesized according to Example 52, using [4-(3,5-dimethylphenyl)-5-(2,6-dimethyl-4-pyridyl)-1,3-thiazol-2-yl] amine, [5-(2-cyclohexylamino-4-pyridyl)-4-(3-methylphenyl)-1,3-thiazol-2-yl]amine, [5-(2-cyclopentylamino-4-pyridyl)-4-(3-methylphenyl)-1,3-thiazol-2-yl]amine and [4-(3-methylphenyl)-5-(2-methyl-4-pyridyl)-1,3-thiazol-2-yl]amine, respectively, instead of [4-(2,6-dimethyl-4-pyridyl)-5-(3-methylphenyl)-1,3-thiazol-2-yl]amine.

Example Compound 53-1

N-[4-(3,5-dimethylphenyl)-5-(2,6-dimethyl-4-pyridyl)-1,3-thiazol-2-yl]-N'-phenylurea
m.p. 219-222° C.

Example Compound 53-2

N-[5-(2-cyclohexylamino-4-pyridyl)-4-(3-methylphenyl)-1,3-thiazol-2-yl]-N'-phenylurea
m.p. 198-199° C.

Example Compound 53-3

N-[5-(2-cyclopentylamino-4-pyridyl)-4-(3-methylphenyl)-1,3-thiazol-2-yl]-N'-phenylurea
m.p. 188-190° C.

Example Compound 53-4

N-[4-(3-methylphenyl)-5-(2-methyl-4-pyridyl)-1,3-thiazol-2-yl]-N'-phenylurea
m.p. 168-169° C.

Example 54

4-(3-methylphenyl)-5-(2-methyl-4-pyridyl)-2-(4-methylsulfinylphenyl)-1,3-thiazole
To a solution of 4-(3-methylphenyl)-5-(2-methyl-4-pyridyl)-2-[4-(methylthio)phenyl]-1,3-thiazole (0.55 g, 1.4 mmol) in acetic acid (15 mL) was added a solution of potassium persulfate (0.43 g, 1.6 mmol) in water (8 mL), and the mixture was stirred for 14 hours at room temperature. An aqueous sodium hydrogen carbonate solution was poured into the reaction mixture, and extracted with ethyl acetate. The extracts were washed with water, dried, then, the solvent was distilled off. The residue was purified by column chromatography (filler: Chromatorex NH DM1020 (trade name, manufactured by Fuji Silysia Chemical Ltd.), hexane-ethyl acetate=1:4), and recrystallized from ethyl acetate-hexane to obtain a title compound (0.15 g, yield 26%).
m.p. 128-130° C.

Example 55

5-(2,6-dimethyl-4-pyridyl)-4-(3-methylphenyl)-2-(4-methylsulfinylphenyl)-1,3-thiazole
To a solution of 5-(2,6-dimethyl-4-pyridyl)-4-(3-methylphenyl)-2-[4-(methylthio)phenyl]-1,3-thiazole (0.41 g, 1.0 mmol) in N,N-dimethylformamide (15 mL) was added m-chloroperbenzoic acid (0.25 g, 1.0 mmol), and the mixture was stirred for 1 hour at room temperature. A 8N aqueous sodium hydroxide solution was poured into the reaction mixture, and extracted with ethyl acetate. The extracted solution was washed with brine, dried, then, the solvent was distilled off. The residue was purified by column chromatography (filler: Chromatorex NH DM1020 (trade name, manufactured by Fuji Silysia Chemical Lte.), hexane-ethyl acetate=1:2), to obtain a title compound (0.41 g, yield 97%).
m.p. 133-134° C.

Example 56

The following example compounds 56-1 and 56-2 were synthesized according to Example 55, using 4-(3,5-dimethylphenyl)-5-(2-methyl-4-pyridyl)-2-[4-(methylthio)phenyl]-1,3-thiazole and 4-(3,5-dimethylphenyl)-5-(2,6-dimethyl-4-pyridyl)-2-[4-(methylthio)phenyl]-1,3-thiazole instead of instead of 5-(2,6-dimethyl-4-pyridyl)-4-(3-methylphenyl)-2-[4-(methylthio)phenyl]-1,3-thiazole Example Compound 56-1

4-(3,5-dimethylphenyl)-5-(2-methyl-4-pyridyl)-2-(4-methylsulfinylphenyl)-1,3-thiazole
m.p. 151-153° C.

Example Compound 56-2

4-(3,5-dimethylphenyl)-5-(2,6-dimethyl-4-pyridyl)-2-(4-methylsulfinylphenyl)-1,3-thiazole
m.p. 151-154° C.

Example 57

4-(3-methylphenyl)-5-(2-methyl-4-pyridyl)-2-(4-methylsulfonylphenyl)-1,3-thiazole
To a solution of 4-(3-methylphenyl)-5-(2-methyl-4-pyridyl)-2-[4-(methylthio)phenyl]-1,3-thiazole (0.61 g, 1.6 mmol) in N,N-dimethylformamide (15 mL) was added m-chloroperbenzoic acid (0.87 g, 3.6 mmol), and the mixture was stirred for 30 minutes at room temperature. An aqueous sodium hydrogen carbonate solution was poured into the reaction mixture, and extracted with ethyl acetate. The extracts were washed with water, dried, then, the solvent was distilled off. The residue was purified by silica gel column chromatography (hexane-ethyl acetate=1:1), and recrystallized from ethanol to obtain a title compound (0.39 g, yield 59%).
m.p. 134-138° C.

Example 58

The following example compounds 58-1 to 58-8 were synthesized according to Example 57, using 4-(3,5-dimethylphenyl)-5-(2-methyl-4-pyridyl)-2-[4-(methylthio)phenyl]-1,3-thiazole, 5-(2,6-dimethyl-4-pyridyl)-4-(3-methylphenyl)-2-[4-(methylthio)phenyl]-1,3-thiazole, 4-(3,5-dimethylphenyl)-5-(2,6-dimethyl-4-pyridyl)-2-[4-(methylthio)phenyl]-1,3-thiazole, 5-(2-fluoro-4-pyridyl)-4-(3-methylphenyl)-2-[4-(methylthio)phenyl]-1,3-thiazole, 4-(4-fluoropheyl)-5-(2-methyl-4-pyridyl)-2-[4-(methylthio)phenyl]-1,3-thiazole, N-[4-[4-(3-chlorophenyl)-2-[4-(methylthio)phenyl]-1,3-thiazol-5-yl]-2-pyridyl]acetamide, N-[4-[4-(3-chlorophenyl)-2-[4-(methylthio)phenyl]-1,3-thiazol-5-yl]-2-pyridyl]propionamide and N-[4-[4-(3-chlorophenyl)-2-[4-(methylthio)phenyl]-1,3-thiazol-5-yl]-2-pyridyl]pivalamide.

Example Compound 58-1

4-(3,5-dimethylphenyl)-5-(2-methyl-4-pyridyl)-2-(4-methylsulfonylphenyl)-1,3-thiazole,
m.p. 196-197° C.

Example Compound 58-2

5-(2,6-dimethyl-4-pyridyl)-4-(3-methylphenyl)-2-(4-methylsulfonylphenyl)-1,3-thiazole,
m.p. 182-184° C.

Example Compound 58-3

4-(3,5-dimethylphenyl)-5-(2,6-dimethyl-4-pyridyl)-2-(4-methylsulfonylphenyl)-1,3-thiazole,
m.p. 217-220° C.

Example Compound 58-4

5-(2-fluoro-4-pyridyl)-4-(3-methylphenyl)-2-(4-methylsulfonylphenyl)-1,3-thiazole,
m.p. 195-199° C.

Example Compound 58-5

4-(4-fluorophenyl)-5-(2-methyl-4-pyridyl)-2-(4-methylsulfonylphenyl)-1,3-thiazole,
m.p. 190-192° C.

Example Compound 58-6

N-[4-[4-(3-chlorophenyl)-2-(4-methylsulfonylphenyl)-1,3-thiazol-5-yl]-2-pyridyl]acetamide,
m.p. 216-217° C.

Example Compound 58-7

N-[4-[4-(3-chlorophenyl)-2-(4-methylsulfonylphenyl)-1,3-thiazol-5-yl]-2-pyridyl]propionamide,
m.p. 224-225° C.

Example Compound 58-8

N-[4-[4-(3-chlorophenyl)-2-(4-methylsulfonylphenyl)-1,3-thiazol-5-yl]-2-pyridyl]pivalamide,
m.p. 122-123° C.

Example 59

4-[4-(3,5-dimethylphenyl)-2-(4-methylsulfonylphenyl)-1,3-thiazol-5-yl]-2-methylpyridine N-oxide To a solution of 4-[4-(3,5-dimethylphenyl)-5-(2-methyl-4-pyridyl)-2-[4-(methylthio)phenyl]-1,3-thiazole (0.60 g, 1.5 mmol) in N,N-dimethylformamide (20 mL) was added m-chloroperbenzoic acid (0.80 g, 3.2 mmol), and the mixture was stirred for 30 minutes at room temperature. m-Chloroperbenzoic acid (0.11 g, 0.45 mmol) was added to the reaction mixture, and the mixture was further stirred for 20 minutes at room temperature. m-Chloroperbenzoic acid (0.38 g, 1.5 mmol) was added to the reaction mixture, and the mixture was further stirred for 20 minutes at room temperature. An aqueous sodium hydrogen carbonate solution was poured, and extracted with ethyl acetate. The extracts were washed with water, dried, then, the solvent was distilled off. The residue was purified by silica gel column chromatography (hexane-ethyl acetate=1:4), and recrystallized from ethanol to obtain a title compound (0.30 g, yield 44%).
m.p. 255-256° C.

Example 60

N-[4-[4-(3-chlorophenyl)-2-(1-methylpiperidin-4-yl)-1,3-thiazol-5-yl]-2-pyridyl]propionamide dihydrochloride To a solution of N-[4-[4-(3-chlorophenyl)-2-(4-piperidyl)-1,3-thiazol-5-yl]-2-pyridyl]propionamide (0.31 g, 0.72 mmol) in N,N-dimethylformamide (8 mL) were added potassium carbonate (0.11 g, 0.82 mmol) and methyl iodide (0.045 mL, 0.72 mmol) were added sequentially, and stirred at room temperature for 20 hours. Aqueous sodium hydrogen carbonate was added to the reaction mixture and extracted with ethyl acetate. The extracts were washed with brine, dried, and concentrated. The residue was purified by column chromatography (filler: Chromatorex NH DM1020 (trade name, manufactured by Fuji Silysia Chemical Ltd.), hexane-ethyl acetate=1:1) and treated with 10% solution of hydrogen chloride in methanol to obtain hydrochloride. The crude crystalline was washed with ethyl acetate to give a title compound (0.12 g, yield 32%).
m.p. 248-253° C.

Example 61

The following example compound 61 was synthesized according to Example 53, using 2-chloroethyl isocyanate instead of phenyl isocyanate.

Example Compound 61

N-(2-chloroethyl)-N'-[5-(2-methyl-4-pyridyl)-4-(3-methylphenyl)-1,3-thiazol-2-yl]urea
m.p. 149-151° C.

Example 62

The following example compound 62 was synthesized according to Example 39, using 2-chloroethyl chloroformate instead of acetyl chloride

Example Compound 62

2-chloroethyl[4-(3-methylphenyl)-5-(2-methyl-4-pyridyl)-1,3-thiazol-2-yl]carbamate
m.p. 156-158° C.

Example 63

N-methoxy-N'-[4-(3-methylphenyl)-5-(2-methyl-4-pyridyl)-1,3-thiazol-2-yl]urea

To a solution of [4-(2-methyl-4-pyridyl)-3-(3-methylphenyl)-1,3-thiazol-2-yl]amine (0.50 g, 1.8 mmol) in N,N-dimethylacetamide (20 mL) was added 1,1-carbonyldiimidazole (0.43 g, 2.7 mmol), and the mixture was stirred for 3 hours at room temperature. A 0-methylhydroxylamine hydrochloride (0.22 g, 2,7 mmol) was added to the reaction mixture, and the mixture was stirred for 24 hours at room temperature. An aqueous sodium hydrogen carbonate solution was poured into the reaction mixture, and the produced solid was filtrated. This solid was washed with water, and dried. The crude product was purified by column chromatography (filler: Chromatorex NH DM1020 (trade name, manufactured by Fuji Silysia Chemical Ltd.), ethyl acetate). The resulted crystal was recrystallized from ethyl acetate to obtain a title compound (0.16 g, yield 25%).
m.p. 194-195° C.

Example 64

The following example compound 64 was synthesized according to Example 63, using 0-phenylhydroxylamine hydrochloride instead of 0-methylhydroxylamine hydrochloride.

Example Compound 64

N-[4-(3-methylphenyl)-5-(2-methyl-4-pyridyl)-1,3-thiazol-2-yl]-N'-phenyloxyurea
m.p. 154-155° C.

Example 65

3-[4-(3-methylphenyl)-5-(2-methyl-4-pyridyl)-1,3-thiazol-5-yl]-oxazolidin-2-one
To a solution of 2-chloroethyl[4-(3-methylphenyl)-5-(2-methyl-4-pyridyl)-1,3-thiazol-2-yl]carbamate (0.30 g, 0.80 mmol) in N,N-dimethylformamide (3 mL) was added potassium tert-butoxide (0.12 g, 1.1 mmol), and the mixture was stirred at room temperature for 1 hour. An aqueous sodium hydrogen carbonate solution was poured into the reaction mixture, and extracted with ethyl acetate. The extracts were washed with water, dried, and concentrated. The residue was purified by silica gel column chromatography (hexane-ethyl acetate=4:1) to obtain a crystal. This crystal was recrystallized from hexane-ethyl acetate, to obtain a title compound (0.20 g, yield 72%).
m.p. 80-82° C.

Example 66

The following example compound 66 was synthesized according to Example 65, using N-(2-chloroethyl)-N'-[5-(2-methyl-4-pyridyl)-4-(3-methylphenyl)-1,3-thiazol-2-yl]urea instead of 2-chloroethyl[4-(3-methylphenyl)-5-(2-methyl-4-pyridyl)-1,3-thiazol-2-yl]carbamate.

Example Compound 66

1-[4-(3-methylphenyl)-5-(2-methyl-4-pyridyl)-1,3-thiazol-2-yl]imidazolidin-2-one
m.p. 200-201° C.

Example 67

1-[4-(3-methylphenyl)-5-(2-methyl-4-pyridyl)-1,3-thiazol-2-yl]-3-phenylimidazolidin-2-one
To a suspension of 1-[4-(3-methylphenyl)-5-(2-methyl-4-pyridyl)-1,3-thiazol-2-yl]-3-imidazolidin-2-one (0.42 g, 1.2 mmol), copper powder (0.23 g, 3.6 mmol), copper chloride (0.01 g, 0.12 mmol) and potassium acetate (0.23 g, 2.4 mmol) in N,N-dimethylacetamide (10 mL) was added bromobenzene (0.56 g, 3.6 mmol), and the mixture was stirred at 150° C. for 4 hours. After filtration, water was added, and extracted with ethyl acetate. The extracts were washed with water, then, dried, and concentrated. The residue was purified by silica gel column chromatography (hexane-ethyl acetate=4:1) to obtain crude crystal. This crude crystal was recrystallized from ethyl acetate, to obtain a title compound (0.18 g, yield 35%).
m.p. 180-182° C.

Example 68

The following example compounds 68-1 and 68-2 were synthesized according to Example 59, using 4-(3-methylphenyl)-5-(2-methyl-4-pyridyl)-2-[4-(methylthio)phenyl]-1,3-thiazole and 2-ethyl-4-(3-methylphenyl)-5-(2-methyl-4-pyridyl)-1,3-thiazole instead of 4-(3,5-dimethylphenyl)-5-(2-methyl-4-pyridyl)-2-[4-(methylthio)phenyl]-1,3-thiazole.

Example Compound 68-1

4-[4-(3-methylphenyl)-2-(4-methylsulfonylphenyl)-1,3-thiazol-5-yl]-2-methylpyridine N-oxide
m.p. 197-198° C.

Example Compound 68-2

[2-ethyl-4-(3-methylphenyl)-1,3-thiazol-5-yl]-2-methylpyridine N-oxide
Oil
$^1$H-NMR (CDCl$_3$) δ: 1.41 (3H, t, J=7.6 Hz), 2.34 (3H, s), 2.46 (3H, s), 3.09 (2H, q, J=7.6 Hz), 7.01 (1H, dd, J=2.2, 7.0 Hz), 7.12-7.24 (4H, m), 8.10 (1H, d, J=2.0 Hz).

Example 69

5-(2-chloro-4-pyridyl)-2-ethyl-4-(3-methylphenyl)-1,3-thiazole
A solution of 4-[2-ethyl-4-(3-methylphenyl)-1,3-thiazol-5-yl]pyridine N-oxide (1.00 g, 3.37 mmol) in phosphorus oxychloride (6.5 mL) was stirred at 100° C. for 2 hours. The reaction solution was cooled, and poured into a saturated aqueous sodium hydrogen carbonate solution, and extracted with ethyl acetate. The extracts were washed with brine, then, dried, and concentrated. The residue was purified by silica gel column chromatography (hexane-ethyl acetate=2:1) to obtain a title compound (0.90 g, yield 81%).
Oil
$^1$H-NMR (CDCl$_3$) δ: 1.42 (3H, t, J=7.8 Hz), 2.35 (3H, s), 3.10 (2H, q, J=7.8 Hz), 7.09 (1H, dd, J=1.4, 5.2 Hz), 7.12-7.30 (4H, m), 7.37 (1H, s), 8.22-8.27 (1H, m).

Example 70

A solution of 4-[2-ethyl-4-(3-methylphenyl)-1,3-thiazol-5-yl]pyridine N-oxide (1.0 g, 3.2 mmol) in phosphorus oxychloride (8 mL) was stirred at 100° C. for 1 hour. The reaction solution was cooled, and poured into a saturated aqueous sodium hydrogen carbonate solution, and extracted with ethyl acetate. The extracts were washed with brine, then, dried, and concentrated. The residue was purified by silica gel column chromatography (hexane-ethyl acetate=10:1 to 2:1) to 5-(2-chloro-6-methyl-4-pyridyl)-2-ethyl-4-(3-methylphenyl)-1,3-thiazole (0.60 g, yield 57%) and 5-(2-chloromethyl-4-pyridyl)-2-ethyl-4-(3-methylphenyl)-1,3-thiazole (0.20 g, yield 19%).

Example Compound 70-1

5-(2-chloro-6-methyl-4-pyridyl)-2-ethyl-4-(3-methylphenyl)-1,3-thiazole
Oil
$^1$H-NMR (CDCl$_3$) δ: 1.45 (3H, t, J=7.8 Hz), 2.35 (3H, s), 2.45 (3H, s), 3.09 (2H, q, J=7.8 Hz), 6.98 (1H, s), 7.06 (1H, s), 7.12-7.24 (3H, m), 7.38 (1H, s).

Example Compound 70-2

5-(2-chloromethyl-4-pyridyl)-2-ethyl-4-(3-methylphenyl)-1,3-thiazole
Oil $^1$H-NMR (CDCl$_3$) δ: 1.46 (3H, t, J=7.6 Hz), 2.33 (3H, s), 3.10 (2H, q, J=7.6 Hz), 4.59 (2H, s), 7.10-7.23 (4H, m), 7.35-7.40 (2H, m), 8.42-8.47 (1H, m).

Example 71

5-(2-cyanomethyl-4-pyridyl)-2-ethyl-4-(3-methylphenyl)-1,3-thiazole

A suspension of 5-(2-chloromethyl-4-pyridyl)-2-ethyl-4-(3-methylphenyl)-1,3-thiazole (0.40 g, 1.2 mmol), potassium cyanide (0.095 g, 1.5 mmol), 18-crown-6 (0.14 g, 0.51 mmol) in acetonitrile (5 mL) was heated under reflux for 6 hours. After cooling, an aqueous potassium carbonate solution was added, and extracted with ethyl acetate. The extracts were washed with brine, then, dried, and concentrated. The residue was purified by silica gel column chromatography (hexane-ethyl acetate=2:1). The resulting crystal was washed with hexane-isopropyl ether to obtain a title compound (0.19 g, 48%).

m.p. 68-69° C.

Example 72

4-[4-(3-methylphenyl)-2-(4-methylsulfonylphenyl)-1,3-thiazol-5-yl]-2-pyridylmethanol To a solution of 4-[4-(3-methylphenyl)-2-(4-methylsulfonylphenyl)-1,3-thiazol-5-yl]pyridine N-oxide (0.43 g, 1.0 mmol) in methylene chloride (10 mL) was added trimethyloxonium tetrafluoroborate (0.17 g, 1.2 mmol), and the mixture was stirred for 2 hours. The reaction mixture was concentrated under reduced pressure, and methanol (15 mL) was added to the residue. To the mixture was added a solution of ammonium persulfate (0.05 g, 0.22 mmol) in water (1 mL) under reflux, and the mixture was heated to reflux for 30 minutes. A solution of ammonium persulfate (0.03 g, 0.11 mmol) in water. (1 mL) was added to the reaction mixture, and the mixture was further heated to reflux for 13 hours. The reaction mixture was cooled to room temperature, then, concentrated under reduced pressure. To the residue was added an aqueous sodium hydrogen carbonate solution, and extracted with ethyl acetate. The extracts were washed with brine, dried over magnesium sulfate, and filtrated and concentrated under reduced pressure. The residued was purified by column chromatography (filler: Chromatorex NH DM1020 (trade name, manufactured by Fuji Silysia Chemical Ltd.), ethyl acetate) to obtain a title compound (0.26 g, yield 61%).

m.p. 172-173° C.

Example 73

2-(4-methylsulfonylphenyl)-4-(3-methylphenyl)-5-[2-(1-pyrrolidinylmethyl)-4-pyridyl]-1,3-thiazole dihydrochloride To a solution of 4-[4-(3-methylphenyl)-2-(4-methylsulfonylphenyl)-1,3-thiazol-5-yl]-2-pyridylmethanol (0.43 g, 1.0 mmol) in tetrahydrofuran (20 mL) was added thionyl chloride (0.08 mL, 1.0 mmol), and the mixture was stirred for 20 minutes. The reaction mixture was concentrated under reduced pressure, and the residue was added to a suspension of pyrrolidine (0.09 mL, 1.1 mmol) and potassium carbonate (0.36 g, 2.6 mmol) in N,N-dimethylformamide (10 mL), and the mixture was stirred for 27 hours at room temperature. To the mixture was added an aqueous sodium hydrogen carbonate solution, and extracted with ethyl acetate. The extracts were washed with brine, dried over magnesium sulfate, and filtrated and concentrated under reduced pressure. The residue was purified by column chromatography (filler: Chromatorex NH DM1020 (trade name, manufactured by Fuji Silysia Chemical Ltd.), hexane-ethyl acetate=1:2). The resulted oil was dissolved in methanol (10 mL), and to this was added a 10% hydrogen chloride-methanol solution (5 mL), and the mixture was stirred for 1 hour at room temperature. The reaction mixture was concentrated under reduced pressure, and the resulting solid was washed with ethanol, to obtain a title compound (yield 17%).

Amorphous $^1$H-NMR (CDCl$_3$) δ: 1.90-2.10 (4H, m), 2.33 (3H, s), 3.31 (3H, s), 4.10-4.40 (4H, m), 4.53 (2H, s), 7.28 (3H, s), 7.43-7.47 (2H, m), 7.67 (1H, s), 8.12 (2H, d, J=8.0 Hz), 8.30 (2H, d, J=8.0 Hz), 8.68 (1H, d, J=5.2 Hz).

Example 74

2-ethyl-4-(3-methylphenyl)-5-[2-(1-pyrrolidinylmethyl)-4-pyridyl]-1,3-thiazole dihydrochloride To a solution of 5-(2-chloromethyl-4-pyridyl)-2-ethyl-4-(3-methylphenyl)-1,3-thiazole (0.20 g, 0.61 mmol) in pyrrolidine (0.5 mL) was stirred for 1 hour at 80° C. After cooling, to this was added an aqueous potassium carbonate solution, and extracted with ethyl acetate. The extracts were washed with brine, then, dried and concentrated. The residue was purified by alumina column chromatography (hexane-ethyl acetate=2:1). The resulting oil was made into a hydrochloride by using a solution of 4N-hydrogen chloride in ethyl acetate, and recrystallized from ethanol-isopropyl ether, to obtain a title compound (0.23 g, 85%).

m.p. 146-151° C.

Example 75

To a solution of 2-bromo-1-(3-bromophenyl)-2-[2-(tert-butoxycarbonylamino)-4-pyridyl]ethanone hydrobromide (22 g, 51 mmol) in N,N,-dimethylformamide (100 mL) was added thiopropionamide (4.3 g, 49 mmol), and the mixture was stirred for 2 hours at room temperature. Into the reaction mixture was poured an aqueous sodium hydrogen carbonate solution, and extracted with ethyl acetate. The extracts were washed with water, then, dried and concentrated. The residue was purified by silica gel column chromatography (hexane-ethyl acetate=4:1), then, recrystallized from hexane-ethyl acetate to obtain 4-(3-bromophenyl)-5-[2-(tert-butoxycarbonylamino)-4-pyridyl]-2-ethyl-1,3-thiazole (6.0 g, yield 27%) and 5-(2-amino-4-pyridyl)-4-(3-bromophenyl)-2-ethyl-1,3-thiazole (1.4 g, yield 8%).

Example Compound 75-1

4-(3-bromophenyl)-5-[2-(tert-butoxycarbonylamino)-4-pyridyl]-2-ethyl-1,3-thiazole m.p. 172-174° C.

Example Compound 75-2

4-[4-(3-bromophenyl)-2-ethyl-1,3-thiazol-5-yl]-2-pyridylamine m.p. 132-134° C.

Example 76

4-[4-(3-cyanophenyl)-2-ethyl-1,3-thiazol-5-yl]-2-pyridylamine

To a solution of 4-(3-bromophenyl)-5-[2-(tert-butoxycarbonylamino)-4-pyridyl]-2-ethyl-1,3-thiazole (0.5 g, 1.1 mmol) in N,N-dimethylformamide (10 mL) was added copper cyanide (0.25 g, 1.6 mmol), and the mixture was stirred for 20 hours at 150° C. under argon atmosphere. Into the reaction mixture was poured ammonia water, and the deposit was removed, then, extracted with ethyl acetate. The extracts were washed with water, then, dried and concentrated. The residue was purified by silica gel column chromatography (hexane-ethyl acetate=4:1) to obtain a crystal. This crystal was washed with hexane-ethyl acetate to obtain a title compound (0.19 g, yield 57%).

m.p. 178-179° C.

Example 77

3-[5-(2-amino-4-pyridyl)-2-ethyl-1,3-thiazol-4-yl]benzoic acid

To a solution of 5-(2-amino-4-pyridyl)-4-(3-cyanophenyl)-2-ethyl-1,3-thiazole (0,50 g, 1.6 mmol) in acetic acid (5 mL) was added 50% sulfuric acid (2.0 mL), and the mixture was stirred for 6 hours at 110° C. The reaction mixture was basified with aqueous sodium hydroxide solution and washed with ethylacetate. The aqueous phase was neutralized with hydrochloric acid, and the deposited crystal was washed with water and ethyl ether to obtain a title compound (0.45 g, yield 84%).

m.p. 273-274° C.

Example 78

Methyl 3-[5-(2-amino-4-pyridyl)-2-ethyl-1,3-thiazol-4-yl]benzoate

To a solution of 3-[5-(2-amino-4-pyridyl)-4-(3-cyanophenyl)-2-ethyl-1,3-thiazol-4-yl]benzoic acid (0.3 g, 1.0 mmol) in methanol (10 mL) was added concentrated sulfuric acid (0.1 mL) and the mixture was stirred for 5 hours at 70° C. The reaction mixture was basified with sodium hydroxide solution and extracted with ethyl acetate. The extracts were washed with water, then, dried and concentrated. The residue was washed with hexane-ethyl acetate to obtain a title compound (0.29 g, yield 85%).

m.p. 173-174° C.

Example 79

To a solution of 4-(3-bromophenyl)-5-[2-(tert-butoxycarbonylamino)-4-pyridyl]-2-ethyl-1,3-thiazole (1.0 g, 2.2 mmol) in tetrahydrofuran (20 mL) was added dropwise a 1.5 M n-butyllithium hexane solution (2.9 mL, 4.3 mmol), and the mixture was stirred for 15 minutes. The reaction mixture was poured onto dry ice, and extracted with ethyl acetate-tetrahydrofuran. The extracts were washed with an aqueous sodium hydroxide solution, then, dried and concentrated. The residue was recrystallized from hexane-ethyl acetate to obtain 5-[2-(tert-butoxycarboylamino)-4-pyridyl]-2-ethyl-4-phenyl-1,3-thiazole (0.29 g, yield 35%). The aqueous layer was made acidic with hydrochloric acid, then, extracted with ethyl acetate-tetrahydrofuran. The extracts were washed with water, then, dried and concentrated. The residue was washed with ethyl acetate to obtain [5-[2-(tert-butoxycarboylamino)-4-pyridyl]-2-ethyl-1,3-thiazol-4-yl]benzoic acid (0.21 g, yield 23%).

Example Compound 79-1

5-[2-(tert-butoxycarbonylamino)-4-pyridyl]-2-ethyl-4-phenyl-1,3-thiazole m.p. 154-155° C.

Example Compound 79-2

3-[5-[2-(tert-butoxycarbonylamino)-4-pyridyl]-2-ethyl-1,3-thiazol-4-yl]benzoic acid $^1$H-NMR (CDCl$_3$) δ: 1.37 (3H, t, J=7.5 Hz), 1.45 (9H, s), 3.08 (2H, q, J=7.5 Hz), 6.83 (1H, dd, J=1.4, 5.0 Hz), 7.34-7.37 (2H, m), 7.42-7.49 (2H, m), 7.86 (1H, s), 8.16 (1H, d, J=5.0 Hz), 9.91 (1H, s).

Example 80

4-[2-(1-tert-butoxycarbonylpiperidin-4-yl)-4-(3-chlorophenyl)-1,3-thiazol-5-yl]-2-pyridylamine A solution of 2-(2-amino-4-pyridyl)-2-bromo-1-(3-chlorophenyl)ethanone hydrobromide (2.74 g, 8.36 mmol) and 1-tert-butoxycarbonylpiperidine-4-carbothioamide in N,N-dimethylformamide (50 mL) was stirred at room temperature for 3 hours. Aqueous sodium hydrogen carbonate was added to the reaction mixture and extracted with ethyl acetate. The extracts were washed with water, dried, and concentrated. The residue was purified by silica gel column chromatography (ethyl acetate) and then purified by column chromatography (filler: Chromatorex NH DM1020 (trade name, manufactured by Fuji Silysia Chemical Ltd.), ethyl acetate). The obtained crude crystalline was recrystallized from ethyl acetate-hexane to give a title compound (1.94 g, yield 50%).

m.p. 143-145° C.

Example 81

N-[4-[2-(1-tert-butoxycarbonylpiperidin-4-yl)-4-(3-chlorophenyl)-1,3-thiazol-5-yl]-2-pyridyl]acetamide To a solution of [4-[2-(1-tert-butoxycarbonylpiperidin-4-yl)-4-(3-chlorophenyl)-1,3-thiazol-5-yl]-2-pyridylamine (1.60 g, 3.40 mmol) in tetrahydrofuran (20 mL) were added acetyl chloride (0.25 mL, 3.52 mmol) and triethylamine (0.50 mL, 3.58 mmol) at 0° C. sequentially, and the resulting mixture was stirred at room temperature for 3 hours. Aqueous sodium hydrogen carbonate was added to the reaction mixture and extracted with ethyl acetate. The extracts were washed with brine, dried, and concentrated. The residue was purified by column chromatography (filler: Chromatorex NH DM1020 (trade name, manufactured by Fuji Silysia Chemical Ltd.), hexane-ethyl acetate=1:1) to give a title compound (1.79 g, yield 98%).

Amorphous Solid $^1$H-NMR(CDCl$_3$) d: 1.49 (9H, s), 1.68-1.88 (2H, m), 2.13-2.21 (5H, m), 2.91 (2H, br t, J=12.0 Hz), 3.12-3.25 (1H, m). 4.20-4.27 (2H, m), 6.87 (1H, dd, J=1.8, 5.4 Hz), 7.18-7.35 (3H, m), 7.56 (1H, t, J=1.8 Hz), 8.15 (1H, d, J=5.4 Hz), 8.27-8.33 (2H, m).

Example 82

The following reference example compounds 82-1 to 82-12 were synthesized according to Example 81, using 4-(2-ethyl-4-phenyl-1,3-thiazol-5-yl)-2-pyridylamine, 4-[2-ethyl-4-(4-fluorophenyl)-1,3-thiazol-5-yl]-2-pyridylamine, 4-[2-ethyl-4-(3-trifluoromethylphenyl)-1,3-thiazol-5-yl]-2-pyridylamine, 4-[2-ethyl-4-(4-fluoro-3-methylphenyl)-1,3-thiazol-5-yl]-2-pyridylamine, 4-[2-ethyl-4-(3-fluorophenyl)-1,3-thiazol-5-yl]-2-pyridylamine, 4-[2-ethyl-4-(4-chlorophenyl)-1,3-thiazol-5-yl]-2-pyridylamine, 4-[2-ethyl-4-(3-ethylphenyl)-1,3-thiazol-5-yl]-2-pyridylamine, 4-[2-ethyl-4-[3-(1-methylethyl)phenyl]-1,3-thiazol-5-yl]-2- pyridylamine, 4-[2-ethyl-4-(3-propylphenyl)-1,3-thiazol-5-yl]-2-pyridylamine, 4-[2-methyl-4-(3methylphenyl)-1,3-thiazol-5-yl]-2-pyridylamine, 4-[4-(3-methylphenyl)-1,3-thiazol-5-yl]-2-pyridylamine and 4-[4-(3-methylphenyl)-2-[4-(methylthio)phenyl]-1,3-thiazol-5-yl]-2-pyridylamine, respectively, instead of 4-[2-(1-tert-butoxycarbonylpiperidin-4-yl)-4-(3-chlorophenyl)-1,3-thiazol-5-yl]-2-pyridylamine.

Example Compound 82-1

N-[4-(2-ethyl-4-phenyl-1,3-thiazol-5-yl)-2-pyridyl]acetamide
m.p. 175-176° C.

Example Compound 82-2

N-[4-[2-ethyl-4-(4-fluorophenyl)-1,3-thiazol-5-yl]-2-pyridyl]acetamide
m.p. 190-191° C.

Example Compound 82-3

N-[4-[2-ethyl-4-(3-trifluoromethylphenyl)-1,3-thiazol-5-yl]-2-pyridyl]acetamide
m.p. 146-147° C.

Example Compound 82-4

N-[4-[2-ethyl-4-(4-fluoro-3-methylphenyl)-1,3-thiazol-5-yl]-2-pyridyl]acetamide
m.p. 142-143° C.

Example Compound 82-5

N-[4-[2-ethyl-4-(3-fluorophenyl)-1,3-thiazol-5-yl]-2-pyridyl]acetamide
m.p. 141-142° C.

Example Compound 82-6

N-[4-[4-(4-chlorophenyl)-2-ethyl-1,3-thiazol-5-yl]-2-pyridyl]acetamide
m.p. 190-191° C.

Example Compound 82-7

N-[4-[2-ethyl-4-(3-ethylphenyl)-1,3-thiazol-5-yl]-2-pyridyl]acetamide
m.p. 112-113° C.

Example Compound 82-8

N-[4-[2-ethyl-4-[3-(1-methylethyl)phenyl]-1,3thiazol-5-yl]-2-pyridyl]acetamide
m.p. 116-117° C.

Example Compound 82-9

N-[4-[2-ethyl-4-(3-propylphenyl)-1,3-thiazol-5-yl]-2-pyridyl]acetamide
m.p. 121-122° C.

Example Compound 82-10

N-[4-[2-methyl-4-(3-methylphenyl)-1,3-thiazol-5-yl]-2-pyridyl]acetamide
m.p. 162-163° C.

Example Compound 82-11

N-[4-[4-(3-methylphenyl)-1,3-thiazol-5-yl]-2-pyridyl]acetamide
m.p. 149-150° C.

Example Compound 82-12

N-[4-[4-(3-methylphenyl)-2-[4-(methylthio)phenyl]-1,3-thiazol-5-yl]-2-pyridyl]acetamide
m.p. 181-182° C.

Example 83

The following example compound 83 was synthesized according to Example 81, using propionyl chloride instead of acetyl chloride.

Example Compound 83

N-[4-[2-(1-tert-butoxycarbonylpiperidin-4-yl)-4-(3-chlorophenyl)-1,3-thiazol-5-yl]-2-pyridyl]propionamide
Amorphous Solid
$^1$H-NMR(CDCl$_3$) d: 1.25 (3H, t, J=7.5 Hz), 1.49 (9H, s), 1.66-1.89 (2H, m), 2.08-2.22 (2H, m), 2.44 (2H, q, J=7.5 Hz), 2.82-3.00 (2H, m), 3.11-3.24 (1H, m). 4.18-4.30 (2H, m), 6.84 (1H, dd, J=1.8, 5.0 Hz), 7.19-7.36 (3H, m), 7.56. (1H, t, J=3.2 Hz), 8.13 (1H, d, J=5.0 Hz), 8.18 (1H, br s), 8.33 (1H, s).

Example 84

The following reference example compounds 84-1 to 84-9 were synthesized according to Example 83, using 4-(2-ethyl-4-phenyl-1,3-thiazol-5-yl)-2-pyridylamine, 4-[2-ethyl-4-(4-fluorophenyl)-1,3-thiazol-5-yl]-2-pyridylamine, 4-[2-ethyl-4-(3-trifluoromethylphenyl)-1,3-thiazol-5-yl]-2-pyridylamine, 4-[2-ethyl-4-(4-fluoro-3-methylphenyl)-1,3-thiazol-5-yl]-2-pyridylamine, 4-[2-ethyl-4-(3-fluorophenyl)-1,3-thiazol-5-yl]-2-pyridylamine, 4-[2-ethyl-4-(4-chlorophenyl)-1,3-thiazol-5-yl]-2-pyridylamine, 4-[2-ethyl-4-[3-(1-methylethyl)phenyl]-1,3-thiazol-5-yl]-2-pyridylamine, 4-[2-ethyl-4-(3-propylphenyl)-1,3-thiazol-5-yl]-2-pyridylamine and 4-[4-(3-methylphenyl)-2-[4-(methylthio)phenyl]-1,3-thiazol-5-yl]-2-pyridylamine, respectively, instead of 4-[2-(1-tert-butoxycarbonylpiperidin-4-yl)-4-(3-chlorophenyl)-1,3-thiazol-5-yl]-2-pyridylamine.

Example Compound 84-1

N-[4-(2-ethyl-4-phenyl-1,3-thiazol-5-yl)-2-pyridyl]propionamide
m.p. 139-140° C.

Example Compound 84-2

N-[4-[2-ethyl-4-(4-fluorophenyl)-1,3-thiazol-5-yl]-2-pyridyl]propionamide
m.p. 156-157° C.

Example Compound 84-3

N-[4-[2-ethyl-4-(3-trifluoromethylphenyl)-1,3-thiazol-5-yl]-2-pyridyl]propionamide
m.p. 126-127° C.

Example Compound 84-4

N-[4-[2-ethyl-4-(4-fluoro-3-methylphenyl)-1,3-thiazol-5-yl]-2-pyridyl]propionamide
m.p. 105-107° C.

Example Compound 84-5

N-[4-[2-ethyl-4-(3-fluorophenyl)-1,3-thiazol-5-yl]-2-pyridyl]propionamide
m.p. 121-122° C.

Example Compound 84-6

N-[4-[4-(4-chlorophenyl)-2-ethyl-1,3-thiazol-5-yl]-2-pyridyl]propionamide
m.p. 152-153° C.

Example Compound 84-7

N-[4-[2-ethyl-4-[3-(1-methylethyl)phenyl]-1,3-thiazol-5-yl]-2-pyridyl]propionamide
m.p. 93-94° C.

Example Compound 84-8

N-[4-[2-ethyl-4-(3-propylphenyl)-1,3-thiazol-5-yl]-2-pyridyl]propionamide
m.p. 124-125° C.

Example Compound 84-9

N-[4-[4-(3-methylphenyl)-2-[4-(methylthio)phenyl]-1,3-thiazol-5-yl]-2-pyridyl]propionamide
m.p. 171-172° C.

Example 85

The following example compound 85 was synthesized according to Example 28, using butyryl chloride instead of cyclohexanecarbonyl chloride.

Example Compound 85

N-[4-[2-ethyl-4-(3-methylphenyl)-1,3-thiazol-5-yl]-2-pyridyl]butyramide
m.p. 88-89° C.

Example 86

The following example compound 86 was synthesized according to Example 85, using 4-[4-(3-chlorophenyl)-2-ethyl-1,3-thiazol-5-yl]-2-pyridylamine instead of 4-[2-ethyl-4-(3-methylphenyl)-1,3-thiazol-5-yl]-2-pyridylamine.

Example Compound 86

N-[4-[4-(3-chlorophenyl)-2-ethyl-1,3-thiazol-5-yl]-2-pyridyl]butyramide
m.p. 119-120° C.

Example 87

The following example compounds 87-1 and 87-2 were synthesized according to Example 85, using valeryl chloride and hexanoyl chloride, respectively, instead of butyryl chloride.

Example Compound 87-1

N-[4-[2-ethyl-4-(3-methylphenyl)-1,3-thiazol-5-yl]-2-pyridyl]valeramide
m.p. 81-82° C.

Example Compound 87-2

N-[4-[2-ethyl-4-(3-methylphenyl)-1,3-thiazol-5-yl]-2-pyridyl]hexanamide
m.p. 84-85° C.

Example 88

The following example compounds 88-1 and 88-2 were synthesized according to Example 86, using valeryl chloride and hexanoyl chloride, respectively, instead of butyryl chloride.

Example Compound 88-1

N-[4-[4-(3-chlorophenyl)-2-ethyl-1,3-thiazol-5-yl]-2-pyridyl]valeramide
m.p. 109-110° C.

Example Compound 88-2

N-[4-[4-(3-chlorophenyl)-2-ethyl-1,3-thiazol-5-yl]-2-pyridyl]hexanamide
m.p. 114-115° C.

Example 89

The following example compound 89 was synthesized according to Example 28, using butyryl chloride instead of cyclopentylacetyl chloride.

Example Compound 89

N-[4-[2-ethyl-4-(3-methylphenyl)-1,3-thiazol-5-yl]-2-pyridyl]cyclopentylacetamide
m.p. 85-86° C.

Example 90

The following example compounds 90-1 and 90-2 were synthesized according to Example 89, using 4-[4-(3-chlorophenyl)-2-ethyl-1,3-thiazol-5-yl]-2-pyridylamine and 4-[4-(4-chlorophenyl)-2-ethyl-1,3-thiazol-5-yl]-2-pyridylamine, respectively, instead of 4-[2-ethyl-4-(3-methylphenyl)-1,3-thiazol-5-yl]-2-pyridylamine.

Example Compound 90-1

N-[4-[4-(3-chlorophenyl)-2-ethyl-1,3-thiazol-5-yl]-2-pyridyl]cyclopentylacetamide
m.p. 121-122° C.

Example Compound 90-2

N-[4-[4-(4-chlorophenyl)-2-ethyl-1,3-thiazol-5-yl]-2-pyridyl]cyclopentylacetamide
m.p. 149-150° C.

Example 91

N-[4-[4-(3-chlorophenyl)-2-(4-piperidyl)-1,3-thiazol-5-yl]-2-pyridyl]acetamide dihydrochloride To a solution of N-[4-[2-(1-tert-butoxycarbonylpiperidin-4-yl)-4-(3-chlorophenyl)-1,3-thiazol-5-yl]-2-pyridylacetamide (1.44 g, 2.81 mmol) in methanol (10 mL) was added 2N-hydrochloric acid (4 mL) and stirred at 80° C. for an hour. The solvent was removed under reduced pressure and the residue was recrystallized from methanol to give a title compound (0.87 g, yield 64%).

m.p. 193-195° C.

Example 92

The following example compound 92 was synthesized according to Example 91, using N-[4-[2-(1-tert-butoxycarbonylpiperidin-4-yl)-4-(3-chlorophenyl)-1,3-thiazol-5-yl]-2-pyridylpropionamide instead of N-[4-[2-(1-tert-butoxycarbonylpiperidin-4-yl)-4-(3-chlorophenyl)-1,3-thiazol-5-yl]-2-pyridylacetamide.

Example Compound 92

N-[4-[4-(3-chlorophenyl)-2-(4-piperidyl)-1,3-thiazol-5-yl]-2-pyridyl]propionamide dihydrochloride
m.p. 202-203° C.

Example 93

N-[4-[2-(1-acetylpiperidin-4-yl)-4-(3-chlorophenyl)-1,3-thiazol-5-yl]-2-pyridyl]acetamide To a suspension of N-[4-[4-(3-chlorophenyl)-2-(4-piperidyl)-1,3-thiazol-5-yl]-2-pyridyl]acetamide dihydrochloride (0.41 g, 0.84 mmol) in tetrahydrofuran (20 mL) were added acetyl chloride (0.13 mL, 1.8 mmol) and triethylamine (0.50 mL, 3.6 mmol) sequentially, and the resulting mixture was stirred at room temperature for 30 minutes. Aqueous sodium hydrogen carbonate was added to the reaction mixture and extracted with ethyl acetate. The extracts were washed with water, dried, and concentrated. The residue was recrystallized from ethyl acetate-hexane to give a title compound (0.24 g, yield 62%).

m.p. 143-145° C.

Example 94

The following example compound 94 was synthesized according to Example 93, using N-[4-[4-(3-chlorophenyl)-2-(4-piperidyl)-1,3-thiazol-5-yl]-2-pyridyl]propionamide dihydrochloride instead of N-[4-[4-(3-chlorophenyl)-2-(4-piperidyl)-1,3-thiazol-5-yl]-2-pyridyl]acetamide dihydrochloride.

Example Compound 94

N-[4-[2-(1-acetylpiperidin-4-yl)-4-(3-chlorophenyl)-1,3-thiazol-5-yl]-2-pyridyl]propionamide
m.p. 174-175° C.

Example 95

The following example compound 95 was synthesized according to Example 11, using 2-bromo-1-(3-ethylphenyl)-2-(2-fluoro-4-pyridyl)ethanone hydrobromide instead of 2-bromo-2-(2-fluoro-4-pyridyl)-1-(3-methylphenyl)ethanone hydrobromide.

Example Compound 95

2-ethyl-4-(3-ethylphenyl)-5-(2-fluoro-4-pyridyl)-1,3-thiazole
Oil $^1$H-NMR(CDCl$_3$) d: 1.18 (3H, t, J=7.6 Hz), 1.46 (3H, t, J=7.6 Hz), 2.62 (2H, q, J=7.6 Hz), 3.10 (2H, q, J=7.6 Hz), 6.86 (1H, t, J=1.4 Hz), 7.07 (1H, dt, J=1.4, 5.2 Hz), 7.16-7.30 (3H, m), 7.33 (1H, s), 8.10 (1H, d, J=5.2 Hz).

Example 96

N-cyclopentyl-4-[2-ethyl-4-(3-ethylphenyl)-1,3-thiazol-5-yl]-2-pyridyl]amine 2-ethyl-4-(3-ethylphenyl)-5-(2-fluoro-4-pyridyl)-1,3-thiazole (0.51 g, 1.6 mmol) and cyclopentylamine (1.6 mL, 16 mmol) were stirred at 140° C. for 12 hours. Aqueous sodium hydrogen carbonate was added to the reaction mixture and extracted with ethyl acetate. The extracts were washed with aqueous sodium hydrogen carbonate and brine, in order, dried, and concentrated. The residue was purified by silica gel column chromatography (hexane-ethyl acetate=4:1). The obtained crude crystalline was recrystallized from isopropyl ether to give a title compound (0.40 g, yield 66%).

m.p. 77-79° C.

Example 97

The following example compound 97 was synthesized according to Example 96, using cyclohexylamine instead of cyclopentylamine.

Example Compound 97

N-cyclohexyl-4-[2-ethyl-4-(3-ethylphenyl)-1,3-thiazol-5-yl]-2-pyridyl]amine
m.p. 115-116° C.

Example 98

The following example compounds 98-1 and 98-2 were synthesized according to Example 57, using N-[4-[4-(3-methylphenyl)-2-[4-(methylthio)phenyl]-1,3-thiazol-5-yl]-2-pyridyl]acetamide and N-[4-[4-(3-methylphenyl)-2-[4-(methylthio)phenyl]-1,3-thiazol-5-yl]-2-pyridyl]propionamide, respectively, instead of 4-(3-methylphenyl)-5-(2-methyl-4-pyridyl)-2-[4-(methylthio)phenyl]-1,3-thiazole.

Example Compound 98-1

N-[4-[4-(3-methylphenyl)-2-(4-methylsulfonylphenyl)-1,3-thiazol-5-yl]-2-pyridyl]acetamide
m.p. 222-223° C.

Example Compound 98-2

N-[4-[4-(3-methylphenyl)-2-(4-methylsulfonylphenyl)-1,3-thiazol-5-yl]-2-pyridyl]propionamide
m.p. 238-239° C.

Example 99

The following example compounds 99-1 and 99-2 were synthesized according to Example 17, using 3-(methylthio)thiopropionamide and 2-amino-1-methyl-2-thioxoethyl benzoate instead of 2-chlorothiobenzamide.

Example Compound 99-1

4-[4-(3-methylphenyl)-2-[2-(methylthio)ethyl]-1,3-thiazol-5-yl]-2-pyridylamine
m.p. 98-99° C.

Example Compound 99-2

1-[5-(2-amino-4-pyridyl)-4-(3-methylphenyl)-1,3thiazol-2-yl]ethyl benzoate
m.p. 89-91° C.

Example 100

The following example compounds 100-1 and 100-2 were synthesized according to Example 99, using 2-(2-amino-4-pyridyl)-2-bromo-1-(3-chlorophenyl)ethanone hydrobromide instead of 2-(2-amino-4-pyridyl)-2-bromo-1-(3-methylphenyl)ethanone hydrobromide.

Example Compound 100-1

4-[4-(3-chlorophenyl)-2-[2-(methylthio)ethyl]-1,3-thiazol-5-yl]-2-pyridylamine
m.p. 96-97° C.

Example Compound 100-2

1-[5-(2-amino-4-pyridyl)-4-(3-chlorophenyl)-1,3-thiazol-2-yl]ethyl benzoate
Amorphous
$^1$H-NMR(CDCl$_3$) d: 1.89 (3H, d, J=6.4 Hz), 4.50 (2H, br s), 6.38-6.47 (2H, m), 6.56 (1H, dd, J=1.4, 5.6 Hz), 7.23-7.38 (3H, m), 7.45-7.53 (2H, m), 7.58-7.66 (2H, m), 8.01 (1H, d, J=5.6 Hz), 8.11-8.16 (2H, m).

Example 101

The following example compounds 101-1 and 101-2 were synthesized according to Example 100, using (methylthio)thioacetamide and 2,2-difluorothiopropionamide instead of 3-(methylthio)thiopropionamide.

Example Compound 101-1

4-[4-(3-chlorophenyl)-2-(methylthio)methyl-1,3-thiazol-5-yl]-2-pyridylamine
m.p. 111-112° C.

Example Compound 101-2

4-[4-(3-chlorophenyl)-2-(1,1-difluoroethyl)-1,3-thiazol-5-yl]-2-pyridylamine
m.p. 131-132° C.

Example 102

The following example compounds 102-1 to 102-6 were synthesized according to Example 83, using 4-[4-(3-methylphenyl)-2-[2-(methylthio)ethyl]-1,3-thiazol-5-yl]-2-pyridylamine, 4-[4-(3-chlorophenyl)-2-[2-(methylthio)ethyl]-1,3-thiazol-5-yl]-2-pyridylamine, 4-[4-(3-chlorophenyl)-2-(methylthio)methyl-1,3-thiazol-5-yl]-2-pyridylamine, 4-[4-(3-chlorophenyl)-2-(1,1-difluoroethyl)-1,3-thiazol-5-yl]-2-pyridylamine, 1-[5-(2-amino-4-pyridyl)-4-(3-methylphenyl)-1,3-thiazol-2-yl]ethyl benzoate and 1-[5-(2-amino-4-pyridyl)-4-(3-chlorophenyl)-1,3-thiazol-2-yl]ethyl benzoate respectively, instead of 4-[2-(1-tert-butoxycarbonylpiperidin-4-yl)-4-(3-chlorophenyl)-1,3-thiazol-5-yl]-2-pyridylamine.

Example Compound 102-1

N-[4-[4-(3-methylphenyl)-2-[2-(methylthio)ethyl]-1,3-thiazol-5-yl]-2-pyridyl]propionamide
m.p. 85-86° C.

Example Compound 102-2

N-[4-[4-(3-chlorophenyl)-2-[2-(methylthio)ethyl]-1,3-thiazol-5-yl]-2-pyridyl]propionamide
m.p. 91-92° C.

Example Compound 102-3

N-[4-[4-(3-chlorophenyl)-2-(methylthio)methyl-1,3-thiazol-5-yl]-2-pyridyl]propionamide
m.p. 118-119° C.

Example Compound 102-4

N-[4-[4-(3-chlorophenyl)-2-(1,1-difluoroethyl)-1,3-thiazol-5-yl]-2-pyridyl]propionamide
m.p. 141-142° C.

Example Compound 102-5

1-[4-(3-methylphenyl)-5-(2-propionylamino-4-pyridyl)-1,3-thiazol-2-yl]ethyl benzoate
m.p. 102-103° C.

Example Compound 102-6

1-[4-(3-chlorophenyl)-5-(2-propionylamino-4-pyridyl)-1,3-thiazol-2-yl]ethyl benzoate
m.p. 124-127° C.

Example 103

The following example compounds 103-1 and 103-2 were synthesized according to Example 81, using 1-[5-(2-amino-4-pyridyl)-4-(3-chlorophenyl)-1,3-thiazol-2-yl]ethyl benzoate and ethyl [5-(2-amino-4-pyridyl)-4-(3-chlorophenyl)-1,3-thiazol-2-yl]acetate instead of [4-[2-(1-tert-butoxycarbonylpiperidin-4-yl)-4-(3-chlorophenyl)-1,3-thiazol-5-yl]-2-pyridylamine.

Example Compound 103-1

1-[5-(2-acetylamino-4-pyridyl)-4-(3-chlorophenyl)-1,3-thiazol-2-yl]ethyl benzoate
m.p. 152-154° C.

Example Compound 103-2 ethyl [5-(2-acetylamino-4-pyridyl)-4-(3-chlorophenyl)-1,3-thiazol-2-yl]acetate
m.p. 99-100° C.

Example 104

N-[4-[2-(1-hydroxyethyl)-4-(3-methylphenyl)-1,3-thiazol-5-yl]-2-pyridyl]propionamide An 1N aqueous sodium hydroxide solution was added dropwise to a solution of 1-[4-(3-methylphenyl)-5-(2-propionylamino-4-pyridyl)-1,3-thiazol-2-yl]ethyl benzoate (1.63 g, 3.46 mmol) in methanol (5 mL) and tetrahydrofuran (20 mL) at 0° C. and the reaction mixture was allowed to warm up to room temperature. The resulting mixture was stirred at room temperature for 30 minutes and the solvent was removed under reduced pressure. The residue was treated with aqueous sodium hydrogen carbonate solution and extracted with ethyl acetate. The extracts were washed with aqueous sodium hydrogen carbonate solution and brine. The resulting solution was dried, and concentrated under reduced pressure. The obtained crude crystal was recrystallized from ethyl acetate-hexane to give a title compound (1.12 g, yield 89%).
m.p. 115-116° C.

Example 105

The following example compound 105 was synthesized according to Example 104, using 1-[4-(3-chlorophenyl)-5-(2-propionylamino-4-pyridyl)-1,3-thiazol-2-yl]ethyl benzoate instead of 1-[4-(3-methylphenyl)-5-(2-propionylamino-4-pyridyl)-1,3-thiazol-2-yl]ethyl benzoate.

Example Compound 105

N-[4-[4-(3-chlorophenyl)-2-(1-hydroxyethyl)-1,3-thiazol-5-yl]-2-pyridyl]propionamide
m.p. 131-132° C.

Example 106

N-[4-[2-acetyl-4-(3-methylphenyl)-1,3-thiazol-5-yl]-2-pyridyl]propionamide
A solution of dimethylsulfoxide (0.30 mL, 4.2 mmol) in dichloromethane (1.0 mL) was added to a solution of oxalyl chloride (0.11 mL, 1.26 mmol) at −78° C. and the resulting mixture was stirred for 15 minutes. A solution of N-[4-[2-(1-hydroxyethyl)-4-(3-methylphenyl)-1,3-thiazol-5-yl]-2-pyridyl]propionamide (0.38 g, 1.0 mmol) in dichloromethane (1.5 mL) was added to the mixture and the resulting mixture was stirred for 45 minutes. The reaction mixture was allowed to warm up to −50° C. and triethylamine (0.72 mL, 5.17 mmol) was added dropwise to the mixture. The resulting mixture was stirred for 30 minutes and poured into aqueous sodium hydrogen carbonate. The mixture was extracted with ethyl acetate and the extracts were washed with aqueous sodium hydrogen carbonate solution and brine. The resulting solution was dried, and concentrated under reduced pressure. The residue was purified by silica gel column chromatography (hexane-ethyl acetate=2:1) to obtain a crude crystal. The obtained crude crystal was recrystallized from isopropyl ether to give a title compound (0.22 g, yield 58%).
m.p. 121-123° C.

Example 107

The following example compound 107 was synthesized according to Example 106, using N-[4-[4-(3-chlorophenyl)-2-(1-hydroxyethyl)-1,3-thiazol-5-yl]-2-pyridyl]propionamide instead of N-[4-[2-(1-hydroxyethyl)-4-(3-methylphenyl)-1,3-thiazol-5-yl]-2-pyridyl]propionamide.

Example Compound 107

N-[4-[2-acetyl-4-(3-chlorophenyl)-1,3-thiazol-5-yl]-2-pyridyl]propionamide
m.p. 115-117° C.

Example 108

N-ethyl-N'-[4-[2-ethyl-4-(3-methylphenyl)-1,3-thiazol-5-yl]-2-pyridyl]urea
To A solution of 4-[2-ethyl-4-(3-methylphenyl)-1,3-thiazol-5-yl]-2-pyridylamine (0.50 g, 1.7 mmol) in N,N-dimethylacetamide (10 mL) was added ethyl isocyanate (0.20 mL, 2.5 mmol) and the reaction mixture was stirred at 80° C. for 20 hours. The reaction mixture was poured into aqueous sodium hydrogen carbonate and extracted with ethyl acetate. The extracts were washed with aqueous sodium hydrogen carbonate solution and brine. The resulting solution was dried, and concentrated under reduced pressure. The obtained crude crystal was recrystallized from ethyl acetate-hexane to give a title compound (0.29 g, yield 47%).
m.p. 160-162° C.

Example 109

The following example compound 109 was synthesized according to Example 108, using 4-[4-(3-chlorophenyl)-2-ethyl-1,3-thiazol-5-yl]-2-pyridylamine instead of 4-[2-ethyl-4-(3-methylphenyl)-1,3-thiazol-5-yl]-2-pyridylamine.

Example Compound 109

N-[4-[4-(3-chlorophenyl)-2-ethyl-1,3-thiazol-5-yl]-2-pyridyl]-N'-ethyl-urea
m.p. 177-180° C.

Example 110

The following example compound 110 was synthesized according to Example 81, using 1-[5-(2-amino-4-pyridyl)-4-(3-methylphenyl)-1,3-thiazol-2-yl]ethyl benzoate instead of [4-[2-(1-tert-butoxycarbonylpiperidin-4-yl)-4-(3-chlorophenyl)-1,3-thiazol-5-yl]-2-pyridylamine.

Example Compound 110

1-[5-(2-acetylamino-4-pyridyl)-4-(3-methylphenyl)-1,3-thiazol-2-yl]ethyl benzoate
m.p. 110-113° C.

Example 111

The following example compounds 111-1 and 111-2 were synthesized according to Example 104, using 1-[5-(2-acetylamino-4-pyridyl)-4-(3-methylphenyl)-1,3-thiazol-2-yl]ethyl benzoate and 1-[5-(2-acetylamino-4-pyridyl)-4-(3-chlorophenyl)-1,3-thiazol-2-yl]ethyl benzoate instead of 1-[4-(3-methylphenyl)-5-(2-propionylamino-4-pyridyl)-1,3-thiazol-2-yl]ethyl benzoate.

Example Compound 111-1

N-[4-[2-(1-hydroxyethyl)-4-(3-methylphenyl)-1,3-thiazol-5-yl]-2-pyridyl]acetamide
m.p. 99-102° C.

Example Compound 111-2

N-[4-[4-(3-chlorophenyl)-2-(1-hydroxyethyl)-1,3-thiazol-5-yl]-2-pyridyl]acetamide
m.p. 142-145° C.

Example 112

The following example compound 112 was synthesized according to Example 106, using N-[4-[4-(3-chlorophenyl)-2-(1-hydroxyethyl)-1,3-thiazol-5-yl]-2-pyridyl]acetamide instead of N-[4-[2-(1-hydroxyethyl)-4-(3-methylphenyl)-1,3-thiazol-5-yl]-2-pyridyl]propionamide.

Example Compound 112

N-[4-[2-acetyl-4-(3-chlorophenyl)-1,3-thiazol-5-yl]-2-pyridyl]acetamide
m.p. 180-183° C.

Example 113

The following example compounds 113-1 and 113-2 were synthesized according to Example 101, using 2-(2-amino-4-pyridyl)-2-bromo-1-(3-methylphenyl)ethanone hydrobromide instead of 2-(2-amino-4-pyridyl)-2-bromo-1-(3-chlorophenyl)ethanone hydrobromide Example Compound 113-1

4-[4-(3-methylphenyl)-2-(methylthio)methyl-1,3-thiazol-5-yl]-2-pyridylamine
m.p. 113-114° C.

Example Compound 113-2

4-[2-(1,1-difluoroethyl)-4-(3-methylphenyl)-1,3-thiazol-5-yl]-2-pyridylamine
m.p. 140-141° C.

The compounds produced in Examples 1 to 113 are shown in Tables 1 to 20.

TABLE 1

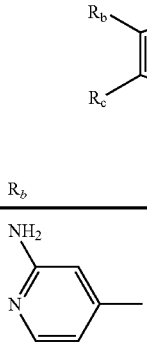

| Example Compound No. | $R_a$ | $R_b$ | $R_c$ | mp/° C. |
|---|---|---|---|---|
| 1 | —NH$_2$ | 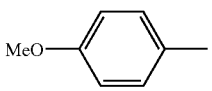 | 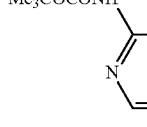 | 251-254 |
| 2 | —NH$_2$ | 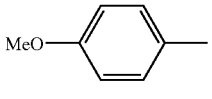 | 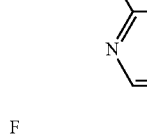 | >270 (dec) |
| 3 | —CH$_2$Me | 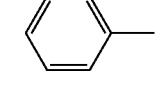 | 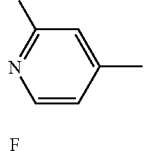 | 162-163 |
| 6 | —NH$_2$ | 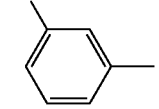 | 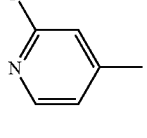 | 214-218 |
| 7-1 | —NH$_2$ | 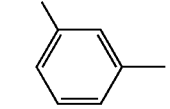 | 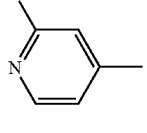 | 190-191 |
| 7-2 | —NH$_2$ | 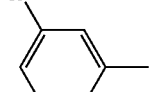 | 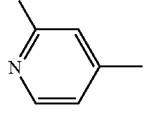 | 227-228 |
| 7-3 | —NH$_2$ | 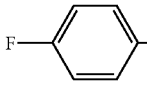 |  | 243-245 |

TABLE 1-continued

| Example Compound No. | $R_a$ | $R_b$ | $R_c$ | mp/° C. |
|---|---|---|---|---|
| 7-4 | —NH$_2$ | 2-Me-pyridin-4-yl | 3-Me-phenyl | 205-206 |
| 7-5 | —NH$_2$ | 2-Me-pyridin-4-yl | 3,5-diMe-phenyl | 219-220 |
| 7-6 | —NH$_2$ | 2,6-diMe-pyridin-4-yl | 3-Me-phenyl | 214-216 |
| 7-7 | —NH$_2$ | 2,6-diMe-pyridin-4-yl | 3,5-diMe-phenyl | 256-258 |
| 7-8 | —NH$_2$ | 2-Me-pyridin-4-yl | 4-F-phenyl | 233-234 |
| 8 | —NHMe | 2-F-pyridin-4-yl | 3-Me-phenyl | 186-187 |

TABLE 2

| Example Compound No. | $R_a$ | $R_b$ | $R_c$ | mp/° C. |
|---|---|---|---|---|
| 9 | —NHMe | 2-Me-pyridin-4-yl | 3-Me-phenyl | 164-165 |

TABLE 2-continued
| Example Compound No. | $R_a$ | $R_b$ | $R_c$ | mp/° C. |
|---|---|---|---|---|
| 10 | —NMe$_2$ | 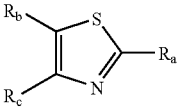 | 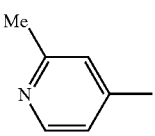 | 77-79 |
| 11 | —CH$_2$Me | 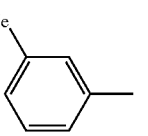 | 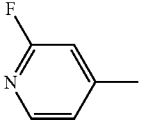 | oil |
| 12 | —CH$_2$Me | 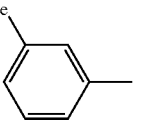 | 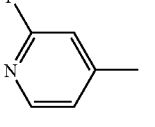 | 102-103 |
| 13 | —CH$_2$Me | 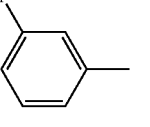 | 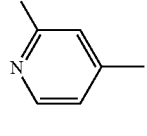 | oil |
| 14-1 | 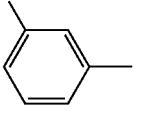 | 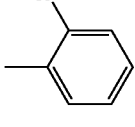 | 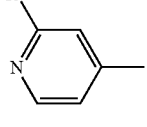 | 83-84 |
| 14-2 | 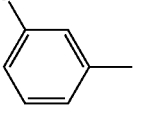 | 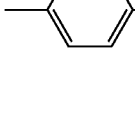 | 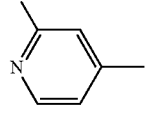 | 104-105 |
| 14-3 | 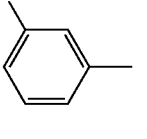 | 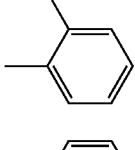 | 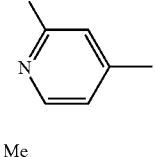 | 73-74 |
| 14-4 | 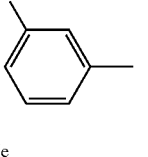 | 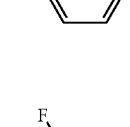 | 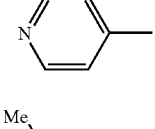 | 89-91 |
| 14-5 | 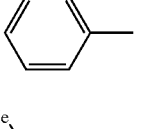 | 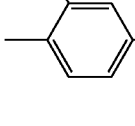 | 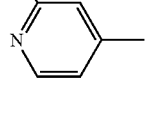 | 90-91 |

TABLE 2-continued
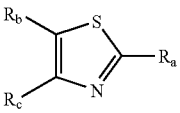
| Example Compound No. | $R_a$ | $R_b$ | $R_c$ | mp/° C. |
|---|---|---|---|---|
| 14-6 | 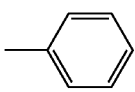 | 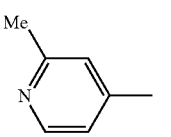 | 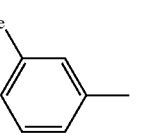 | 79-80 |
| 14-7 | —CH$_2$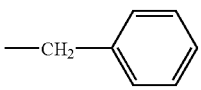 | 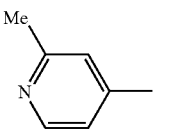 | 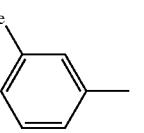 | 82-84 |
| 14-8 | —(CH$_2$)$_2$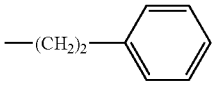 | 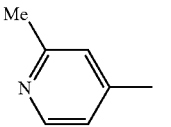 | 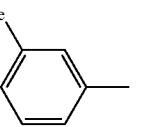 | 64-65 |
| 14-9 | —(CH$_2$)$_3$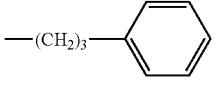 | 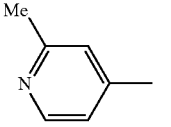 | 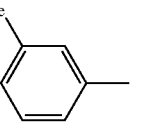 | oil |
TABLE 3
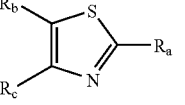
| Example Compound No. | $R_a$ | $R_b$ | $R_c$ | mp/° C. |
|---|---|---|---|---|
| 14-10 | —(CH$_2$)$_3$Me |  | 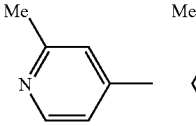 | oil |
| 14-11 | —(CH$_2$)$_2$Me | 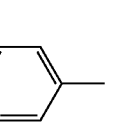 |  | oil |
| 14-12 | —CO$_2$CH$_2$Me | 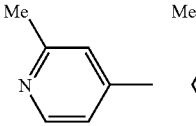 | 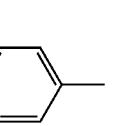 | 97-98 |

TABLE 3-continued
| Example Compound No. | R$_a$ | R$_b$ | R$_c$ | mp/° C. |
|---|---|---|---|---|
| 14-13 | 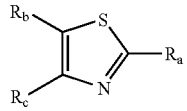 | 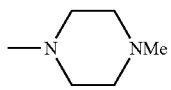 | 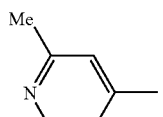 | 115-116 |
| 14-14 | 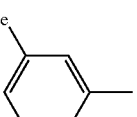 | 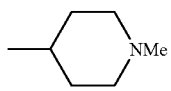 | 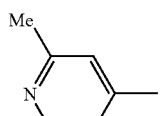 | 127-130 |
| 15 | 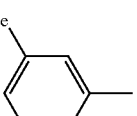 | 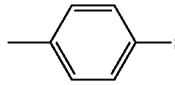 | 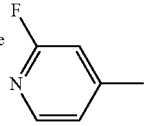 | 97-100 |
| 16-1 | 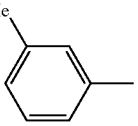 |  | 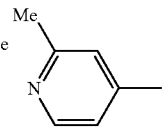 | 119-122 |
| 16-2 | 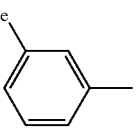 |  | 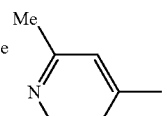 | 123-125 |
| 16-3 | 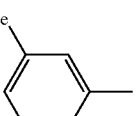 | 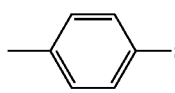 | 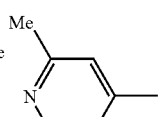 | 112-114 |
| 16-4 | 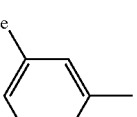 |  | 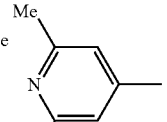 | 134-136 |
| 16-5 | 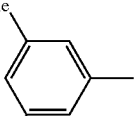 |  | 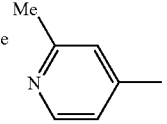 | 99-100 |
| 16-6 | 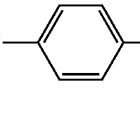 |  | 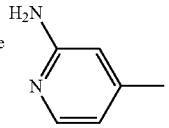 | 183-184 |

TABLE 3-continued
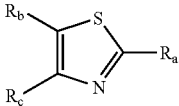
| Example Compound No. | $R_a$ | $R_b$ | $R_c$ | mp/° C. |
|---|---|---|---|---|
| 17 | 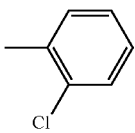 | 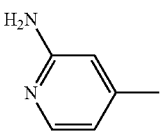 | 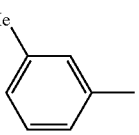 | 175-177 |
TABLE 4
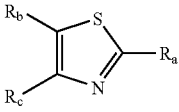
| Example Compound No. | $R_a$ | $R_b$ | $R_c$ | mp/° C. |
|---|---|---|---|---|
| 18-1 | 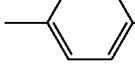 | 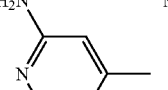 | 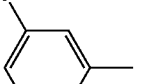 | 160-162 |
| 18-2 | —(CH$_2$)$_3$Me | 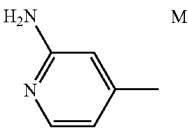 | 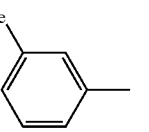 | oil |
| 18-3 | —CH$_2$CF$_3$ | 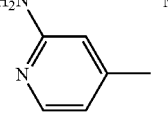 | 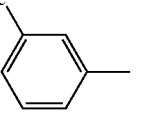 | 131-132 |
| 18-4 | —(CH$_2$)$_2$Me | 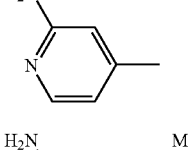 | 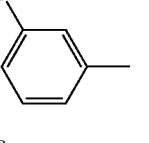 | 113-115 |
| 18-5 | —CH$_2$CO$_2$CH$_2$Me | 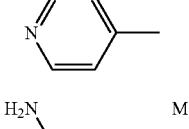 | 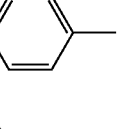 | 128-129 |
| 18-6 | —CO$_2$CH$_2$Me | 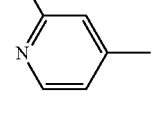 | 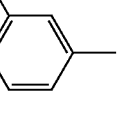 | 147-148 |

TABLE 4-continued
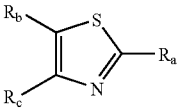
| Example Compound No. | $R_a$ | $R_b$ | $R_c$ | mp/° C. |
|---|---|---|---|---|
| 20-1 | —CH$_2$Me | 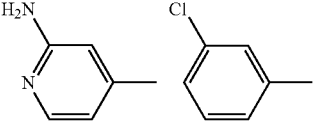 | 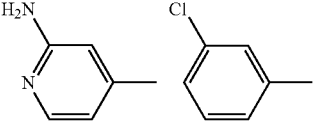 | 131-132 |
| 20-2 | —CH$_2$Me | 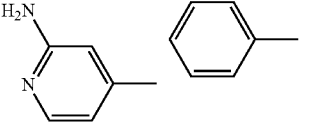 | 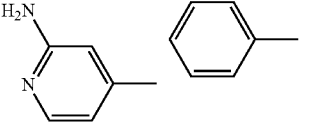 | 158-159 |
| 20-3 | —CH$_2$Me | 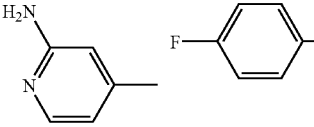 | 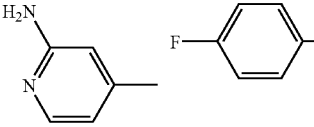 | 140-141 |
| 20-4 | —CH$_2$Me | 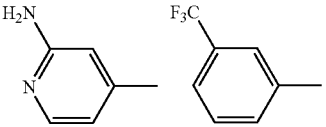 | 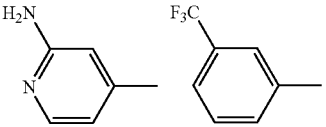 | 117-118 |
| 20-5 | —CH$_2$Me | 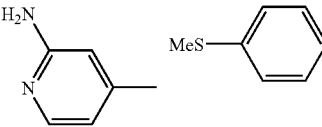 | 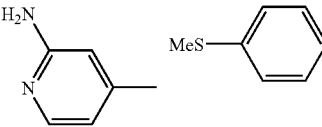 | 119-120 |
| 20-6 | —CH$_2$Me | 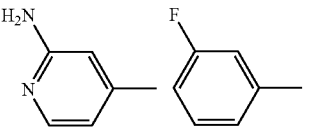 | 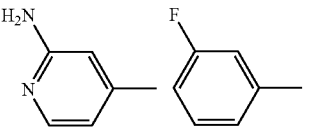 | 153-154 |
| 20-7 | —CH$_2$Me | 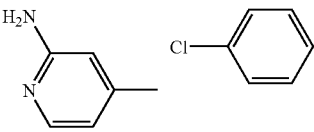 | 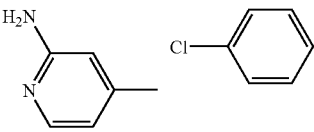 | 136-137 |
| 20-8 | —CH$_2$Me | 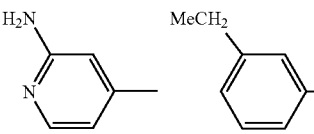 | 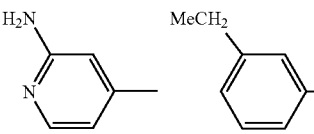 | 128-129 |

TABLE 5
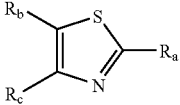
| Example Compound No. | $R_a$ | $R_b$ | $R_c$ | mp/° C. |
|---|---|---|---|---|
| 20-9 | —CH₂Me | 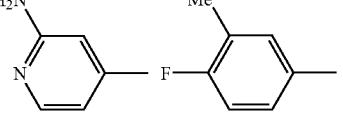 H₂N-pyridine |  Me, F-phenyl | 134-135 |
| 20-10 | —CH₂Me | 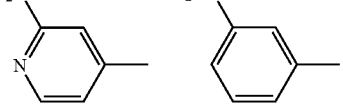 H₂N-pyridine |  Me₂CH-phenyl | 80-81 |
| 20-11 | —CH₂Me | 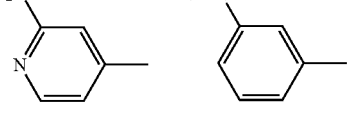 H₂N-pyridine |  Me(H₂C)₂-phenyl | 72-74 |
| 20-12 | —CH₂Me | 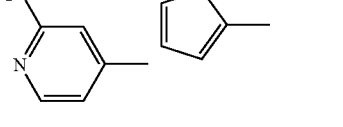 H₂N-pyridine |  thiophene | 159-160 |
| 21-1 | —(CH₂)₂Me | 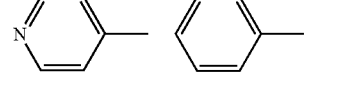 H₂N-pyridine |  Cl-phenyl | 99-100 |
| 21-2 | —CH₂CO₂CH₂Me | 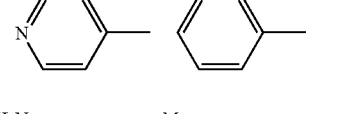 H₂N-pyridine |  Cl-phenyl | 154-155 |
| 22 | —CH₂Me | 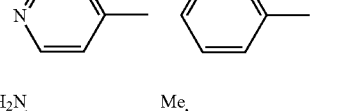 H₂N-pyridine |  Me-phenyl | 144-146 |
| 23-1 | —Me | 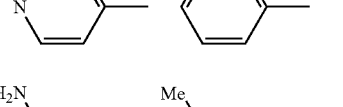 H₂N-pyridine | 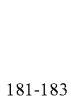 Me-phenyl | 152-153 |
| 23-2 | 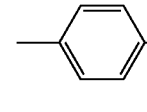 —C₆H₄—SMe | 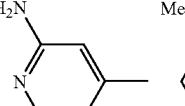 H₂N-pyridine |  Me-phenyl | 181-183 |

TABLE 5-continued
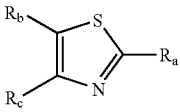
| Example Compound No. | $R_a$ | $R_b$ | $R_c$ | mp/° C. |
|---|---|---|---|---|
| 23-3 | —Me | H₂N-pyridyl | 4-MeO-phenyl | 140-141 |
| 24 | —CH₂CO₂H | H₂N-pyridyl | 3-Me-phenyl | 132-133 |
| 25-1 | —CO₂H | H₂N-pyridyl | 3-Me-phenyl | 156-157 |
| 25-2 | —CO₂H | 2-Me-pyridyl | 3-Me-phenyl | 135-136 |
| 26 | —H | 2-Me-pyridyl | 3-Me-phenyl | oil |
TABLE 6
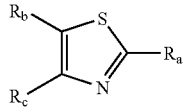
| Example Compound No. | $R_a$ | $R_b$ | $R_c$ | mp/° C. |
|---|---|---|---|---|
| 27-1 | —H | H₂N-pyridyl | 3-Me-phenyl | 91-92 |
| 27-2 | —Me | H₂N-pyridyl | 3-Cl-phenyl | 142-143 |

TABLE 6-continued
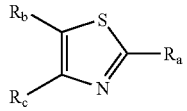
| Example Compound No. | $R_a$ | $R_b$ | $R_c$ | mp/° C. |
|---|---|---|---|---|
| 28 | —CH₂Me | 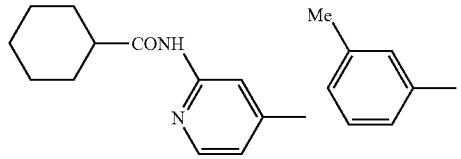 | 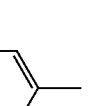 | 98-100 |
| 29-1 | —CH₂Me | 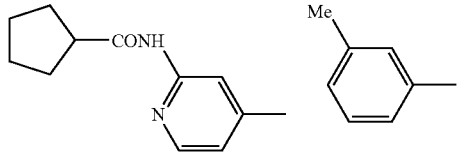 | 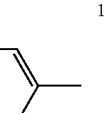 | 123-125 |
| 29-2 | —CH₂Me | 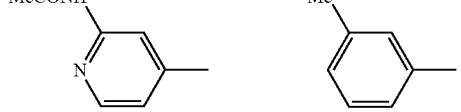 | 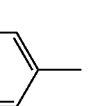 | 119-120 |
| 29-3 | —CH₂Me | 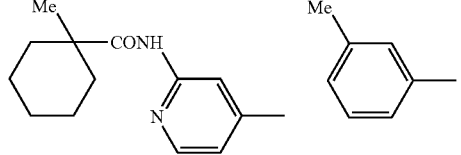 | 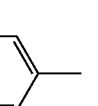 | oil |
| 29-4 | —CH₂Me | 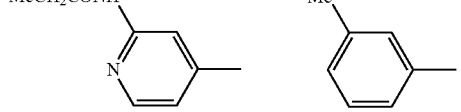 | 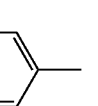 | 103-104 |
| 29-5 | —CH₂Me | 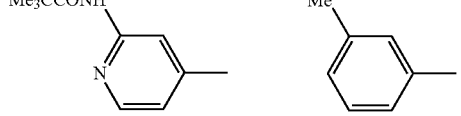 | 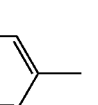 | oil |
| 30-1 | —Me |  | 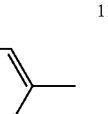 | 112-115 |
| 30-2 | —CH₂Me |  | 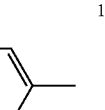 | 149-150 |
| 30-3 | —(CH₂)₂Me |  | 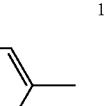 | 144-145 |

TABLE 6-continued
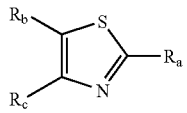
| Example Compound No. | $R_a$ | $R_b$ | $R_c$ | mp/° C. |
|---|---|---|---|---|
| 30-4 | —CH₂Me | MeCONH<br>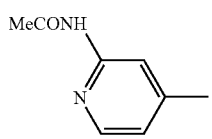 | 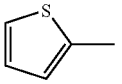 | 154-155 |
| 30-5 | 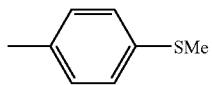 | MeCONH<br>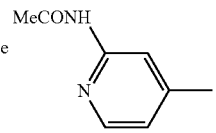 | 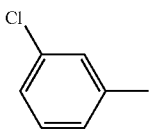 | 207-208 |
TABLE 7
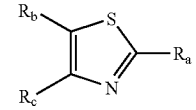
| Example Compound No. | $R_a$ | $R_b$ | $R_c$ | mp/° C. |
|---|---|---|---|---|
| 30-6 | —CH₂Me | 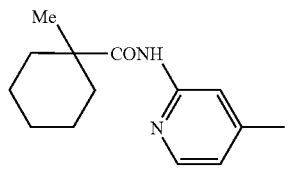 | 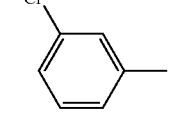 | oil |
| 30-7 | —Me | MeCH₂CONH<br>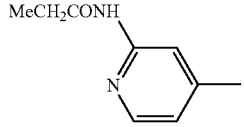 | 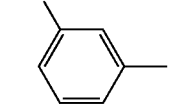 | 134-135 |
| 30-8 | —CH₂Me | MeCH₂CONH<br>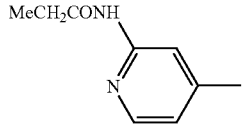 | 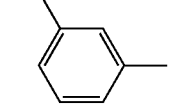 | 132-133 |
| 30-9 | —(CH₂)₂Me | MeCH₂CONH<br>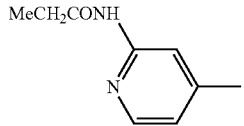 | 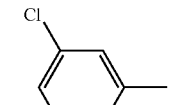 | 103-104 |
| 30-10 | —CH₂Me | MeCH₂CONH<br>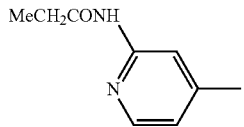 | 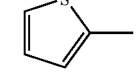 | 187-188 |

TABLE 7-continued
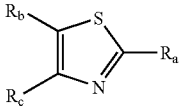
| Example Compound No. | R_a | R_b | R_c | mp/° C. |
|---|---|---|---|---|
| 30-11 | 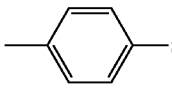 | 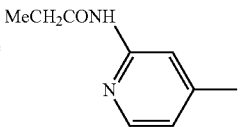 | 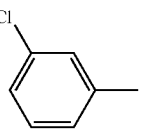 | 187-188 |
| 30-12 | 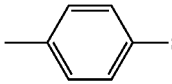 | 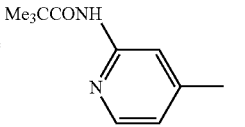 | 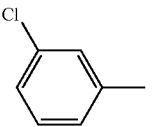 | 119-120 |
| 31 | —CH$_2$Me | 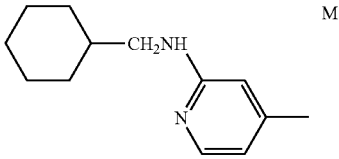 | 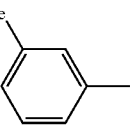 | 74-75 |
| 32 | —CH$_2$Me | 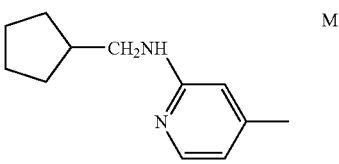 | 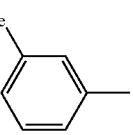 | 67-69 |
| 33 | —NH$_2$ | 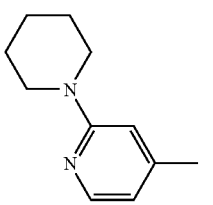 | 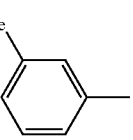 | 181-182 |
| 34-1 | —NH$_2$ | 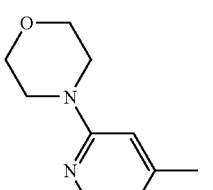 | 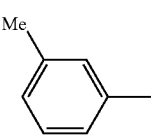 | 188-189 |
| 34-2 | —NH$_2$ | 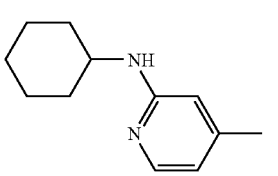 | 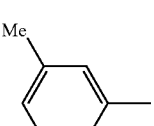 | 168-169 |

TABLE 8
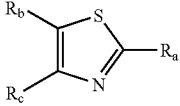
| Example Compound No. | $R_a$ | $R_b$ | $R_c$ | mp/° C. |
|---|---|---|---|---|
| 34-3 | —NH$_2$ | 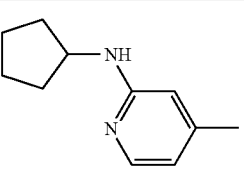 | 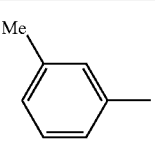 Me | 169-170 |
| 35-1 | —NH$_2$ | 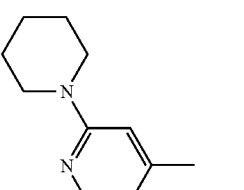 | 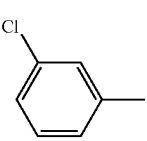 Cl | 206-208 |
| 35-2 | 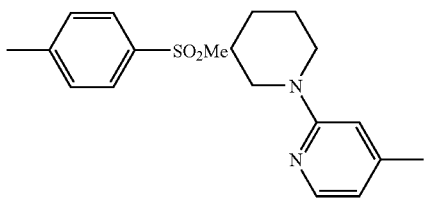 —SO$_2$Me | 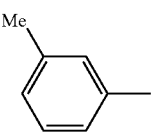 | 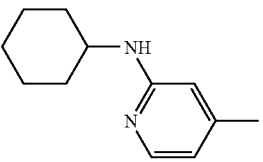 Me | 155-157 |
| 36-1 | —NH$_2$ | 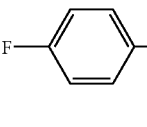 | 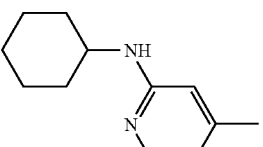 F | 194-195 |
| 36-2 | —NHMe | 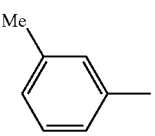 | 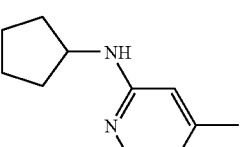 Me | 211-212 |
| 36-3 | —NHMe | 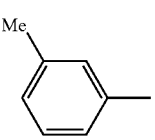 | 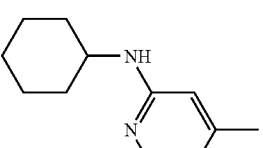 Me | 170-172 |
| 36-4 | —CH$_2$Me | 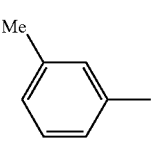 | Me | 110-112 |

TABLE 8-continued

| Example Compound No. | R_a | R_b | R_c | mp/° C. |
|---|---|---|---|---|
| 36-5 | | 4-(MeSO_2)-phenyl-cyclohexyl-NH-(4-methylpyridin-2-yl) | 3-methylphenyl | 197-199 |
| 36-6 | —CH_2Me | cyclopentyl-NH-(4-methylpyridin-2-yl) | 3-methylphenyl | 117-118 |
| 36-7 | | 4-(MeSO_2)-phenyl-cyclopentyl-NH-(4-methylpyridin-2-yl) | 3-methylphenyl | 154-156 |
| 36-8 | | 4-(MeSO_2)-phenyl-morpholinyl-(4-methylpyridin-2-yl) | 3-methylphenyl | 200-202 |

TABLE 9

| Example Compound No. | R_a | R_b | R_c | mp/° C. |
|---|---|---|---|---|
| 36-9 | —CH_2Me | morpholinyl-(4-methylpyridin-2-yl) | 3-methylphenyl | 69-71 |
| 36-10 | —CH_2Me | cyclohexyl-NH-(4-methylpyridin-2-yl) | 3-chlorophenyl | 106-107 |

TABLE 9-continued

| Example Compound No. | $R_a$ | $R_b$ | $R_c$ | mp/° C. |
|---|---|---|---|---|
| 36-11 | —CH₂Me | cyclopentyl-NH-(4-methylpyridin-2-yl) | 3-Cl-phenyl | 110-111 |
| 37-1 | —CH₂Me | pyrrolidin-1-yl-(4-methylpyridin-2-yl) | 3-Me-phenyl | 108-109 |
| 37-2 | 4-methylphenyl | 4-(SO₂Me)phenyl-cyclohexyl-NMe-(4-methylpyridin-2-yl) | 3-Me-phenyl | 173-174 |
| 37-3 | 4-methylphenyl | 4-(SO₂Me)phenyl-cyclohexyl-CH₂NH-(4-methylpyridin-2-yl) | 3-Me-phenyl | 157-159 |
| 37-4 | 4-methylphenyl | 4-(SO₂Me)phenyl-pyrrolidinyl-(4-methylpyridin-2-yl) | 3-Me-phenyl | 199-201 |
| 37-5 | 4-methylphenyl | 4-(SO₂Me)phenyl-4-Me-piperazinyl-(4-methylpyridin-2-yl) | 3-Me-phenyl | 153-154 |
| 38 | —NHCOMe | MeCONH-(4-methylpyridin-2-yl) | 4-MeO-phenyl | 262-264 |
| 39 | —NHCOMe | 2-Me-(4-methylpyridin-2-yl) | 3-Me-phenyl | 230-231 |

TABLE 9-continued
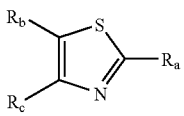
| Example Compound No. | $R_a$ | $R_b$ | $R_c$ | mp/° C. |
|---|---|---|---|---|
| 40-1 | —NHCOMe | 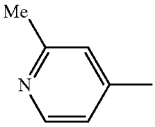 | 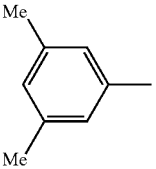 | 236-237 |
TABLE 10
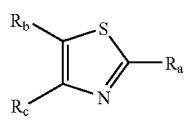
| Example Compound No. | $R_a$ | $R_b$ | $R_c$ | mp/° C. |
|---|---|---|---|---|
| 40-2 | —NHCOMe | 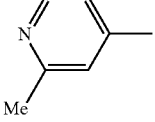 | 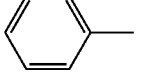 | 185-187 |
| 40-3 | —NHCOMe | 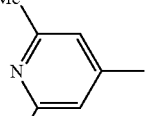 | 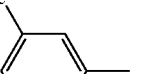 | 266-267 |
| 41 | 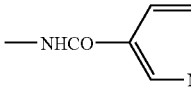 | 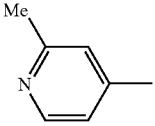 | 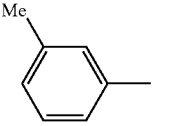 | 175-178 |
| 42-1 | 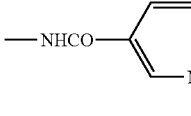 | 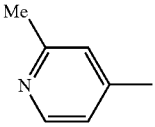 | 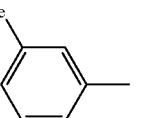 | 203-206 |
| 42-2 | 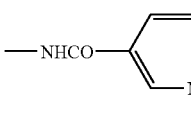 | 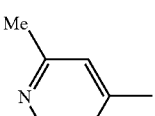 | 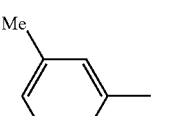 | 267-268 |

TABLE 10-continued
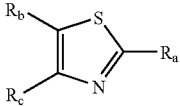
| Example Compound No. | $R_a$ | $R_b$ | $R_c$ | mp/° C. |
|---|---|---|---|---|
| 42-3 | 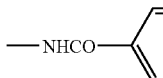 | 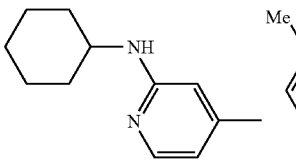 | 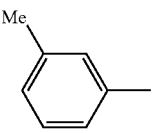 | 201-203 |
| 42-4 |  | 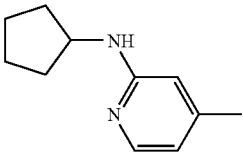 | 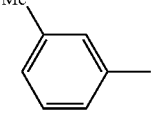 | 215-216 |
| 42-5 | 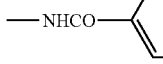 | 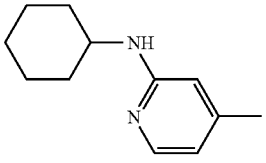 | 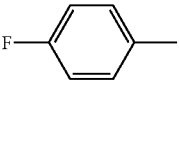 | 136-138 |
| 42-6 | 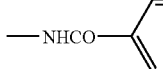 | 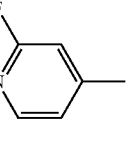 | 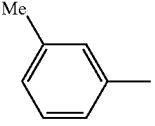 | 229-231 |
| 42-7 | 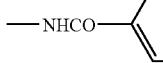 | 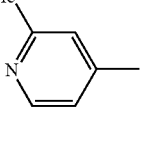 | 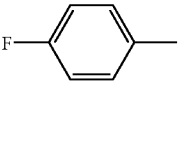 | 261-262 |
| 42-8 | 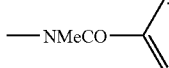 | 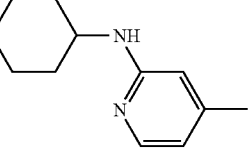 | 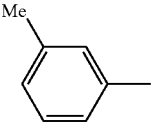 | 147-148 |

TABLE 11
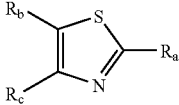
| Example Compound No. | $R_a$ | $R_b$ | $R_c$ | mp/° C. |
|---|---|---|---|---|
| 42-9 | 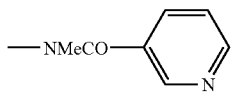 | 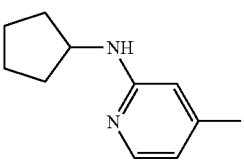 | 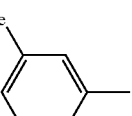 | 148-149 |
| 42-10 | 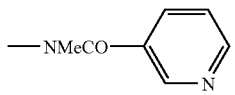 | 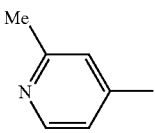 | 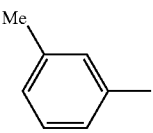 | oil |
| 43 | 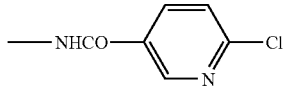 | 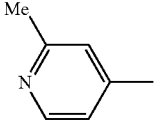 | 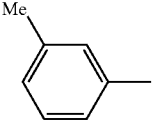 | 228-230 |
| 44-1 | 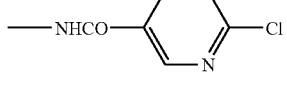 | 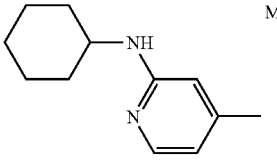 | 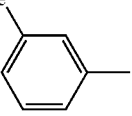 | 255-256 |
| 44-2 | 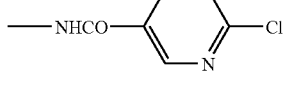 | 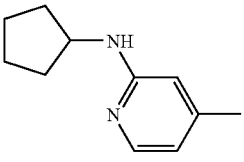 | 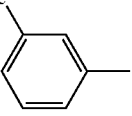 | 211-212 |
| 44-3 | 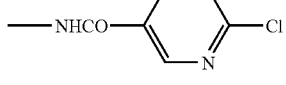 | 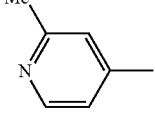 | 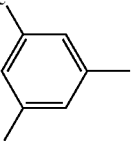 | 271-273 |
| 44-4 | 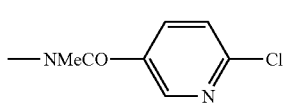 | 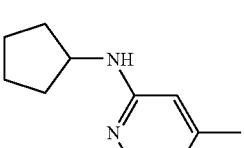 | 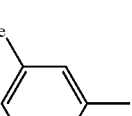 | 171-172 |
| 45 | 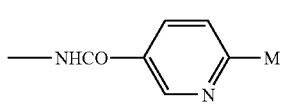 | 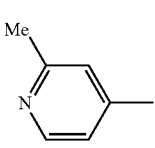 | 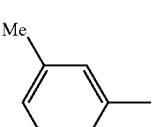 | 233-234 |

TABLE 11-continued
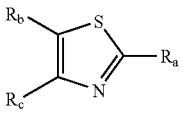
| Example Compound No. | $R_a$ | $R_b$ | $R_c$ | mp/° C. |
|---|---|---|---|---|
| 46-1 | 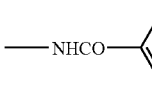 | 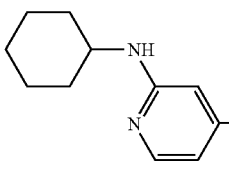 | 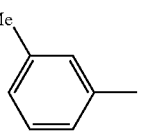 | 242-243 |
| 46-2 | 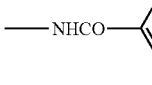 | 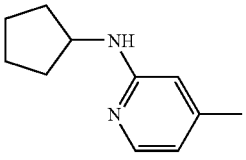 | 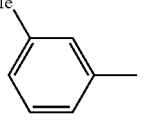 | 213-214 |
| 46-3 | 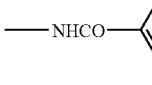 | 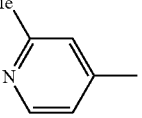 | 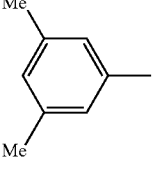 | 252-253 |
| 46-4 | 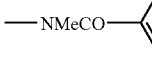 | 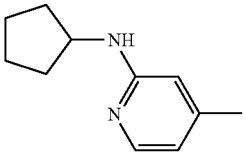 | 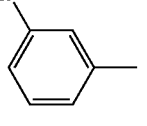 | 176-177 |
TABLE 12
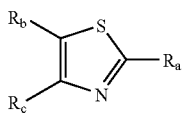
| Example Compound No. | $R_a$ | $R_b$ | $R_c$ | mp/° C. |
|---|---|---|---|---|
| 47 | 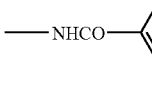 | 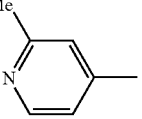 | 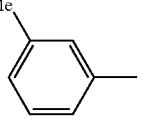 | 224-226 |
| 48-1 | 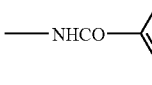 | 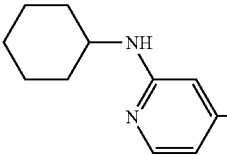 | 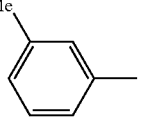 | 191-192 |

TABLE 12-continued

| Example Compound No. | R_a | R_b | R_c | mp/° C. |
|---|---|---|---|---|
| 48-2 | —NHCO-(5-pyridyl, 2-OMe) | cyclopentyl-NH-(2-pyridyl, 4-Me) | 3,5-dimethylphenyl (Me,Me) ... 3-methylphenyl | 219-221 |
| 48-3 | —NHCO-(5-pyridyl, 2-OMe) | 2-Me, 4-Me pyridyl | 3,5-dimethylphenyl | 242-244 |
| 49 | —NHCO-(3-pyridyl, 2-OMe) | 2-Me, 4-Me pyridyl | 3-methylphenyl | 169-170 |
| 50 | —NHCOMe | 2-NH₂, 4-Me pyridyl | 4-MeO-phenyl | 247-250 |
| 51 | —NHCO-phenyl | 2-NH₂, 4-Me pyridyl | 4-MeO-phenyl | 219-222 |
| 52 | —NHCONH-phenyl | 2,6-diMe-4-Me pyridyl | 3-methylphenyl | 173-174 |
| 53-1 | —NHCONH-phenyl | 2,6-diMe-4-Me pyridyl | 3,5-dimethylphenyl | 219-222 |
| 53-2 | —NHCONH-phenyl | cyclohexyl-NH-(2-pyridyl, 4-Me) | 3-methylphenyl | 198-199 |

TABLE 12-continued

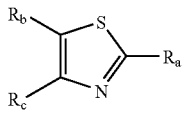

| Example Compound No. | $R_a$ | $R_b$ | $R_c$ | mp/° C. |
|---|---|---|---|---|
| 53-3 | —NHCONH—Ph | cyclopentyl-NH-(4-methylpyridin-2-yl) | 3-methylphenyl | 188-190 |
| 53-4 | —NHCONH—Ph | 2-methyl-4-methylpyridin-? (2,4-dimethylpyridinyl) | 3-methylphenyl | 168-169 |

TABLE 13

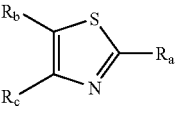

| Example Compound No. | $R_a$ | $R_b$ | $R_c$ | mp/° C. |
|---|---|---|---|---|
| 54 | 4-(SOMe)phenyl | 2-methyl-4-methylpyridinyl | 3-methylphenyl | 128-130 |
| 55 | 4-(SOMe)phenyl | 2-methyl-5-methylpyridinyl | 3-methylphenyl | 133-134 |
| 56-1 | 4-(SOMe)phenyl | 2-methyl-4-methylpyridinyl | 3,5-dimethylphenyl | 151-153 |
| 56-2 | 4-(SOMe)phenyl | 2,6-dimethyl-4-methylpyridinyl | 3,5-dimethylphenyl | 151-154 |
| 57 | 4-(SO$_2$Me)phenyl | 2-methyl-5-methylpyridinyl | 3-methylphenyl | 134-138 |

TABLE 13-continued
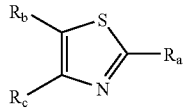

TABLE 14
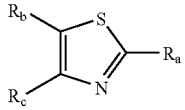
| Example Compound No. | $R_a$ | $R_b$ | $R_c$ | additives | mp/° C. |
|---|---|---|---|---|---|
| 58-8 | 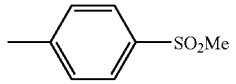 | Me₃CCONH 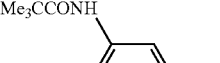 | Cl 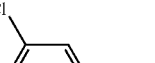 | | 122-123 |
| 59 | 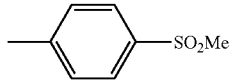 | 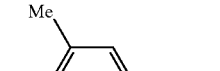 | 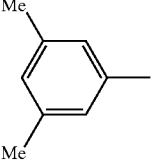 | | 255-256 |
| 60 |  | MeCH₂CONH 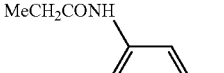 | Cl 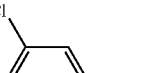 | 2HCl | 248-253 |
| 61 | —NHCONH(CH₂)₂Cl |  |  | | 149-151 |
| 62 | —NHCO₂(CH₂)₂Cl | 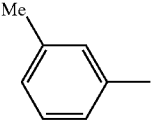 | 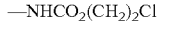 | | 156-158 |
| 63 | —NHCONHOMe |  | 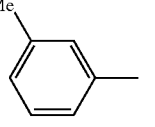 | | 194-195 |
| 64 | —NHCONHO— 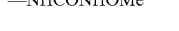 |  | 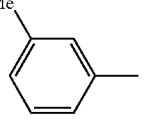 | | 154-155 |
| 65 | 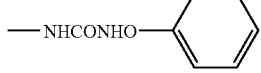 | 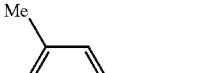 | 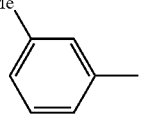 | | 80-82 |
| 66 | 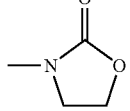 | 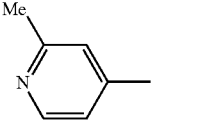 | 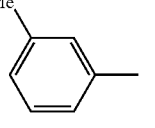 | | 200-201 |

TABLE 14-continued
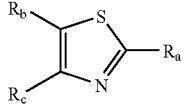
| Example Compound No. | R$_a$ | R$_b$ | R$_c$ | additives | mp/° C. |
|---|---|---|---|---|---|
| 67 | 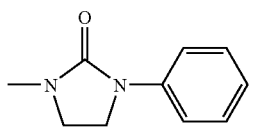 | 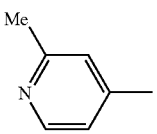 | 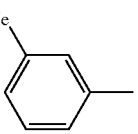 | | 180-182 |
| 68-1 | 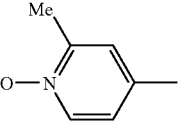 | 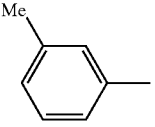 | 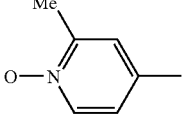 | | 197-198 |
| 68-2 | —CH$_2$Me | 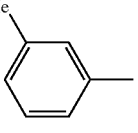 | 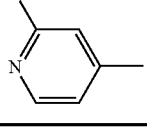 | | oil |
| 69 | —CH$_2$Me | 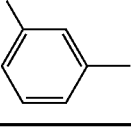 | 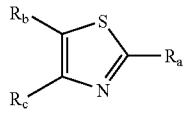 | | oil |
TABLE 15
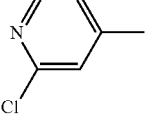
| Example Compound No. | R$_a$ | R$_b$ | R$_c$ | additives | mp/° C. |
|---|---|---|---|---|---|
| 70-1 | —CH$_2$Me | 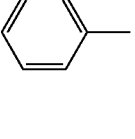 | 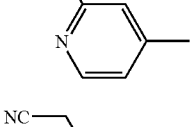 | | oil |
| 70-2 | —CH$_2$Me | 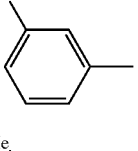 | 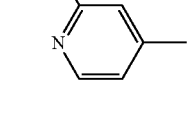 | | oil |
| 71 | —CH$_2$Me | 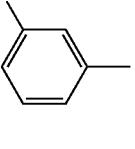 | | | 68-69 |

TABLE 15-continued
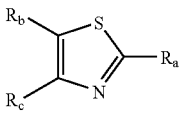
| Example Compound No. | $R_a$ | $R_b$ | $R_c$ | additives | mp/° C. |
|---|---|---|---|---|---|
| 72 | 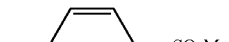 | 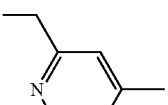 | 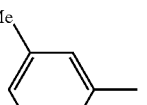 | | 172-173 |
| 73 | 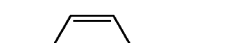 | 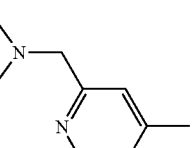 | 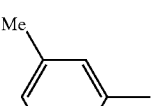 | 2HCl | amorphous |
| 74 | —CH$_2$Me | 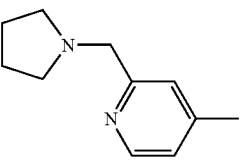 | 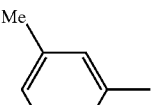 | 2HCl | 146-151 |
| 75-1 | —CH$_2$Me | 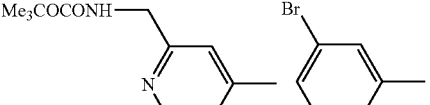 | 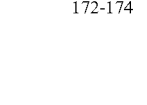 | | 172-174 |
| 75-2 | —CH$_2$Me |  | 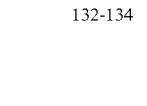 | | 132-134 |
| 76 | —CH$_2$Me |  | 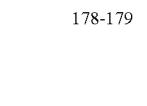 | | 178-179 |
| 77 | —CH$_2$Me |  | 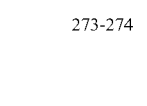 | | 273-274 |
| 78 | —CH$_2$Me |  | 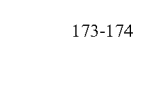 | | 173-174 |
| 79-1 | —CH$_2$Me | 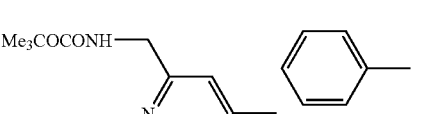 | 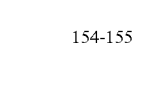 | | 154-155 |

TABLE 15-continued

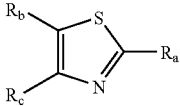

| Example Compound No. | $R_a$ | $R_b$ | $R_c$ | additives | mp/° C. |
|---|---|---|---|---|---|
| 79-2 | —CH$_2$Me | 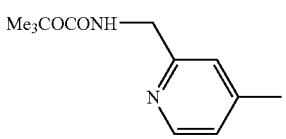Me$_3$COCONH— on pyridine (N at 2, Me at 4) | 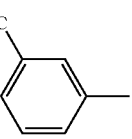 HO$_2$C on benzene (3-position methyl) | | amorphous |

TABLE 16

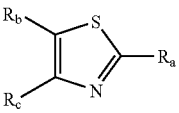

| Example Compound No. | $R_a$ | $R_b$ | $R_c$ | mp/° C. |
|---|---|---|---|---|
| 80 | 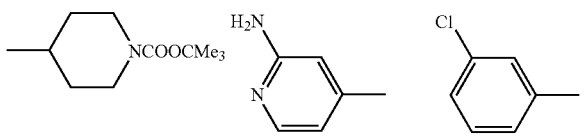 piperidine-NCOOCMe$_3$ | H$_2$N-pyridine-4-Me | 3-Cl-phenyl | 143-145 |
| 81 | 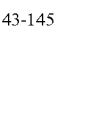 piperidine-NCOOCMe$_3$ | MeCONH-pyridine-4-Me | 3-Cl-phenyl | amorphous |
| 82-1 | —CH$_2$Me | MeCONH-pyridine-4-Me | phenyl | 175-176 |
| 82-2 | —CH$_2$Me | MeCONH-pyridine-4-Me | 4-F-phenyl | 190-191 |
| 82-3 | —CH$_2$Me | MeCONH-pyridine-4-Me | 3-CF$_3$-phenyl | 146-147 |
| 82-4 | —CH$_2$Me | MeCONH-pyridine-4-F | 2-Me-4-... phenyl | 142-143 |

TABLE 16-continued

| Example Compound No. | $R_a$ | $R_b$ | $R_c$ | mp/° C. |
|---|---|---|---|---|
| 82-5 | —CH₂Me | MeCONH-pyridyl- | 2-F-4-methylphenyl | 141-142 |
| 82-6 | —CH₂Me | MeCONH-pyridyl- | 4-Cl-phenyl | 190-191 |
| 82-7 | —CH₂Me | MeCONH-pyridyl- | 3-MeCH-phenyl | 112-113 |
| 82-8 | —CH₂Me | MeCONH-pyridyl- | 3-Me₂CH-phenyl | 118-117 |
| 82-9 | —CH₂Me | MeCONH-pyridyl- | 3-Me(CH₂)₂-phenyl | 121-122 |
| 82-10 | —Me | MeCONH-pyridyl- | 3-Me-phenyl | 162-163 |
| 82-11 | —H | MeCONH-pyridyl- | 3-Me-phenyl | 149-150 |
| 82-12 | 4-SMe-phenyl | MeCONH-pyridyl- | 3-Me-phenyl | 181-182 |

TABLE 17
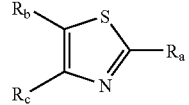
| Example Compound No. | $R_a$ | $R_b$ | $R_c$ | mp/°C |
|---|---|---|---|---|
| 83 | 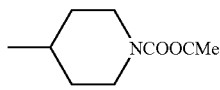 | MeCH$_2$CONH 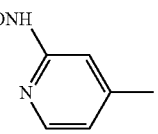 | 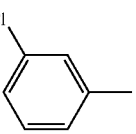 | amorphous |
| 84-1 | —CH$_2$Me | MeCH$_2$CONH 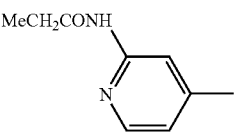 | 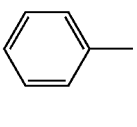 | 139-140 |
| 84-2 | —CH$_2$Me | MeCH$_2$CONH 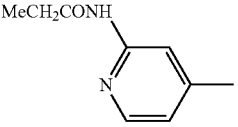 | 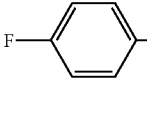 | 156-157 |
| 84-3 | —CH$_2$Me | MeCH$_2$CONH 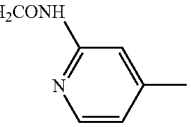 | 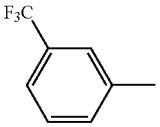 | 126-127 |
| 84-4 | —CH$_2$Me | MeCH$_2$CONH 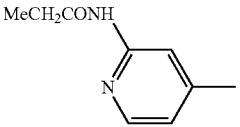 | 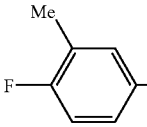 | 105-107 |
| 84-5 | —CH$_2$Me | MeCH$_2$CONH 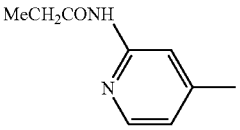 | 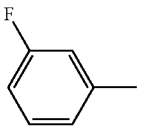 | 121-122 |
| 84-6 | —CH$_2$Me | MeCH$_2$CONH 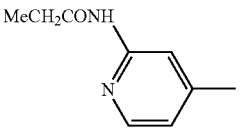 | 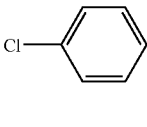 | 152-153 |
| 84-7 | —CH$_2$Me | MeCH$_2$CONH 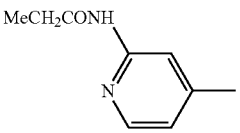 | 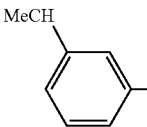 | 93-94 |
| 84-8 | —CH$_2$Me | MeCH$_2$CONH 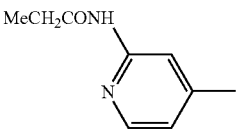 | 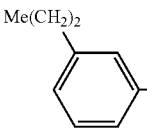 | 124-125 |

TABLE 17-continued
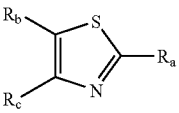
| Example Compound No. | $R_a$ | $R_b$ | $R_c$ | mp/° C. |
|---|---|---|---|---|
| 84-9 | 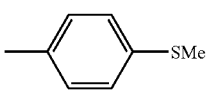 | MeCH$_2$CONH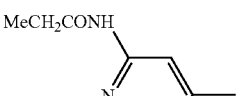 | Me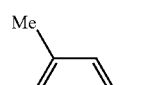 | 171-172 |
| 85 | —CH$_2$Me | Me(CH$_2$)$_2$CONH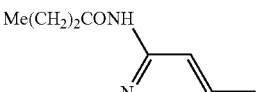 | Me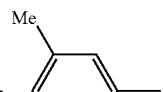 | 88-89 |
| 86 | —CH$_2$Me | Me(CH$_2$)$_2$CONH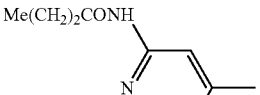 | Cl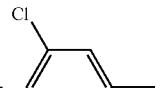 | 119-120 |
| 87-1 | —CH$_2$Me | Me(CH$_2$)$_3$CONH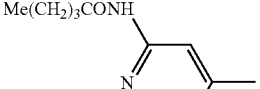 | Me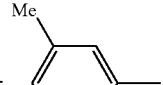 | 81-82 |
TABLE 18
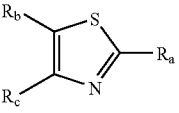
| Example Compound No. | $R_a$ | $R_b$ | $R_c$ | additives | mp/° C. |
|---|---|---|---|---|---|
| 87-2 | —CH$_2$Me | Me(CH$_2$)$_4$CONH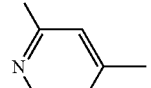 | Me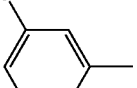 | | 84-85 |
| 88-1 | —CH$_2$Me | Me(CH$_2$)$_3$CONH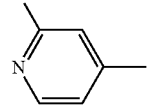 | Cl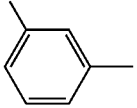 | | 109-110 |
| 88-2 | —CH$_2$Me | Me(CH$_2$)$_4$CONH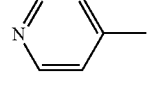 | Cl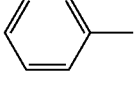 | | 114-115 |

TABLE 18-continued
| Example Compound No. | R$_a$ | R$_b$ | R$_c$ | additives | mp/° C. |
|---|---|---|---|---|---|
| 89 | —CH$_2$Me | 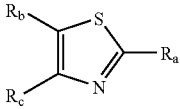—CH$_2$CONH—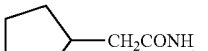 | Me—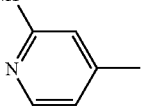 | | 85-86 |
| 90-1 | —CH$_2$Me | 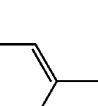—CH$_2$CONH—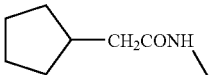 | Cl—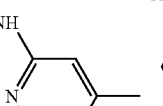 | | 121-122 |
| 90-2 | —CH$_2$Me | 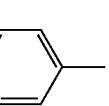—CH$_2$CONH—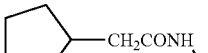 | Cl—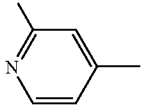 | | 149-150 |
| 91 | 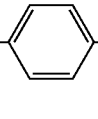 | MeCONH—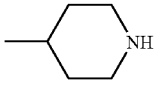 | Cl—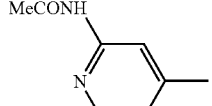 | 2HCl | 193-195 |
| 92 | 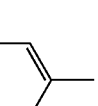 | MeCH$_2$CONH—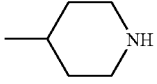 | Cl—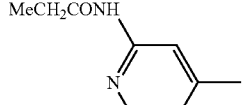 | 2HCl | 202-203 |
| 93 | 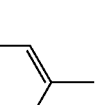 | MeCONH—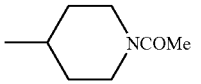 | Cl—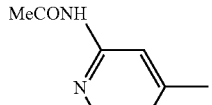 | | 160-161 |
| 94 | 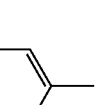 | MeCH$_2$CONH—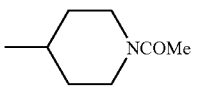 | Cl—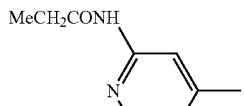 | | 174-175 |
| 95 | —CH$_2$Me | 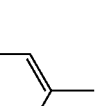 | MeCH—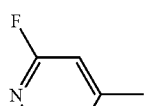 | | oil |
| 96 | —CH$_2$Me | 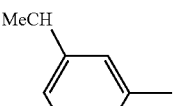—NH— | MeCH—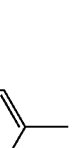 | | 77-79 |

TABLE 18-continued

[Thiazole structure with Rb at position 5, Ra at position 2, Rc at position 4]

| Example Compound No. | Ra | Rb | Rc | additives | mp/° C. |
|---|---|---|---|---|---|
| 97 | —CH₂Me | cyclohexyl-NH-(4-methylpyridin-2-yl) | 3-methylphenyl (MeCH) | | 115-116 |

TABLE 19

[Thiazole structure with Rb at position 5, Ra at position 2, Rc at position 4]

| Example Compound No. | Ra | Rb | Rc | mp/° C. |
|---|---|---|---|---|
| 98-1 | 4-(SO₂Me)phenyl | MeCONH-(4-methylpyridin-2-yl) | 3-methylphenyl | 222-223 |
| 98-2 | 4-(SO₂Me)phenyl | MeCH₂CONH-(4-methylpyridin-2-yl) | 3-methylphenyl | 238-239 |
| 99-1 | —CH₂CH₂SMe | | 3-methylphenyl | 98-99 |
| 99-2 | —CH(Me)OCO-phenyl | | 3-methylphenyl | 89-91 |
| 100-1 | —CH₂CH₂SMe | | 3-chlorophenyl | 96-97 |
| 100-2 | —CH(Me)OCO-phenyl | | 3-chlorophenyl | amorphous |

TABLE 19-continued
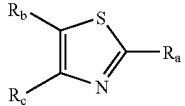
| Example Compound No. | R$_a$ | R$_b$ | R$_c$ | mp/° C. |
|---|---|---|---|---|
| 101-1 | —CH$_2$SMe | | 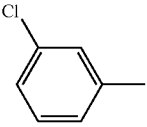 | 111-112 |
| 101-2 | —CF$_2$Me | | 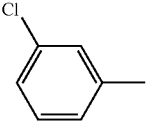 | 131-132 |
| 102-1 | —CH$_2$CH$_2$SMe | MeCH$_2$CONH— 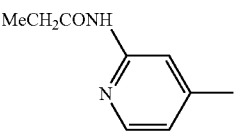 | 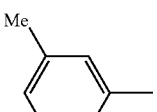 | 85-86 |
| 102-2 | —CH$_2$CH$_2$SMe | MeCH$_2$CONH— 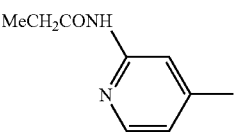 | 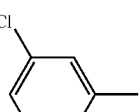 | 91-92 |
| 102-3 | —CH$_2$SMe | MeCH$_2$CONH— 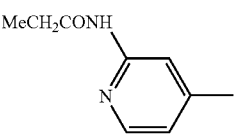 | 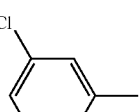 | 118-119 |
| 102-4 | —CF$_2$Me | MeCH$_2$CONH— 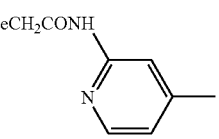 | 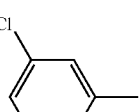 | 141-142 |
| 102-5 | —CH(Me)OCO— 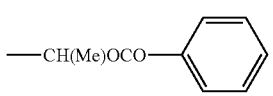 | MeCH$_2$COHN— 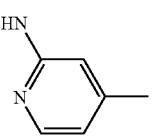 | 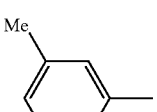 | 102-103 |
| 102-6 | —CH(Me)OCO— 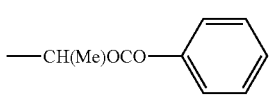 | MeCH$_2$COHN— 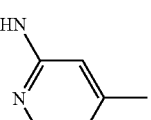 | 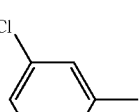 | 124-127 |

TABLE 20

| Example Compound No. | R$_a$ | R$_b$ | R$_c$ | mp/° C. |
|---|---|---|---|---|
| 103-1 | —CH(Me)OCO-phenyl | MeCOHN-(4-methylpyridin-2-yl) | 3-Cl-phenyl | 152-154 |
| 103-2 | —CH$_2$CO$_2$CH$_2$Me | MeCOHN-(4-methylpyridin-2-yl) | 3-Cl-phenyl | 99-100 |
| 104 | —CH(OH)Me | MeCOHN-(4-methylpyridin-2-yl) | 3-Me-phenyl | 115-116 |
| 105 | —CH(OH)Me | MeCH$_2$COHN-(4-methylpyridin-2-yl) | 3-Cl-phenyl | 131-132 |
| 106 | —COMe | MeCH$_2$COHN-(4-methylpyridin-2-yl) | 3-Me-phenyl | 121-123 |
| 107 | —COMe | MeCH$_2$COHN-(4-methylpyridin-2-yl) | 3-Cl-phenyl | 115-117 |
| 108 | —CH$_2$Me | MeCH$_2$COHN-(4-methylpyridin-2-yl) | 3-Me-phenyl | 177-180 |
| 109 | —CH$_2$Me | MeCH$_2$NHCOHN-(4-methylpyridin-2-yl) | 3-Cl-phenyl | 160-162 |
| 110 | —CH(Me)OCO-phenyl | MeCOHN-(4-methylpyridin-2-yl) | 3-Me-phenyl | 110-113 |

TABLE 20-continued

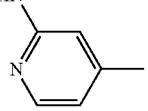

| Example Compound No. | $R_a$ | $R_b$ | $R_c$ | mp/° C. |
|---|---|---|---|---|
| 111-1 | —CH(OH)Me | MeCOHN—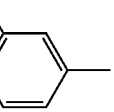 | Me—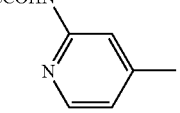 | 99-102 |
| 111-2 | —CH(OH)Me | MeCOHN—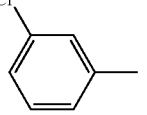 | Cl—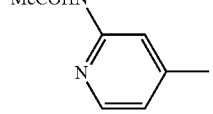 | 142-145 |
| 112 | —COMe | MeCOHN—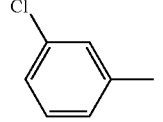 | Cl—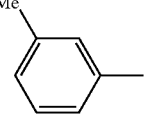 | 180-183 |
| 113-1 | —CH$_2$SMe | | Me—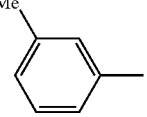 | 113-114 |
| 113-2 | —CF$_2$Me | | Me— | 140-141 |

Preparation Example 1

| (1) Example compound 29-2 | 10.0 mg |
|---|---|
| (2) Lactose | 60.0 mg |
| (3) Corn starch | 35.0 mg |
| (4) Gelatin | 3.0 mg |
| (5) Magnesium stearate | 2.0 mg |

10.0 mg of Example Compound 29-2, 60.0 mg of lactose and 35.0 mg of Corn starch are granulated through a 1 mm mesh sieve using 0.03 ml of a 10% gelatin aqueous solution (3.0 g in terms of gelatin), then, dried at 40° C. and sieved again. Thus obtained granules are mixed with 2.0 mg of magnesium stearate and compressed. The resulted core tablets are coated with sugar coating made from a water suspension of sucrose, titanium dioxide, talc and Arabic gum. The coated tables are endowed with gloss by bees wax to give coated tablets.

Preparation Example 2

| (1) Example compound 29-2 | 10.0 mg |
|---|---|
| (2) Lactose | 70.0 mg |
| (3) Corn starch | 50.0 mg |
| (4) Soluble starch | 7.0 mg |
| (5) Magnesium stearate | 3.0 mg |

10.0 mg of Example Compound 29-2 and 3.0 mg of magnesium stearate are granulated with 0.07 ml of an aqueous solution of soluble starch (7.0 mg in terms of soluble starch), then, dried, and mixed with 70.0 mg of lactose and 50.0 mg of corn starch. The mixture is compressed to obtain tablets.

Preparation Example 3

| (1) Example compound 29-2 | 5.0 mg |
|---|---|
| (2) Sodium Chloride | 20.0 mg |
| (3) Distilled water | | amount to give total amount of 2 ml 5.0 mg of Example compound 29-2 and 20.0 mg of sodium chloride are dissolved in distilled water, and to this was added water to give a total amount of 2.0 ml. The solution is filtrated,

Reference Preparation Example 1

| | |
|---|---|
| (1) Lofecoxiv | 5.0 mg |
| (2) Sodium chloride | 20.0 mg |
| (3) Distilled water | | amount to give total amount of 2 ml 5.0 mg of lofecoxiv and 20.0 mg of sodium chloride are dissolved in distilled water, and to this is added water to give a total amount of 2.0 ml. The solution is filtrated, and a 2 ml ampule is filled with the filtrate under sterile condition. The ampule is disinfected, then, sealed to give an injection solution.

Reference Preparation Example 2

| | |
|---|---|
| (1) Lofecoxiv | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethylcellulose | 20 mg |
| Total | 120 mg |

The above-described components (1) to (6) are mixed according to a normal method, and tabletted by a tabletting machine to obtain tablets.

Preparation Example 4

Any of preparations of Preparation Examples 1 to 3 and any of preparations of Reference Preparation Examples 1 and 2 are combined.

Experiment 1

Genetic manipulation methods described below are based on methods described in Maniatis et al., Molecular Cloning, ColdSpring Harbor Laboratory, 1989, and the appended reagent protocol.

(1) Cloning of Human p38 MAP Kinase Gene and Preparation of Recombinant Baculovirus Cloning of human p38 MAP kinase gene was conducted by a PCR method using primer set p38-U: 5'-

[SEQ ID No. 1]
ACCACTCGAGATGGACTACAAGGACGACGATGACAAGTCTCAGGAGAGGC
CCACGTTCTACC-3' and

[SEQ ID No. 2]
PAG-L: 5'-ACCCGGTACCACCAGGTGCTCAGGACTCCATCTCT-3' synthesized referring to the nucleotide sequence of p38 MAP kinase gene of Han et al., Science 265 (5173), 808-811 (1994), utilizing kidney cDNA (QUICK-Clone cDNA, manufactured by Toyobo Co., Ltd.) as a template.

A PCR reaction was performed according to Hot Start method using AmpliWax PCR Gem 100 (Takara Shuzo Co., Ltd.). For preparing lower layer mixed liquid, 2 µL of 10×LA PCR Buffer, 3 µL of 2.5 mM dNTP solution, each 2.5 µL of 12.5 µM primer solution, and 10 µL of sterile distilled water were mixed. For preparing upper layer mixed liquid, 1 µL of human heart cDNA (1 ng/mL) as a template, 3 µL of 10×LA PCR Buffer, 1 µL of 2.5 mM dNTP solution, 0.5 µL of TaKaRa LA Taq DNA polymerase (Takara Shuzo Co., Ltd.) and 24.5 µL of sterile distilled water were mixed. To the prepared lower mixed liquid was added one AmpliWax PCR Gem 100 (Takara Shuzo Co., Ltd.) treated for 5 minutes at 70° C. and 5 minutes in ice, then, the upper mixed liquid was added, to prepare a reaction solution for PCR. A tube filled with the reaction solution was set on Thermal Cycler (Perkin Elmer), then, treated for 2 minutes at 95° C. Further, a cycle including 15 seconds at 95° C. and 2 minutes at 68° C. was repeated 35 times, then, treated for 8 minutes at 72° C. The resulted PCR product was subjected to agarose gel (1%) electrophoresis, a 1.1 kb DNA fragment containing a p38 MAP kinase gene was recovered from the gel, then, pT7Blue-T vector (Takara Shuzo Co., Ltd.) was inserted to prepare a plasmid pHP38.

4.8 kb XhoI-KpnI fragment of plasmid pFASTBAC1 (CIBCOBRL) and 1.1 kb XhoI-Kpn fragment of the above-mentioned plasmid pHP38 were ligated to construct plasmid pFBHP38.

Plasmid pFBHP38 and BAC-TO-BAC Baculovirus Expression System (GIBCOBRL) were used to prepare virus stock BAC-HP38 of recombinant baculovirus.

(2) Cloning of Human MKK3 Gene and Preparation of Recombinant Baculovirus

Cloning of human MKK3 gene was conducted by a PCR method using primer set MKK-U: 5'-

[SEQ ID No. 3]
ACAAGAATTCATAACATATGGCTCATCATCATCATCATCATTCCAAGCCA
CCCGCACCCAA-3' and

[SEQ ID No. 4]
TCCCGTCTAGACTATGAGTCTTCTCCCAGGAT-3' synthesized referring to the nucleotide sequence of MKK3 gene of Derijard, B. et al., Science 267 (5198), 682-685 (1995), utilizing kidney cDNA (QUICK-Clone cDNA, manufactured by Toyobo Co., Ltd.) as a template.

A PCR reaction was performed according to Hot Start method using AmpliWax PCR Gem 100 (Takara Shuzo Co., Ltd.). For preparing lower layer mixed liquid, 2 µL of 10×LA PCR Buffer, 3 µL of 2.5 mM dNTP solution, each 2.5 µL of 12.5 µM primer solution, and 10 µL of sterile distilled water were mixed. For preparing upper layer mixed liquid, 1 µL of human kidney cDNA (1 ng/mL) as a template, 3 µL of 10×LA PCR Buffer, 1 µL of 2.5 mM dNTP solution, 0.5 µL of TaKaRa LA Taq DNA polymerase (Takara Shuzo Co., Ltd.) and 24.5 µL of sterile distilled water were mixed. To the prepared lower mixed liquid was added one AmpliWax PCR Gem 100 (Takara Shuzo Co.,Ltd.), treated for 5 minutes at 70° C. and 5 minutes in ice, then, the upper mixed liquid was added, to prepare a reaction solution for PCR. A tube filled with the reaction solution was set on Thermal Cycler (Perkin Elmer), then, treated for 2 minutes at 95° C. Further, a cycle including 15 seconds at 95° C. and 2 minutes at 68° C. was repeated 35 times, then, treated for 8 minutes at 72° C. The resulted PCR product was subjected to agarose gel (1%) electrophoresis, a 1.0 kb DNA fragment containing a MKK3 gene was recovered from the gel, then, pT7Blue-T vector (Takara Shuzo Co., Ltd.) was inserted to prepare a plasmid pHMKK3.

For converting MKK3 into constitutively active type (Ser at 189 is converted into Glu, and. Thr at 193 is converted into Glu), mutation was introduced by QuikChange Site-Directed Mutagenesis Kit (Stratagene) using primer set SER-U: 5'-

GGCTACTTGGTGGACGAGGTGGCCAAGGAGATGGATGCCGGCTGC-3' and  [SEQ ID No. 5]

SER-L: 5'-GCAGCCGGCATCCATCTCCTTGGCCACCTCGTCCACCAAGTAGCC-3', [SEQ ID No. 6]
to obtain pcaMKK3.

4.8 kb EcoRI-XbaI fragment of plasmid pFASTBAC1 (CIBCOBRL) and 1.0 kb EcoRI-XbaI fragment of the above-mentioned plasmid pcaMKK3 were ligated to construct plasmid pFBcaMKK3.

Plasmid pFBcaMKK3 and BAC-TO-BAC Baculovirus Expression System (GIBCOBRL) were used to prepare virus stock BAC-caMKK3 of recombinant baculovirus.

(3) Preparation of Active Type p38 MAP Kinase

Sf-21 cells were inoculated on 100 mL Sf-900II SF medium (GIBCOBRL) to give $1\times10^6$ cells/mL, then, cultured for 24 hours at 27° C. Each 0.2 mL of virus stocks BAC-HP38 and BAC-caMKK3 of the recombinant baculovirus were added, then, cultured for further 48 hours. Cells were separated from the culture solution by centrifugal separation (3000 rpm, 10 min.), then, washed with PBS twice. The cells were suspended in 10 mL of Lysis buffer (25 mM HEPES (pH7.5), 1% TritonX, 130 mM NaCl, 1 mM EDTA, 1 mM DTT, 25 mM β-glycerophosphate, 20 mM leupeptin, 1 mM APMSF, 1 mM Sodium orthovanadate), then, treatment by Homogenizer (POLYTRON) for 2 minutes at 20000 rpm was performed twice to lyse the cells. Active type p38 MAP kinase was purified from the supernatant obtained by centrifugal separation (40000 rpm, 45 minutes), by using Anti-FLAG M2 Affinity Gel (Eastman Chemical).

(4) To 37.5 µL of a reaction solution (25 mM HEPES (pH 7.5), 10 mM Magnesium Acetate) containing 260 ng of active type p38 MAP kinase and 1 µg of Myelin Basic Protein was added 2.5 µL of a sample compound dissolved in DMSO, then, the mixture was kept at 30° C. for 5 minutes. The reaction was initiated by adding 10 µL of an ATP solution (2.5 µM ATP, 0.1 µCi[γ-$^{32}$P] ATP). After reaction for 60 minutes at 30° C., the reaction was terminated by adding 50 µL of a 20% TCA solution. The reaction solution was left for 20 minutes at 0° C., then, acid insoluble fraction was transferred to GF/C filter (Packard Japan) using Cell Harvester (Packard Japan), and washed with 250 mM $H_3PO_4$. After drying for 60 minutes at 45° C., 40 µL of Microscint 0 (Packard Japan) was added, and radiation activity was measured by Top Counter (Packard Japan). The concentration ($IC_{50}$ value) of a sample compound necessary for inhibiting 50% of incorporation into the acid insoluble fraction of $^{32}$p was calculated by PRISM 2.01 (GraphPad Software).

The results are shown below.

TABLE 21

| Example Compound No. | $IC_{50}$ (µM) |
| --- | --- |
| 30-2 | 0.010 |
| 34-2 | 0.0099 |

TABLE 21-continued

| Example Compound No. | $IC_{50}$ (µM) |
| --- | --- |
| 36-10 | 0.0011 |
| 46-4 | 0.017 |
| 58-7 | 0.0084 |

Experiment 2

Measurement of Inhibitory Activity of TNF-α Production

THP-1 cells cultured in a PRMI 1640 medium (Life Technologies, Inc., USA) containing 1% inactivated fetal bovine serum (Life Technologies, Inc.) and 10 mM HEPES (pH 7.5) were inoculated on a 96 well plate to give $1\times10^5$ cells/well, then, 1 µL of a sample compound dissolved in DMSO was added. After incubation for 1 hour at 37° C. in a $CO_2$ incubator, LPS (Wako Pure Chemical Industries Ltd.) was added to give a final concentration of 5 µg/mL. After incubation for 4 hours at 37° C. in a $CO_2$ incubator, the supernatant was obtained by centrifugal separation. The TNF-α concentration in the supernatant was measured by ELISA (R&D Systems, Quantikine Kit). The concentration ($IC_{50}$ value) of a sample compound necessary for inhibiting 50% of TNF-α production was calculated by PRISM 2.01 (GraphPad Software).

The results are shown below.

TABLE 22

| Example Compound No. | $IC_{50}$ (µM) |
| --- | --- |
| 30-2 | 0.12 |
| 34-2 | 0.002 |
| 36-10 | 0.055 |
| 46-4 | 0.082 |
| 58-7 | 0.021 |

From the above-described results, it is known that compounds of the present invention have excellent inhibitory activity of p38 MAP kinase and TNF-α production.

INDUSTRIAL APPLICABILITY

The compound (Ia), (Ib) or (Ic) of the present invention or a salt thereof or a pro-drug thereof has an excellent p38 MAP kinase inhibitory activity, TNF-α inhibitory activity and the like, and can be used as a pharmaceutical composition for preventing or treating cytokine-mediated diseases such as p38 MAP kinase-mediated diseases, TNF-α-mediated diseases and the like, and as a pharmaceutical composition for preventing or treating adenosine receptor-mediated diseases.

What is claimed is:

1. A compound which is:

5-[2(tert-butoxycarbonylamino)-4-pyridyl]-2-ethyl-4-(3-methylphenyl)-1,3-thiazole,

[4-(3-methylphenyl)-5-(2-methyl-4-pyridyl)-1,3-thiazol-2-yl]amine, 2-ethyl-5-(2-fluoro-4-pyridyl)-4-(3-methylphenyl)-1,3-thiazole, 5-(2-fluoro-4-pyridyl)-4-(3-methylphenyl)-2-[4-(methylthio)phenyl]-1,3-thiazole, 4-(3-methylphenyl)-5-(2-methyl-4-pyridyl)-2-[4-(methylthio)phenyl]-1,3-thiazole, 4-[2-ethyl-4-(3-methylphenyl)-1,3-thiazol-5-yl]-2-pyridylamine, N-[4-[2-ethyl-4-(3-methylphenyl)-1,3-thiazol-5-yl]-2-pyridyl]acetamide, N-[4-[2-ethyl-4-(3-methylphenyl)-1,3-thiazol-5-yl]-2-pyridyl]propionamide, N-[4-[4-(3-chlorophenyl)-2-methyl-1,3-thiazol-5-yl]-2-pyridyl]acetamide, N-[4-[4-(3-chlorophenyl)-2-ethyl-1,3-thiazol-5-yl]-2-pyridyl]acetamide, N-[4-[4-(3-chlorophenyl)-2-propyl-1,3-thiazol-5-yl]-2-pyridyl]acetamide, N-[4-[4-(3-chlorophenyl)-2-methyl-1,3-thiazol-5-yl]-2-pyridyl]propionamide, N-[4-[4-(3-chlorophenyl)-2-ethyl-1,3-thiazol-5-yl]-2-pyridyl]propionamide, N-[4-[4-(3-chlorophenyl)-2-propyl-1,3-thiazol-5-yl]-2-pyridyl]propionamide, N-cyclohexyl-4-[2-ethyl-4-(3-methylphenyl)-1,3-thiazol-5-yl]-2-pyridylamine, N-cyclohexyl-4-[4-(3-methylphenyl)-2-(4-methylsulfonylphenyl)-1,3-thiazol-5-yl]-2-pyridylamine, N-cyclopentyl-4-[-2-ethyl-4-(3-methylphenyl)-1,3-thiazol-5-yl]-2-pyridylamine, N-cyclopentyl-4-[4-(3-methylphenyl)-2-(4-methylsulfonylphenyl)-1,3-thiazol-5-yl]-2-pyridylamine, 4-[4-(3-chlorophenyl)-2-ethyl-1,3-thiazol-5-yl]-N-cyclohexyl-2-pyridylamine, 4-[4-(3-chlorophenyl)-2-ethyl-1,3-thiazol-5-yl]-N-cyclopentyl-2-pyridylamine, N-[4-(3-methylphenyl)-5-(2-methyl-4-pyridyl)-1,3-thiazol-2-yl]acetamide, 4-(3-methylphenyl)-5-(2-methyl-4-pyridyl)-2-(4-methylsulfinylphenyl)-1,3-thiazole, 4-(3-methylphenyl)-5-(2-methyl-4-pyridyl)-2-(4-methylsulfonylphenyl)-1,3-thiazole, 5-(2-fluoro-4-pyridyl)-4-(3-methylphenyl)-2-(4-methylsulfonylphenyl)-1,3-thiazole, N-[4-[4-(3-chlorophenyl)-2-(4-methylsulfonylphenyl)-1,3-thiazol-5-yl]-2-pyridyl]acetamide, N-[4-[4-(3-chlorophenyl)-2-(4-methylsulfonylphenyl)-1,3-thiazol-5-yl]-2-pyridyl]propionamide, or N-[4-[4-(3-chlorophenyl)-2-(4-methylsulfonylphenyl)-1,3-thiazol-5-yl]-2-pyridyl]pivalamide, or a salt thereof.

2. A pharmaceutical composition comprising the compound as claimed in claim 1 and a pharmacologically acceptable carrier.

* * * * *

SEQUENCE LISTING

<160> NUMBER OF SEQ ID NOS: 6

<210> SEQ ID NO 1
<211> LENGTH: 62
<212> TYPE: DNA
<213> ORGANISM: Artificial Sequence

```
<220> FEATURE:
<223> OTHER INFORMATION: Description of Artificial Sequence: PRIMER p38-
      U

<400> SEQUENCE: 1
accactcgag atggactaca aggacgacga tgacaagtct caggagaggc ccacgttcta      60
cc                                                                    62

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: PRIMER PAG-
      L

<400> SEQUENCE: 2
acccggtacc accaggtgct caggactcca tctct                                35

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence: PRIMER MKK-
      U

<400> SEQUENCE: 3
acaagaattc ataacatatg gctcatcatc atcatcatca ttccaagcca cccgcaccca      60
a                                                                     61

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: PRIMER MKK-
      L

<400> SEQUENCE: 4
tcccgtctag actatgagtc ttctcccagg at                                   32

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: PRIMER SER-
      U

<400> SEQUENCE: 5
ggctacttgg tggacgaggt ggccaaggag atggatgccg gctgc                     45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: PRIMER SER-
      L

<400> SEQUENCE: 6
gcagccggca tccatctcct tggccacctc gtccaccaag tagcc                     45
```